United States Patent [19]

Morishige et al.

[11] Patent Number: 6,022,888
[45] Date of Patent: Feb. 8, 2000

[54] IRIDOID DERIVATIVES AND NEOVASCULARIZATION INHIBITORS CONTAINING THE SAME AS ACTIVE INGREDIENT

[75] Inventors: Hideaki Morishige; Yukiko Kurita; Yousuke Yamazaki; Chiaki Sakakibara; Masaharu Kigawa, all of Ibaragi, Japan

[73] Assignee: Tsumura & Co., Tokyo, Japan

[21] Appl. No.: 09/142,493

[22] PCT Filed: Mar. 5, 1997

[86] PCT No.: PCT/JP97/00675

§ 371 Date: Sep. 8, 1998

§ 102(e) Date: Sep. 8, 1998

[87] PCT Pub. No.: WO97/32868

PCT Pub. Date: Sep. 12, 1997

[30] Foreign Application Priority Data

Mar. 6, 1996 [JP] Japan ................................. 8-075419

[51] Int. Cl.[7] .................... A61K 31/34; A61K 31/35; C07D 303/06; C07D 311/78
[52] U.S. Cl. .................... 514/455; 514/456; 514/473; 514/475; 549/332; 549/387; 549/396; 549/546; 549/551; 549/554
[58] Field of Search ..................... 514/455, 456, 514/473, 475; 549/332, 387, 396, 546, 551, 554

[56] References Cited

U.S. PATENT DOCUMENTS 4,954,496  9/1990  Oku et al. .

5,374,653 12/1994 Fujii et al. .

OTHER PUBLICATIONS

Beilstein Handbook of Organic Chem. 5th Supplementary Series, vol. 18, part six (1987) p. 267.

Djerassi et al. J. Org. Chem. vol. 26 (1961) pp. 1192–1206.

*Primary Examiner*—Johann Richter
*Assistant Examiner*—Tadfiq A. Solola
*Attorney, Agent, or Firm*—Sughrue, Mion, Zinn, Macpeak & Seas, PLLC

[57] ABSTRACT

Novel iridoid derivatives represented by general formula (I):

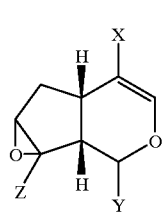

(I)

and a vascularization inhibitor having for its active ingredient said derivative are disclosed. This vascularization inhibitor has remarkable vascularization inhibitory effects unaccompanied by serious adverse side effects, which is useful for the treatment and prevention of various diseases accompanied by abnormal acceleration of vascularization.

7 Claims, 1 Drawing Sheet

IRIDOID DERIVATIVES AND NEOVASCULARIZATION INHIBITORS CONTAINING THE SAME AS ACTIVE INGREDIENT

This appln is a 371 of PCT/JP97/00675 filed Mar. 5, 1997.

TECHNICAL FIELD

The present invention relates to novel iridoid derivatives and a vascularization inhibitor having for its active ingredient said derivative.

BACKGROUND ART

Although vascularization occurs in the normal physiological state of humans and animals, such as during blastogenesis and ovulation or placenta formation in accordance with the female estrus cycle, as well as in the normal state during wound healing and in the healing process of inflammations and so on, it is also known to occur in numerous pathological states that cause rapid increases and expansion of capillaries resulting in serious tissue damage. For example, it is described in N. Engl. J. Med., 285: 1182, 1971 that the growth of tumor cells occurs dependent on an increase in capillary vascularization of tumor tissue. In addition, Matsubara, et al. reported in Jpn. J. Inflammation, Vol. 10, No. 4, July 1990, p. 241–245 that, during the course of an inflammation, there is a correlation between neogenesis of small blood vessels such as capillaries and postcapillary venules and cellular invasion by monocytes and lymphocytes, and neogenesis of small blood vessels as nutrient vessels is essential for granulation growth.

In addition, known examples of other diseases related to abnormal acceleration of vascularization include diabetic retinopathy, retrolental fibroplasia, vascularization accompanying corneal transplant, glaucoma, ophthalmic tumor and trachoma in the field of ophthalmology, angioma and fibrous angioma in the field of pediatrics, hypertrophic cicatrix and granulation in the field of surgery, rheumatoid arthritis and edemic scleroma in the field of internal medicine, and atherosclerosis and various types of tumors in the case of heart diseases.

Consequently, the use of drugs that inhibit vascularization as pharmaceuticals for the treatment of various types of the above diseases has recently attracted attention. Namely, neogenesis of small vessels is known to occur during the course of disease. For example, drugs having vascularization inhibitory effects are useful in the treatment of various diseases such as cancer, chronic inflammations such as chronic rheumatoid arthritis, diabetic retinopathy, pronatal retinopathy, various thrombotic diseases within the retina, arteriosclerosis, angioma, angiofibroma and psoriasis.

Tetrahydrocortisol is disclosed in, for example, the above-mentioned Jpn. J. Inflammation, Vol. 10, No. 4, July 1990, p. 241–245 as an example of a drug having vascularization inhibitory effects. In addition, several anti-rheumatic agents used in the treatment of chronic rheumatoid arthritis are disclosed as also having vascularization inhibitory effects. Examples of these anti-rheumatic agents include SH compounds such as gold sodium thiomaleate, auranofin and D-penicillamine.

However, drugs having vascularization inhibitory effects as described above also have various clinical problems. For example, it is necessary for tetrahydrocortisol to be used concomitant to heparin, which has vascularization promotion effects, in order for it to demonstrate vascularization inhibitory effects.

On the other hand, many of the anti-rheumatic agents having the vascularization inhibitory effects described above have serious adverse side effects, making their application difficult in terms of managing their administration.

In consideration of these problems of the prior art, the present invention provides a novel compound having remarkable vascularization inhibitory effects unaccompanied by serious adverse side effects, which is useful for the treatment and prevention of various diseases accompanied by abnormal acceleration of vascularization, along with a vascularization inhibitor having for its active ingredient said compound.

DISCLOSURE OF THE INVENTION

As a result of earnest research repeatedly conducted by the inventors of the present invention on a compound having vascularization inhibitory effects in order to solve the problems of the prior art described above, a novel compound was discovered that has vascularization inhibitory effects, thereby leading to completion of the present invention. The present invention is as described below.

(1) Novel iridoid derivatives represented with the following general formula (I):

(I)

[wherein,

X represents a $(C_{1-5})$ alkyl group or —$COR^1$

{$R^1$ is:

(a) a hydroxyl group or —OM (—OM is a pharmacologically allowed salt or M is an alkali metal atom), (b) a $(C_{1-10})$ alkoxyl group, $(C_{2-10})$ alkenyloxyl group or $(C_{4-15})$ alkedienyloxyl group (each may or may not be substituted with a phenyl group), (c) a furfuryloxyl group, phenoxyl group or $(C_{3-10})$ cycloalkyloxyl group, or (d) —$NR^4R^5$ (wherein $R^4$ and $R^5$ may be respectively identical or different, and substituted with a hydrogen atom, $(C_{3-10})$ cycloalkyl group, phenyl group, a five-memberd or six-memberd ring system containing one or a plurality of nitrogen atom (s), oxygen atom (s) or sulfur atom (s) as a heteroatom, $(C_{1-10})$ alkyl group (which may or may not be substituted with a mercapto group, —$CO_2R^6$ (wherein $R^6$ is a $(C_{1-5})$ alkyl group), phenyl group or nitrogen-containing aromatic group), or $R^4$ and $R^5$ are bonded to form a heterocycloalkyl group, and said heterocycloalkyl group is a five-memberd or six-memberd ring system that is able to contain only the nitrogen atom at which a heteroatom is bonded with $R^4$ and $R^5$ or a different nitrogen atom or oxygen atom [which may or may not be substituted with a $(C_{1-5})$ alkyl group (which may or may not be substituted with a hydroxyl group or —OCONH —$R^7$ (wherein $R^7$ is a hydrogen atom or $(C_{1-5})$ alkyl group)]}, Y represent a hydrogen atom or the following formula:

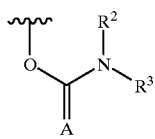

{wherein R² and R³ may be respectively identical or different, and represent:

(a) a hydrogen atom, ($C_{1-10}$) alkyl group (which may be a straight or branched chain), ($C_{2-10}$) alkenyl group, ($C_{3-10}$) cycloalkyl group, ($C_{1-10}$) alkylamino group, ($C_{1-10}$) alkoxyl group, ($C_{3-10}$) heterocycloalkyl group, phenyl group, phenyl ($C_{1-5}$) alkyl group, naphthyl group, or cyclic amino group containing a nitrogen atom, oxygen atom or sulfur atom as a heteroatom (each of which may or may not be substituted with a halogen atom, hydroxyl group, mercapto group, nitro group, cyano group, —$SO_2NH_2$ group, hydroxy ($C_{1-5}$) alkoxyl group, ($C_{1-5}$) alkylamino group, ($C_{1-5}$) alkylcarbonyl group, ($C_{1-5}$) alkylthio group, benzylthio group, halogenated ($C_{1-5}$) alkyl group, halogenated ($C_{1-5}$) alkoxyl group, —$CO_2R^8$ (wherein $R^8$ is a ($C_{1-5}$) alkyl group, ($C_{3-10}$) cycloalkyl group or five-memberd or six-memberd ring system that may be condensed with a benzene ring and contains one or a plurality of nitrogen atom (s), oxygen atom (s) or sulfur atom (s) as heteroatom (s)), (b) —$COR^9$ (wherein $R^9$ is a ($C_{1-5}$) alkyl group (which may or may not be substituted with a halogen atom) or a phenyl group), or, (c) R² and R³ are bonded to form a heterocycloalkyl group or heterocycloalkenyl group, and said heterocycloalkyl group or heterocycloalkenyl group is a four-memberd, five-memberd or six-memberd ring system that may be condensed with a benzene ring, and contains either only a nitrogen atom at which a heteroatom is bonded with R² and R³ or a different nitrogen atom, oxygen atom or sulfur atom (which may or may not be substituted with a ($C_{1-5}$) alkyl group, hydroxy ($C_{1-5}$)alkyl group, phenyl group, phenyl ($C_{1-5}$) alkyl group, halogenated phenyl group, ($C_{1-5}$) alkoxyphenyl group or halogenated ($C_{1-5}$) alkylphenyl group), and A represents an oxygen atom or sulfur atom}, and Z represents a ($C_{1-10}$) alkyl group [which may or may not be substituted with a hydroxyl group, halogen atom, —O—$R^{10}$, —OCO—$R^{11}$, —OCOO—$R^{12}$ or —OCONH—$R^{13}$ (wherein, $R^{10}$ through $R^{13}$ may be a hydrogen atom or ($C_{1-5}$) alkyl group that may be substituted with a halogen atom)] or —CO—$R^{14}$ or —$CH_2$—S—$R^{15}$ (wherein $R^{14}$ and $R^{15}$ may be substituted with a five-memberd or six-memberd ring system that may be condensed with a benzene ring and can contain one or a plurality of nitrogen atom (s), oxygen atom (s) or sulfur atom (s) as heteroatom (s), or a hydroxy ($C_{1-5}$) alkyl group)}].

(2) Novel iridoid derivatives represented with the following general formula (II):

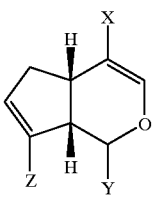

(II)

(wherein X, Y and Z are the same as previously defined).

(3) Novel iridoid derivatives represented with the following general formula (III):

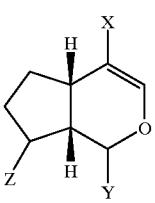

(III)

(wherein X, Y and Z are the same as previously defined).

(4) Novel iridoid derivatives represented with the following general formula (IV):

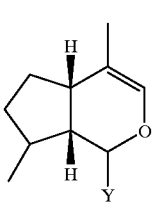

(IV)

(wherein, Y is the same as previously defined).

(5) Novel iridoid derivatives represented with the following general formula (V):

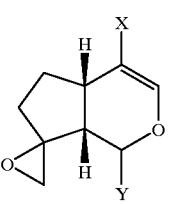

(V)

(wherein, X and Y are the same as previously defined).

(6) Novel iridoid derivatives represented with the following general formula (VI):

(VI)

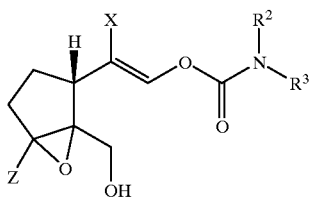

(wherein, R², R³, X and Z are the same as previously defined).

(7) Novel iridoid derivatives represented with the following general formula (VII):

(VII)

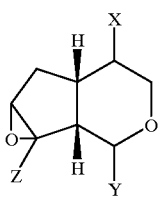

(wherein, X, Y and Z are the same as previously defined).

(8) Novel iridoid derivatives represented with the following general formula (VIII):

(VIII)

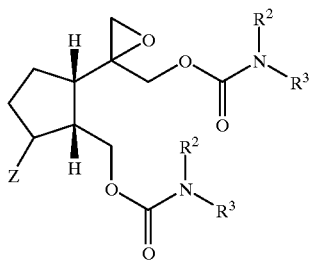

(wherein, R², R³ and Z are the same as previously defined).

(9) Novel iridoid derivatives represented with the following general formula (IX):

(IX)

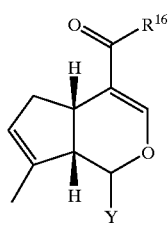

{wherein, Y is the same as previously defined, and R¹⁶ represents a hydroxyl group, methoxyl group or —OM (—OM is a pharmacologically allowed salt or M is an alkali metal atom)}.

(10) Novel iridoid derivatives represented with the following general formula (X):

(X)

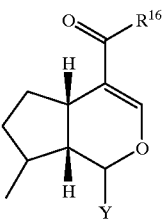

(wherein, Y and R¹⁶ are the same as previously defined).

(11) A vascularization inhibitor having for its active ingredient the novel iridoid derivatives or a mixture thereof according to any of the iridoid derivatives described in (1) through (10) above.

BEST MODE FOR CARRYING OUT THE INVENTION

Figure 1:
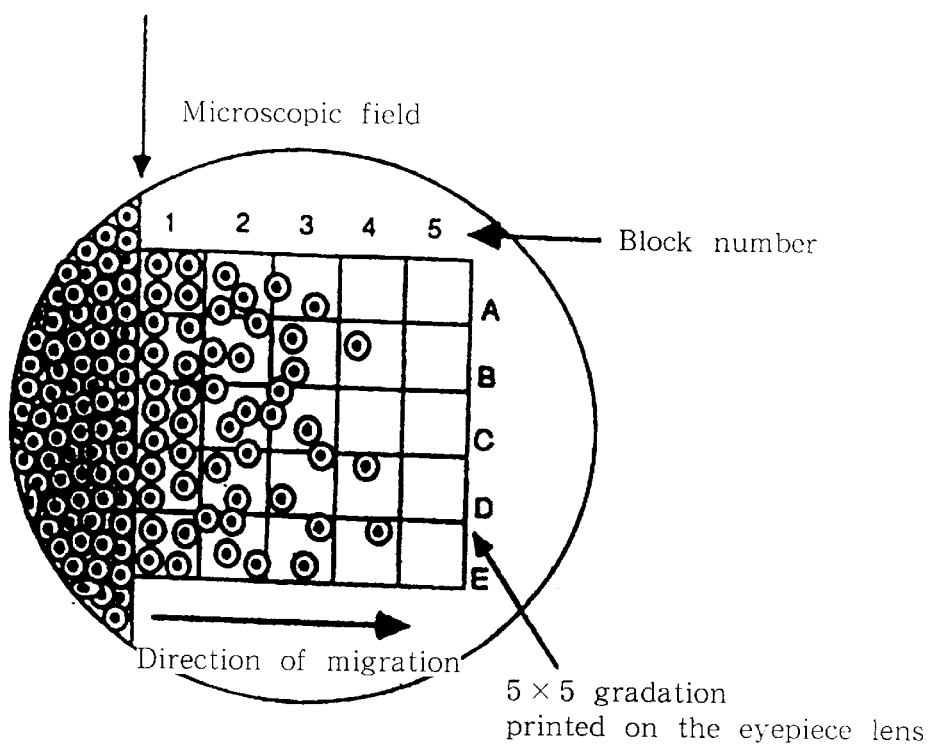
FIG. 1 is an explanatory drawing showing the migrating state of cells as viewed by microscopy in a cell migration inhibition (CMA) test.

The novel iridoid derivatives represented with general formulas (I) through (X) of the present invention can be produced in the manner described in (1) through (75) below.

(1) After hydrolyzing the methoxycarbonyl group of known compound (2) to form a carboxylic acid, it is converted to benzylester. By additionally removing the protecting group of the hydroxyl group, the compound is converted to compound (3). After carbamoylating the hydroxyl group of (3), the five-membered ring double bond is oxidized to produce compound (4a). Moreover, the benzylester is removed by reduction to form carboxylic acid (5a). Carboxylic acid (5a) can be converted to its sodium salt by treating with sodium methoxide, converted to compound (7) be esterification, and converted to compound (8) by amidation, respectively.

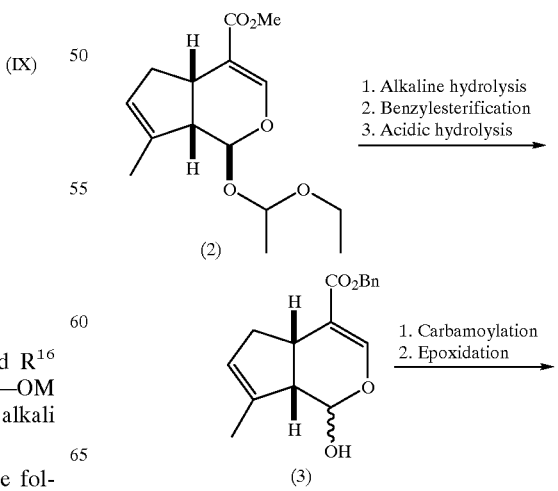

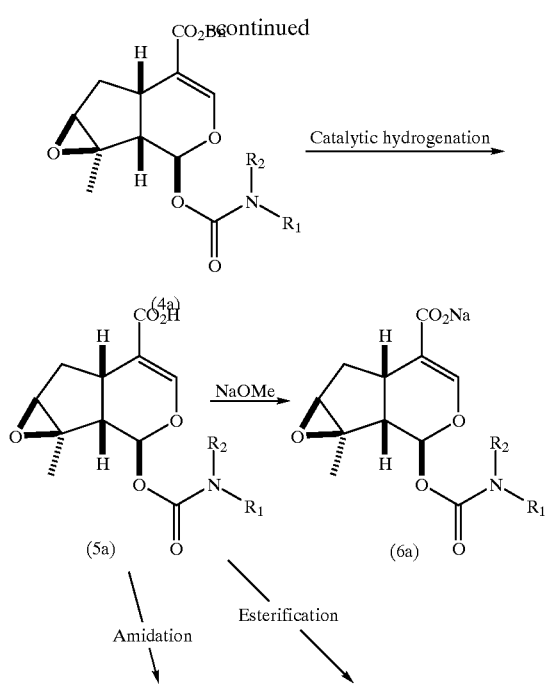

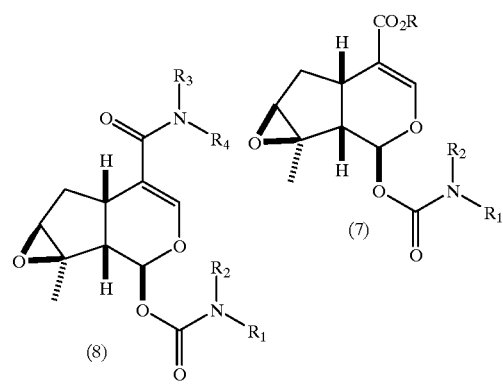

(2) In addition, compound (4b) is obtained by isolating the stereoisomer of the epoxide when obtaining the above-mentioned (4a). This compound (4b) can be converted to an ester (7b) and a sodium salt (6b) in the same manner.

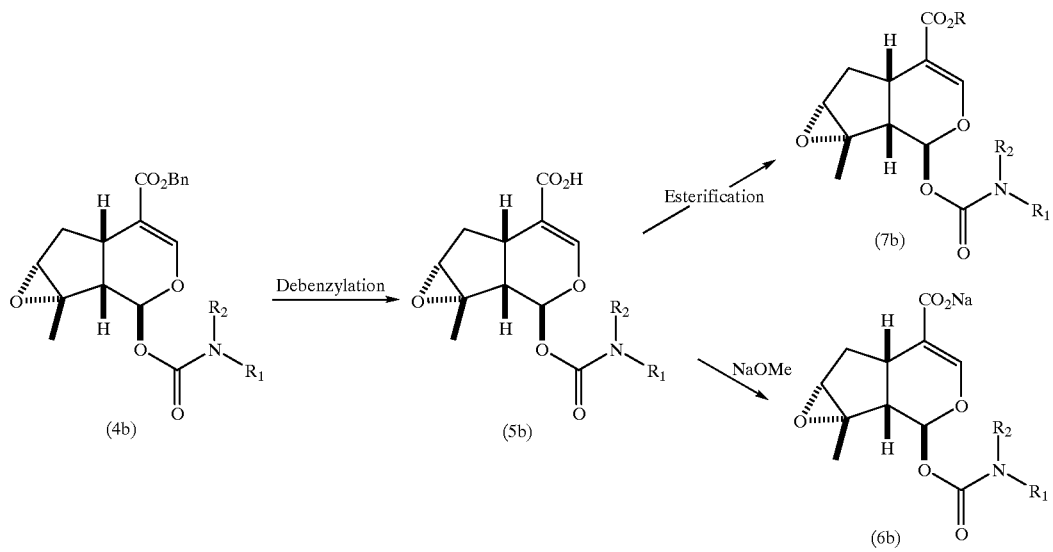

(3) After converting known compound (9) to compound (10), compound (10) is converted to carbamoyl derivative (11) by reacting with a primary or secondary amine. In addition, carbamoyl derivative (11) can be obtained by reacting compound (9) with a corresponding alkylisocyanate.

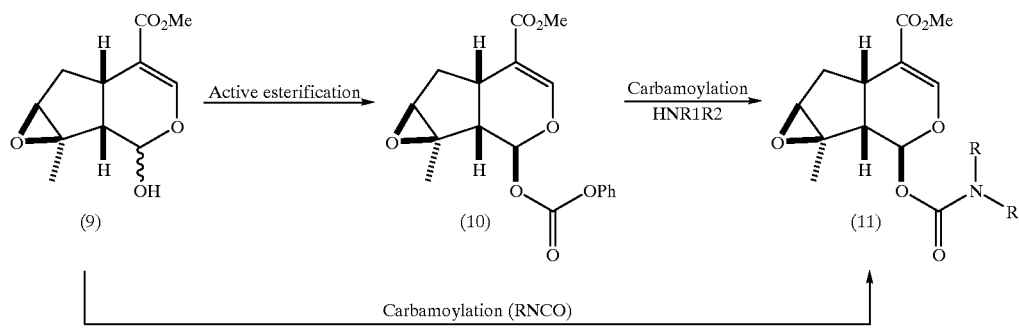

(4) A known genipin is converted to compound (12) through several steps. After alkylation of the formyl group of compound (12), the resulting hydroxyl group is removed by reduction, the ethoxyethyl group is converted to a carbamoyl group and the double bond is oxidized which allows production of compound (13).

(5) Compound (14) is produced from a known genipin through several steps. Compounds (15), (16) and (17) can respectively be produced by performing various alkylations on the hydroxyl group of compound (14). In addition, compound (19) can be produced by carbamoylation of the primary hydroxyl group of epoxide (18) derived from genipin.

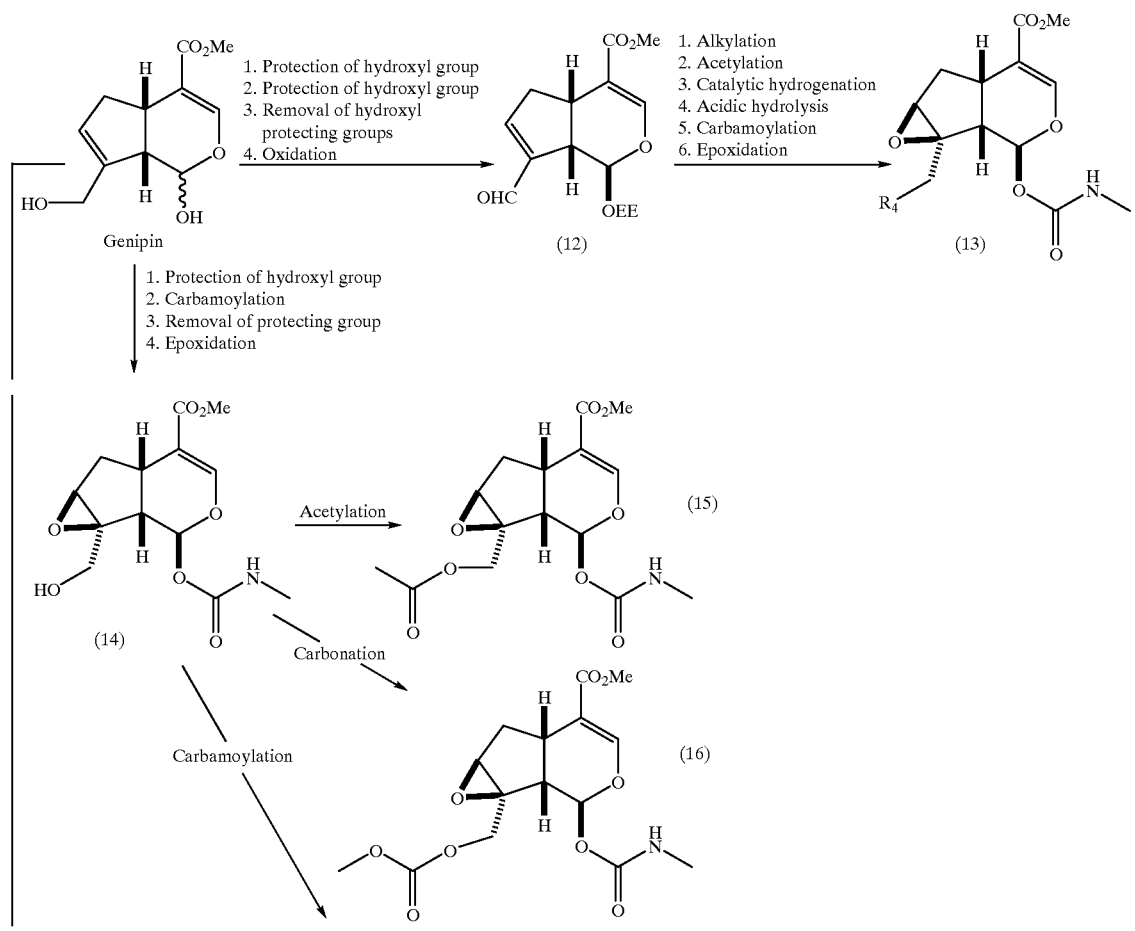

-continued

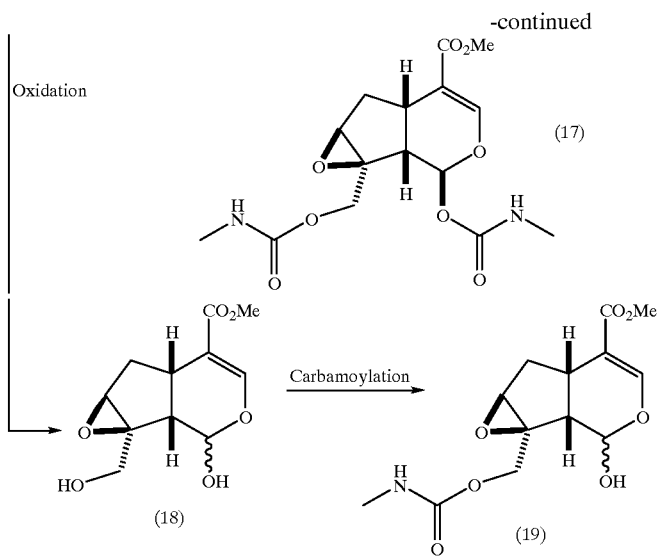

(6) After halogenating compound (20) converted from genipin in three steps, compound (21) can be produced by epoxidating the double bonds on five-memberd ring.

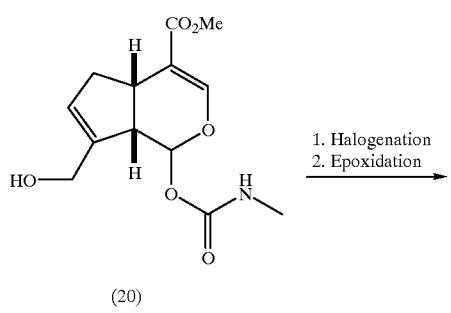

-continued

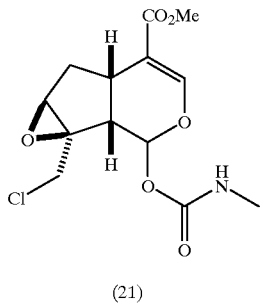

(7) After alkylating the primary hydroxyl group of known compound (22), the ethoxyethyl group is removed by acidic hydrolysis to carbamoylate the resulting hydroxyl group. Next, compound (23) is produced by oxidizing the double bonds on the five-memberd ring.

(8) After similarly halogenation of the primary hydroxyl group of compound (22), the ethoxyethyl group is removed by acidic hydrolysis to carbamoylate the resulting hydroxyl group. Next, compound (24) is produced by oxidizing the double bonds on the five-memberd ring.

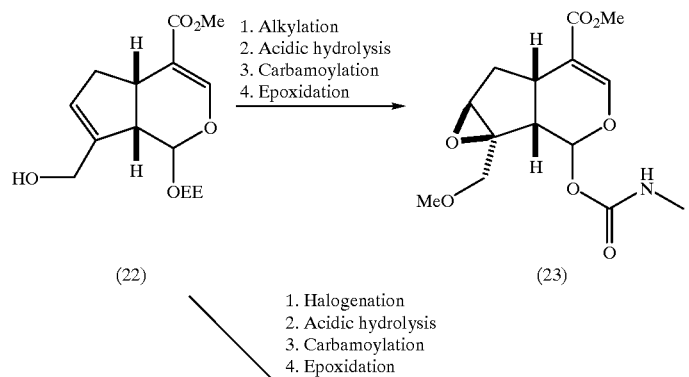

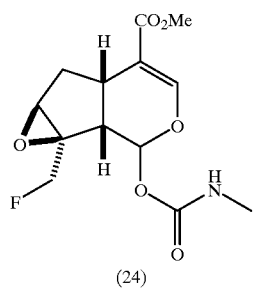
(24)
(9) After converting known compound (25) to compound (26), carbamoyl derivative (27) can be produced by reacting with a primary or secondary amine. In addition, compound (27) can be produced by reacting compound (25) with a corresponding alkylisocyanate.
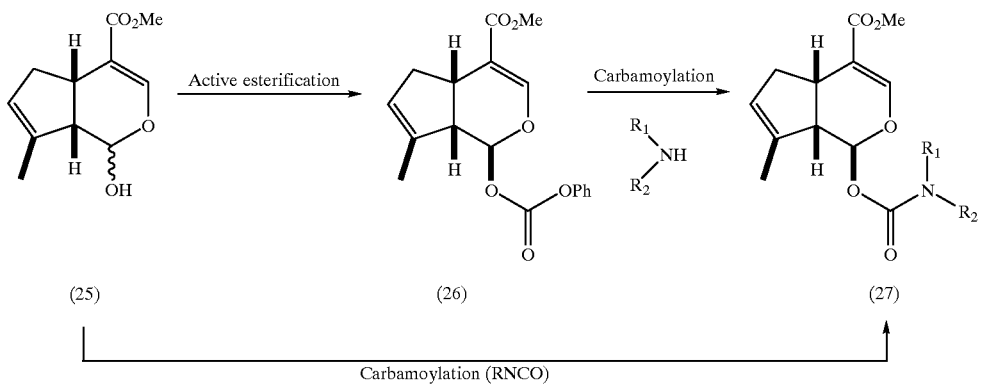
(10) Carbamoyl derivative (30) can be produced from compound (28) using the same method as described above.
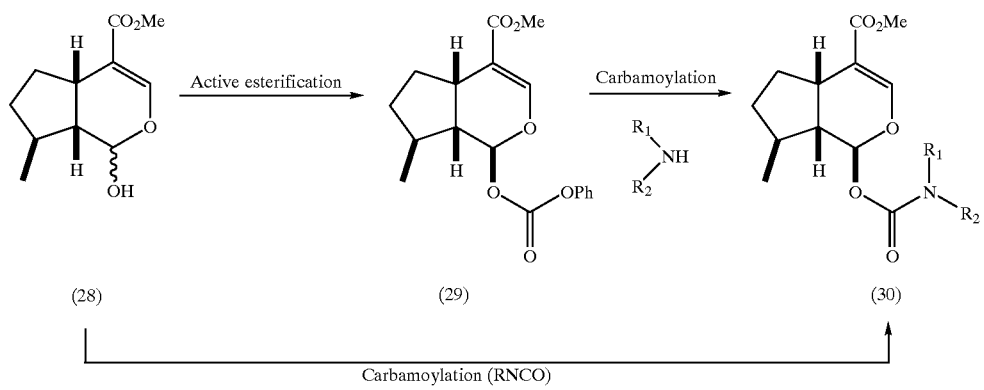

(11) Compound (31) can be produced by carbamoylation of a known Nepetalactol.

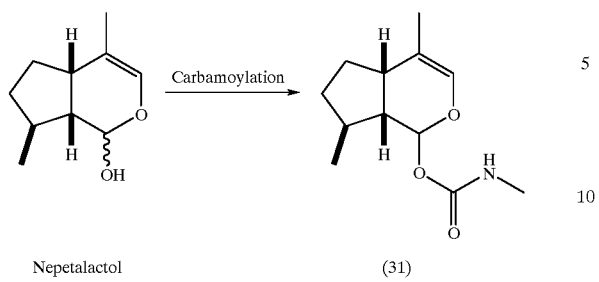

(12) Compound (33) can be produced by conversion in several steps after converting a known genipin to the ethylester derivative (32).

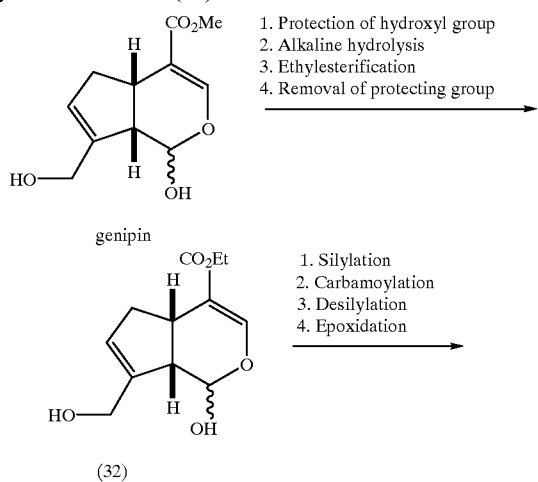

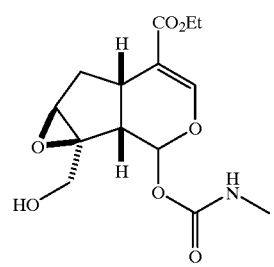

(13) Known compound (34) can be converted to compound (35) by carbamoylation. In addition, after protection of the hydroxyl group of this compound (34), the methoxycarbonyl group is alkalinehydrolyzed. After protection of the resulting carboxyl group by benzylation, the hydroxyl protecting group is removed and the resulting hydroxyl group is carbamoylated. Moreover, compound (36) is obtained by debenzylation. Compound (37) can be produced by amidating compound (36), sodium salt (38) can be produced by treatment of compound (37) with sodium methoxide, and compound (39) can be produced by conversion of the carboxyl group to a methyl group by reduction.

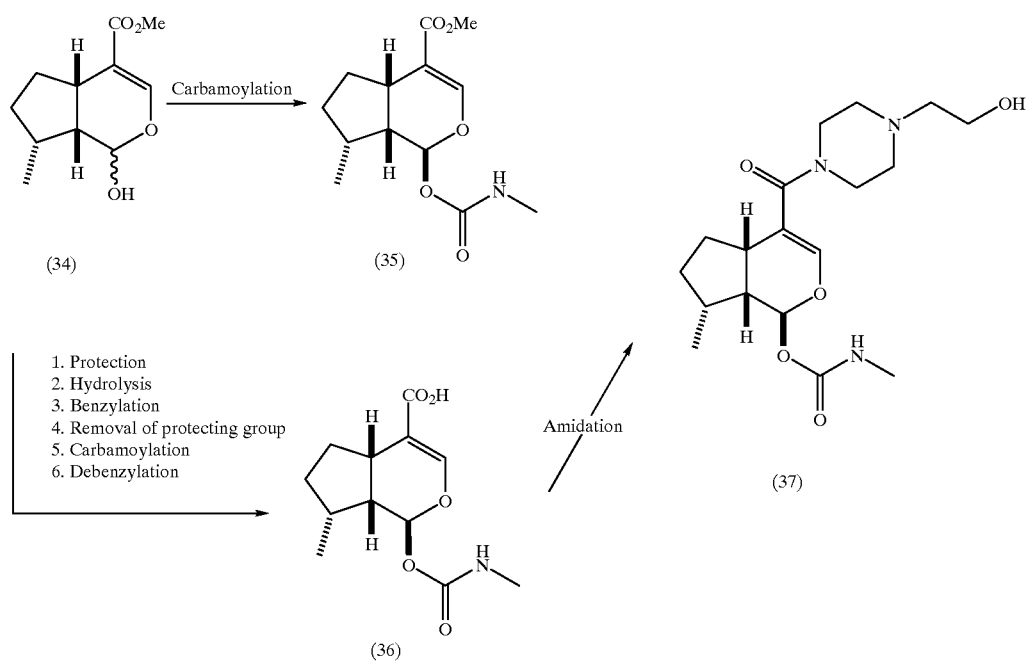

-continued
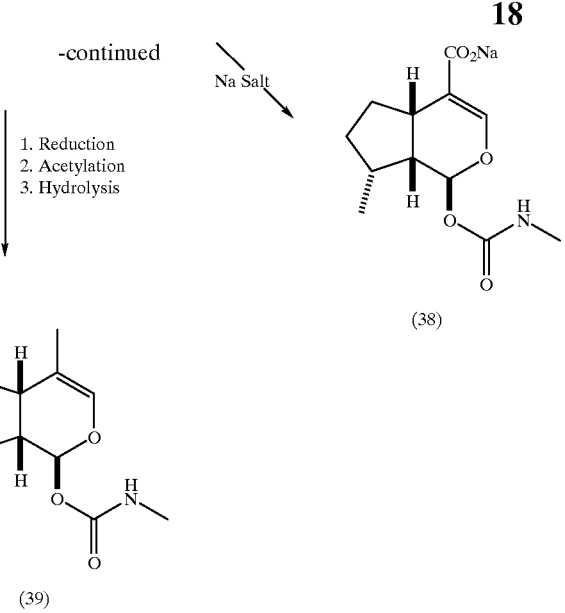
1. Reduction
2. Acetylation
3. Hydrolysis
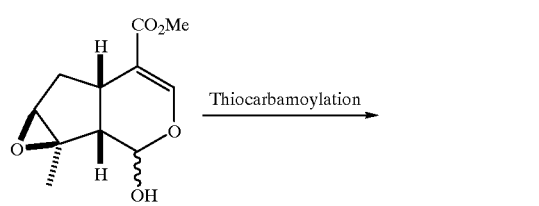
(14) Compound (40), its stereoisomer (41) and compound (42), etc. can be produced by thiocarbamoylation of known compound (9).
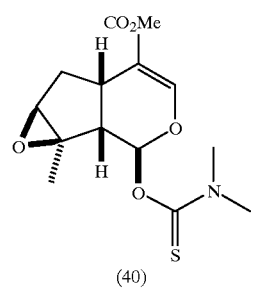
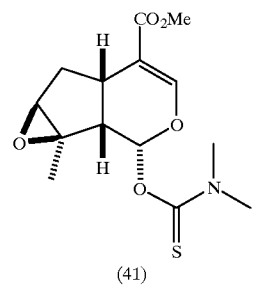
-continued
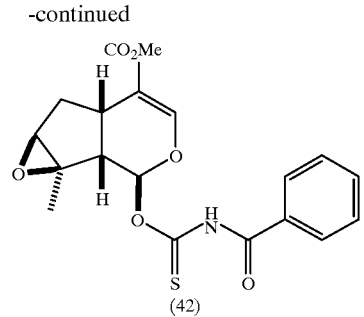
(15) Compound (43) and compound (44), etc. can be produced by carbamoylation of a known genipin.
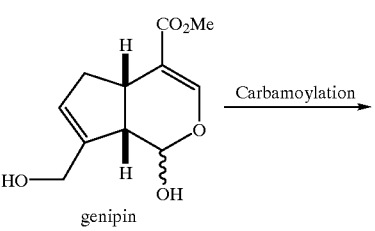
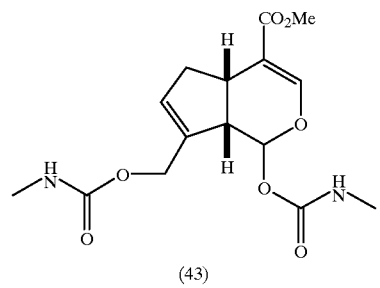

-continued

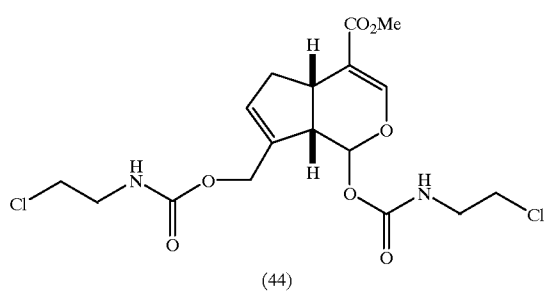
(44)

(16) Compound (46) can be obtained by deacetylation after reductive deacetalation of known compound (45) by reduction. Compound (47) can be produced by epoxidation of this compound (46), and compound (48) can be produced by carbamoylation of this compound (47).

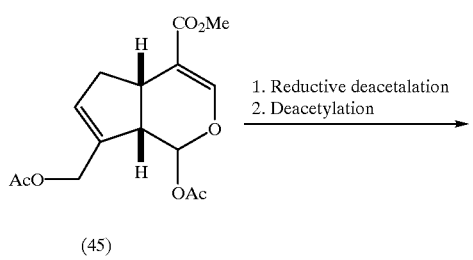
(45)

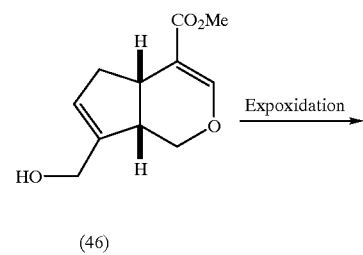
(46)

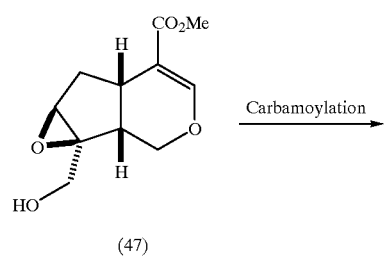
(47)

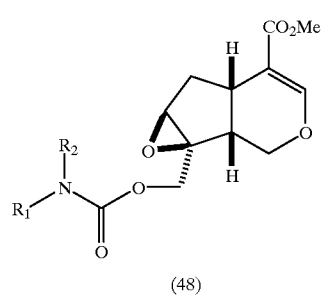
(48)

(17) Compound (49) can be produced by substituting the hydroxyl group of previously obtained compound (46) with a halogen, and then reacting with a sodium mercaptobenzothiazole salt.

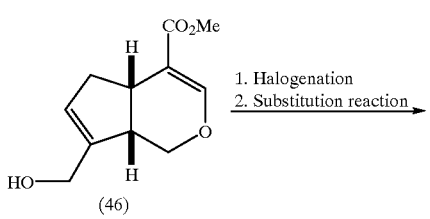
(46)

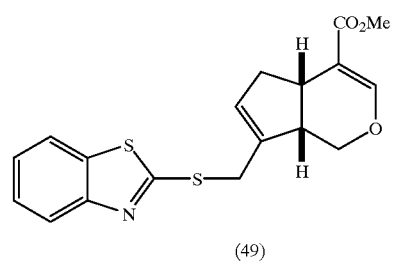
(49)

(18) Compound (50) can be produced by oxidation of the primary hydroxyl group of previously obtained compound (46) to a carboxyl group followed by amidation.

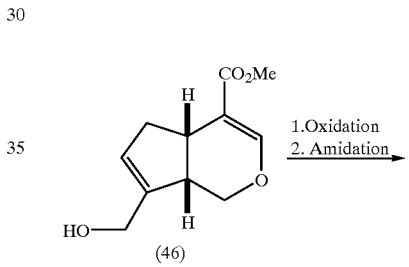
(46)

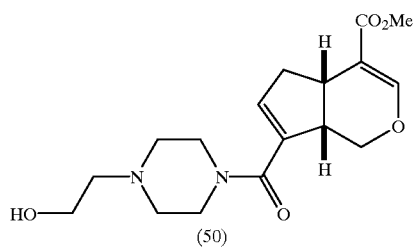
(50)

(19) Compound (51) can be produced by oxidation of the primary hydroxyl group of previously obtained compound (46) to a formyl group followed by a carbon increasing reaction and hydrogenation to a resulting double bond.

(20) Compound (53) can be produced by conversion of compound (46) to compound (52) by carbamoylation followed by catalytic hydrogenation to compound (52).

(21) Compound (54) can be produced by protection of the hydroxyl group of compound (46), hydrolyzing the methoxycarbonyl group, amidation and then removal of the protecting group.

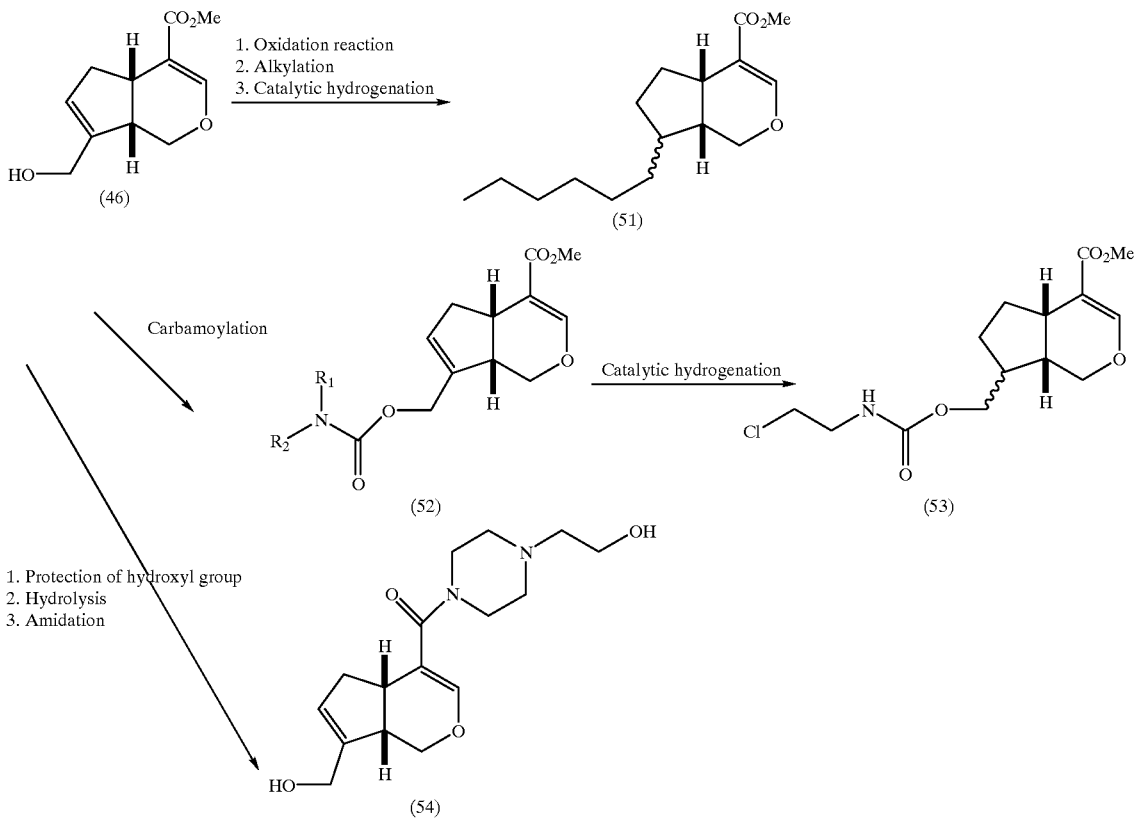

(22) Compound (55) can be produced by oxidizing the hydroxyl group of previously obtained compound (47) to a formyl group, and hydrogenating the resulting double bond after increasing the number of carbon atoms by alkylation.

(23) Known compound (56) is converted to compound (57) by performing several conversion steps. Compound (57) can be converted to isomeric mixture (58), which is difficult to isolate, by Catalytic hydrogenation of compound (57).

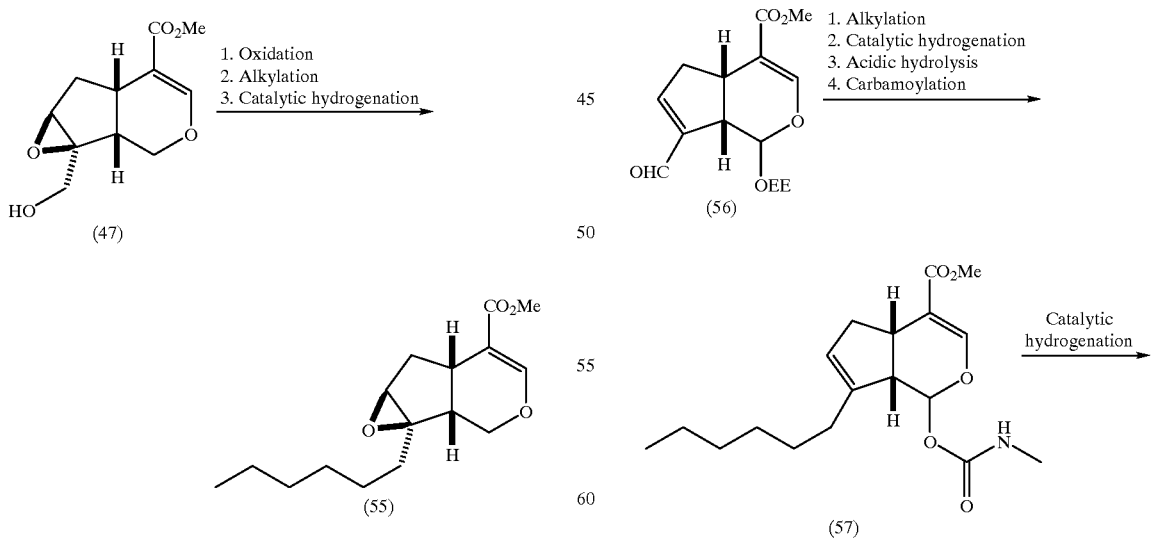

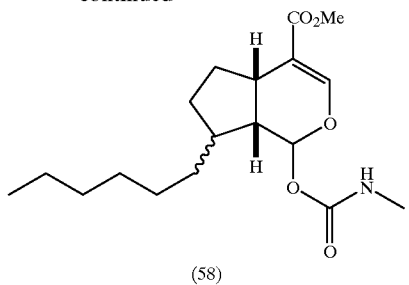

(58)

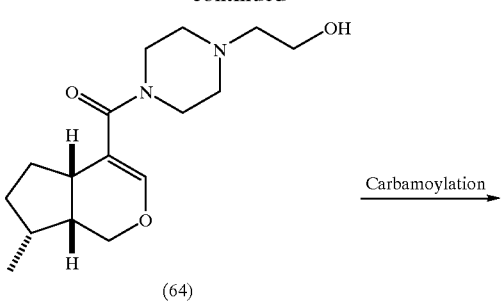

(64)

(24) Compound (60) can be produced by reductive deacetalation of known compound (59). Compound (61) can be produced by epoxidation of this compound (60). In addition, compound (62) can be produced from compound (60) in several steps.

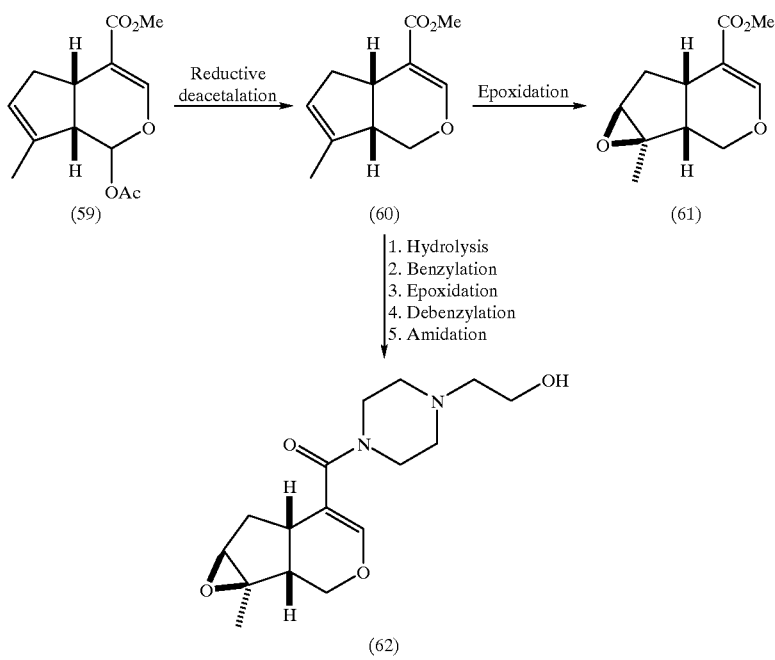

(25) Known compound (63) is converted to compound (64) by hydrolysis and amidation. Moreover, compound (65) can be produced by carbamoylation of this compound (64).

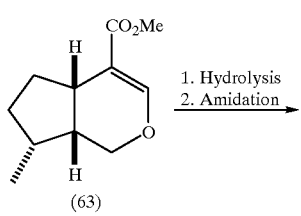

(63)

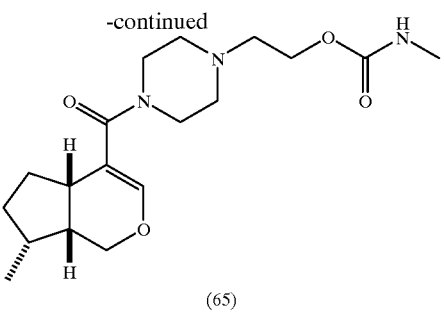

(65)

(26) The methoxycarbonyl group of known compound (2) is hydrolyzed followed by protection of the resulting carboxyl group. Moreover, after removal of the ethoxyethyl group of hydrolysis under acidic condition followed by carbamoylation of the resulting hydroxyl group, compound (66) can be produced by conversion of the ester to a carboxyl group.

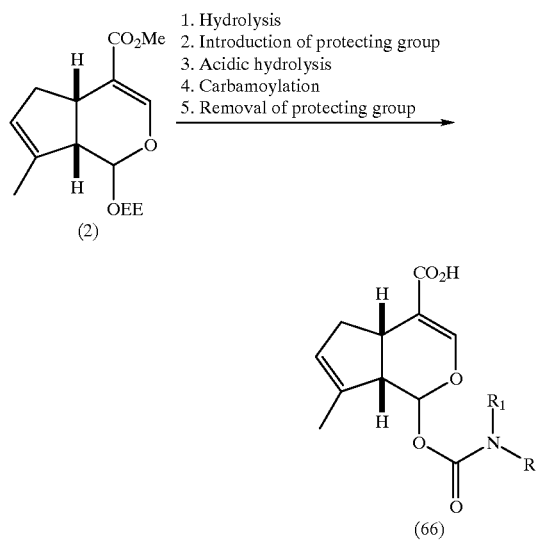

(27) Compound (66) can be converted to compound (67) by amidation, to compound (68) by esterification, and to sodium salt (69) by treatment with sodium methoxide.

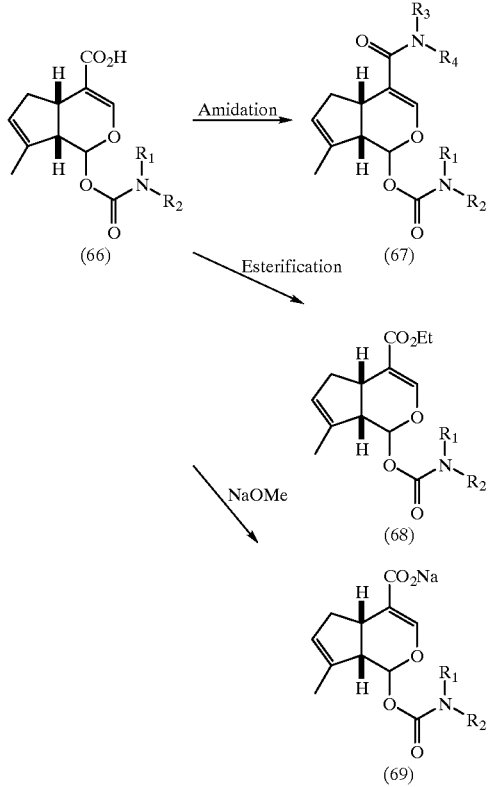

(28) Compound (70) can be produced by hydrating compound (20) followed by tosylation and epoxidation.

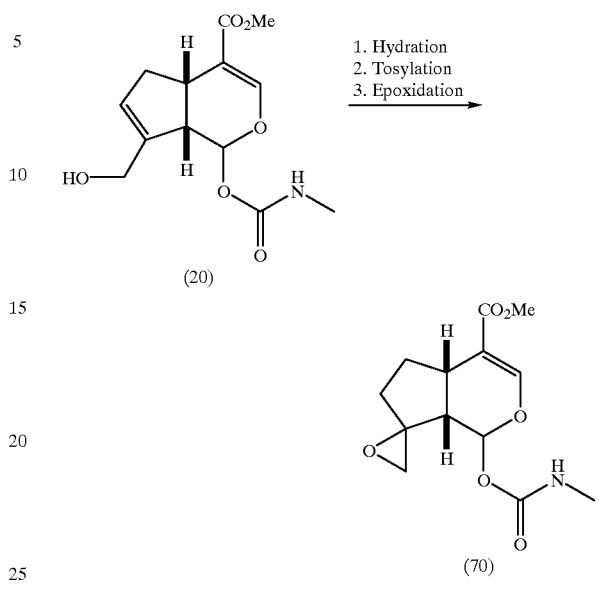

(29) Known compound (71) can be converted to compound (72) by carbamoylation followed by two steps consisting of reduction and oxidation.

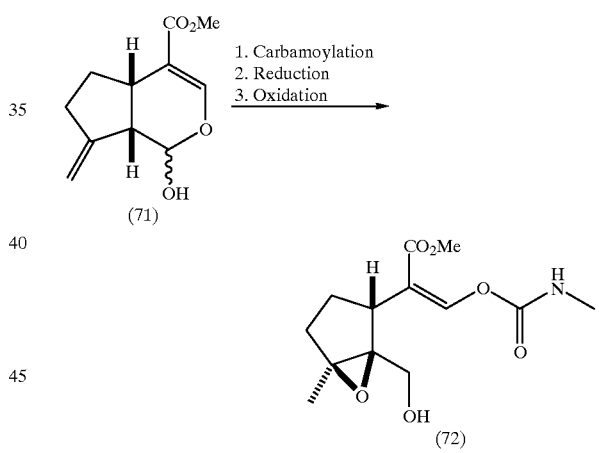

(30) Compound (73) can be produced by reduction of the conjugated double bond of compound (11).

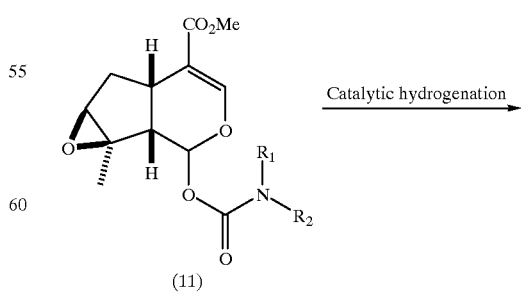

-continued

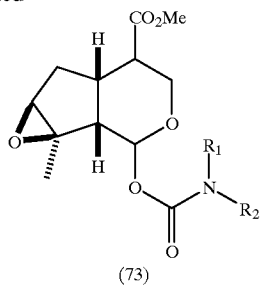

(73)

(31) Compounds (74) and (75) can be produced from known compounds (28) and (34) by employing several conversion steps.

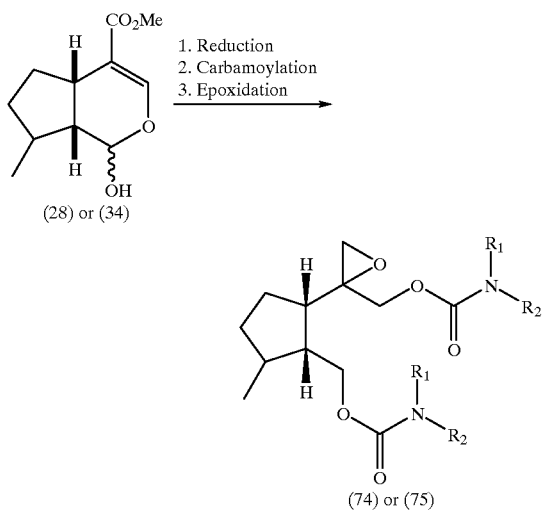

1. Hydroxyl Group Acetylation

Acetylation is carirred out at in the range of 0° C. to room temperature for 1 hour or more using, for example, acetic anhydride or acetyl chloride for the acetylation agent, using, for example, triethylamine, diisopropylethylamine, pyridine, lutidine, collidine, diazabicycloundecene, 4-dimethylaminopyridine or other amines either alone or as a mixture for the base, and using, for example, organic halides such as chloroform and dichloromethane, ethers such as ether and tetrahydrofuran, or aromatic hydrocarbons such as benzene and toluene, which themselves do not react with the reagents, for the solvent.

2. Acidic Hydrolysis

Hydrolysis may be performed by any method provided it is typical acidic hydrolysis. Examples of acids used include hydrochloric acid, sulfuric acid, pyridium p-toluenesulfonate, acetic acid, boron trifluoride ether complex and hydrofluoric acid. Hydrolysis is carirred out in water or an organic solvent containing water at from 0° C. to about 100° C. for 30 minutes or more.

3. Alkaline Hydrolysis

Alkaline hydrolysis may be performed by using any method provided it is typical alkaline hydrolysis. Alkaline hydrolysis is achieved by using an alkaline metal hydroxide such as sodium hydroxide, potassium hydroxide or lithium hydroxide and reacting in water or an organic solvent such as methanol, ethanol or propanol that contains water at from 0° C. to about 100° C. for 30 minutes or more.

4. Oxidation

Oxidation of a double bond to an epoxyl group may be performed by using any method provided it is a typically used reaction. Oxidation is achieved by using an organic peroxide such as metachloroperbenzoic acid, magnesium monoperoxyphthalate, peracetic acid, cumene hydroperoxide and t-butyl hydroperoxide in the presence of a typically known buffer such as sodium bicarbonate or potassium hydrogen phosphate if necessary, combining with a catalyst such as vanadylacetyl acetate, tungstic acid or hexacarbonyl molybdenum if necessary, using an organic halide such as chloroform or dichloromethane, an aromatic hydrocarbon such as benzene or toluene, or an alcohol such as methanol or ethanol for the solvent, and reacting from at 0° C. to about room temperature for 10 minutes or more.

Oxidation of a hydroxyl group to a carbonyl group may be performed by using any method provided it is a typically used reaction. Oxidation is carirred out at room temperature for 30 minutes or more using oxidant such as manganese dioxide, pyridium chlorochromate, chromium trioxide or a dimethylsulfoxide—based oxidant, and using aromatic hydrocarbones such as benzene and toluene or an organic halide such as chloroform and dichloromethane as solvent.

Oxidation of a formyl group to a carboxyl group may also be performed by using any method provided it is a typically used reaction. Oxidation is carirred out at from 0° C. to about room temperature for 10 minutes or more in the presence of an oxidant such as a combination of sodium chlorite, chromic acid, ruthenium oxide and sodium periodate, and if necessary, disodium hydrogen phosphate and sulfaminic acid, in a solvent such as water, alcohol or a halide such as dichloromethane.

5. Reduction 5-1 The methods described in (1) through (3) below can be suitably selected according to the substrate for the reduction method.

(1) A method wherein reduction is carirred out at from 0° C. to about 100° C. for 5 hours or more using for the catalyst palladium chloride, platinum dioxide, palladium, palladium hydroxide, rhodium or bis(triphenylphosphine) palladium chloride, and using for the reductant hydrogen, cyclohexadiene, ammonium formate, sodium formate or hydrazine, in solvent such as ethyl acetate, benzene, toluene, methanol, tetrahydrofuran, dioxane or water either alone or as a mixture thereof (catalytic reduction method).

(2) A method wherein reduction is carirred out at from 0° C. to about room temperature for 10 minutes or more using sodium borohydride or sodium cyanoborohydride, and using water, an alcohol such as methanol, ethanol and isopropanol, or an acidic solution such as aqueous acetic acid or aqueous hydrochloric acid as solvent.

(3) A method wherein reduction is carirred out at from −80° C. to about room temperature for 10 minutes or more using an aluminum hydride such as lithium aluminum hydride, diisobutyl aluminum hydride and sodium bi (methoxyethoxy) aluminum hydride, in a solvent such as an ether such as diethylether, tetrahydrofuran and dimethoxyethane, or a hydrocarbon such as benzene and toluene.

5-2 Reduction Deacetalation

There are many cases in which the purpose of a typical reductive deacetalation reaction is achieved by using the action of a reductant under acidic conditions. Thus, although there are no particular limitations on the method provided it is suitable for the particular objective, according to a report in the literature, it can be carirred out at from −20° C. to about room temperature using for the reductant hydrogen, sodium cyanoborohydride or triethylsilane in the presence of a Lewis acid such as trimethylsilyltrifluoromethanesulfonate, boron trifluoride ether complex and titanium tetrachloride, or a protic acid such as hydrochloric acid and toluene sulfonic acid, and in a solvent such as dichloromethane and tetrahydrofuran.

5-3 Reduction of a Carboxyl Group to a Methyl Group

Since it is difficult to reduce a carboxyl group directly to a methyl group, there are many cases in which the purpose is achieved by employing several conversion steps. For example, a carboxyl group can be converted to a methyl group by first reducing the carboxyl group to a primary hydroxyl group followed by removal of the hydroxyl group.

6. Protection of a Hydroxyl Group and Removal of the Protecting Group

A known method is used for hydroxyl group protection and removal of the protecting group (Reference Literature: T. W. Greene., "Protective Groups in Organic Synthesis", John Wiley & Sons Inc., New York (1981). Examples of protecting groups that can be used include silyl-type protecting groups such as a t-butyldimethylsilyl group and t-butyldiphenylsily group, acetal-type protecting groups such as an ethoxyethyl group, tetrahydropyranyl group and methoxyethoxymethyl group, or acyl-type protecting groups such as an acetal group and benzoyl group. Introduction of a silyl-type protecting group can be carried out at from −30° C. to about room temperature for 5 minutes or more using for the reagent a typical silylating agent such as t-butyldimethylsilyl chloride, t-butyldiphenylsilyl chloride and t-butyldimethylsilyl triflate in the presence of triethylamine, imidazole, 4-dimethylaminopyridine, lutidine, silver nitrate or the like, and in a typical organic solvent such as chloroform, dichloromethane, dimethylformamide or benzene.

Introduction of an acetal-type protecting group can be carirred out at from 0° C. to about room temperature for 30 minutes or more using for the reagent a vinyl ether such as ethylvinyl ether or dihydropyrane or a halide such as methoxyethoxymethyl chloride, in a typical organic solvent that does not itself react with the reagent, examples of which include dichloromethane, chloroform, benzene, toluene, ether and tetrahydrofuran, under acidic conditions using as catalyst para-toluenesulfonic acid, camphorsulfonic acid or sulfuric acid or the like, or under basic conditions using as catalyst diisopropylethylamine or triethylamine or the like. Introduction of an acyl-type protecting group can be performed in accordance with the acetylation method previously described using as reagent acetyl chloride, acetic anhydride, benzoyl chloride, benzoyl bromide or benzoic anhydride and so forth.

Alkaline hydrolysis (3 above), acidic hydrolysis (2 above), catalytic reduction (5 above), methods using fluoride ions and so forth can be used for removal of protecting groups, and the method that is used differs depending on the type of protecting group. Removal of a protecting group using fluoride ions can be carried out at from −20° C. to about room temperature for 30 minutes or more using for the reagent, for example, tetra-n-butylammonium fluoride (TBAF), aqueous hydrofluoric acid solution, potassium fluoride, hydrogen fluoride-pyridine or hydrogen fluoride-triethylamine, in a solvent such as tetrahydrofuran, acetonitrile or cyclohexane, and, if necessary, in the presence of a buffer such as phenol or benzoic acid.

7. Carbamoylation

Carbamoylation can be achieved by using a method wherein isocyanate is reacted with a substrate alcohol, or using a method wherein substrate alcohol is reacted with chloroformate ester, or the like to form an active ester followed by reacting with a primary or secondary amine which act as a nucleophilic substitution agent.

7-1 Method Using Isocyanate

Carbamoylation using isocyanate can be carried out at from −40° C. to about room temperature for 30 minutes or more normally using about 1 mole to 5 moles of alkyl-substituted isocyanate corresponding to the target substance to 1 mole of substrate alcohol, normally using a catalytic amount to 5 moles of a base to 1 mole of substrate alcohol in the form of an amine such as triethylamine, diisopropylethylamine, pyridine, lutidine, collidine, diazabicycloundecene or 4-dimethylaminopyridine either alone or as a mixture thereof, and in an organic solvent that does itself typically react with the reagent, such as acetonitrile, dichloromethane, chloroform, benzene, toluene, ether or tetrahydrofuran. In addition, there are cases in which the use of thiocyanate instead of isocyanate at this time allows conversion to the thiocarbamate.

7-2 Method Going Through an Active Ester 7-2 Method via Active EstersAn active ester form can be obtained by reaction of substrate alcohol with from 1 to 5 moles of chloroformate ester (such as phenyl chloroformate or methyl chloroformate) to one mole of substrate alcohol in the presence of from 1 to 5 moles of amine as base, such as triethylamine, diisopropylamine, pyridine, lutidine, collidine, diazabicycloundecene or 4-dimethylaminopyridine, either alone or as a mixture thereof at 0° to about room temperature for 30 minutes or more in a typical organic solvent which itself does not react with reagents, such as dichloromethane, chloroform, benzene, toluene, ether, or tetrahydrofuran. The carbamoyl derivative can be obtained by reaction of active ester derivative, thus obtained, which may be isolated, with from 1 to 5 moles of primary or secondary amine corresponding to the desired product at −40° to about room temperature for 30 minutes or more in a typical organic solvent which itself does not react with reagents, such as dichloromethane, chloroform, benzene, toluene, ether, or tetrahydrofuran in the presence of from 1 to 5 moles of amine, if necessary, as base, such as triethylamine, diisopropylamine, pyridine, lutidine, collidine, diazabicycloundecene or 4-dimethylaminopyridine.

8. Esterification

A method wherein substrate carboxylic acid and alcohol are condensed, and the other method wherein alkylation agent is allowed to act on substrate carboxylic acid are used for esterification.

8-1 Substrate Carboxylic Acid and Alcohol Condensation Method

A method in which condensation is carried out under acidic conditions and a method in which condensation is carried out by using a condensation agent are used as methods for condensing substrate carboxylic acid and alcohol.

In the case of the method in which condensation is carried out under acidic conditions, condensation may be carried out by using for the acid catalyst hydrochloric acid, sulfuric acid, formic acid, trifluoroacetic acid, aromatic sulfonic acid or boron trifluoride ether complex as acid catalyst, and using an organic solvent that is azeotropic with water such as benzene or toluene or using an excess amount of substrate alcohol for the solvent, while removing water or the target ester from the system. In addition, it is preferable that the reaction temperature be from 0° C. to reflux temperature. This reaction is frequently carried out from 30 minutes to 20 hours or more.

In the case of a method using a condensation agent, the reaction is carried out from 0° C. to about room temperature for 30 minutes or more using normally from about 1 mole to 5 mole of alcohol to 1 mole of substrate carboxylic acid, using for the condensation agent normally from about 1 mole to 5 moles of a condensation agent such as dicyclohexylcarbodiimide, 2-chloro-1, 3-dimethylimidazolinium chloride, diethylchlorophosphate, diethylcyanophosphate or diphenylphospholylazide to 1 mole of substrate carboxylic acid, and using as base normally from about 1 mole to 5 moles of an amine such as triethylamine, diisopropylethylamine, pyridine, lutidine, collidine, diazabicycloundecene or 4-dimethylaminopyridine, either alone or as a mixture thereof, to 1 mole of substrate carboxylic acid, in a solvent which itself does not react with the reagents that is a typical organic solvent such as dichloromethane, chloroform, benzene, toluene, ether or tetrahydrofuran.

8-2 Esterification Method Using an Alkylation Agent

Esterification can be carirred out at from 0° C. to about room temperature for 30 minutes or more using for the alkylation agent normally from about 1 mole to 5 moles of, for example, an dialkylsulfate such as dimethylsulfate or diethylsulfate or an alkyl halide such as methyl iodide, benzyl bromide or n-hexyl iodide to 1 mole of substrate carboxylic acid, and using for the base normally from about 1 mole to 5 moles or an amine such as triethylamine, diisopropylethylamine, pyridine, lutidine, collidine, diazabicycloundecene or 4-dimethylaminopyridine or an alkaline metal carbonate to 1 mole of substrate alcohol, in a solvent which itself does not react with the reagents that is a typical organic solvent such as dichloromethane, chloroform, benzene, toluene, ether, tetrahydrofuran or dimethylformamide.

9. Amidation

Amidation is carirred out at from 0° C. to about room temperature for 30 minutes or more using normally from about 1 mole to 5 moles of primary or secondary amine to 1 mole of substrate carboxylic acid, using as condensation agent normally from about 1 mole to 5 moles of a condensation agent such as dicyclohexylcarbodiimide, 2-chloro-1,3-dimethylimidazolinium chloride, diethylchlorophosphate, diethylcyanophosphate or diphenylphospholylazide to 1 mole of substrate carboxylic acid, and using for the base normally from about 1 mole to 5 moles of an amine such as triethylamine, diisopropylethylamine, pyridine, lutidine, collidine, diazabicycloundecene or 4-dimethylaminopyridine, either alone or as a mixture thereof, to 1 mole of substrate carboxylic acid, in a solvent which itself does not react with the reagents that is a typical organic solvent such as dichloromethane, chloroform, benzene, toluene, ether or tetrahydrofuran.

10. Alkylation

Alkylation of a hydroxyl group is carried by using the alkylation agents described in 8-2 above. Alkylation can be carirred out at from 0° C. to about room temperature for 10 minutes or more using normally from about 1 mole to 5 moles of alkylation agent to 1 mole of substrate alcohol, and using for the base normally from about 1 mole to 5 moles of a tertiary amine such as triethylamine or diisopropylethylamine or an alkaline metal hydroxide to 1 mole of substrate alcohol, in a solvent which itself does not react with the reagents that is a typical organic solvent such as dichloromethane, chloroform, benzene, toluene, ether or tetrahydrofuran. Alkylation of a carbonyl group can be carried out by reacting from −78° C. to about room temperature for 30 minutes or more using for the alkylation reagent normally from about 1 mole to 5 moles of an alkylation agent such as alkyl copper complex, alkyl alkaline metal, alkyl alkaline earth metal. Grignard's reagent or alkyltriphenylphosphonium halide, examples of Grignard's reagent including alkylmagnesium bromides, and alkylmagnesium iodides such as methylmagnesium bromide and n-heptylmagnesium bromide, to 1 mole of substrate aldehyde, in a solvent which itself does not react with the reagents that is a typical organic solvent such as dichloromethane, chloroform, benzene, toluene, ether or tetrahydrofuran. Alkylation using alkylphosphonium halide is carirred out at from −78° C. to about room temperature for 30 minutes or more in the presence of a base such as an alkyl lithium such as n-butyllithium, etc. or a potassium tert-butoxide, in a solvent such as ether, tetrahydrofuran or tert-butanol.

11. Halogenation of a Hydroxyl Group

Any method may be used for halogenation of a hydroxyl group provided it is a typically used method. For example, halogenation can be carried out at from 0° C. to about room temperature for 30 minutes or more using for the halogenation agent normally from about 1 mole to 5 moles of a halogenation agent such as thionylchloride, N-halosuccinyl imide, carbon tetrachloride or alkylsulfonic acid halide to 1 mole of substrate alcohol, and using for the base normally from about 1 mole to 5 moles of a base such as tetra-n-butylammonium fluoride (TBAF) or triethylamine to 1 mole of substrate alcohol, in a solvent which itself does not react with the reagents that is a typical organic solvent such as dichloromethane, chloroform, benzene, toluene, ether or tetrahydrofuran.

12. Conversion of Carboxylic Acid to Sodium Salt

Conversion to a sodium salt can be carried out by ordinary known method. For example, conversion can be achieved by stirring at from 0° C. to about room temperature for 30 minutes or more using sodium methoxide, sodium carbonate, sodium bicarbonate, etc., in alcohol such as methanol or ethanol (which may be mixed with other organic solvents).

13. Hydration Reaction

Hydration may be performed using ordinary known method. Although an example of a typical method involves obtaining a hydrate by performing hydroboration to a double bond followed by oxidative treatment, in another method, hydration can be achieved according to the method described in S. Isayama and T. Mukaiyama, Chem. Lett., 1989, 1071–1074, etc.

There are no particular limitations on the administration form of the vascularization inhibitor having for its active ingredient novel iridoid derivatives of the present invention, and said administration form can be suitably selected as necessary. Examples of administration forms include oral preparations such as tablets, capsules, granules, grains, powders and liquids, or parenteral preparations such as injections and suppositories.

The vascularization inhibitor of the present invention can be administered orally. In this case, although the weight of active ingredient within the vascularization inhibitor of the present invention varies according to the patient's age, sex and body weight or the severity of the disease, the normal adult does is within a range of 30–1000 mg per day, and this dose is preferably divided into several administrations per day.

Although the present compound is used alone in the case of oral preparations, it can be manufactured in accordance with routine methods by using a vehicle like, for example, starch, lactose, sucrose, mannitol, carboxymethylcellulose, cornstarch or inorganic salt. Binder, disintegrating agent, surface active agent, lubricant, fluidity promoter, crosslinking agent, colorant or fragrance, etc. may be suitably selected and used in addition to the vehicle described above.

Examples of binders include starch, dextrin, gum Arabic powder, gelatin, hydroxypropyl starch, methylcellulose, sodium carboxymethylcellulose, hydroxypropylcellulose, crystalline cellulose, ethylcellulose, polyvinylpyrrolidine and macrogol.

In addition, examples of disintegrating agents that can be used include starch, hydroxypropyl starch, sodium carboxymethylcellulose, calcium carboxymethylcellulose, carboxymethylcellulose and low-substituted hydroxypropylcellulose.

In addition, examples of surface active agents include sodium laurylsulfate, soy bean lecithin, sucrose fatty acid ester and polysorbate 80.

In addition, examples of lubricants include talc, waxes, hydrogenated vegetable oil, sucrose fatty acid ester, magnesium stearate, calcium stearate, aluminum stearate and polyethylene glycol. In addition, examples of fluidity promoters include light silicic anhydride, dry aluminum hydroxide gel, synthetic aluminum silicate and magnesium silicate.

Moreover, the vascularization inhibitor of the present invention can also be administered in the form of a suspension, emulsion, syrup or elixir. In the case of such preparation forms, a flavoring agent or colorant may be contained.

The vascularization inhibitor of the present invention can also be administered in the form of a parenteral preparation. In this case, although the weight of active ingredient within the vascularization inhibitor of the present invention varies according to the patient's age, sex and body weight or the severity of the disease, the normal adult does is within a range of 1–300 mg per day, and this dose is preferably administered by intravenous injection, intravenous drip, subcutaneous injection or intramuscular injection.

Parenteral preparations can be used by diluting the present compound with a suitable diluent. Typical examples of diluents that can be used include distilled water for injection, physiological saline, aqueous glucose solution, vegetable oil for injection, sesame oil, peanut oil, soy bean oil, corn oil, propylene glycol and polyethylene glycol. Disinfectant, preservative or stabilizer may also be added as necessary to parenteral preparations.

Among these, from the viewpoint of storage stability, injection preparations in particular can be frozen after filling into vials, etc., moisture can be removed by ordinary freeze-drying techniques, the injections can be stored in the form of a freeze-dried product, and a liquid can be reconstituted from the freeze-dried product immediately prior to use. Isotonic agent, stabilizer, preservative, analgesic, etc. may also be added to injection preparations as necessary. Other examples of parenteral preparations include externally applied liquids, ointments and other applications, or suppositories for intrarectal administration. These preparations can be manufactured in accordance with routine methods.

As has been explained above, the vascularization inhibitor of the present invention contains as its active ingredient the present compound having vascularization inhibitory effects, and is extremely useful in the improvement of the course of diseases having a correlation with vascularization. For example, it is useful in the inhibition of the growth of tumor cells, inflammation healing, and the inhibition of the granulation growth. In addition, it is also widely applied in the treatment of diseases having a correlation with vascularization.

The following provides a description of the production process and physicochemical properties of the novel compound of the present invention.

The proton nuclear magnetic resonance ($^1$H-NMR) spectra of the compounds shown in the following table were all measured in $CDCl_3$ with the exception of those indicated below.

Compound measured in $CD_3OD$: No. 2 in Table 1; compounds measured in $D_2O$: No. I-67 and I-69 in Table 17, No. I-281 in Table 60 and No. I-313 in Table 66; compounds measured in DMSO-$d_6$: No. I-81 in Table 20, No. I-86 and I-90 in Table 21, No. I-93 in Table 22, No. I-122 in Table 28, No. I-184 in Table 40, No. I-189 in Table 41, No. I-193 in Table 42, No. I-198 in Table 43 and No. I-227 in Table 49; compound measured in $CDCl_3$-$CD_3OD$: No. I-133 in Table 30.

In addition, the following abbreviations are used in the descriptions of $^1$H-NMR data: s: singlet, d: doublet, t: triplet, q: quartet, m: multiplet, dd: double doublet, br: broad, br s: broad singlet, ABq: AB quartet, and J: coupling constant.

Furthermore, substitution groups, etc. may be abbreviated with symbols in the structural formulas shown below. The meanings of those symbols are as follows:

TBDMS: tert-butyldimethylsilyl, Ac: acetyl, MEM: methoxyethoxymethyl, Me: methyl, Et: ethyl and Ph: phenyl,

[EXAMPLES 1–28]

Example 1

[Step 1]

Water was added to 6.52 g of a known (1S,4aS,7aR)-1-[1-(ethoxy)ethoxy]-7-methyl-1,4a,5,7-tetrahydrocyclopenta [c]-pyrane-4-carboxylic acid methyl ester followed by addition of 4.6 g of lithium hydroxide-1-hydrate and refluxing for 2 hours. After washing the reaction mixture with ether, the aqueous phase was acidified with dilute hydrochloric acid and extracted with ethyl acetate. After washing the organic phase with brine, it was dried over anhydrous magnesium sulfate. The solvent was distilled off under reduced pressure to obtain a brown oil (7.33 g).

[Step 2]

7.33 g of the above a brown oil were dissolved in dimethylformamide followed by addition of 3.9 g of potassium carbonate and 3.4 ml of benzyl bromide and stirring for 3 hours at room temperature. After filtering out the insoluble matter, the filtrate was extracted with ethyl acetate. After washing the organic phase with brine, it was dried over anhydrous magnesium sulfate. After concentration, the residue was purified by silica gel chromatography to obtain a colorless oil from the hexane-ether eluate in the form of (1S,4aS,7aR)-1-[1-(ethoxy)ethoxy]-7-methyl-1,4a,5,7a-tetrahydrochloric[c]-pyrane-4-carboxylic acid benzyl ester (7.06 g, yield: 86%). The physicochemical properties of this compound are shown below.

$^1$H-NMR (δ ppm, in $CDCl_3$): 1.10–1.42 (3H,m), 1.30–1.42 (3H, m), 1.84 (3H,m), 1.98–2.16 (1H,m), 2.47 (1H,m), 2.70–2.88 (1H, m), 3.17–3.26 (1H,m), 3.40–3.90 (2H,m), 4.70–5.10 (2H,m), 5.17 (2H,s), 5.52 (1H,m), 7.30–7.42 (5H,m), 7.53–7.60 (1H,m)

[Step 3]

Dilute hydrochloric acid was added to a tetrahydrofuran solution of (1S,4aS,7aR)-1-[1-(ethoxy)ethoxy]-7-methyl-1, 4a,5,7a-tetrahydrocyclopenta [c]-pyrane-4-carboxylaic acid benzyl ester (7.06 g) followed by stirring for 1 hour at room temperature. The reaction mixture was then extracted with ether. After washing the organic phase with saturated aqueous sodium bicarbonate and brine, it was dried over anhydrous magnesium sulfate. After distilling off the solvent under reduced pressure, the residue was purified by silica gel chromatography to obtain a colorless oil from the hexane-ethyl acetate eluate in the form of (1S,4aS,7aR)-1-hydroxy-7-methyl-1,4a,5,7a-tetrahydrocyclopenta [c]-pyrane-4-carboxylic acid benzyl ester (4.98 g, yield: 87%). The physicochemical properties of this compound are shown below.

$^1$H-NMR (δ ppm, in CDCl$_3$): 1.85 (3H,d,J=1 Hz), 1.90–2.10 (1H, m), 2.37 (1H,t,J=8 Hz), 2.73–2.85 (1H,m), 3.18 (1H,m), 4.11 (1H, s), 4.86 (1H,t,J=7 Hz), 5.17 (2H,s), 5.52 (1H,m), 7.30–7.42 (5H, m), 7.54 (1H,d,J=1 Hz)

[Step 4]

9.2 ml of triethylamine and 2.4 ml of methylisocyanate were added to an acetonitrile solution containing 4.98 g of (1S,4aS,7aR)-1-hydroxy-7-methyl-1,4a,5,7a-tetrahydrocyclopenta [c]-pyrane-4-carboxylic acid benzyl ester followed by stirring for 1 hour at room temperature. The reaction mixture was then extracted with ethyl acetate. After washing the organic phase with brine, it was dried over anhydrous magnesium sulfate. After distilling off the solvent under reduced pressure, the residue was purified by silica gel chromatography to obtain a colorless oil from the hexane-ethyl acetate eluate in the form of (1S,4aS,7aR)-7-methyl-1-(methylcarbamoyloxy)-1,4-a,5,7a-tetrahydrocyclopenta [c]-pyrane-4-carboxylic acid benzyl ester of 5.10 g (yield: 86%). The physicochemical properties of this compound are shown below.

$^1$H-NMR (δ ppm, in CDCl$_3$): 1.76 (3H,s), 2.18 (1H,m), 2.62 (1H, m), 2.70–2.88 (1H,m), 2.82 (3H,d,J=5 Hz), 3.21 (1H,m), 5.17 (2H, s), 5.51 (1H,m), 5.87 (1H,d,J=7 Hz), 7.29–7.45 (5H,m), 7.50 (1H, d,J=1 Hz)

[Step 5]

15 g of potassium dihydrogen phosphate and 50 g of magnesium monoperphthalate were added to a methanol solution containing 4.46 g of (1S,4aS,7aR)-7-methyl-1-(methylcarbamoyloxy)-1,4a,5,7a-tetrahydrocycropenta [c]-pyrane-4-carboxylic acid benzyl ester followed by stirring for 1 hour. The reaction mixture was then extracted with ethyl acetate. After washing the organic phase with water, saturated aqueous sodium bicarbonate, aqueous sodium thiosulfate and brine, it was dried over anhydrous magnesium sulfate. After distilling off the solvent under reduced pressure, the residue was purified by silica gel chromatography to obtain a colorless oil from the hexane-ethyl acetate eluate in the form of (1S,4aS,6S,7R,7aR)-6,7-epoxy-7-methyl-1-(methylcarbamoyloxy)-1,4a,5,6,7,7a-hexahydrocyclopenta [c]-pyrane-4-carboxylic acid benzyl ester (2.78 g, yield: 60%), and the stereoisomer with respect to the epoxyl group in the form of (1S,4aS,6R,7S,7aR)-6,7-epoxy-7-methyl-1-(methylcarbamoyloxy)-1,4a,5,6,7,7a-hexahydrocyclopenta[c]-pyrane-4-carboxylic acid benzyl ester (0.53 g, yield: 11%). The physicochemical properties of the former compound above is shown in Table 3, Compound No. 11, while those of the latter compound above are shown below.

$^1$H-NMR (δ ppm, in CDCl$_3$): 1.42 (3H,s), 1.40–1.54 (1H,m), 2.31 (1H,dd,J=7,10 Hz), 2.63 (1H,dd,J=8,14 Hz), 2.87 (3H,d,J=5 Hz), 2.80–2.98 (1H,m), 3.28 (1H,s), 5.04–5.10 (1H,br), 5.16–5.26 (2H, m), 5.74 (1H,d,J=10 Hz), 7.32–7.42 (5H,m), 7.45 (1H,s)

[Step 6]

35 mg of 5% palladium-carbon catalyst were added to an ethyl acetate solution containing 350 mg of (1S,4aS,6S,7R,7aR)-6,7-epoxy-7-methyl-1-(methylcarbamoyloxy)-1,4a,5,6,7,7a-hexahydrocyclopenta [c]-pyrane-4-carboxylic acid benzyl ester followed by stirring for 2 hours at room temperature under hydrogen gas atmosphere at 1 atm. After filtering out the insoluble matter, the filtrate was concentrated under reduced pressure to obtain a colorless powder in the form of (1S,4aS,6S,7R,7aR)-6,7-epoxy-1,4a,5,6,7,7a-hexahydro-7-methyl-1-(methylcarbamoyloxy) cyclopenta [c]-pyrane-4-carboxylic acid (298 mg; yield: 99%). The physicochemical properties of this compound are described in Table 1, Compound No. 1.

Example 2

40 mg of sodium methoxide were added to a methanol solution containing 197 mg of (1S,4aS,6S,7R,7aR)-6,7-epoxy-1,4a,5,6,7,7a-hexahydro-7-methyl-1-(methylcarbamoyloxy) cyclopenta [c]-pyrane-4-carboxylic acid described in Example 1 followed by stirring for 1 hour at room temperature. The solvent was distilled off from the reaction solution to obtain a colorless powder in the form of sodium (1S,4aS,6S,7R,7aR)-6,7-epoxy-1,4a,5,6,7,7a-hexahydro-7-methyl-1-(methylcarbamoyloxy) cyclopenta [c]-pyrane-4-carboxylic acid (210 mg, yield: 98%). The physicochemical properties of this compound are described in Table 1, Compound No. 2.

Example 3

0.15 ml of triethylamine and 60 μl of methylisocyanate were added to an acetonitrile solution containing 200 mg of a known (4aS, 6S,7R,7aR)-6,7-epoxy-1,4a,5,6,7,7a-hexahydro-1-hydroxy-7-methylcyclopenta [c] pyrane-4-carboxylic acid methylester followed by stirring for 1 hour at room temperature. After adding 1 ml of methanol to the reaction mixture, it was concentrated under reduced pressure. The residue was purified by silica gel chromatography to obtain colorless needles from the hexane-ether eluate in the form of (1S,4aS,6S,7R,7aR)-6,7-epoxy-1,4a,5,6,7,7a-hexahydro-1-methylcarbamoyloxyo-7-methylcyclopenta [c] pyrane-4-carboxylic acid methylester (55 mg, yield: 22%). The physicochemical properties of this compound are described in Table 1, Compound No. 3).

Example 4

130 mg of potassium carbonate and 121 μl of diethyl sulfate were added to an acetonitrile solution containing 210 mg of (1S, 4aS,6S,7R,7aR)-6,7-epoxy-1,4a,5,6,7,7a-hexahydro-7-methyl-1-(methylcarbamoyloxy) cyclopenta [c]-pyrane-4-carboxylic acid described in Example 1 followed by heating and stirring for 1 hour at 70° C. The reaction mixture was then extracted with ethyl acetate. After washing the organic phase with dilute hydrochloric acid, saturated aqueous sodium bicarbonate and brine, it was dried over anhydrous magnesium sulfate. After distilling off the solvent under reduced pressure, the residue was purified by silica gel chromatography to obtain a colorless oil from the hexane-ethyl acetate eluate in the form of (1S,4aS,6S, 7R,7aR)-6,7-epoxy-1, 4a,5,6,7,7a-hexahydro-7-methyl-1-(methylcarbamoyloxy) cyclopenta [c]-pyrane-4-carboxylic acid ethylester (204 mg, yield: 88%). The physicochemical properties of this compound are described in Table 1, Compound No. 4.

Example 5

124 mg of potassium carbonate and 0.10 ml of n-hexyliodide were added to a dimethylformamide solution containing 200 mg of (1S,4aS,6S,7R,7aR)-6,7-epoxy-1,4a, 5,6,7,7a-hexahydro-7-methyl-1-(methylcarbamoyloxy) cyclopenta [c]-pyrane-4-carboxylic acid described in Example 1 followed by heating and stirring for 1 hour at 70° C. The reaction mixture was then extracted with ethyl acetate. After washing the organic phase with dilute hydrochloric acid, saturated aqueous sodium bicarbonate and brine, it was dried over anhydrous magnesium sulfate. After distilling off the solvent under reduced pressure, the residue was purified by silica gel chromatography to obtain a colorless oil from the hexane-ethyl acetate eluate in the form of (1S,4aS,6S,7R,7aR)-6,7-epoxy-1,4a,5,6,7,7a-hexahydro-7-methyl-1-(methylcarbamoyloxy) cyclopenta [c]-pyrane-4-carboxylic acid n-hexylester (210 mg, yield: 80%). The physicochemical properties of this compound are described in Table 1, Compound No. 5.

Example 6

0.5 ml of triethylamine and 0.45 ml of diethylchlorophosphate were added to a dichloromethane solution containing 331 mg of (1S,4aS,6S,7R,7aR)-6,7-epoxy-1,4a,5,6,7,7a-hexahydro-7-methyl-1-(methylcarbamoyloxy)cyclopenta [c]-pyrane-4-carboxylic acid described in Example 1. After stirring for 30 minutes at room temperature, 0.42 ml of geraniol and 17 mg of 4-dimethylaminopyridine (to be abbreviated as DMAP) were added followed by stirring for 5 hours at room temperature. The reaction mixture was then extracted with dichloromethane. After washing the organic phase with dilute hydrochloric acid, saturated aqueous sodium bicarbonate and brine, it was dried over anhydrous magnesium sulfate. After distilling off the solvent under reduced pressure, the residue was purified by silica gel chromatography to obtain a colorless oil from the hexane-ethyl acetate eluate in the form of (1S,4aS,6S,7R,7aR)-6,7-epoxy-1,4a,5,6,7,7a-hexahydro-7-methyl-1-(methylcarbamoyloxy)cyclopenta[c]-pyrane-4-carboxylic acid geranyl ester (280 mg, yield: 50%). The physicochemical properties of this compound are described in Table 2, Compound No. 6.

(1S,4aS,6S,7R,7aR)-6,7-epoxy-1,4a,5,6,7,7a-hexahydro-7-methyl-1-(methylcarbamoyloxy)cyclopenta[c]-pyrane-4-carboxylic acid 4-pentenylester (Table 2, Compound No. 7), (1S,4aS,6S,7R,7aR)-6,7-epoxy-1,4a,5,6,7,7a-hexahydro-7-methyl-1-(methylcarbamoyloxy)cyclopenta[c]-pyrane-4-carboxylic acid 3-butenylester (Table 2, Compound No. 8), (1S,4aS,6S,7R,7aR)-6,7-epoxy-1,4a,5,6,7,7a-hexahydro-7-methyl-1 -(methylcarbamoyloxy)cyclopenta[c]-pyrane-4-carboxylic acid allylester (Table 2, Compound No. 9), (1S,4aS,6S,7R,7aR)-6,7-epoxy-1,4a,5,6,7,7a-hexahydro-7-methyl-1-(methylcarbamoyloxy) cyclopenta[c]-pyrane-4-carboxylic acid furfurylester (Table 2, Compound No. 10), (1S,4aS,6S,7R,7aR)-6,7-epoxy-1,4a,5,6,7,7a-hexahydro-7-methyl-1-(methylcarbamoyloxy)cyclopenta[c]-pyrane-4-carboxylic acid phenylethylester (Table 3, Compound No. 12), (1S,4aS,6S,7R,7aR)-6,7-epoxy-1,4a,5,6,7,7a-hexahydro-7-methyl-1-(methylcarbamoyloxy)cyclopenta [c]-pyrane-4-carboxylic acid phenylester (Table 3, Compound No. 13), (1S,4aS,6S,7R,7aR)-6,7-epoxy-1,4a,5,6,7, 7a-hexahydro-7-methyl-1-(methylcarbamoyloxy) cyclopenta[c]-pyrane-4-carboxylic acid ethylamide (Table 4, Compound No. 16), (1S,4aS,6S,7R,7aR)-6,7-epoxy-1,4a, 5,6,7,7a-hexahydro-7-methyl-1-(methylcarbamoyloxy) cyclopenta[c]-pyrane-4-carboxylic acid n-hexylamide (Table 4, Compound No. 17), (1S,4aS,6S,7R,7aR)-6,7-epoxy-1,4a,5,6,7,7a-hexahydro-7-methyl-1-(methylcarbamoyloxy)cyclopenta[c]-pyrane-4-carboxylic acid cyclohexylamide (Table 5, Compound No. 21), (1S, 4aS,6S,7R,7aR)-6,7-epoxy-1,4a,5,6,7,7a-hexahydro-7-methyl-1-(methylcarbamoyloxy)cyclopenta[c]-pyrane-4-carboxylic acid morpholylamide (Table 5, Compound No. 23), (1S,4aS,6S,7R,7aR)-6,7-epoxy-1,4a,5,6,7,7a-hexahydro-7-methyl-1-(methylcarbamoyloxy)cyclopenta [c]-pyrane-4-carboxylic acid 2,6-dimethylmorpholylamide (Table 5, Compound No. 24), (1S,4aS,6S,7R,7aR)-6,7-epoxy-1,4a,5,6,7,7a-hexahydro-7-methyl-1-(methylcarbamoyloxy)cyclopenta[c]-pyrane-4-carboxylic acid piperidylamide (Table 6, Compound No. 26), and (1S,4aS,6S,7R,7aR)-6,7-epoxy-1,4a,5,6,7,7a-hexahydro-7-methyl-1-(methylcarbamoyloxy)cyclopenta[c]-pyrane-4-carboxylic acid phenylethylamide (Table 6, Compound No. 28) were produced in the same manner from (1S,4aS,6S, 7R,7aR)-6,7-epoxy-1,4a,5,6,7,7a-hexahydro- 7-methyl-1-(methylcarbamoyloxy)cyclopenta[c]-pyrane-4-carboxylic acid.

Example 7

A dichloromethane solution containing 395 mg of (1S, 4aS,6S,7R,7aR)-6,7-epoxy-1,4a,5,6,7,7a-hexahydro-7-methyl-1-(methylcarbamoyloxy)cyclopenta[c]-pyrane-4-carboxylic acid described in Example 1 was cooled with ice followed by addition of 0.49 ml of triethylamine, 0.38 ml of diphenylphosphate azide and 118 mg of methylamine hydrochloride and stirring for 15 hours at room temperature. The reaction mixture was then extracted with dichloromethane. After washing the organic phase with dilute hydrochloric acid, saturated aqueous sodium bicarbonate and brine, it was dried over anhydrous magnesium sulfate. After distilling off the solvent under reduced pressure, the residue was purified by silica gel chromatography to obtain colorless needles from the dichloromethane-methanol eluate in the form of (1S,4aS,6S,7R,7aR)-6,7-epoxy-1,4a,5,6,7,7a-hexahydro-7-methyl-1-(methylcarbamoyloxy)cyclopenta[c]-pyrane-4-carboxylic acid methylamide (194 mg, yield: 47%). The physicochemical properties of this compound are described in Table 3, Compound No. 15.

(1S,4aS,6S,7R,7aR)-6,7-epoxy-1,4a,5,6,7,7a-hexahydro-1-(methylcarbamoyloxy)cyclopenta[c]-pyrane-4-carboxylic acid dimethylamide (Table 4, Compound No. 18), (1S,4aS, 6S,7R,7aR)-6,7-epoxy-1,4a,5,6,7,7a-hexahydro-7-methyl-1-(methylcarbamoyloxy)cyclopenta[c]-pyrane-4-carboxylic acid dimethylamide (Table 4, Compound No. 19), (1S,4aS, 6S,7R,7aR)-6,7-epoxy-1,4a,5,6,7,7a-hexahydro-7-methyl-1-(methylcarbamoyloxy)cyclopenta[c]-pyrane-4-carboxylic acid pyrrolidylamide (Table 5, Compound No. 25), and (1S,4aS,6S,7R,7aR)-6,7-epoxy-1,4a,5,6,7,7a-hexahydro-7-methyl-1-(methylcarbamoyloxy)cyclopenta[c]-pyrane-4-carboxylic acid benzylamide (Table 6, Compound No. 27) were produced in the same manner from (1S,4aS,6S,7R, 7aR)-6,7-epoxy-1,4a,5,6,7,7a-hexahydro-7-methyl-1-(methylcarbamoyloxy)cyclopenta[c]-pyrane-4-carboxylic acid. The physicochemical properties of the above compounds are described in the attached tables (corresponding to Table No. and Compound No.).

Example 8

0.28 ml of piperazylethanol, 273 mg of DMAP and 461 mg of dicyclohexylcarbodiimide were added to a dichloromethane solution containing 400 mg of (1S,4aS,6S,7R, 7aR)-6,7-epoxy-1,4a,5,6,7,7a-hexahydro-7-methyl-1-(methylcarbamoyloxy)cyclopenta[c]-pyrane-4-carboxylic acid described in Example 1 followed by stirring for 15 hours at room temperature. The reaction mixture was then extracted with dichloromethane. After washing the organic phase with saturated aqueous sodium bicarbonate and brine, it was dried over anhydrous magnesium sulfate. After distilling off the solvent under reduced pressure, the residue was purified by silica gel chromatography to obtain a colorless amorphous substance from the dichloromethane-methanol eluate in the form of (1S,4aS,6S,7R,7aR)-6,7-epoxy-1,4a,5,6,7,7a-hexahydro-7-methyl-1-(methylcarbamoyloxy)cyclopenta[c]-pyrane-4-carboxylic acid 4-(2-hyroxyethyl) piperazylamide (276 mg, yield: 49%). The physicochemical properties of this compound are described in Table 5, Compound No. 22.

Example 9

A dichloromethane solution containing 400 mg of (1S,4aS,6S,7R,7aR)-6,7-epoxy-1,4a,5,6,7,7a-hexahydro-7-methyl-1-(methylcarbamoyloxy)cyclopenta[c]-pyrane-4-carboxylic acid described in Example 1 was cooled with ice followed by addition of 0.20 ml of 1-methylpiperazine, 2 ml of triethylamine and 301 mg of 2-chloro-1,3-dimethylimidazolinium chloride and stirring for 15 hours at room temperature. The reaction mixture was then extracted with dichloromethane. After washing the organic phase with saturated aqueous sodium bicarbonate and brine, it was dried over anhydrous magnesium sulfate. After distilling off the solvent under reduced pressure, the residue was purified by silica gel chromatography to obtain a colorless powder from the dichloromethane-methanol eluate in the form of (1S,4aS,6S,7R,7aR)-6,7-epoxy-1,4a,5,6,7,7a-hexahydro-7-methyl-1-(methylcarbamoyloxy)cyclopenta[c]-pyrane-4-carboxylic acid 4-methylpiperazylamide (264 mg, yield: 50%). The physicochemical properties of this compound are described in Table 5, Compound No. 20.

(1S,4aS,6S,7R,7aR)-6,7-epoxy-1,4a,5,6,7,7a-hexahydro-7-methyl-1-(methylcarbamoyloxy)cyclopenta[c]-pyrane-4-carboxylic acid cyclohexylester was produced in the same manner from (1S,4aS,6S,7R,7aR)-6,7-epoxy-1,4a,5,6,7,7a-hexahydro-7-methyl-1-(methylcarbamoyloxy)cyclopenta[c]-pyrane-4-carboxylic acid. The physicochemical properties of this compound are described in Table 3, Compound No. 14.

Example 10

1.2 mg of DMAP and 0.9 ml of chlorophenylformate were added to a dichloromethane solution containing 1.12 g of a known (4aS,6S,7R,7aR)-6,7-epoxy-1,4a,5,6,7,7a-hexahydro-1-hydroxy-7-methylcyclopenta[c]pyrane-4-carboxylic acid methylester followed by stirring for 1 hour at room temperature. The reaction mixture was then extracted with dichloromethane. After washing the organic phase with dilute hydrochloric acid and brine, it was dried over anhydrous magnesium sulfate. After distilling off the solvent under reduced pressure, the residue was purified by silica gel chromatography to obtain a colorless powder from the hexane-ethyl acetate eluate in the form of (1S,4aS,6S,7R,7aR)-6,7-epoxy-1,4a,5,6,7,7a-hexahydro-7-methyl-1-(phenoxycarbonyloxy)cyclopenta[c]pyrane-4-carboxylic acid methylester (1.16 g, yield: 70%). The physicochemical properties of this compound are as shown below.

$^1$H-NMR (δ ppm, in CDCl$_3$): 1.38–1.48 (1H,m), 1.54 (3H,s), 2.46 (1H,dd,J=7.10 Hz), 2.66 (1H,m), 2.90 (1H,m), 3.31 (1H,s), 3.72 (3H,s), 5.72 (1H,d,J=10 Hz), 7.14–7.34 (3H,m), 7.34–7.50 (3H,m).

Example 11

5 ml of a 50% aqueous dimethylamine solution were added to a dichloromethane solution containing 198 mg of (1S,4aS,6S,7R,7aR)-6,7-epoxy-1,4a,5,6,7,7a-hexahydro-7-methyl-1-(phenoxycarbonyloxy)cyclopenta[c]-pyrane-4-carboxylic acid methylester described in Example 10 followed by stirring for 10 minutes at room temperature. The reaction mixture was then extracted with dichloromethane. After washing the organic phase with brine, it was dried over anhydrous magnesium sulfate. After distilling off the solvent under reduced pressure, the residue was purified by silica gel chromatography to obtain a colorless powder from the hexane-ethyl acetate eluate in the form of (1S,4aS,6S,7R,7aR)-1-(dimethylcarbamoyloxy)-6,7-epoxy-1,4a,5,6,7,7a-hexahydrocyclopenta[c]pyrane-4-carboxylic acid methyl-ester (140 mg, yield: 83%). The physicochemical properties of this compound are described in Table 7, Compound No. 31.

(1S,4aS,6S,7R,7aR)-1-(carbamoyloxy)-6,7-epoxy-1,4a,5,6,7,7a-hexahydro-7-methylcyclopenta[c]pyrane-4-carboxylic acid methylester was produced in the same manner from (1S,4aS,6S,7R,7aR)-6,7-epoxy-1,4a,5,6,7,7a-hexahydro-7-methyl-1-(phenoxycarbonyloxy)cyclopenta[c]pyrane-4-carboxylic acid methylester. The physicochemical properties of this compound are described in Table 6, Compound No. 29.

Example 12

0.11 ml of n-hexylamine were added to a dichloromethane solution containing 246 mg of (1S,4aS,6S,7R,7aR)-6,7-epoxy-1,4a,5,6,7,7a-hexahydro-7-methyl-1-(phenoxycarbonyloxy)cyclopenta[c]pyrane-4-carboxylic acid methylester described in Example 10 followed by stirring for 1 hour at room temperature. The reaction mixture was then extracted with dichloromethane. After washing the organic phase with brine, it was dried over anhydrous magnesium sulfate. After distilling off the solvent under reduced pressure, the residue was purified by silica gel chromatography to obtain a colorless powder from the hexane-ethyl acetate eluate in the form of (1S,4aS,6S,7R,7aR)-6,7-epoxy-1-(n-hexylcarbamoyloxy)-1,4a,5,6,7,7a-hexahydro-7-methylcyclopenta[c]pyrane-4-carboxylic acid methylester (87 mg, yield: 35%). The physicochemical properties of this compound are described in Table 7, Compound No. 33.

(1S,4aS,6S,7R,7aR)-6,7-epoxy-1,4a,5,6,7,7a-hexahydro-7-methyl-1-(morpholinocarbonyloxy)cyclopenta[c]pyrane-4-carboxylic acid methylester was produced in the same manner from (1S,4aS,6S,7R,7aR)-6,7-epoxy-1,4a,5,6,7,7a-hexahydro-7-methyl-1-(phenoxycarbonyloxy)cyclopenta[c]pyrane-4-carboxylic acid methylester. The physicochemical properties of this compound are described in Table 8, Compound No. 38.

Example 13

An acetonitrile solution containing 790 mg of a known (4aS,6S,7R,7aR)-6,7-epoxy-1,4a,5,6,7,7a-hexahydro-1-hydroxy-7-methylcyclopenta[c]pyrane-4-carboxylic acid methylester was cooled with ice followed by addition of 0.54 ml of triethylamine and 0.23 ml of methylisocyanate and stirring for 15 hours at room temperature. The reaction mixture was then extracted with ethyl acetate. After washing the organic phase with brine, it was dried over anhydrous magnesium sulfate. After distilling off the solvent under reduced pressure, the residue was purified by silica gel chromatography to obtain a colorless powder from the hexane-ethyl acetate eluate in the form of (1S,4aS,6S,7R,7aR)-6,7-epoxy-1,4a,5,6,7,7a-hexahydro-7-methyl-1-(methylcarbamoyloxy)cyclopenta[c]pyrane-4-carboxylic acid methylester (610 mg, yield: 61.7%). The physicochemical properties of this compound are described in Table 1, Compound No. 3.

(1S,4aS,6S,7R,7aR)-6,7-epoxy-1-(ethylcarbamoyloxy)-1,4a,5,6,7,7a-hexahydro-7-methylcyclopenta[c]pyrane-4-carboxylic acid methylester (Table 6, Compound No. 30), (1S,4aS,6S,7R,7aR)-1-[(2-chloroethyl) carbamoyloxy]-6,7-epoxy-1,4a,5,6,7,7a-hexahydro-7-methylcyclopenta[c] pyrane-4-carboxylic acid methylester (Table 7, Compound No. 32), (1S,4aS,6S,7R,7aR)-6,7-epoxy-1,4a,5,6,7,7a-hexahydro-1-(isopropylcarbamoyloxy)-7-methylcyclopenta[c]pyrane-4-carboxylic acid methylester (Table 6, Compound No. 34), (1S,4aS,6S,7R,7aR)-6,7-epoxy-1,4a,5,6,7,7a-hexahydro-7-methyl-1-(phenoxycarbamoyloxy)cyclopenta[c]pyrane-4-carboxylic acid methylester (Table 7, Compound 35), (1S,4aS,6S,7R,7aR)-6,7-epoxy-1,4a,5,6,7,7a-hexahydro-1-[(4-fluorophenyl) carbamoyloxy]-7-methylcyclopenta[c]pyrane-4-carboxylic acid methylester (Table 8, Compound No. 36), (1S,4aS,6S,7R,7aR)-6,7-epoxy-1,4a,5,6,7,7a-hexahydro-7-methyl-1-[(1-naphtyl) carbamoyloxy]cyclopenta[c]pyrane-4-carboxylic acid methylester (Table 8, Compound No. 37), (1S,4aS,6S,7R,7aR)-1-(chloroacetylcarbamoyloxy-6,7-epoxy-1,4a,5,6,7,7a-hexahydro-7-methylcyclopenta[c]pyrane-4-carboxylic acid methylester (Table 8, Compound 39), and (1S,4aS,6S,7R,7aR)-1-(benzoylcarbamoyloxy)-6,7-epoxy-1,4a,5,6,7,7a-hexahydro-7-methylcyclopenta[c]pyrane-4-carboxylic acid methylester (Table 9, Compound No. 41) were produced in the same manner from (4aS,6S,7R,7aR)-6,7-epoxy-1,4a,5,6,7,7a-hexahydro-1-hydroxy-7-methylcyclopenta[c]pyrane-4-carboxylic acid methylester.

Example 14

A dichloromethane solution containing 100 mg of a known (4aS,6S,7R,7aR)-6,7-epoxy-1,4a,5,6,7,7a-hexahydro-1-hydroxy-7-methylcyclopenta[c]pyrane-4-carboxylic acid methylester was cooled with ice followed by addition of chloroacetylisocyanate (45 ml) and stirring for 15 hours at room temperature. The reaction mixture was then extracted with dichloromethane. After washing the organic phase with brine, it was dried over anhydrous magnesium sulfate. After distilling off the solvent under reduced pressure, the residue was purified by silica gel chromatography to obtain a colorless powder from the hexane-ethyl acetate eluate in the form of (1R,4aS,6S,7R,7aR)-1-(chloroacetylcarbamoyloxy)-6,7-epoxy-1,4a,5,6,7,7a-hexahydro-7-methylcyclopenta[c]pyrane-4-carboxylic acid methylester (137 mg, yield: 91%). The physicochemical properties of this compound are described in Table 8, Compound No. 40.

(1S,4aS,6S,7R,7aR)-1-(benzoylcarbamoyloxy-6,7-epoxy-1,4a,5,6,7,7a-hexahydro-7-methylcyclopenta[c]pyrane-4-carboxylic acid methylester was produced in the same manner from (4aS,6S,7R,7aR)-6,7-epoxy-1,4a,5,6,7,7a-hexahydro-1-hydroxy-7-methylcyclopenta[c]pyrane-4-carboxylic acid methylester. The physicochemical properties of this compound are described in Table 9, Compound No. 42.

Example 15

[Step 1]

An anhydrous tetrahydrofuran solution containing 100 mg of (1S,4aS,7aR)-1-[1-(ethoxy)ethoxy]-7-formyl-1,4a,5,7a-tetrahydrocyclopenta[c]pyrane-4-carboxylic acid methylester was cooled to −78° C. under argon gas atmosphere followed by dropping 0.38 ml of magnesium methyliodide (0.98 M tetrahydrofuran solution). Two hours later, saturated aqueous ammonium chloride solution was added to the reaction mixture followed by extraction with ethyl acetate. After washing the organic phase with brine, it was dried over magnesium sulfate. After distilling off the solvent under reduced pressure, the residue was purified by silica gel chromatography to obtain a pale yellow oil from the hexane-ether eluate in the form of (1S,4aS,7aR)-1-[1-(ethoxy)ethoxy]-7-[2-(hydroxy)ethyl]-1,4a,5,7a-tetrahydrocyclopenta[c]pyrane-4-carboxylic acid methylester (81 mg, yield: 77%). the physicochemical properties of this compound are described below. $^1$H-NMR (δ ppm, in CDCl$_3$): 1.03–1.39 (9H,m), 1.68–3.24 (5H,m), 3.72 (3H,s), 3.40–3.88 (2H,m), 4.72–5.08 (2H,m), 5.52 (1H,br,s), 7.47–7.49 (1H,m)

[Step 2]

1.63 g of the above (1S,4aS,7aR)-1-[1-(ethoxy)ethoxy]-7-[2-(hydroxy)ethyl]-1,4a,5,7a-tetrahydrocyclopenta[c]pyrane-4-carboxylic acid methylester were dissolved in dichloromethane followed by addition of 1.7 ml of pyridine and DMAP. Next, 1.0 ml of acetic anhydride were added followed by stirring for 3 hours at room temperature. The reaction mixture was then extracted with ether. After washing the organic phase with 2N aqueous hydrochloric acid, saturated aqueous sodium bicarbonate and brine, it was dried over anhydrous magnesium sulfate. After distilling off the solvent under reduced pressure, the residue was purified by silica gel chromatography to obtain a colorless oil from the hexane-ether eluate in the form of (1S,4aS,7aR)-7-[2-(acetoxy)ethyl]-1-[1-(ethoxy)ethoxy]-1,4a,5,7a-tetrahydrocyclopenta[c]pyrane-4-carboxylic acid methylester (1.65 g, yield: 89%). The physicochemical properties of this compound are described below.

$^1$H-NMR (δ ppm, in CDCl$_3$): 1.13–1.23 (3H,m), 1.33–1.45 (3H,m), 2.08 (3H,s), 2.50–2.68 (1H,m), 2.78–2.94 (2H,m), 3.12–3.28 (1H,m), 3.73 (3H,s), 3.40–3.94 (2H,m), 4.70 (0.5H,d,J=8 Hz), 4.90 (0.5H,d,J=8 Hz), 4.92–5.12 (1H,m), 5.60 (1H,br s), 5.68–5.90 (1H, m), 7.48–7.51 (1H,m)

[Step 3]

1.65 g of the above (1S,4aS,7aR)-7-[2-(acetoxy)ethyl]-1-[1-(ethoxy)ethoxy]-1,4a,5,7a-tetrahydrocyclopenta[c]pyrane-4-carboxylic acid methylester were dissolved in a mixed solvent of tetrahydrofuran and water followed by addition of 80 mg of 10% palladium carbon catalyst and 3.2 g of sodium formate and refluxing for 24 hours at 80° C. Insoluble matter in the reaction mixture was removed by filtration followed by concentration of the filtrate. The filtrate was then extracted with ethyl acetate. After washing the organic phase with brine, it was dried over magnesium sulfate. After distilling off the solvent under reduced pressure, the residue was used in the next reaction.

[Step 4]

The above residue (1.25 g) was dissolved in tetrahydrofuran followed by addition of aqueous 2N hydrochloric acid and stirring for 5 hours at room temperature. After neutralization of the reaction mixture, it was extracted with ethyl acetate. After washing the organic phase with brine, it was dried over magnesium sulfate. After distilling off the solvent under reduced pressure, the residue was purified by silica gel chromatography to obtain a colorless oil from the hexane-ether eluate in the form of a mixture of double bond regioisomers that are separated with difficulty of (1S,4aS,7aR)-7-ethyl-1-hydroxy-1,4a,5,7a-tetrahydrocyclopenta[c]pyrane-4-carboxylic acid methylester (major component) (882 mg, yield: 93%). The physicochemical properties of this compound are described below.

$^1$H-NMR (δ ppm, CDCl$_3$): 0.88–3.36 (10H,m), 3.73 (3H, s), 4.88 (1H,m), 5.55–5.62 (1H,m), 7.44–7.50 (1H,m)

[Step 5]

Colorless needles in the form of a mixture of double bond regioisomers of (1S,4aS,7aR)-7-ethyl-1-(methylcarbamoyloxy)-1,4a,5,7a-tetrahydrocyclopenta[c]pyrane-4-carboxylic acid methylester (major component) (1.09 g, yield: 98.5%) were obtained by performing the same procedure as Step 4 of Example 1 on 882 mg of the above (1S,4aS,7aR)-7-ethyl-1-hydroxy-1,4a,5,7a-tetrahydrocyclopenta[c]pyrane-4-carboxylic acid methylester. The physicochemical properties of this compound are described below.

$^1$H-NMR ($\delta$ ppm, in CDCl$_3$): 0.88–3.28 (9H,m), 2.84 (3H,d,J=5 Hz), 3.73 (3H,s), 4.88 (1H,br s), 5.52 (1H,br s), 5.76–5.89 (1H,m), 7.40–7.47 (1H,m)

[Step 6]

Colorless needles in the form of (1S,4aS,6S,7R,7aR)-6,7-epoxy-7-ethyl-1,4a,5,6,7,7a-hexahydro-1-hexahydro-1-(methylcarbamoyloxy)cyclopenta[c]pyrane-4-carboxylic acid methylester (432 mg, yield: 37.5%) were obtained by performing the same procedure as Step 5 of Example 1 on 1.09 g of the above (1S,4aS,7aR)-7-ethyl-1-(methylcarbamoyloxy)-1,4a,5,7a-tetrahydrocyclopenta[c]pyrane-4-carboxylic acid methylester. The physicochemical properties of this compound are described in Table 9, Compound No. 43.

Example 16

1.55 g of (1S,4aS,7aR)-1-[1-(ethoxy)ethoxy]-7-formyl-1,4a,5,7a-tetrahydrocyclopenta[c]pyrane-4-carboxylic acid methylester were dissolved in anhydrous tetrahydrofuran followed by dropping 20 ml of magnesium pentylbromide (0.3 M tetrahydrofuran solution) while stirring and cooling at −78° C., and then stirring for 4 hours at the same temperature. After addition of saturated aqueous ammonium chloride solution to the reaction mixture, it was extracted with ethyl acetate. After washing the organic phase with brine, it was dried over magnesium sulfate. After distilling off the solvent under reduced pressure, the residue was purified by silica gel chromatography to obtain a colorless oil from the hexane-ether eluate in the form of (1S,4aS,7aR)-1-[1-(ethoxy)ethoxy]-7-formyl-1,4a,5,7a-tetrahydrocyclopenta[c]pyrane-4-carboxylic acid methylester (1.46 g, yield: 76%). The physicochemical properties of this compound are described below.

$^1$H-NMR ($\delta$ ppm, in CDCl$_3$): 0.84–0.96 (3H,m), 1.12–1.48 (14H,m), 2.00–3.26 (4H,m), 3.44–3.92 (2H,m), 3.73 (3H,s), 4.74 (1H,d,J=8 Hz), 4.92 (1H,q,J=5 Hz), 5.94 (1H,br s), 7.51 (1H,s)

Continuing, (1R,4aS,6S,7R,7aR)-6,7-epoxy-7-n-hexyl-1,4a,5,6,7,7a-hexahydro-1-(methylcarbamoyloxy)cyclopenta[c]pyrane-4-carboxylic acid methylester was produced by following the same procedure as steps 2 through 6 for producing (1S,4aS,6S,7R,7aR)-6,7-epoxy-7-ethyl-1,4a,5,6,7,7a-hexahydro-1-(methylcarbamoyloxy)cyclopenta[c]pyrane-4-carboxylic acid methylester in Example 14 using the above (1S,4aS,7aR)-1-[1-(ethoxy)ethoxy]-7-(2-hydroxy)-n-hexyl]-1,4a,5,7a-tetrahydrocyclopenta[c]pyrane-4-carboxylic acid methylester. The physicochemical properties of this compound are described in Table 9, Compound No. 44.

Example 17

30.0 g of a known (4aS,7aR)-7-(tert-butyldimethylsilyloxymethyl)-1-hydroxy-1,4a,5,7a-tetrahydrocyclopenta[c]pyrane-4-carboxylic acid methylester were converted to colorless crystals in the form of (1S,4aS,7aR)-7-(tert-butyldimethylsilyloxymethyl)-1-(methylcarbamoyloxy)-1,4a,5,7a-tetrahydrocyclopenta[c]pyrane-4-carboxylic acid methylester (31.6 g, yield: 90.2%) by performing the same procedure as step 4 of Example 1. The physicochemical properties of this compound are described below.

$^1$H-NMR ($\delta$ ppm, in CDCl$_3$): 0.07 (6H,s), 0.91 (9H,s), 2.10–3.32 (4H,m), 2.84 (3H,d,J=5 Hz), 3.72 (3H,s), 4.22 (2H,br s), 4.84 (1H,br), 5.78 (1H,br s), 5.88 (1H,d,J=7 Hz), 7.45 (1H,s)

28.5 g of the above (1S,4aS,7aR)-7-(tert-butyldiemthylsilyloxymethyl)-1-(methylcarbamoyloxy)-1,4a,5,7a-tetrahydrocyclopenta[c]pyrane-4-carboxylic acid methylester were dissolved in tetrahydrofuran followed by addition of 35 g of benzoic acid. Next, 143 ml of tetra-n-butylammonium fluoride (1.0 M, tetrahydrofuran solution) were dropped in followed by stirring for 24 hours at room temperature. The reaction mixture was then extracted with ethyl acetate. After washing the organic phase with saturated aqueous sodium bicarbonate and brine, it was dried over magnesium sulfate. After distilling off the solvent under reduced pressure, the residue was purified by silica gel chromatography to obtain a colorless powder from the hexane-ether eluate in the form of (1S,4aS,7aR)-7-(hydroxymethyl)-1-(methylcarbamoyloxy)-1,4a,5,7a-tetrahydrocyclopenta[c]pyrane-4-carboxylic acid methylester (20.0 g, yield: 98.4%). The physicochemical properties of this compound are described in Table 66, Compound No. I-315.

85 mg of vanadium oxyacetylacetonate were dissolved in dichloromethane followed by dropping 7.1 ml of t-butylhydroperoxide (3.0 M, 2,2,4-trimethylpentane solution) and stirring for 20 minutes. Next, a dichloromethan solution of 3.0 g of (1S,4aS,7aR)-7-(hydroxymethyl)-1-(methylcarbamoyloxy)-1,4a,5,7a-tetrahydrocyclopenta[c]pyrane-4-carboxylic acid methylester was dropped thereinto followed by stirring for 17 hours at room temperature. The reaction mixture was poured into saturated aqueous sodium thiosulfate solution and extracted with ethyl acetate. After washing the organic phase with brine, it was dried over magnesium sulfate. After distilling off the solvent under reduced pressure, the residue was purified by silica gel chromatography to obtain colorless needles from the hexane-ether eluate in the form of (1S,4aS,6S,7R,7aR)-6,7-epoxy-7-(hydroxymethyl)-1-(methylcarbamoyloxy)-1,4a,5,6,7,7a-hexahydrocyclopenta[c]pyrane-4-carboxylic acid methylester (2.9 g, yield: 89%). The physicochemical properties of this compound are described in Table 9, Compound No. 45.

Example 18

500 mg of the (1S,4aS,6S,7R,7aR)-6,7-epoxy-7-(hydroxymethyl)-1-(methylcarbamoyloxy)-1,4a,5,6,7,7a-hexahydrocyclopenta[c]pyrane-4-carboxylic acid methylester were dissolved in dichloromethane followed by addition of 0.4 ml of pyridine and 50 mg of DMAP. Next, 0.32 ml of acetic anhydride were dropped in followed by stirring for 4 hours at room temperature. The reaction mixture was then extracted with ethyl acetate. After washing the organic phase with 2N aqueous hydrochloric acid, saturated aqueous sodium bicarbonate and brine, it was dried over magnesium sulfate. After distilling off the solvent under reduced pressure, the residue was purified by silica gel chromatography to obtain a colorless foamy substance from the hexane-ether eluate in the form of (1S,4aS,6S,7R,7aR)-7-

(acetoxymethyl)-6,7-epoxy-1-(methylcarbamoyloxy-1,4a,5,6,7,7a-hexahydro[c]pyrane-4-carboxylic acid methylester (465 mg, yield: 82%). The physicochemical properties of this compound are described in Table 10, Compound No. 46.

500 mg of (1S,4aS,6S,7R,7aR)-6,7-epoxy-7-(hydroxymethyl)-1-(methylcarbamoyloxy)-1,4a,5,6,7,7a-hexahydrocyclopenta[c]pyrane-4-carboxylic acid methylester were converted to a colorless foamy substance in the form of (1S,4aS,6S,7R,7aR)-6,7-epoxy-7-(methoxycarbonyloxymethyl)-1-(methylcarbamoyloxy)-1,4a,5,6,7,7a-hexahydrocyclopenta[c]pyrane-4-carboxylic acid methylester (415 mg, yield: 70%) by treating using methylchlorocarbonic acid in the same manner as above. The physicochemical properties of this compound are described in Table 10, Compound No. 47.

500 mg of the above (1S,4aS,6S,7R,7aR)-6,7-epoxy-7-(hydroxymethyl)-1-(methylcarbamoyloxy)-1,4a,5,6,7,7a-hexahydrocyclopenta[c]pyrane-4-carboxylic acid methylester were converted to colorless needles in the form of (1S,4aS,6S,7R,7aR)-6,7-epoxy-1-(methylcarbamoyloxy)-7-(methylcarbamoyloxymethyl)-1,4a,5,6,7,7a-hexahydrocyclopenta[c]pyrane-4-carboxylic acid methylester (547 mg, yield: 91%) by treating according to the same method as Step 4 of Example 1. The physicochemical properties of this compound are described in Table 10, Compound No. 48.

1.12 g of a known (4aS,7aR)-7-(methoxymethyl)-1-hydroxy-1,4a,5,6,7,7a-hexahydro[c]pyrane-4-carboxylic acid methylester were converted to a colorless powder in the form of (1A,4aS,7aR)-7-methoxymethyl)-1-(methylcarbamoyloxy)-1,4a,5,7a-tetrahydrocyclopenta[c]pyrane-4-carboxylic acid methylester (1.3 g, yield: 93.8%) by performing the same procedure as Step 4 of Example 1. The physicochemical properties of this compound are described below.

$^1$H-NMR (δ ppm, in CDCl$_3$): 1.88–3.28 (4H,m), 2.84 (3H,d,J=5 Hz), 3.32 (3H,s), 3.73 (3H,s), 3.98 (2H, br s), 4.98 (1H,br), 5.85 (1H,br s), 5.90 (1H,d,J=7 Hz), 7.46 (1H,d,J= 1Hz).

The above (1S,4aS,7aR)-7-(methoxymethyl)-1-(methylcarbamoyloxy)-1,4a,5,7a-tetrahydrocyclopenta[c]pyrane-4-carboxylic acid methylester (1.50 g) was converted to a colorless power in the form of (1S,4aS,6S,7R,7aR)-6,7-epoxy-7-(methoxymethyl)-1-(methylcarbamoyloxy)-1,4a,5,6,7,7a-hexahydrocyclopenta[c]pyrane-4-carboxylic acid methylester (630 mg, yield: 40%) by treating in the same manner as Step 4 of Example 1. The physicochemical properties of this compound are described in Table 10, Compound No. 49.

Example 20

100 mg of a known (1S,4aS,7aR)-1-[1-(ethoxy)ethoxy]-7-(hydroxymethyl)-1,4a,5,7a-tetrahydrocyclopenta[c]pyrane-4-carboxylic acid methylester were dissolved in tetrahydrofuran followed by addition of molecular sieve 4A (powder, 500 mg), 0.67 ml of tetra-n-butylammonium fluoride (1.0 M, tetrahydrofuran solution) and 88 mg of p-toluenesulfonylfluoride and by stirring for 24 hours at room temperature. After filtering out the insoluble matter, the filtrate was extracted with ethyl acetate. After washing the organic phase with brine, it was dried over magnesium sulfate. After distilling off the solvent under reduced pressure, the residue was purified by silica gel chromatography to convert to a pale yellow oil from the hexane-ether eluate in the form of (1S,4aS,7aR)-1-[1-(ethoxy)ethoxy]-7-(fluoromethyl)-1,4s,5,7a-tetrahydrocyclopenta[c]pyrane-4-carboxylic acid methylester (61 mg, yield: 61%). the physicochemical properties of this compound are described below.

$^1$H-NMR (δ ppm, in CDCl$_3$): 1.08–1.44 (6H,m), 2.04–3.32 (4H, m), 3.40–3.92 (2H,m), 3.73 (3H,s), 4.82–5.20 (4H,m), 5.99 (1H,br s), 7.49 (0.5H,d,J=1Hz), 7.51 (0.5H,d,J=1 Hz).

670 mg of the above (1S,4aS,7aR)-1-[1-(ethoxy)ethoxy]-7-(fluoromethyl)-1,4a,5,7a-tetrahydrocyclopenta[c]pyrane-4-carboxylic acid methylester were dissolved in tetrahydrofuran followed by addition of 2N aqueous hydrochloric acid and stirring for 2 hours at room temperature. The reaction mixture was neutralized after adding water, and then extracted with ethyl acetate. After washing the organic phase with brine, it was dried over magnesium sulfate. After distilling off the solvent under reduced pressure, the residue was purified by silica gel chromatography to obtain a pale yellow oil from the hexane-ether eluate in the form of (4aS,7aR)-7-(fluoromethyl)-1-hydroxy-1,4a,5,7a-tetrahydrocyclopenta[c]pyrane-4-carboxylic acid methylester (500 mg, yield: 98%). The physicochemical properties of this compound are described below.

$^1$H-NMR (δ ppm, in CDCl$_3$): 1.98–3.56 (5H,m), 3.74 (3H,s), 4.80–4.92 (1H,m), 4.96 (1H,br s), 5.20 (1H,br s), 5.99 (1H, br s), 7.52 (1H,d,J=1 Hz).

562 mg of the above (4aS,7aR)-7-(fluoromethyl)-1-hydroxy-1,4a,5,7a-tetrahydrocyclopenta[c]pyrane-4-carboxylic acid methylester were converted to a colorless powder in the form of (1S,4aS,7aR)-7-(fluoromethyl)-1-(methylcarbamoyloxy)- 1,4a,5,7a-tetrahydrocyclopenta[c]pyrane-4-carboxylic acid methylester (665 mg, yield: 95%) by performing the same treatment as Step 4 of Example 1. The physicochemical properties of this compound are described in Table 66, Compound No. I-314.

660 mg of the above (1S,4aS,7aR)-7-(fluoromethyl)-1-(methylcarbamoyloxy)-1,4a,5,7a-tetrahydrocyclopenta[c] pyrane-4-carboxylic acid methylester were converted to a colorless powder in the form of (1S,4aS,6S,7R,7aR)-6,7-epoxy-7-(fluoromethyl)-1-(methylcarbamoyloxy)-1,4a,5,6,7,7a-hexahydrocyclopenta[c]pyrane-4-carboxylic acid methylester (306 mg, yield: 44%) by performing the same treatment as Step 5 of Example 1. The physicochemical properties of this compound are described in Table 10, Compound No. 50.

Example 21

2.0 g of (1S,4aS,6S,4R,7aR)-6,7-epoxy-7-(hydroxymethyl)-1-(methylcarbamoyloxy)-1,4a,5,6,7,7a-hexahydrocyclopenta[c]pyrane-4-carboxylic acid methylester described in Example 19 were dissolved in dichloromethane followed by addition of 2.5 ml of triethylamine and 1.4 ml of methanesulfonylchloride while stirring and cooling with ice. After stirring for 12 hours at the same temperature, the reaction mixture was extracted with ethyl acetate. After washing the organic phase with saturated aqueous sodium bicarbonate and brine, it was dried over magnesium sulfate. After distilling off the solvent under reduced pressure, the residue was purified by silica gel chromatography to obtain a pale yellow oil from the hexane-ether eluate in the form of (1S,4aS,7aR)-4-(chloromethyl)-1-(methylcarbamoyloxy)-1,4a,5,7a-tetrahydrocyclopenta[c] pyrane-4-carboxylic acid methylester (770 mg, yield: 24%). The physicochemical properties of this compound are described below.

$^1$H-NMR (δ ppm, in CDCl$_3$): 2.12–2.24 (1H,m), 2.85 (3H,d,J=5 Hz), 2.92–3.06 (2H,m), 3.22–3.38 (1H,m), 3.37

47

(3H,s), 4.94 (1H, br), 5.06–5.28 (2H,m), 5.84 (1H,d,J=7 Hz), 5.99 (1H, br s), 7.46 (1H,d,J=1Hz).

770 mg of (1S,4aS,7aR)-7-(chloromethyl)-1-(methylcarbamoyloxy)-1,4a,5,7a-tetrahydrocyclopenta[c]pyrane-4-carboxylic acid methylester were converted to a colorless powder in the form of (1S,4aS,6S,7R,7aR)-6,7-epoxy-7-(chloromethyl)-1-(methylcarbamoyloxy)-1,4a,5,6,7,7a-hexahydrocyclopenta[c]pyrane-4-carboxylic acid methylester (86 mg, yield: 11%) by treating in the same manner as Step 5 of Example 1. The physicochemical properties of this compound are described in Table 11, Compound No. 51.

Example 22

2.0 g of (1S,4aS,6S,7R,7aR)-6,7-epoxy-7-(hydroxymethyl)-1-(methylcarbamoyloxy)-1,4a,5,6,7,7a-hexahydrocyclopenta[c]pyrane-4-carboxylic acid methylester described in Example 19 were dissolved in dichloromethane followed by addition of 5.7 ml of pyridine and dropping 1.4 ml of methanesulfonylchloride with stirring and cooling in an ice bath. After stirring for 12 hours at the same temperature, the reaction mixture was extracted with ethyl acetate. The organic phase was washed with 2N aqueous hydrochloric acid, saturated aqueous sodium bicarbonate and brine, and dried over magnesium sulfate. After distilling off the solvent under reduced pressure, the residue was dissolved in a 1:1 mixture of tetrahydrofuran and isopropanol followed by addition of 400 mg of cobaltacetylacetonate and 1.3 ml of phenylsilane and stirring for 48 hours at room temperature under an oxygen gas atmosphere at 1 atm. After concentrating the reaction mixture, it was extracted with ethyl acetate. After washing the organic phase with saturated aqueous sodium bicarbonate and brine, it was dried over magnesium sulfate. After distilling off the solvent under reduced pressure, the resulting residue was dissolved in methanol followed by addition of 200 mg of potassium carbonate and stirring for 2 hours at room temperature. After addition of saturated aqueous ammonium chloride solution, the reaction mixture was extracted with ethyl acetate. After washing the organic phase with brine, it was dried over magnesium sulfate. After distilling off the solvent under reduced pressure, the residue was purified by silica gel chromatography to obtain a colorless powder from the hexane-ether eluate in the form of (1S,4aS,7R,7aR)-1-(methylcarbamoyloxy)-1,4a,5,6,7,7a-hexahydrospiro[cyclopenta[c]pyrane -7(1H),2'-oxirane]-4-carboxylic acid methylester (250 mg, yield: 25.0%), along with a colorless powder in the form of (1S,4aS,7S,7aR)-1-(methylcarbamoyloxy)-1,4a,5,6,7,7a-hexahydrospiro[cyclopenta[c]pyrane-7(1H,),2'-oxirane]-4-carboxylic acid methylester (90 mg, yield: 9.0%). The physicochemical properties of the former compound are described in Table 11, Compound No. 52, while those of the latter compound are described in Table 9, Compound No. 53.

Example 23

2.0 g of a known (4aS,7aR)-1-hydroxy-7-methylene-1,4a,5,6,7a-pentahydrocyclopenta[c]pyrane-4-carboxylic acid methylester were dissolved in acetonitrile followed by addition of 1.6 ml of triethylamine, addition of 0.67 ml of methylisocyanate and stirring for 2 hours at room temperature. After adding 1 ml of methanol to the reaction mixture and stirring for 30 minutes, the reaction mixture was concentrated. The residue was dissolved in methanol followed by addition of 1.22 g of cerium chloride (7 hydrate) and stirring at 0° C. 180 mg of sodium borohydride were added followed by stirring for 2 hours at the same temperature. After addition of saturated ammonium chloride solution to the reaction mixture, it was extracted with ethyl acetate. After washing the organic phase with brine, it was dried over magnesium sulfate. After distilling off the solvent under reduced pressure, the residue was purified by silica gel chromatography to obtain a colorless oil from the hexane-ether eluate in the form of 2-[(1S)-2-(hydroxymethyl)-3-methyl-2-cyclopentenyl]-3-[(methylcarbamoyl)oxy]methylacrylate (440 mg, yield: 16.3%). The physicochemical properties of this compound are shown below.

$^1$H-NMR (δ ppm, in CDCl$_3$): 1.74 (3H, br s), 1.80–2.96 (6H,m), 2.87 (3H,d,J=5 Hz), 3.73 (3H,s), 3.82–4.20 (2H,m), 5.29 (4H,br), 8.20 (1H,s).

3mg of vanadylacetylacetonate were dissolved in dichloromethane followed by dropping 0.25 ml of t-butylhydroperoxide (3.0 M, 2,2,4-trimethylpentane solution) and stirring for 20 minutes. Next, a dichloromethane solution containing 100 mg of 2-[(1S)-2-(hydroxymethyl)-3-methyl-2-cyclopentenyl]-3-[(methylcarbamoyl)oxy]methylacrylate was added dropwise in followed by stirring for 4 hours at room temperature. The reaction mixture was poured into saturated aqueous sodium thiosulfate solution and extracted with ethyl acetate. After washing the organic phase with brine, it was dried over magnesium sulfate. After distilling off the solvent under reduced pressure, the residue was purified by silica gel chromatography to obtain an amorphous powder from the hexane-ether eluate in the form of 2-[(1S,2R,3S)-2,3-epoxy-2-(hydroxymethyl)-3-methyl-2-cyclopentyl]-3-[(methylcarbamoyl)oxy]methylacrylate (39 mg, yield: 37%). The physicochemical properties of this compound are described in Table 11, Compound No. 54.

Example 24

500 mg of (1S,4aS,6S,7R,7aR)-6,7-epoxy-1,4a,5,6,7,7a-hexahydro-7-methyl-1-(methylcarbamoyloxy)cyclopenta[c]pyrane-4-carboxylic acid methylester descried in Example 3 were dissolved in methanol followed by the suspension of 50 mg of 20% palladium-carbon hydroxide catalyst and stirring for 12 hours under hydrogen gas atmosphere at 1 atm. After filtering out the insoluble matter, the filtrate was concentrated. The residue was purified by silica gel chromatography to obtain a colorless powder from the hexane-ether eluate in the form of (1S,4R,4aS,6S,4R,7aR)-6,7-epoxy-7-methyl-1-(methylcarbamoyloxy)-1,3,4,4a,5,6,7,7a-octahydrocyclopenta[c]pyrane-4-carboxylic acid methylester (375 mg, yield: 74%), and a colorless powder in the form of (1S,4S,4aS,6S,7R, 7aR)-6,7-epoxy-7-methyl-1-(methylcarbamoyloxy)-1,3,4,4a,5,6,7,7a-octahydrocyclopenta[c]pyrane-4-carboxylic acid methylester (68 mg, yield: 14%). The physicochemical properties of the former compound are described in Table 11, Compound No. 55, while those of the latter compound are described in Table 12, Compound No. 56.

Example 25

1.35 g of (1S,4aS,6R,7S,7aR)-6,7-epoxy-7-methyl-1-(methylcarbamoyloxy)-1,4a,5,7a-tetrahydrocyclopenta[c]pyrane-4-carboxylic acid benzylester described in Step 5 of Example 1 were dissolved in ethyl acetate followed by suspension of 60 mg of 5% palladium-carbon catalyst and stirring for 24 hours under hydrogen gas atmosphere at 1 atm. After filtering out the insoluble matter, the filtrate was concentrated. The residue was dissolved in methanol-ether followed by dropwise addition of 3.0 ml of trimethylsilyl-diazomethane (2.0 M, hexane solution) and stirring for 30 minutes at room temperature. The reaction mixture was then extracted with ethyl acetate. After washing the organic phase with brine, it was dried over magnesium sulfate. After distilling off the solvent under reduced pressure, the residue was purified by silica gel chromatography to obtain a colorless powder from the hexane-ether eluate in the form of (1S,4aS,6R,7S,7aR)-6,7-epoxy-7-methyl-1-(methylcarbamoyloxy-1,4a,5,6,7,7a-hexahydrocyclopenta[c]pyrane-4-carboxylic acid methylester (720 mg, yield: 68%). The physicochemical properties of this compound are described in Table 12, Compound No. 57.

Example 26

200 mg of a known 2-[(1S,2R,3R)-2-(hydroxymethyl)-3-methylcyclopento-1-yl]-propene-1-ole were converted to a colorless oil in the form of 2-[(1S,2R,3R)-2-(hydroxymethyl)-3-methylcyclopento-1-yl]-2,3-epoxy-propane-1-ole (180 mg, yield: 79%) according to the same method as in Step 54 of Example 1. The physicochemical properties of this compound are described below.

$^1$H-NMR (δ ppm, in CDCl$_3$): 0.98 (3H,d,J=7 Hz), 1.24–1.80 (2H, m), 2.01–2.54 (5H,m), 2.77–2.80 (1H,m), 3.47–4.13 (6H,m).

80 mg of the above 2-[(1S,2R,3R)-2-(hydroxymethyl)-3-methylcyclopento-1-yl]-2,3-epoxy-propane-1-ole were converted to a colorless powder in the form of 2-[(1S,2R,3R)-2-(methylcarbamoyloxy)methyl-3-methylcyclopento-1-yl]-2,3-epoxy-propane-1-methylcarbamate (110 mg, yield: 85.3%) by performing the same procedure as in Step 4 of Example 1. The physicochemical properties of this compound are described in Table 12, Compound No. 58.

Example 27

100 mg of a known 2-[(1S,2R,3S)-2-(hydroxymethyl)-3-methylcyclopento-1-yl]-2,3-epoxy-propane-1ole were converted to a colorless powder in the form of 2-[(1S,2R,3S)-2-(methylcarbamoyloxy)methyl-3-methylcyclopento-1-yl]-2,3-epoxy-propane-1-methylcarbamate (100 mg, yield: 62%) according to the same method as Step 4 of Example 1. The physicochemical properties of this compound are described in Table 12, Compound No. 59.

Example 28

A known (4aS,6S,7R,7aR)-6,7-epoxy-1-hydroxy-7-hydroxymethyl-1,4a,5,6,7a-pentahydro[c]pyrane-4-carboxylic acid methylester (50 mg) was dissolved in 2 ml of dichloromethane followed by addition of 85 μl of pyridine and 60 μl of methylisocyanate and stirring for 18 hours at room temperature. The reaction mixture was then extracted with ethyl acetate. After washing the organic phase with 2 N aqueous hydrochloric acid, saturated aqueous sodium bicarbonate and brine, it was dried over magnesium sulfate. After distilling off the solvent under reduced pressure, the residue was purified by silica gel chromatography to obtain a product from the hexane-ether eluate in the form of (4aS,6S,7R,7aR)-6,7-epoxy-1-hydroxy-7-methylcarbamoyloxymethyl-1,4a,5,6,7a-pentahydro[c]pyrane-4-carboxylic acid methylester. Moreover, colorless needles (20 mg, yield: 32%) were obtained by recrystallizing from hexane-ethyl acetate. The physicochemical properties of this compound are described in Table 12, Compound No. 60.

TABLE 1

| Compound No. | Structural Formulas | $^1$H-NMR (δ ppm in CDCl$_3$) | MS |
|---|---|---|---|
| 1 | (structure with CO$_2$H) | 1.43(3H, s), 1.40–1.50(1H, m), 2.34(1H, m), 2.89(3H, d, J=5Hz), 2.60–2.90(2H, m), 3.29(1H, s), 4.90(1H, br), 5.76(1H, d, J=12Hz), 7.49(1H, s), 8.30(1H, br) | +FAB270.1 (M$^+$ + 1), −FAB268.1 (M$^+$ − 1) |
| 2 | (structure with CO$_2$Na) | $^1$H-NMR (δ ppm in CD$_3$OD) 1.29(3H, s), 1.24–1.39(1H, m), 2.12(1H, dd, J−7, 10Hz), 2.50(1H, dd, J=8, 14Hz), 2.61–2.76(4H, m), 3.20(1H, s), 5.55(1H, d, J=10Hz), 7.13(1H, s) | +FAB292.1 (M$^+$ + 1), −FAB290.1 (M$^+$ − 1) |

TABLE 1-continued

| Compound No. | Structural Formulas | ¹H-NMR (δ ppm in CDCl₃) | MS |
|---|---|---|---|
| 3 | | 1.43(3H, s), 1.38–1.51(1H, m), 2.31(1H, dd, J=7, 10Hz), 2.64(1H, dd, J=7, 14Hz), 2.89(3H, d, J=5Hz), 2.77–2.90(1H, m), 3.29(1H, s), 3.71(1H, s), 5.04(1H, br), 5.74(1H, d, J=10Hz), 7.40(1H, d, J=1Hz) | 283(M⁺), 252, 226, 208, 197, 165 |
| 4 | | 1.27(3H, t, J=7Hz), 1.43(3H, s), 1.40–1.52(1H, m), 2.31(1H, dd, J=7, 10Hz), 2.64(1H, dd, J=7, 14Hz), 2.89(3H, d, J=5Hz), 2.78–2.94(1H, m), 3.29(1H, s), 4.17(2H, q, J=7Hz), 5.00(1H, br), 5.74(1H, d, J=10Hz), 7.40(1H, d, J=1Hz) | 297(M⁺), 252, 240, 222, 211, 193, 171 |
| 5 | | 0.89(3H, t, J=6Hz), 1.43(3H, s), 1.24–1.76(9H, m), 2.07(1H, dd, J=7, 10Hz), 2.64(1H, dd, J=7, 14Hz), 2.89(3H, d, J=5Hz), 2.76–2.96(1H, m), 3.29(1H, s), 4.07–4.14(2H, m), 5.02(1H, br), 5.73(1H, d, J=10Hz), 7.32(1H, s) | 353(M⁺), 296, 267, 249, 236, 222, 209, 165 |

TABLE 2

| Compound No. | Structural Formulas | ¹H-NMR (δ ppm in CDCl₃) | MS |
|---|---|---|---|
| 6 | | 1.43(3H, s), 1.34–1.56(1H, m), 1.60(3H, s), 1.68(3H, s), 1.70(3H, s), 1.96–2.20(4H, m), 2.30(1H, dd, J=7, 10Hz), 2.64(1H, dd, J=8, 14Hz), 2.88(3H, d, J=5Hz), 2.76–2.92(1H, m), 3.28(1H, s), 4.58–4.68(2H, m), 4.92–5.12(2H, m), 5.30–5.37(1H, m), 5.73(1H, d, J=10Hz). | 405(M⁺), 336, 279, 252, 212, 195, 178, 136, 121, 93 |

TABLE 2-continued

| Compound No. | Structural Formulas | $^1$H-NMR ($\delta$ ppm in CDCl$_3$) | MS |
| --- | --- | --- | --- |
| 7 | | 1.43(3H, s), 1.36–1.52(1H, m), 1.76(2H, m), 2.11(2H, m), 2.30(1H, m), 2.61(1H, m), 2.87(3H, d, J=5Hz), 2.74–2.94(1H, m), 3.30(1H, s), 4.13(2H, m), 4.95–5.10(2H, m), 5.52(1H, br), 5.74(1H, d, J=10Hz), 5.84–5.92(1H, m), 7.40(1H, s) | 337(M$^+$), 280, 262, 251, 233, 212, 193, 165 |
| 8 | | 1.43(3H, s), 1.40–1.54(1H, m), 2.26–2.48(3H, m), 2.63(1H, dd, J=8,14Hz), 2.87(3H, d, J=5Hz), 2.74–2.94(1H, m), 3.29(1H, m), 4.08–4.28(2H, m), 5.06–5.18(2H, m), 5.38(1H, br), 5.73(1H, d, J=10Hz), 5.68–5.90(1H, m), 7.40(1H, d, J=1Hz) | 323(M$^+$), 266, 237, 219, 195, 165 |
| 9 | | 1.43(3H, s), 1.40–1.54(1H, m), 2.31(1H, dd, J=7, 10Hz), 2.65(1H, dd, J=8, 14Hz), 2.88(3H, d, J=5Hz), 2.76–2.94(1H, m), 3.29(1H, s), 4.60–4.64(2H, m), 5.10(1H, br), 5.18–5.36(2H, m), 5.75(1H, d, J=10Hz), 5.82–6.04(1H, m), 7.44(1H, d, J=1Hz) | 309(M$^+$), 279, 252, 223, 205, 193, 165 |
| 10 | | 1.42(3H, s), 1.38–1.50(1H, m), 2.29(1H, dd, J=4, 10Hz), 2.62(1H, dd, J=7, 14Hz), 2.87(3H, d, J=5Hz), 2.74–2.92(1H, m), 3.27(1H, s), 4.98–5.11(3H, m), 5.73(1H, d, J=10Hz), 6.33–6.40(2H, m), 7.40–7.42(2H, m) | 349(M$^+$), 310, 274, 253, 228, 193, 178 |

TABLE 3

| Compound No. | Structural Formulas | ¹H-NMR (δ ppm in CDCl₃) | MS |
| --- | --- | --- | --- |
| 11 | | 1.42(3H, s), 1.40–1.54(1H, m), 2.31(1H, dd, J=7, 10Hz), 2.63(1H, dd, J=8, 14Hz), 2.87(3H, d, J=5Hz), 2.80–2.98(1H, m), 3.28(1H, s), 5.04–5.10(1H, br), 5.16–5.26(2H, m), 5.74(1H, d, J=10Hz), 7.32–7.42(5H, m), 7.45(1H, s) 12Hz), 7.49(1H, s), 8.30(1H, br) | 359(M⁺), 302, 273, 253, 211, 193, 165, 151 |
| 12 | | 1.41(3H, s), 1.36–1.50(1H, m) 2.27(1H, dd, J=7, 10Hz), 2.51(1H, dd, J=8, 14Hz), 2.85(3H, d, J=5Hz), 2.64–3.02(1H, m), 3.25(1H, s), 3.84(2H, m), 4.32(2H, m), 5.18(1H, br), 5.71(1H, d, J=10Hz), 7.12–7.38(6H, m) | 298(M⁺-MeNHCOO) 269, 256, 229 |
| 13 | | 1.45(3H, s), 1.44–1.62(1H, m), 2.38(1H, dd, J=7, 10Hz), 2.73(1H, dd, J=8, 14Hz), 2.87(3H, d, J=5Hz), 2.80–3.04(1H, m), 3.32(1H, s), 5.12(1H, br), 5.82(1H, d, J=10Hz), 7.04–7.42(5H, m), 7.64(1H, s) | 345(M⁺), 270, 252, 241, 225, 195 |
| 14 | | 1.10–1.60(7H, m), 1.43(3H, s), 1.60–1.94(4H, m), 2.31(1H, dd, J=7, 10Hz), 2.64(1H, dd, J=8, 14Hz), 2.88(3H, d, J=5Hz), 2.72–2.90(1H, m), 3.29(1H, s), 4.83(1H, m), 5.08(1H, br), 5.73(1H, d, J=10Hz), 7.40(1H, d, J=1Hz) | 351(M⁺), 294, 264, 247, 230, 195, 165, 183, 165 |
| 15 | | 1.35(3H, s), 1.40–1.54(1H, m), 2.19(1H, dd, J=7, 10Hz), 2.47(1H, dd, J=8, 14Hz), 2.70(3H, d, J=3Hz), 2.79(3H, d, J=5Hz), 2.60–2.90(1H, m), 3.29(1H, s), 5.67(1H, d, J=10Hz), 6.70(1H, br), 6.90(1H, br), 7.12(1H, d, J=1Hz) | 282(M⁺), 252, 225, 212, 196, 176, 165, 151, 138, 127 |

TABLE 4

| Compound No. | Structural Formulas | $^1$H-NMR (δ ppm in CDCl$_3$) | MS |
| --- | --- | --- | --- |
| 16 | | 1.15(1H, t, J=7Hz), 1.44(3H, s), 1.44–1.60(1H, m), 2.34(1H, dd, J=7, 10Hz), 2.51(1H, dd, J=8, 14Hz), 3.26–3.42(3H, m), 5.02(1H, br), 5.46(1H, br), 5.71(1H, d, J=10Hz), 7.16(1H, s) | 296(M$^+$), 281, 252, 239, 226, 192, 165 |
| 17 | | 0.88(3H, t, J=7Hz), 1.20–1.40(8H, m), 1.44(3H, s), 1.40–1.60(1H, m), 2.34(1H, dd, J=8, 10Hz), 2.49(1H, dd, J=8, 14Hz), 2.88(3H, d, J=5Hz), 2.76–2.92(1H, m), 3.22–3.40(3H, m), 4.99(1H, br), 5.45(1H, br), 5.71(1H, d, J=10Hz), 7.16(1H, s) | 352(M$^+$), 295, 277, 266, 248, 225, 208, 197 |
| 18 | | 1.43(3H, s), 1.40–1.57(1H, m), 2.35–2.46(2H, m), 2.88(3H, d, J=5Hz), 3.01(6H, s), 2.90–3.08(1H, m), 3.27(1H, s), 5.02(1H, br), 57.4(1H, d, J=10Hz), 6.52(1H, d, J=1Hz) | 296(M$^+$), 281, 252, 239, 222, 210, 195, 176, 165, 152, 141 |
| 19 | | 1.13(6H, t, J=7Hz), 1.43(3H, s), 1.48–1.60(1H, m), 2.31–2.42(2H, m), 2.88(3H, d, J=5Hz), 2.84–3.02(1H, m), 3.27(1H, s), 3.40(4H, q, J=7Hz), 4.98(1H, br), 5.73(1H, d, J=10Hz), 6.47(1H, d, J=2Hz) | 324(M$^+$), 295, 267, 250, 238, 220, 195, 169, 154 |

TABLE 4-continued

| Compound No. | Structural Formulas | ¹H-NMR (δ ppm in CDCl₃) | MS |
|---|---|---|---|
| 20 | | 1.43(3H, s), 1.40–1.56(1H, m), 2.30(3H, s), 2.24–2.50(6H, m), 2.89(3H, d, J=5Hz), 2.84–3.06(1H, m), 3.28(1H, s), 3.50–3.74(4H, m), 4.98(1H, br), 5.73(1H, d, J=10Hz), 6.49(1H, d, J=1Hz) | 351(M⁺), 336, 294, 277, 247, 206, 177, 149, 125 |

TABLE 5

| Compound No. | Structural Formulas | ¹H-NMR (δ ppm in CDCl₃) | MS |
|---|---|---|---|
| 21 | | 1.44(3H, s), 1.00–2.00(10H, m), 2.34(1H, dd, J=7, 10Hz), 2.48(1H, dd, J=8, 14Hz), 2.88(3H, d, J=5Hz), 2.80–2.92(1H, m), 3.30(H, s), 3.82(1H, m), 4.98(1H, br), 5.29(1H, br), 5.70(1H, d, J–10Hz), 7.14(1H, s) | 350(M⁺), 293, 275, 246, 223, 195 |
| 22 | | 1.43(3H, s), 1.43–1.55(1H, m), 1.98(1H, br), 2.30–2.64(8H, m), 2.88(3H, d, J=5Hz), 2.88–3.03(1H, m), 3.28(1H, s), 3.50–3.94(6H, m), 4.95(1H, br), 5.73(1H, d, J=10Hz), 6.50(1H, d, J=1Hz) | 381(M⁺), 350, 324, 307, 293, 275, 237, 195 |

TABLE 5-continued

| Compound No. | Structural Formulas | ¹H-NMR (δ ppm in CDCl₃) | MS |
| --- | --- | --- | --- |
| 23 | | 1.43(3H, s), 1.43–1.54(1H, m), 2.30–2.48(2H, m), 2.89(3H, d, J=5Hz), 2.88–3.04(1H, m), 3.28(1H, s), 3.44–3.76(8H, m), 4.96(1H, br), 5.73(1H, d, J=10Hz), 6.51(1H, d, J=1Hz) | 338(M⁺), 281, 264, 234, 195, 183, 148, 125 |
| 24 | | 1.19(6H, d, J=6Hz), 1.43(3H, s), 1.43–1.53(1H, m), 2.33–2.70(4H, m), 2.89(3H, d, J=5Hz), 2.89–3.04(1H, m), 3.28(1H, s), 3.36–3.62(2H, m), 4.01–4.23(2H, m), 5.00(1H, br), 5.75(1H, d, J=10Hz), 6.48(1H, d, J=1Hz) | 366(M⁺), 351, 323, 309, 292, 252, 211, 195, 176, 148, 115 |
| 25 | | 1.43(3H, s), 1.40–1.52(1H, m), 1.70–2.00(4H, m), 2.35(1H, dd, J=7, 10Hz), 2.41–2.52(1H, m), 2.89(3H, d, J=4Hz), 3.05(1H, m), 3.27(1H, s), 3.40–3.64(4H, m), 4.98(1H, br), 5.73(1H, d, J=10Hz), 6.67(1H, d, J=1Hz) | 322(M⁺), 265, 232, 207, 195, 178, 150, 134 |

TABLE 6

| Compound No. | Structural Formulas | $^1$H-NMR (δ ppm in CDCl$_3$) | MS |
|---|---|---|---|
| 26 | | 1.43(3H, s), 1.36–1.76(7H, m), 2.30–2.46(2H, m), 2.88(3H, d, J=5Hz), 2.86–3.02(1H, m), 3.27(1H, s), 3.40–3.64(4H, m), 5.18(1H, br), 5.73(1H, d, J=10Hz), 6.47(1H, d, J=2Hz) | 336(M$^+$), 279, 262, 250, 209, 193, 181, 166, 138, 112, 84 |
| 27 | | 1.43(3H, s), 1.43–1.60(1H, m), 2.33(1H, dd, J=7, 10Hz), 2.49(1H, dd, J=8, 14Hz), 2.87(3H, d, J=5Hz), 2.75–2.87(1H, m), 3.28(1H, s), 4.38–4.60(2H, m), 5.01(1H, br), 5.71(1H, d, J=10Hz), 5.78(1H, br), 7.21(1H, s), 7.25–7.42(5H, m) | 358(M$^+$), 301, 283, 254, 227, 203, 178, 165, 122, 106, 91 |
| 28 | | 1.41(3H, s), 1.34–1.47(1H, m), 2.22–2.36(2H, m), 2.68–2.87(3H, m), 2.88(3H, d, J=5Hz), 3.25(1H, s), 3.41–3.71(2H, m), 5.02(1H, br), 5.47(1H, br), 5.67(1H, d, J=10Hz), 7.07(1H, d, J=1Hz), 7.08–7.36(5H, m) | 372(M$^+$), 315, 297, 280, 268, 252, 224, 195, 177, 149, 125, 104 |
| 29 | | 1.46(3H, s), 1.38–1.50(1H, m), 2.34(1H, dd, J=7, 10Hz), 2.65(1H, dd, J=8, 14Hz), 2.78–2.91(1H, m), 3.31(1H, s), 3.72(3H, s), 5.15(2H, br), 5.72(1H, d, J=10Hz), 7.41(1H, m) | 269(M$^+$), 238, 197, 179, 165, 139 |

TABLE 6-continued

| Compound No. | Structural Formulas | $^1$H-NMR ($\delta$ ppm in CDCl$_3$) | MS |
| --- | --- | --- | --- |
| 30 | | 1.20(3H, t, J=7Hz), 1.43(3H, s), 1.39–1.45(1H, m), 2.31(1H, dd, J=7, 10Hz), 2.65(1H, dd, J=7, 14Hz), 2.77–2.90(1H, m), 3.22–3.36(3H, m), 3.71(3H, s), 4.98(1H, br), 5.74(1H, d, J=10Hz), 7.41(1H, d, J=1Hz) | 297(M$^+$), 266, 226, 208, 197, 179, 165 |

TABLE 7

| Compound No. | Structural Formulas | $^1$H-NMR ($\delta$ ppm in CDCl$_3$) | MS |
| --- | --- | --- | --- |
| 31 | | 1.44(3H, s), 1.39–1.51(1H, m), 2.77(1H, dd, J=7.10Hz), 2.63(1H, dd, J=8, 14Hz), 2.80–2.92(1H, m), 3.00(3H, s), 3.02(3H, s), 3.29(1H, s), 3.71(3H, s), 5.75(1H, d, J=10Hz), 7.40(1H, m) | 297(M$^+$), 266, 225 208, 193, 179, 148, 139 |
| 32 | | 1.44(3H, s), 1.38–1.51(1H, m), 2.33(1H, dd, J=7, 10Hz), 2.65(1H, dd, J=8, 14(Hz), 2.78–2.90(1H, m), 3.30(1H, s), 3.56–3.71(4H, m), 3.71(3H, s), 5.60(1H, br), 5.73(1H, d, J=10Hz), 7.40(1H, d, J=2Hz) | 331(M$^+$), 300, 238, 226, 208, 197, 179, 165 |
| 33 | | 0.89(3H, t, J=7Hz), 1.43(3H, s), 1.22–1.64(9H, m), 2.30(1H, dd, J=7, 10Hz), 2.64(1H, dd, J=8, 14Hz), 2.78–2.92(1H, m), 3.20–3.34(3H, m), 3.71(3H, s), 5.04(1H, br), 5.74(1H, d, J=10Hz), 7.40(1H, d, J=1Hz) | 353(M$^+$), 322, 290, 249, 226, 208, 197, 179, 165 |
| 34 | | 1.22(3H, d, J=7Hz), 1.23(3H, d, J=7Hz), 1.43(3H, s), 1.36–1.50(1H, m), 2.33(1H, dd, J=7, 10Hz), 2.64(1H, dd, J=8, 14Hz), 2.77–2.92(1H, m), 3.29(1H, s), 3.71(3H, s), 3.80–3.98(1H, m), 4.80(1H, br), 5.73(1H, d, J=10Hz), 7.40(1H, m) | 311(M$^+$), 280, 252, 226, 208, 197, 179, 165 |

TABLE 7-continued

| Compound No. | Structural Formulas | $^1$H-NMR ($\delta$ ppm in CDCl$_3$) | MS |
|---|---|---|---|
| 35 | | 1.48(3H, s), 1.41–1.53(1H, m), 2.38(1H, dd, J=7, 10Hz), 2.67(1H, dd, J=8, 14Hz), 2.80–2.94(1H, m), 3.32(1H, s), 3.72(3H, s), 5.84(1H, d, J=10Hz), 6.96(1H, br), 7.10–7.20(1H, m), 7.31–7.50(5H, m) | 345(M$^+$), 301, 258, 226, 212, 197, 165 |

TABLE 8

| Compound No. | Structural Formulas | $^1$H-NMR ($\delta$ ppm in CDCl$_3$) | MS |
|---|---|---|---|
| 36 | | 1.48(3H, s), 1.41–1.53(1H, m), 2.37(1H, dd, J=7, 10Hz), 2.67(1H, dd, J=8, 14Hz), 2.78–2.94(1H, m), 3.32(1H, s), 3.72(3H, s), 3.72(3H, s), 7.82(1H, d, J=10Hz), 6.85(1H, br), 7.01–7.13(2H, m), 7.33–7.46(3H, m) | 363(M$^+$), 209, 197, 179, 165, 151, 137 |
| 37 | | 1.56(3H, s), 1.44–1.66(1H, m), 2.16–2.54(1H, m), 2.62–2.76(1H, m), 2.80–3.02(1H, m), 3.33(1H, s), 3.73(3H, s), 5.89(1H, d, J=10Hz), 7.22(1H, br), 7.46–7.96(8H, m) | 395(M$^+$), 226, 197, 183, 169 |
| 38 | | 1.43(3H, s), 1.40–1.52(1H, m), 2.37(1H, dd, J=7, 10Hz), 2.65(1H, dd, 7, 14Hz), 2.78–2.84(1H, m), 3.30(1H, s), 3.42–3.76(8H, m), 3.71(3H, s), 5.75(1H, d, J=10Hz), 7.40(1H, m) | 339(M$^+$), 308, 278, 245, 229, 213, 191, 179 |

TABLE 8-continued

| Compound No. | Structural Formulas | $^1$H-NMR (δ ppm in CDCl$_3$) | MS |
|---|---|---|---|
| 39 | | 1.44(3H, s), 1.41–1.55(1H, m), 2.39(1H, dd, J=7, 10Hz), 2.67(1H, dd, J=8, 14Hz), 2.76–2.90(1H, m), 3.34(1H, s), 3.73(3H, s), 4.53(2H, s), 5.76(1H, d, J=10Hz), 7.39(1H, s), 8.70(1H, br) | 345(M$^+$), 314, 208, 197, 179, 165, 139 |
| 40 | | 1.45(3H, s), 1.72–1.84(1H, m), 2.52–2.65(2H, m), 2.74–2.82(1H, m), 3.40(1H, s), 3.74(3H, s), 4.52(2H, d, J=2Hz), 6.46(1H, d, J=3Hz), 7.34(1H, d, J=2Hz), 8.54(1H, br) | 345(M$^+$), 314, 285, 262, 226, 208, 176, 165, 139 |

TABLE 9

| Compound No. | Structural Formulas | $^1$H-NMR (δ ppm in CDCl$_3$) | MS |
|---|---|---|---|
| 41 | | 1.42(3H, s), 1.38–1.52(1H, m), 2.29(1H, dd, J=7, 10Hz), 2.60(1H, dd, J=7, 14Hz), 2.74–2.86(1H, m), 3.30(1H, s), 3.69(3H, s), 5.84(1H, d, J=10Hz), 7.27(1H, s), 7.37–7.67(3H, m), 7.94–8.05(2H, m), 9.51(1H, br) | 268(M$^+$), 226, 197, 183, 165, 147, 123, 105 |
| 42 | | 1.49(3H, s), 1.90–2.04(1H, m), 2.52–2.68(2H, m), 2.70–2.86(1H, m), 3.44(1H, s), 3.73(3H, s), 6.59(1H, d, J=4Hz), 7.39(1H, d, J=2Hz), 7.44–7.68(3H, m), 7.76–7.90(2H, m), 7.99(1H, br) | +FAB374.1 (M$^+$ + 1), −FAB372.1 (M$^+$ − 1) |

TABLE 9-continued

| Compound No. | Structural Formulas | $^1$H-NMR (δ ppm in CDCl$_3$) | MS |
|---|---|---|---|
| 43 | | 0.98(3H, t, J=7Hz), 1.32–2.12(3H, m), 2.36–2.86(3H, m), 2.89(3H, d, J=5Hz), 3.33(1H, s), 3.71(3H, s), 4.96(1H, d, J=10Hz), 5.74(1H, J=10Hz), 7.40(1H, s) | 297(M$^+$), |
| 44 | | 0.88–0.98(3H, m), 1.24–1.60(10H, m), 1.88–3.10(4H, m), 2.89(3H, d, J=5Hz), 3.30(1H, s), 3.71(3H, s), 4.94(1H, brs), 5.75(1H, d, J=10Hz), 7.40(1H, s) | 353(M$^+$), |
| 45 | | 1.50(1H, dd, J=10, 13Hz), 1.92–2.84(4H, m), 2.87(3H, d, J=5Hz), 3.54(1H, s), 3.71(1H, ABq, J=13Hz), 3.72(3H, s), 4.00(1H, ABq, J=13Hz), 5.32(1H, br), 5.73(1H, d, J=10Hz), 7.41(1H, s) | 242(M$^+$ − NHCOCH$_3$) |

TABLE 10

| Compound No. | Structural Formulas | $^1$H-NMR (δ ppm in CDCl$_3$) | MS |
|---|---|---|---|
| 46 | | 1.50(1H, dd, J=10Hz), 2.10(3H, s), 2.44–2.82(3H, m), 2.86(3H, d, J=5Hz), 3.51(1H, s), 3.72(3H, s), 3.97(1H, ABq, J=12Hz), 4.67(1H, ABq, 12Hz), 5.14(1H, br s), 5.69(1H, d, J=10Hz), 7.42(1H, s) | 341(M$^+$), |

TABLE 10-continued

| Compound No. | Structural Formulas | ¹H-NMR (δ ppm in CDCl₃) | MS |
| --- | --- | --- | --- |
| 47 | | 1.50(1H, dd, J=10, 13Hz), 2.52–2.82(3H, m), 2.87(3H, d, J=5Hz), 3.52(1H, s), 3.72(3H, s), 3.81(3H, s), 4.12(1H, ABq, J=12Hz), 4.68(1H, J=12Hz), 5.18(1H, br), 5.69(1H, d, J=10Hz), 7.42(1H, d, J=1Hz) | 357(M⁺) |
| 48 | | 1.50(1H, dd, J=10, 12Hz), 2.24–2.76(3H, m), 2.81(3H, d, J=5Hz), 2.86(3H, d, J=5Hz), 3.49(1H, s), 3.72(3H, s), 3.93(1H, ABq, J=12Hz), 4.70(1H, ABq, J=12Hz), 4.94(1H, br), 5.66(1H, br), 5.67(1H, d, J=10Hz), 7.43(1H, s) | 356(M⁺), |
| 49 | | 1.50(1H, dd, J=10, 13Hz), 2.48–2.88(3H, m), 2.89(3H, d, J=5Hz), 3.37(3H, s), 3.41(1H, s), 3.42(1H, ABq, J=12Hz), 3.71(3H, s), 3.72(1H, ABq, J=12Hz), 5.09(1H, br), 5.77(1H, d, J=10Hz), 7.41(1H, s) | 313(M⁺), |
| 50 | | 1.49–2.65(4H, m), 2.89(3H, d, J=5Hz), 3.49(1H, s), 3.72(3H, s), 4.36–4.77(2H, m), 5.02(1H, br), 5.94(1H, d, J=10Hz), 7.42(1H, s) | 301(M⁺) |

TABLE 11

| Compound No. | Structural Formulas | ¹H-NMR (δ ppm in CDCl₃) | MS |
| --- | --- | --- | --- |
| 51 | | 1.40–2.80(4H, m), 2.89(3H, d, J=5Hz), 3.56(1H, ABq, J=12Hz), 3.72(3H, s), 3.92(1H, ABq, J=12Hz), 4.72(1H, br), 5.74(1H, d, J=10Hz), 7.42(1H, s) | 317(M⁺), |

TABLE 11-continued

| Compound No. | Structural Formulas | ¹H-NMR (δ ppm in CDCl₃) | MS |
|---|---|---|---|
| 52 | | 1.62–2.42(6H, m), 2.78(1H, ABq, J=4Hz), 2.84(3H, d, J=5Hz), 3.60(1H, ABq, J=4Hz), 3.14–3.28(1H, m), 3.74(3H, s), 4.78(1H, br), 5.93(1H, d, J=6Hz), 7.44(1H, d, J=1Hz) | 283(M⁺) |
| 53 | | 1.72–2.52(5H, m), 2.82(3H, d, J=5Hz), 2.76–2.88(2H, m), 2.94–3.06(1H, m), 3.74(3H, s), 4.70(1H, br), 5.91(1H, d, J=5Hz), 7.52(1H, s) | 283(M⁺), |
| 54 | | 1.47(3H, s), 1.32–2.36(6H, m), 2.87(3H, d, J=5Hz), 3.73(3H, s), 3.58–3.90(2H, m), 5.62(1H, br), 8.22(1H, s) | 228(M⁺-NHCOCH₃) |
| 55 | | 1.38(3H, s), 1.68–2.26(2H, m), 2.20(1H, dd, J=7, 8Hz), 2.52–2.72(1H, m), 2.90–3.02(1H, m), 3.29(1H, s), 3.67(3H, s), 3.68(1H, t, J=12Hz), 4.02(1H, dd, J=5, 12Hz), 4.86(1H, br), 5.42(1H, d, J=9Hz) | 227(M⁺-NHCOCH₃) |

TABLE 12

| Compound No. | Structural Formulas | ¹H-NMR (δ ppm in CDCl₃) | MS |
|---|---|---|---|
| 56 | | 1.38(3H, s), 1.60–2.82(5H, m), 2.83(3H, d, J=5Hz), 3.29(1H, s), 3.71(1H, dd, J=3, 12Hz), 3.72(3H, s), 4.28(1H, d, J=12Hz), 4.86(1H, br), 5.41(1H, d, J=9Hz) | |

TABLE 12-continued

| Compound No. | Structural Formulas | $^1$H-NMR (δ ppm in CDCl$_3$) | MS |
|---|---|---|---|
| 57 | | 1.55(3H, s), 2.16(2H, m), 2.43(1H, dd, J=1, 12Hz), 2.82(3H, d, J=9Hz), 2.96(1H, m), 3.27(1H, s), 3.70(3H, s), 4.72(1H, br s), 6.44(1H, d, J=1Hz), 7.27(1H, s) | 283(M$^+$) |
| 58 | | 1.01(3H, d, J=7Hz), 1.12–2.60(7H, m), 2.79(6H, d, J=5Hz), 3.62–4.22(6H, m), 4.72(2H, br) | |
| 59 | | 0.97(3H, d, J=7Hz), 1.14–2.64(7H, m), 2.79(6H, d, J=5Hz), 3.70–4.08(6H, m), 4.76(2H, br s) | |
| 60 | | 1.64–1.80(1H, m), 2.30–2.72(3H, m), 2.80(3H, d, j=8Hz), 3.53(1H, br s), 3.73(3H, s), 3.92(1H, d, J=12Hz), 3.92(1H, d, J=12Hz), 4.90(1H, br s), 4.96(1H, d, J=12Hz), 5.00(1H, d, J=12Hz), 7.38(1H, s) | 299(M$^+$) |

Test Example

A cell proliferation assay (CPA) test, cell migration assay (CMA) test and tube formation assay (TFA) test were conducted on the above-mentioned compounds serving as the active ingredient of the vascularization inhibitor of the present invention. The following provides an explanation of each test method.

Furthermore, the sample liquids of compounds used in the CPA and CMA tests were prepared in the manner described below. Firstly, after weighing out each compound, a calculated amount of DMSO was added. After dissolving the compound in the DMSO, phosphate buffered physiological saline (PBS (−)) was added to bring the sample concentration to 1 mg/ml in PBS (−). The amount of DMSO used to dissolve the compounds was adjusted in advance to that the concentration of DMSO at that time was 5%. The resulting liquids were diluted 10-fold with 5% DMSO-PBS (−) solution to prepare sample solutions having a concentration of 0.1 mg/ml. In the TFA test, 320 μl of the prepared 1 mg/ml sample solutions were removed followed by addition of 680 μl of PBS (−) to prepare samples having a concentration of 10 μg/ml. Moreover, 100 μl of this solution was removed followed by addition of 900 μl of PBS (−) to dilute 10-fold and prepare samples having a concentration of 1 μg/ml.

Cell Proliferation Assay (CPA) Test

100 μl of the 7th subculture obtained from first generation human umbilical-vein endothelial cells (HUVEC) were disseminated in the wells (N=3) of a 96-well plate (Iwaki, Cat. #4860-010) at a cell concentration of 5×10$^4$ cells/ml. M-199 medium containing +20% FCS, 10 ng/ml of b-FGF and 10 ng/ml of EGF (abbreviated as "M199 (2+)") was used for the medium.

After culturing for 24 hours at 37° C. in the presence of 5% CO$_2$ under the above conditions, 20 μl/well of MTT solution (solution containing 5 mg/ml of PBS (−)) were added to the control well followed by accurately culturing for 4 hours at 37° C. in the presence of 5% $CO_2$. Following completion of culturing, 100 μl/well of a stop solution (0.001 N aqueous HCl solution containing 10% SDS) were added. On the other hand, 10 μl/well of sample solutions at concentrations of 1 mg/ml and 0.1 mg/ml were added to the other wells.

After culturing for 24 hours at 37° C. in the presence of 5% $CO_2$, the medium was replaced and 100 μl/well of M199 (2+) were added. The samples were also replaced in each well at this time.

Moreover, after additionally culturing for 48 hours at 37° C. in the presence of 5% $CO_2$, 20 μl/well of MTT solution were added to the wells containing sample and the control well followed by accurately culturing for 4 hours at 37° C. and adding 100 μl/well of stop solution.

After allowing to stand undisturbed overnight at 37° C., the absorbance of each well at 540 nm was measured with an ELISA reader followed by analysis of the resulting data to determine the $IC_{50}$ values.

Cell Migration Assay (CMA) Test

After disseminating the 7th subculture of HUVEC obtained from the first generation in the same manner as above at 4ml/well (3.0×10$^5$ cells/well) in a collagen-coated 6-well plate (NUNC), the cells were cultured for 48 hours at 37° C. in the presence of 5% $CO_2$. The cells reached nearly a completely confluent state as a result of this culturing.

A double-edged, disposable razor blade was divided into four sections, of which one of those sections was pinched between a pair of forceps. Using this piece of razor blade, the cell surface in the above confluent state was scraped off. Two areas of the cell surface were scraped off in each well.

After washing the surface of the wells from which the cells had been scraped off with medium, 4.0 ml of fresh M199 (2+) medium were added followed by addition of 40 μl or 4 μl of sample solution (1 mg/ml). The cells were cultured for 24 hours at 37° C. in the presence of 5% $CO_2$. After discarding the culture liquid, the cells were fixed for 30 minutes with methanol. Next, after staining the cells for 4 hours with Giemsa stain, the plates were washed with tap water and air dried.

Measurement of cell migration was performed by microscopically counting the number of cells that had newly migrated within the range of a 1 mm×1 mm block. More specifically, as shown in FIG. 1, a line on the edge of the gradation (block) was aligned with the line formed as a result of scraping off the cells, and, for example, the number of cells in block 1 (1–A,B,C,D,E) were all counted within a 5×5 gradation (1 square=200 μm×200 μm) printed on the eyepiece lens, and that number was taken to be the number of cells of block 1. The total number of cells counted in blocks 1 through 5 were then totaled to determine the overall total number of cells. Four fields were counted for each well.

Evaluation was performed determining the cell migration (%) according to the following formula.

Cell migration rate=number of migrating cells to which sample was added×100/number of migrating of control (+)

If this value was 60% or less, the sample was determined to demonstrate remarkable cell migration inhibitory effects. Control (+) indicates the number of migrating cells in the control well containing M199 (2+).

Tube Formation Assay (TFA) Test

To begin with, 8 volumes of Type 1-A cell matrix (manufactured by Gibco Co.), 1 volume of 10×M119, and 1 volume of reconstituted buffer [200 mM HEPES, 0.05 N sodium hydroxide, 260 mM sodium bicarbonate] were slowly mixed under cooling with ice while avoiding bubbling to form a collagen gel. This collagen gel was distributed in a NUNC 24-well plate at 310 μl/well followed by allowing to stand undisturbed for 2 hours at 37° C. to solidify the gel.

Next, the 7th subculture of HUVEC (1×10$^5$ cells/ml) obtained from the first generation in the same manner as above were disseminated at 500 μl/well. The cells were cultured for 2 hours at 37° C. to allow the cells to make contact with the collagen. After then removing the medium by aspiration, 50 μl of sample solution were added followed by addition of 310 μl/well of freshly prepared collagen gel and culturing for 1 hour and 10 minutes at 37° C. to solidify the double-layer gel.

1 ml/well of M-199 medium containing 20% FCS, 30 ng/ml of b-FGF and 0.1 μM PMA were added to the wells followed by culturing for 20 hours at 37° C. in the presence of 5% $CO_2$.

Tube formation by the cells was evaluated by photographing the portion in the center of the wells that exhibited clear contrast using ASA400 film, and then analyzing the resulting photographs. Measurement of the lengths of the formed tubes was performed using the public domain NIH Image with a computer.

Evaluation was performed by calculating the inhibition rate (%) of tube formation according to the following formula.

Inhibition rate (%)=100−((formed tube length in presence of sample−formed tube length in presence of control (−))×100/ (formed tube length in presence of control (+)−formed tube length in presence of control (−)))

If the value calculated from the above formula was 40% or less, the sample was judged to exhibit remarkable tube formation inhibitory effects.

The results of each test are shown in Tables 13 and 14 below.

TABLE 13

| Compound No. | CPA ($IC_{50}$ μg/ml) | CMA (% relative to control) | | TFA (inhibition rate, %) | |
|---|---|---|---|---|---|
| | | 10 μg/ml | 1 μg/ml | 10 μg/ml | 1 μg/ml |
| 1 | >100.0 | 93.5 | 98.5 | 37.8 | 49.8 |
| 2 | <100.0 | 95.8 | 88.4 | 56.9 | 69.1 |
| 3 | <100.0 | 57.3 | 68.5 | 33.5 | 33.0 |
| 4 | <100.0 | 53.0 | 70.8 | 5.6 | 40.5 |
| 5 | 44.9 | 82.0 | 98.6 | 34.5 | 20.8 |
| 6 | >100.0 | 105.0 | 106.3 | 8.7 | 24.2 |
| 7 | 90.6 | 79.7 | 82.6 | 18.2 | 25.8 |
| 8 | 60.5 | 60.5 | 75.4 | 93.2 | 27.3 |
| 9 | >100.0 | 116.4 | 110.7 | 16.5 | 11.0 |
| 10 | 93.3 | 103.3 | 101.3 | 27.7 | 28.6 |
| 11 | >100.0 | 85.5 | 101.5 | 40.3 | 20.7 |
| 12 | >100.0 | 89.8 | 100.6 | 32.5 | 32.7 |
| 13 | 53.3 | 94.0 | 94.1 | 36.8 | 36.3 |
| 14 | >100.0 | 101.7 | 99.4 | 48.7 | 38.2 |
| 15 | >100.0 | 58.3 | 71.1 | −8.0 | −16.0 |
| 16 | >100.0 | 102.3 | 98.1 | 21.6 | 30.7 |
| 17 | 69.1 | 114.0 | 94.4 | 23.4 | 19.0 |
| 18 | >100.0 | 71.5 | 90.3 | 27.7 | 28.6 |

TABLE 13-continued

| Compound | CPA | CMA (% relative to control) | | TFA (inhibition rate, %) | |
|---|---|---|---|---|---|
| No. | ($IC_{50}$ µg/ml) | 10 µg/ml | 1 µg/ml | 10 µg/ml | 1 µg/ml |
| 19 | >100.0 | 93.5 | 96.4 | 21.3 | 23.6 |
| 20 | >100.0 | 89.5 | 97.4 | 19.6 | 34.3 |
| 21 | >100.0 | 101.0 | 105.3 | 23.2 | 29.5 |
| 22 | >100.0 | 97.7 | 93.4 | 74.9 | 50.8 |
| 23 | — | — | — | — | — |
| 24 | >100.0 | 112.3 | 96.9 | 24.2 | 41.3 |
| 25 | >100.0 | 87.5 | 91.8 | 14.5 | 31.8 |
| 26 | >100.0 | 103.9 | 84.0 | 30.8 | 41.2 |
| 27 | >100.0 | 103.1 | 94.5 | 32.7 | 29.1 |
| 28 | >100.0 | 113.9 | 94.3 | 36.8 | 41.3 |
| 29 | >100.0 | 88.0 | 89.9 | 29.3 | 17.7 |
| 30 | >100.0 | 104.6 | 90.0 | 36.0 | 16.5 |

TABLE 14

| Compound | CPA | CMA (% relative to control) | | TFA (inhibition rate, %) | |
|---|---|---|---|---|---|
| No. | ($IC_{50}$ µg/ml) | 10 µg/ml | 1 µg/ml | 10 µg/ml | 1 µg/ml |
| 31 | >100.0 | 107.2 | 97.2 | 26.5 | 15.2 |
| 32 | >100.0 | 97.0 | 93.0 | 30.0 | 68.8 |
| 33 | >100.0 | 102.5 | 108.7 | n.d. | n.d. |
| 34 | >100.0 | 95.2 | 98.2 | -14.1 | 16.8 |
| 35 | >100.0 | 67.2 | 84.4 | 20.0 | -3.3 |
| 36 | >100.0 | 99.7 | 95.0 | -18.3 | 6.9 |
| 37 | >100.0 | 88.6 | 102.0 | 22.6 | 14.1 |
| 38 | >100.0 | 61.8 | 92.3 | -10.0 | 15.3 |
| 39 | 55.0 | 94.6 | 110.5 | 39.7 | 37.6 |
| 40 | 58.1 | 66.8 | 77.3 | 23.8 | 32.8 |
| 41 | 56.1 | 95.0 | 102.2 | 37.6 | 46.7 |
| 42 | >100.0 | 70.6 | 90.4 | 18.7 | 12.5 |
| 43 | >100.0 | 89.3 | 99.9 | 9.1 | 12.4 |
| 44 | >100.0 | 98.2 | 99.4 | 71.4 | 69.7 |
| 45 | — | — | — | — | — |
| 46 | >100.0 | 103.4 | 105.1 | 1.5 | -0.8 |
| 47 | >100.0 | 60.5 | 95.9 | 2.6 | -27.3 |
| 48 | >100.0 | 107.3 | 93.3 | 54.1 | 51.5 |
| 49 | >100.0 | 104.0 | 101.5 | 12.8 | 21.2 |
| 50 | >100.0 | 63.5 | 87.9 | 23.2 | 9.5 |
| 51 | >100.0 | 100.8 | 101.9 | -1.4 | 19.1 |
| 52 | >100.0 | 103.0 | 100.6 | -6.5 | 21.7 |
| 53 | >100.0 | 94.1 | 100.4 | 9.7 | 26.0 |
| 54 | >100.0 | 86.2 | 90.5 | -12.2 | -8.6 |
| 55 | >100.0 | 91.8 | 97.8 | 3.8 | 13.9 |
| 56 | — | — | — | — | — |
| 57 | >100.0 | 93.0 | 96.0 | 13.5 | 17.7 |
| 58 | >100.0 | 97.0 | 121.6 | 22.3 | 20.6 |
| 59 | >100.0 | 92.5 | 99.3 | -4.5 | 5.9 |
| 60 | >100.0 | 96.3 | 87.1 | 41.5 | 32.7 |

For the sake of comparison, similar tests were performed ion known substances having vascularization inhibitory effects, namely b-FGF inhibitor (Protamine), collagenase inhibitor (Minocycline), anti-rheumatic agent (Methotrexate (MTX)), 5-fluorouracil (5-FU) and Fumagilline. Those results are shown in Table 15 below.

TABLE 15

| Compound | CPA | CMA (% relative to control) | | TFA (inhibition rate, %) | |
|---|---|---|---|---|---|
| No. | ($IC_{50}$ µg/ml) | 10 µg/ml | 1 µg/ml | 10 µg/ml | 1 µg/ml |
| Protamine | 52.7 | 50.0 | 69.2 | 25.4 | 41.0 |
| Minocycline | — | 51.6 | 67.3 | 56.7 | 42.1 |
| MTX | 0.04 | 103.2 | 102.1 | 42.6 | 37.5 |

TABLE 15-continued

| Compound | CPA | CMA (% relative to control) | | TFA (inhibition rate, %) | |
|---|---|---|---|---|---|
| No. | ($IC_{50}$ µg/ml) | 10 µg/ml | 1 µg/ml | 10 µg/ml | 1 µg/ml |
| 5-FU | 3.5 | 92.9 | 101.5 | 52.3 | 42.4 |
| Fumagilline | 33.3 | 74.2 | 95.5 | — | — |

As can be understood from the test example described above, in nearly all cases, the compounds of the present invention exhibited $IC_{50}$ values in the CPA test of 100 or higher. Thus, despite not having cytotoxicity, effects were observed in the CMA ad TFA tests. In contrast, although all of the comparative compounds were observed to have effects in the CMA and TFA tests, $IC_{50}$ values in the CPA test were extremely low, thus indicating the existence of cytotoxicity.

EXAMPLES 29–48

Example 29

200 mg of the compound described in Example 1 (Table 1, Compound No. 1) were dissolved in dichloromethane followed by addition of 0.2 ml of triethylamine, 0.24 ml of diphenylphosphate azide and 0.07 ml of 28% aqueous ammonia and stirring for 18 hours at room temperature. The reaction mixture was poured into water and extracted with ethyl acetate. After washing the organic phase with brine, it was dried over magnesium sulfate. After distilling off the solvent under reduced pressure, the residue was purified by silica gel chromatography to obtain Compound No. I-61 (18 mg) from the hexane-ether eluate.

Compounds No. I-62, I-63 and I-64 were obtained from the compound described in Example 1 (Table 1, Compound No. 1) in the same manner as described above. The physicochemical properties of these compounds are described in Table 16, Compound No. I-61 through I-64.

100 mg of the compound described in Example 1 (Table 1, Compound No. 1) and 63 mg of glycine ethylester hydrochloride were dissolved in dimethylformamide followed by addition of 0.2 ml of triethylamine and 68 ?l of diethylphosphoric cyanide and stirring for 18 hours at room temperature. The reaction mixture was poured into water and extracted with ethyl acetate. After washing the organic phase with brine, it was dried over magnesium sulfate. After concentration, the residue was purified by silica gel chromatography to obtain colorless needles in the form of Compound No. I-65 (82 mg) from the hexane-ether eluate. The physicochemical properties of this compound are described in Table 16, Compound No. I-65.

Example 30

Step 1

(4aS,7aR)-1-hydroxy-7-methyl-1,4a,5,7a-tetrahydrocyclopenta[c]pyrane-4-carboxylic acid benzylester described in Example 1 was converted to a colorless oil in the form of Compound II-1 according to the same method as Step 4 of Example 1. The physicochemical properties of this compound are described in Table 67, Compound No. II-1.

Compound No. II-1 obtained above was oxidized according to the same method as Step 5 of Example 1, and the products were respectively converted to colorless powders in the form of Compound No. II-2 and Compound No. II-3 by separating by silica gel chromatography. The physicochemical properties of these compound are described in Table 67, Compound No. II-2 and Compound No. II-3.

Compound No. II-2 obtained above was converted to amorphous I-66 according to the same method as Step 6 of Example 1. The physicochemical properties of this compound are described in Table 17, Compound No. I-66.

Compound No. II-3 obtained above was converted to amorphous II-4 according to the same method as Step 6 of Example 1. The physicochemical properties of this compound are described in Table 67, Compound No. II-4.

Compound No. I-66 obtained above was converted to a colorless power I-67 according to the same method as Example 2. The physicochemical properties of this compound are described in Table 17, Compound No. I-67.

Compound No. I-66 obtained above was converted to colorless needles I-68 according to the same method as Example 8. The physicochemical properties of this compound are described in Table 17, Compound No. I-68.

Compound No. II-4 obtained above was converted to a colorless power I-69 according to the same method as Example 2. The physicochemical properties of this compound are described in Table 17, Compound No. I-69.

Example 31

3.84 ml of chlorophenylformate, 3.8 ml of pyridine and 300 mg of 4-dimethylaminopyridine were added to known Compound No. III-1 (5.0 g) indicated in Table 74 followed by stirring for 2 hours at room temperature. The reaction mixture was poured into water and extracted with ethyl acetate. After washing the organic phase with 2 N aqueous hydrochloric acid, saturated aqueous sodium bicarbonate, and brine, it was dried over magnesium sulfate. After concentration, the residue was purified by silica gel chromatography to obtain amorphous solid II-5 from the hexane-ether eluate. The physicochemical properties of this compound are shown in Table 67, Compound No. II-5.

The above Compound No. II-5 (500 mg) was dissolved in acetonitrile followed by addition of 1.0 ml of aqueous ammonia and stirring for 24 hours at room temperature. After concentrating the reaction mixture, the residue was purified by chromatography using silica gel to obtain colorless needs I-70 from the hexane-ether eluate. Compound No. I-71 to I-130 were produced in the same manner. The physicochemical properties of these compounds are described in Table 17 to Table 29, Compound No. I-70 through I-130.

The above Compound No. II-5 (300 mg) was dissolved in acetonitrile followed by addition of 0.5 ml of triethylamine and 2-aminomethylbenzimidazole hydrochloride and the mixture was stirred for 24 hours at room temperature. The reaction mixture was then extracted with ethyl acetate. After washing the organic phase with brine, it was dried over magnesium sulfate. After concentration, the residue was purified by chromatography using silica gel to obtain colorless needles I-131 from the hexane-ether eluate.

Compound No. I-132 to I-150 were produced in the same manner. The physicochemical properties of these compounds are described from Table 30 to Table 33, Compound No. I-131 through I-150.

Known Compound No. III-1 (300 mg) shown in Table 74 was dissolved in acetonitrile followed by addition of 0.12 ml of ethylisocyanate and 60 ml of triethylamine and stirring for 5 hours at room temperature. The reaction mixture was poured into water and extracted with ethyl acetate. After washing the organic phase with brine, it was dried over magnesium sulfate. After concentration, the residue was purified by chromatography using silica gel to obtain colorless needles I-151 from the hexane-ether eluate. Compound No. I-152 through I-174 were produced in the same manner. The physicochemical properties of these compounds are described from Table 34 to Table 38, Compound No. I-151 through I-174.

Example 32

0.89 ml of chlorophenylformate, 0.76 ml of pyridine and 10 mg of 4-dimethylaminopyridine were added to known Compound No. III-2 (1 g) shown in Table 74 followed by stirring for 5 hours at room temperature. The reaction mixture was poured into water and extracted with ethyl acetate. After washing the organic phase with 2 N aqueous hydrochloric acid, saturated aqueous sodium bicarbonate and brine, it was dried over magnesium sulfate. After concentration, the residue was purified by chromatography using silica gel to obtain a pale yellow solid II-6 (768 mg) from the hexane-ether eluate. The physicochemical properties of this compound are shown in Table 68. Compound No. II-6.

The above Compound No. II-6 (300 mg) was dissolved in acetonitrile followed by addition of 0.25 ml of n-hexylamine and stirring for 24 hours at room temperature. After concentrating the reaction mixture, the residue was purified by chromatography using silica gel to obtain a colorless oil I-175 from the hexane-ether eluate. Compound No. I-176 through I-235 were produced in the same manner. The physicochemical properties of these compounds are described from Table 38 to Table 50, Compound No. I-175 through I-235.

Compound No. II-6 (300 mg) obtained above was dissolved in acetonitrile followed by addition of 0.5 ml of triethylamine and 205 mg of aminoethanethiol hydrochloride and stirring for 24 hours at room temperature. The reaction mixture was then extracted with ethyl acetate. After washing the organic phase with brine, it was dried over magnesium sulfate. After concentration, the residue was purified by chromatography using silica gel to obtain a colorless oil I-236 from the hexane-ether eluate. Compound No. I-237 through I-253 were produced in the same manner. The physicochemical properties of these compounds are described from Table 51 to Table 54, Compound No. I-236 through I-253.

Known Compound No. III-2 (1.0 g) shown in Table 74 was dissolved in acetonitrile followed by addition of 0.33 ml of methylisocyanate and 0.2 ml of triethylamine and stirring for 5 hours at room temperature. The reaction mixture was poured into water and extracted with ethyl acetate. After washing the organic phase with brine, it was dried over magnesium sulfate. After concentration, the residue was purified by chromatography using silica gel to obtain colorless needles I-254 from the hexane-ether eluate. Compound No. I-255 through I-277 were produced in the same manner. The physicochemical properties of these compounds are described from Table 54 to Table 59, Compound No. I-254 through I-277.

Example 33

A known Nepetalactol was converted to colorless needles I-278 (110 mg) according to the same method as Step 4 of Example 1. The physicochemical properties of this compound are described in Table 59, Compound No. I-278.

Example 34

A known Compound No. III-3 shown in Table 74 was converted to a colorless oil II-7 according to the same method as Step 1 of Example 1. The physicochemical properties of this compound are described in Table 68, Compound No. II-7.

Compound No. II-7 obtained above was converted to a colorless oil II-8 according to the same method as Example 4. The physicochemical properties of this compound are described in Table 68, Compound No. II-8.

Compound No. II-8 obtained above was converted to amorphous compound II-9 according to the same method as Step 3 of Example 1. The physicochemical properties of this compound are described in Table 68, Compound No. II-9.

Compound No. II-9 obtained above (340 mg) was dissolved in dimethylformamide followed by addition of 145 mg of imidazole and 310 mg of tert-butyldimethylsilylchloride and stirring for 18 hours at room temperature. The reaction mixture was extracted with ethyl acetate. After washing the organic phase with water and brine, it was dried over magnesium sulfate. After concentration, the residue was dissolved in acetonitrile to convert to a colorless oil II-10 according to the same method as Step 4 of Example 1. The physicochemical properties of this compound are described in Table 68, Compound No. II-10.

Compound No. II-10 obtained above was converted to a colorless powder II-11 according to the same method as Example 17. The physicochemical properties of this compound are described in Table 11, Compound No. II-11.

Compound No. II-11 obtained above was converted to colorless needles I-279 according to the same method as Example 17. The physicochemical properties of this compound are described in Table 59, Compound No. I-279.

Example 35

A known Compound No. III-4 shown in Table 7 4was converted to a colorless powder I-280 according to the same method as Step 4 of Example 1. The physicochemical properties of this compound are described in Table 59, Compound No. I-280.

Known Compound No. III-5 shown in Table 7 4was converted to a carboxylic acid according to the same method as Step 1 of Example 1. Moreover, the product obtained in this reaction was converted to a benzylester in the same manner as Step 2 of Example 1. This product was converted to pale yellow oil II-12 according to the same method as Step 3 of Example 1. The physicochemical properties of this compound are described in Table 69, Compound No. II-12.

Compound No. II-12 obtained above was converted to a colorless powder II-13 by performing the same conversion as Step 4 of Example 1. The physicochemical properties of this compound are described in Table 69, Compound No. II-13.

Compound No. 13 obtained above was converted to a colorless powder II-14 according to the same method as Step 6 of Example 1. The physicochemical properties of this compound are described in Table 69, Compound No. II-14.

Compound No. II-14 obtained above was converted to Compound No. I-281 according to the same method as Example 2. The physicochemical properties of this compound are described in Table 1, Compound No. I-281.

Compound No. II-14 obtained above was converted to a colorless powder I-282 according to the same method as Example 8. The physicochemical properties of this compound are described in Table 60, Compound No. I-282.

Example 36

Compound No. II-14 (500 mg) described in Example 35 was dissolved in tetrahydrofuran followed by addition of 0.18 ml of methylchloroformate and 0.27 ml of triethylamine while stirring at −30° C. Next, an aqueous solution containing 185 mg of sodium borohydride was dropped into the above reaction mixture. After warming up to room temperature, saturated aqueous ammonium chloride solution was added followed by extraction with ethyl acetate. After washing the organic phase with brine, it was dried over magnesium sulfate. After concentration, the residue was converted to a colorless oil II-15 according to the same method as Step 1 of Example 18. The physicochemical properties of this compound are described in Table 69, Compound No. II-15.

The above Compound No. II-15 (40 mg) was dissolved in ethyl acetate followed by addition of 10% palladium-carbon and stirring for 3 hours under hydrogen gas atmosphere at 1 atm. After filtering out the insoluble matter, the filtrate was concentrated and the residue was purified by silica gel chromatography to obtain a colorless powder I-283 from the hexane-ether eluate. The physicochemical properties of this compound are described in Table 60, Compound No. I-283.

Example 37

A known Compound No. III-6 (107 mg) shown in Table 74 was dissolved in acetonitrile followed by addition of 65 mg of dimethylthiocarbamoyl chloride, 73 µl of triethylamine and 14 mg of dimethylaminopyridine and stirring for 24 hours at room temperature. The reaction mixture was poured into water and extracted with ethyl acetate. The organic phase was washed with brine and dried over magnesium sulfate. After concentration the residue was purified by silica gel chromatography to obtain colorless powders I-284 and I-285 from the hexane-ether eluate. The physicochemical properties of these compounds are described in Table 60, Compound No. I-284 and I-285.

A known Compound No. III-6 (100 mg) shown in Table 74 was dissolved in acetonitrile followed by addition of 72 µl of triethylamine and 70 µl of benzoylisocynate and stirring for 4 hours at room temperature. The reaction mixture was poured into water and extracted with ethyl acetate. After washing the organic phase with brine, it was dried over magnesium sulfate. After concentration, the residue was purified by silica gel chromatography to obtain an amorphous powder I-286 from the hexane-ether eluate. The physicochemical properties of this compound are described in Table 61, Compound No. I-286.

Example 38

A known genipin was converted to colorless needles I-287 according to the same method as Step 4 of Example 1. The physicochemical properties of this compound are described in Table 61, Compound No. I-287.

A known genipin was converted to colorless needles I-288 according to the same method as Step 4 of Example 1. The physicochemical properties of this compound are described in Table 61, Compound No. I-288.

Example 39

A known Compound No. III-7 (13.0 g) shown in Table 74 was dissolved in dichloromethane followed by the sequential addition of 42 ml of trimethylsilyltrifluoromethane sulfonate, 33.5 ml of triethylsilane and 5.2 ml of boron trifluoride-ether complex and stirring for 18 hours at 0° C. The reaction mixture was poured into saturated aqueous sodium bicarbonate and extracted with ethyl acetate. After washing the organic phase with brine, it was dried over magnesium sulfate. After concentration, the residue was purified by silica gel chromatography to obtain a colorless oil II-16 (4.85 g) from the hexane-ether eluate. The physicochemical properties of this compound are described in Table 70, Compound No. II-16.

Compound No. II-16 (160 mg) obtained above was dissolved in methanol followed by addition of potassium carbonate and stirring for 2 hours at room temperature. After concentrating the reaction mixture, the residue was purified by silica gel chromatography to obtain a colorless oil II-17 (100 mg, yield: 75%) from the hexane-ether eluate. The physicochemical properties of this compound are described in Table 70, Compound No. II-17.

4 mg of vanadylacetylacetonate were dissolved in dichloromethane followed by addition of tert-butylhydroperoxide. After stirring for 20 minutes at room temperature, Compound No. II-17 obtained above (100 mg) was dropped into the dichloromethane solution followed by stirring for 12 hours at the same temperature. The reaction mixture was poured into saturated aqueous sodium thiosulfate solution and extracted with ethyl acetate. After washing the organic phase with brine, it was dried over magnesium sulfate. After concentration, the residue was purified by silica gel chromatography to obtain a colorless oil I-289 (70 mg) from the hexane-ether eluate. The physiochemical properties of this compound are described in Table 61, Compound No. I-289.

Compound No. I-289 (70 mg) obtained above was dissolved in acetonitrile followed by addition of 50 μl of triethylamine and 22 μl of methylisocyanate and stirring for 2 hours at room temperature under argon gas atmosphere. The reaction mixture was poured into water and extracted with ethyl acetate. After washing the organic phase with brine, it was dried over magnesium sulfate. After concentration, the residue was purified by silica gel chromatography to obtain colorless needles I-290 (47 mg) from the hexane-ether eluate. The physiochemical properties of this compound are described in Table 61, Compound No. I-290.

Compound No. I-289 (180 mg) obtained above was dissolved in acetonitrile followed by addition of 133 μl of triethylamine and 82 μl of 2-chloroethylisocyanate and stirring for 2 hours at room temperature. The reaction mixture was poured into water and extracted with ethyl acetate. After washing the organic phase with brine, it was dried over magnesium sulfate. After concentration, the residue was purified by silica gel chromatography to obtain colorless needles I-291 (120 mg) from the hexane-ether eluate. The physiochemical properties of this compound are described in Table 62, Compound No. I-291.

Example 40

Compound No. II-17 described in Example 39 (2.0 g) was dissolved in dichloromethane followed by addition of 0.83 ml of thionylchloride and stirring for 24 hours at room temperature. The reaction mixture was poured into water and extracted with ethyl acetate. After washing the organic phase with saturated aqueous sodium bicarbonate and brine, it was dried over magnesium sulfate. After concentration, the residue was dissolved in methylethylketone followed by addition of 2.8 g of sodium iodide and 1.6 g of sodium bicarbonate and stirring for 3 hours at 60° C. After concentrating the reaction mixture, the residue was purified by silica gel chromatography to obtain a colorless oil II-18 (1.68 g) from the hexane-ether eluate. The physiochemical properties of this compound are described in Table 70, Compound No. II-18.

The above Compound No. II-18 (100 mg) was dissolved in dimethylformamide followed by addition of 71 mg of sodium 2-mercaptobenzthiazole and stirring for 12 hours at room temperature. The reaction mixture was poured into water and extracted with ethyl acetate. After washing the organic phase with water and brine, it was dried over magnesium sulfate. After concentration, the residue was purified by silica gel chromatography to obtain a colorless powder I-292 (91 mg) from the hexane-ether eluate. The physiochemical properties of this compound are described in Table 62, Compound No. I-292.

Example 41

Compound No. II-17 (300 mg) described in Example 39 was dissolved in dichloromethane followed by the suspension of 1.2 g of manganese dioxide and refluxing for 18 hours. After filtering out the insoluble matter, the filtrate was concentrated. The resulting residue was dissolved in tert-butanol followed by addition of 2-methyl-2-butene. Next, an aqueous solution containing 1.17 g of sodium chlorite and 1.6 g of sodium dihydrogen phosphate was dropped into the above solution followed by stirring for 15 hours at room temperature. After concentrating the reaction mixture, it was extracted with ethyl acetate. After washing the organic phase with brine, it was dried over magnesium sulfate. After concentration, the residue was purified by silica gel chromatography to obtain a colorless oil II-19 (323 mg) from the hexane-ether eluate. The physiochemical properties of this compound are described in Table 70, Compound No. II-19.

The above Compound No. II-19 (300 mg) was dissolved in dichloromethane followed by addition of 413 mg of dicyclohexylcarbodiimide, 0.28 ml of triethylamine and 262 mg of 2-piperazinoethanol followed by stirring for 12 hours at room temperature. The reaction mixture was poured into water and extracted with ethyl acetate. After washing the organic phase with brine, it was dried over magnesium sulfate. After concentration, the residue was purified by silica gel chromatography and then purified with dichloromethane-methanol to obtain a colorless powder I-293 (100 mg). The physiochemical properties of this compound are described in Table 62, Compound No. I-293.

Example 42

Compound No. II-17 (300 mg) described in Example 39 was dissolved in dichloromethane followed by suspending of 1.2 g of manganese dioxide therein and refluxing for 18 hours. After filtering out insoluble matter, the filtrate was concentrated. In the other flusk, 0.56 ml of n-butyllithium (1.64 mol solution) were dropped into a solution which was prepared by addition of 380 mg of n-amyltriphenylphosphonium bromide to anhydrous tetrahydrofuran under argon gas atmosphere at −78° C. After heating to room temperature, the solution was again cooled to −78° C. To this solution, tetrahydrofuran solution of the residue obtained from manganese dioxide oxidation above was added dropwise. After heating to room temperature, saturated ammonium chloride solution was added followed by extraction with ethyl acetate. After washing the organic phase with brine, it was dried over magnesium sulfate. After concentration, the residue was purified by silica gel chromatography to obtain a colorless oil II-20 (92 mg) from the hexane-ether eluate. The physicochemical properties of this compound are described in Table 70, Compound No. II-20.

Compound No. II-20 (92 mg) was dissolved in ethyl acetate followed by suspending of 10% palladium-carbon and by stirring for 24 hours under hydrogen gas atmosphere at 1 atm. After filtering out the catalyst, the filtrate was concentrated and the residue was purified by silica gel chromatography to obtain a colorless oil I-294 (87 mg, yield: 93%) from the hexane-ether eluate in the form of an isomeric mixture that was difficult to separate. The physiochemical properties of this compound are described in Table 62, Compound No. I-294.

Compound No. II-17 described in Example 39 was converted to Compound No. I-295 according to the same method as in Step 4 of Example 1. The physicochemical properties of this compound are described in Table 62, Compound No. I-295.

Compound No. II-17 described in Example 39 were converted to Compound No. I-296 according to the same method as in Step 4 of Example 1. The physicochemical properties of this compound are described in Table 63, Compound No. I-296.

The above Compound No. I-296 (350 mg) was dissolved in ethyl acetate followed by suspending of 10 mg of platinum dioxide therein followed by stirring for 24 hours under hydrogen gas atmosphere at 1 atm. After filtering out insoluble matter, the filtrate was concentrated and the residue was purified by silica gel chromatography to obtain a colorless oil I-297 (152 mg) from the hexane-ether eluate. The physicochemical properties of this compound are described in Table 63, Compound No. I-297.

Example 43

0.2 ml of oxalylchloride and 0.24 ml of dimethylsulfoxide were added to dichloromethane while stirring at −78° C. followed by stirring for 15 minutes. Next, the solution was dropped with a dichloromethane solution containing Compound No. I-289 obtained in Example 39 (250 mg) followed by stirring for 1 hour at −45° C. Moreover, 1.53 ml of triethylamine were added and after heating to 0° C., water was added followed by extraction with ethyl acetate. After washing the organic phase with saturated aqueous sodium bicarbonate and brine, it was dried over magnesium sulfate. After concentration, the residue was purified by silica gel chromatography to obtain a colorless oil II-21 (94 mg, yield: 38%) from the hexane-ether eluate. The physicochemical properties of this compound are described in Table 71, Compound No. II-21.

Compound No. II-21 obtained above was converted to Compound No. II-22 according to the same method as Example 42. The physicochemical properties of this compound are described in Table 71, Compound No. II-22.

Compound No. II-22 (84 mg) obtained above was dissolved in ethyl acetate followed by addition of 3 mg of platinum dioxide and stirring for 24 hours under hydrogen gas atmosphere at 1 atm. After filtering out insoluble matter, the filtrate was concentrated and the residue was purified by silica gel chromatography to obtain a colorless oil I-298 (78 mg) from the hexane-ether eluate. The physicochemical properties of this compound are described in Table 63, Compound No. I-298.

Example 44

(Step 1)

Known Compound No. III-8 shown in Table 74 was converted to Compound No. II-23 according to the same method as in Example 42. The physicochemical properties of this compound are described in Table 71, Compound No. II-23.

(Step 2)

Compound No. II-23 obtained above (730 mg) was dissolved in ethyl acetate followed by addition of 10% palladium-carbon and stirring for 24 hours under hydrogen gas atmosphere at 1 atm. After filtering out insoluble matter, the filtrate was concentrated and the residue was purified by silica gel chromatography to obtain a colorless oil II-24 (720 mg) from the hexane-ether eluate. The physicochemical properties of this compound are described in Table 71, Compound No. II-24.

(Step 3)

The above Compound No. II-24 was converted to Compound No. II-25 according to the same method as in Step 3 of Example 1. The physicochemical properties of this compound are described in Table 71, Compound No. II-25.

(Step 4)

Compound No. II-25 obtained above was converted to Compound No. I-299 according to the same method as in Step 4 of Example 1. The physiochemical properties of this compound are described in Table 63, Compound No. I-299.

(Step 5)

Compound No. I-299 obtained in Step 4 above was converted to an isomeric mixture I-300 that was difficult to separate according to the same method as in the above Step 2. The physicochemical properties of this compound are described in Table 63, Compound No. I-300.

Compound No. II-17 described in Example 39 (300 mg) was dissolved in dichloromethane followed by addition of ethylvinyl ether and pyridinium p-toluenesulfonate and stirring for 3 hours at room temperature. The reaction mixture solution was extracted with ethyl acetate. After washing the organic phase with brine, it was dried over magnesium sulfate. After concentration, the residue was used in a hydrolysis according to the same method as in Step 1 of Example 1. Moreover, the product obtained in this reaction was converted to a colorless oil I-301 according to the same method as in Example 8. The physicochemical properties of this compound are described in Table 64, Compound No. I-301.

Example 45

A known Compound No. III-9 shown in Table 74 was converted to a colorless oil I-302 according to the same method as in Example 39. The physicochemical properties of this compound are described in Table 64, Compound No. I-302.

Compound No. I-302 was converted to colorless needles I-303 according to the same method as in Step 5 of Example 1. The physicochemical properties of this compound are described in Table 64, Compound No. I-303.

The above Compound No. I-302 (850 mg) was dissolved in aqueous methanol solution followed by addition of 550 mg of lithium hydroxide and stirring for 3 hours at 60° C. After adding hydrochloric acid to the reaction mixture to acidify the solution, it was extracted with ethyl acetate. After washing the organic phase with brine, it was dried over magnesium sulfate. After concentration, the residue was dissolved in dimethylformamide followed by addition of 0.64 ml of benzylbromide and 730 mg of potassium carbonate and stirring for 2 hours at room temperature. The reaction mixture was then extracted with ethyl acetate. After washing the organic phase with brine, it was dried over magnesium sulfate. After concentrating the residue was dissolved in methanol followed by addition of 4.3 g of magnesium monoperoxyterephthalate and 2.9 g of potassium dihydrogen phosphate and stirring for 24 hours at room temperature. Work-up was done in the same manner as Step 5 of Example 1 to obtain a product. This residue was dissolved in ethyl acetate followed by suspending of 10% palladium-carbon therein and stirring for 12 hours under hydrogen gas atmosphere at 1 atm. After filtering out the catalyst, the filtrate was concentrated and the residue was dissolved in dichloromethane followed by addition of 44 mg of dicyclohexylcarbodiimide, 28 mg of 2-piperazinoethanol and 37 mg of dimethylaminopyridine and stirring for 24 hours at room temperature. The reaction mixture was extracted with ethyl acetate and the organic phase was washed with brine. After drying with magnesium sulfate, the organic phase was concentrated and the residue was purified by silica gel chromatography to obtain a colorless oil I-304 (12 mg) from the hexane-ether eluate. The physiochemical properties of this compound are described in Table 64, Compound No. I-304.

Example 46

A known Compound No. III-10 shown in Table 74 was converted to a colorless oil II-26 according to the same method as in Step 1 of Example 1. The physicochemical properties of this compound are described in Table 72, Compound No. II-26.

The above Compound No. II-26 was converted to a colorless oil I-305 in accordance with the same method as in Example 8. The physicochemical properties of this compound are described in Table 64, Compound No. I-305.

The above Compound No. I-305 was converted to a colorless powder I-306 according to the same method as in Step 4 of Example 1. The physicochemical properties of this compound are described in Table 64, Compound No. I-306.

Example 47

(Step 1)

A known Compound No. III-11 shown in Table 74 was converted to a colorless oil II-27 according to the same method as in Step 1 of Example 1. The physicochemical properties of this compound are described in Table 72, Compound No. II-27.

(Step 2)

Compound No. II-27 obtained above (4.35 g) was dissolved in dichloromethane followed by addition of 5.65 ml of diisopropylethylamine and 2.22 ml of methoxyethoxymethylchloride and stirring for 12 hours at room temperature. The reaction mixture was poured into water and extracted with ethyl acetate. After washing the organic phase with saturated aqueous sodium bicarbonate and brine, it was dried over magnesium sulfate. After concentration, the residue was purified by silica gel chromatography to obtain a colorless oil II-28 from the hexane-ether eluate. The physicochemical properties of this compound are described in Table 72, Compound No. II-28.

(Step 3)

Compound No. II-28 obtained above was converted to a colorless oil II-29 according to the same method as in Step 3 of Example 1. The physicochemical properties of this compound are described in Table 72, Compound No. II-29.

(Step 4)

Compound No. II-29 obtained above was converted to a colorless oil II-30 according to the same method as in Step 4 of Example 1. Compound No. II-31 was similarly produced from Compound No. II-29. The physicochemical properties of these compounds are described in Table 73, Compound No. II-30 and II-31.

(Step 5)

Compound No. II-30 obtained above was dissolved in tetrahydrofuran followed by addition of dilute hydrochloric acid and stirring for 5 hours at room temperature. The reaction mixture was neutralized to a weakly acidic pH with sodium carbonate and then extracted with ethyl acetate. After drying the organic phase with magnesium sulfate, the organic phase was concentrated and the residue was purified by silica gel chromatography to obtain a colorless powder I-307 from the hexane-ether eluate. A colorless powder I-308 was produced in the same manner from Compound No. II-31 obtained above. The physicochemical properties of these compounds are described in Table 65, Compound No. I-307 and I-308.

Example 48

Compound No. I-307 obtained in Example 47 was converted to amorphous solid I-309 according to the same method as in Example 8. The physicochemical properties of this compound are described in Table 65, Compound No. I-309.

Compound No. I-307 obtained in Example 47 was converted to amorphous solid I-310 according to the same method as in Example 7. The physicochemical properties of this compound are described in Table 65, Compound No. I-310.

Compound No. I-307 obtained in Example 47 was converted to amorphous solid I-311 according to the same method as in Example 7. The physicochemical properties of this compound are described in Table 66, Compound No. I-311.

Compound No. I-307 obtained in Example 47 was converted to colorless needles I-312 according to the same method as in Example 4. The physicochemical properties of this compound are described in Table 66, Compound No. I-312.

Compound No. I-307 obtained in Example 47 was to amorphous solid I-313 according to the same method as in Example 2. The physicochemical properties of this compound are described in Table 66, Compound No. I-313.

TABLE 16

| Compound No. | Structural Formulas | ¹H-NMR (δ ppm in CDCl₃) | MS |
|---|---|---|---|
| I-61 | | 1.44(3H, s), 2.00(1H, br), 2.34(1H, dd, J=7, 10Hz), 2.50–2.60(1H, m), 2.83(1H, dt, J=7, 8Hz), 2.88(3H, d, J=5Hz), 3.31(1H, s), 5.17–5.27(1H, m), 5.72(1H, d, J=10Hz), 5.75(2H, br), 7.23(1H, s) | (EI) m/z; 268(M⁺) |
| I-62 | | 1.38(3H, s), 1.84(1H, dd, J=7, 10Hz), 2.31–2.52(2H, m), 2.83(1H, dt, J=8, 9Hz), 2.87(3H, d, J=5Hz), 3.32(1H, s), 5.07–5.17(1H, m), 5.78(1H, d, J=9Hz), 6.78(1H, s), 6.84(1H, d, J=4Hz), 7.31(1H, d, J=4Hz) | |
| I-63 | | 1.40(3H, s), 1.40–1.52(1H, m), 2.67(1H, dd, J=7, 10Hz), 2.47–2.71(1H, m), 2.78(3H, s), 2.87(1H, dt, J=8, 9Hz), 3.31(1H, s), 4.66(2H, s), 5.68(1H, d, J=10Hz), 7.16–7.21(2H, m), 7.30(1H, s), 7.48–7.53(2H, m) | |
| I-64 | | 1.44(3H, s), 1.51(1H, dd, J=7, 10Hz), 2.34(1H, dd, J=7, 10Hz), 2.39–2.60(1H, m), 2.79–2.87(4H, m), 2.88(3H, d, J=5Hz), 3.31(1H, s), 3.50–3.70(2H, m), 5.11–5.21(1H, m), 5.72(1H, d, J=10Hz), 6.38–6.46(1H, m), 7.44(1H, d, J–1Hz) | (EI) m/z; 328(M⁺) |

TABLE 16-continued

| Compound No. | Structural Formulas | $^1$H-NMR ($\delta$ ppm in CDCl$_3$) | MS |
|---|---|---|---|
| I-65 | | 1.29(3H, t, J=7Hz), 1.44(3H, s), 2.36(1H, dd, J=7, 10Hz), 2.52–2.63(1H, m), 2.86(1H, dt, J=8, 9Hz), 2.89(3H, d, J=5Hz), 3.31(1H, s), 4.05–4.17(2H, m), 4.23(2H, q, J=7Hz), 4.90–5.00(1H, m), 5.73(1H, d, J=10Hz), 5.94–6.02(1H, m), 7.24(1H, s) | (EI) m/z; 354(M$^+$) |

TABLE 17

| Compound No. | Structural Formulas | $^1$H-NMR ($\delta$ ppm in CDCl$_3$) | MS |
|---|---|---|---|
| I-66 | | 1.25(3H, s), 1.91–1.95(2H, m), 2.12(1H, dd, J=7, 10Hz), 2.35–2.46(1H, m), 2.60(1H, dt, J=8, 9Hz), 3.18(1H, s), 3.35–3.62(4H, m), 5.64(1H, d, J=10Hz), 7.03(1H, br), 7.28(1H, s) | |
| I-67 | | 1.47(3H, s), 1.50–1.63(1H, m), 2.42–2.80(3H, m), 3.35–3.79(5H, m), 5.69(1H, d, J=10Hz), 7.17(1H, s) | |
| I-68 | | 1.45(3H, s), 1.49–1.63(2H, m), 2.36–2.60(8H, m), 2.96(1H, dt, J=7, 8Hz), 3.29(1H, s), 3.58–3.66(10H, m), 5.36–549(1H, m), 5.73(1H, d, 10Hz), 6.50(1H, d, J=1Hz) | (EI) m/z; 429(M$^+$) |

TABLE 17-continued

| Compound No. | Structural Formulas | $^1$H-NMR (δ ppm in CDCl$_3$) | MS |
|---|---|---|---|
| I-69 | | 1.56(3H, s), 1.91–1.98(1H, m), 2.17–2.28(1H, m), 2.67–2.77(1H, m), 3.03(1H, t, J=9Hz), 3.47–3.69(5H, m), 6.34(1H, s), 6.94(1H, s) | |
| I-70 | | 1.78(3H, d, J=1Hz), 2.07–2.22(1H, m), 2.64–2.80(2H, m), 3.21(1H, dt, J=7, 8Hz), 3.73(3H, s), 4.90(2H, br), 5.53(1H, br), 5.88(1H, d, J=6Hz), 7.45(1H, d, J=1Hz) | (EI) m/z; 222(M$^+$—OMe) |

TABLE 18

| Compound No. | Structural Formulas | $^1$H-NMR (δ ppm in CDCl$_3$) | MS |
|---|---|---|---|
| I-71 | | 1.78(3H, s), 2.07–2.22(1H, m), 2.50–2.86(9H, m), 3.22(1H, dt, J=7, 8Hz), 3.56(4H, t, J=7Hz), 3.64(2H, t, J=5Hz), 3.73(3H, s), 5.54(1H, br), 5.86(1H, d, J=7Hz), 7.46(1H, d, J=1Hz) | (EI) m/z; 366(M$^+$) |
| I-72 | | 0.89(3H, t, J=7Hz), 1.25–1.39(6H, m), 1.48–1.56(2H, m), 1.77(3H, br), 2.08–2.20(1H, m), 2.60–2.85(2H, m), 3.14–3.27(3H, m), 3.72(3H, s), 4.78–4.82(1H, m), 5.52(1H, br), 5.87(1H, d, J=7Hz), 7.45(1H, s) | (EI) m/z; 306(M$^+$—OMe) |

TABLE 18-continued

| Compound No. | Structural Formulas | $^1$H-NMR (δ ppm in CDCl$_3$) | MS |
|---|---|---|---|
| I-73 | | 1.76(3H, br), 2.01–2.21(1H, m), 2.31(3H, s), 2.58–2.89(10H, m), 3.20(1H, dt, J=7, 8Hz), 3.72(3H, s), 5.52(1H, br), 5.83(1H, br), 5.91(1H, d, J=6Hz), 7.43(1H, s) | (EI) m/z; 351(M$^+$) |
| I-74 | | 1.77(3H, br), 2.09–2.14(1H, m), 2.64–2.85(2H, m), 3.20(1H, dt, J=7, 8Hz), 3.72(3H, s), 4.36(2H, d, J=6Hz), 5.24–5.36(1H, m), 5.53(1H, br), 5.93(1H, d, J=6Hz), 7.14(1H, dd, J=2, 9Hz), 7.40(1H, s), 7.41(2H, d, J=9Hz) | |
| I-75 | | 1.78(3H, br), 2.06–2.22(1H, m), 2.68–2.85(2H, m), 3.21(1H, dt, J=7, 8Hz), 3.72(3H, s), 4.54(2H, d, J=5Hz), 5.52(1H, br), 5.92(1H, d, J=6Hz), 6.20–6.32(1H, m), 7.18–7.30(2H, m), 7.45(1H, dJ=1Hz), 7.68(1H, dt, J=2, 8Hz), 8.55(1H, d, J=5Hz) | (EI) m/z; 344(M$^+$) |

TABLE 19

| Compound No. | Structural Formulas | $^1$H-NMR (δ ppm in CDCl$_3$) | MS |
|---|---|---|---|
| I-76 | | 1.76(3H, br), 2.08–2.20(1H, m), 2.64–2.84(2H, m), 3.18(1H, dt, J=7, 8Hz), 3.72(3H, s), 4.43(2H, d, J=6Hz), 5.52(1H, br), 5.74–5.86(1H, m), 5.94(1H, d, J=6Hz), 7.67–7.31(1H, m), 7.44(1H, s), 7.67(1H, d, J=8Hz), 8.51(1H, d, J=1Hz), 8.53(1H, s) | (EI) m/z; 344(M$^+$) |

TABLE 19-continued

| Compound No. | Structural Formulas | $^1$H-NMR ($\delta$ ppm in CDCl$_3$) | MS |
|---|---|---|---|
| I-77 | | 1.75(3H, s), 2.05–2.20(1H, m), 2.62–2.85(2H, m), 3.19(1H, dt, J=7, 8Hz), 3.72(3H, s), 4.41(2H, d, J=6Hz), 5.25–5.35(1H, m), 5.52(1H, br), 5.91(1H, d, J=6Hz), 6.77–6.91(2H, m), 7.28–7.40(1H, m), 7.43(1H, d, J=1Hz) | |
| I-78 | | 1.50–1.60(1H, m), 1.77(3H, s), 1.83–2.20(4H, m), 2.61–2.85(2H, m), 3.09–3.21(2H, m), 3.42–3.47(1H, m), 3.72(3H, s), 3.77–4.01(3H, m), 5.24(1H, t, J=6Hz), 5.52(1H, s), 5.87(1H, d, J=7Hz), 7.45(1H, s) | (FAB) m/z; 338(M$^+$) |
| I-79 | | 1.74(3H, s), 2.08–2.18(1H, m), 2.62(1H, t, J=7Hz), 2.72–2.84(1H, m), 3.02(2H, t, J=6Hz), 3.19(1H, dt, J=7, 8Hz), 3.66(2H, dt, J=6.0, 6.5Hz), 3.72(3H, s), 5.52(1H, s), 5.78–5.81(1H, m), 5.85(1H, d, J=7Hz), 7.15–7.19(2H, m), 7.44(1H, s), 7.63(1H, td, J=2, 8Hz), 8.53–8.56(1H, m) | (FAB) m/z; 359(M$^+$) |
| I-80 | | 1.77(3H, s), 2.02–2.21(1H, m), 2.62–2.85(2H, m), 3.19(1H, dt, J=7, 8Hz), 3.72(3H, s), 4.42(2H, d, J=6Hz), 5.19(1H, t, J=6Hz), 5.53(1H, s), 5.93(1H, d, J=6Hz), 7.26–7.36(5H, m), 7.45(1H, d, J=1Hz) | (FAB) m/z; 344(M$^+$) |

TABLE 20

| Compound No. | Structural Formulas | $^1$H-NMR (δ ppm in CDCl$_3$) | MS |
|---|---|---|---|
| I-81 | | 1.73(3H, s), 2.04–2.16(1H, m), 2.74–2.78(2H, m), 2.95(3H, s), 3.09–3.21(1H, m), 3.67(3H, s), 4.41(1H, d, J=15Hz), 4.54(1H, d, J=15Hz), 5.54(1H, br), 5.90(1H, d, J=6Hz), 7.23–7.36(5H, m), 7.40(1H, s) | (FAB) m/z; 358(MH$^+$) |
| I-82 | | 1.75(3H, s), 2.06–2.26(1H, m), 2.61(1H, t, J=7Hz), 2.72–2.86(1H, m), 2.89(2H, t, J=7Hz), 3.18(1H, dt, J=7, 8Hz), 3.43–3.55(2H, m), 3.72(3H, s), 4.93(1H, t, J=6Hz), 5.52(1H, s), 5.85(1H, d, J=7Hz), 6.99–7.26(4H, m), 7.45(1H, d, J=1Hz) | (FAB) m/z; 376(MH$^+$) |
| I-83 | | 1.76(3H, s), 2.08–2.20(1H, m), 2.61–2.85(2H, m), 3.19(1H, dt, J=7, 8Hz), 3.72(3H, s), 3.80(3H, s), 4.34(2H, d, J=6Hz), 5.12(1H, t, J=6Hz), 5.52(1H, s), 5.92(1H, d, J=6Hz), 6.88(2H, d, J=9Hz), 7.22(2H, d, J=9Hz), 7.45(1H, s) | (FAB) m/z; 374(MH$^+$) |
| I-84 | | 1.77(3H, s), 1.93(1H, br), 2.08–2.21(1H, m), 2.63–2.85(2H, m), 3.20(1H, dt, J=7, 8Hz), 3.40(2H, dt, J=5, 6Hz), 3.72(3H, s), 3.72–3.79(2H, m), 5.31(1H, s), 5.53(1H, s), 5.89(1H, d, J=6Hz), 7.45(1H, s) | (FAB) m/z; 298(MH$^+$) |
| I-85 | | 1.78(3H, s), 2.07–2.22(1H, m), 2.64–2.86(2H, m), 3.22(1H, dt, J=7, 8Hz), 3.51–3.55(4H, m), 3.64–3.75(4H, m), 3.73(3H, s), 5.54(1H, s), 5.91(1H, d, J=4Hz), 7.46(1H, d, J=1Hz) | (FAB) m/z; 324(MH$^+$) |

TABLE 21

| Compound No. | Structural Formulas | $^1$H-NMR (δ ppm in $CDCl_3$) | MS |
|---|---|---|---|
| I-86 | | 1.73(3H, d, J=1Hz), 2.12–2.21(1H, m), 2.16(6H, s), 2.39(2H, t, J=7Hz), 2.71–2.78(2H, m), 2.88(3H, s), 3.12–3.40(3H, m), 3.64(3H, s), 5.52(1H, s), 5.84(1H, d, J=6Hz), 7.38(1H, s) | (FAB) m/z; 339($MH^+$) |
| I-87 | | 0.93(6H, d, J=7Hz), 1.69–1.89(1H, m), 1.77(3H, s), 2.07–2.20(1H, m), 2.60–2.86(2H, m), 3.05(2H, t, J=7Hz), 3.20(1H, dt, J=7, 8Hz), 3.72(3H, s), 4.90(1H, s), 5.53(1H, s), 5.87(1H, d, J=7Hz), 7.45(1H, d, J=1Hz) | (FAB) m/z; 310($MH^+$) |
| I-88 | | 0.84–1.00(2H, m), 1.16–1.33(3H, m), 1.44–1.51(1H, m), 1.70–1.76(8H, m), 1.07–2.20(1H, m), 2.59–2.85(2H, m), 3.06(2H, t, J=6.5Hz), 3.20(1H, dt, J=7, 8Hz), 3.72(3H, s), 4.89(1H, br), 5.52(1H, s), 5.87(1H, d, J=7Hz), 7.45(1H, d, J=1Hz) | (FAB) m/z; 350($MH^+$) |
| I-89 | | 1.45–1.64(2H, m), 1.76(3H, s), 1.91–2.19(5H, m), 2.60–2.84(4H, m), 3.20(1H, dt, J=7, 8Hz), 3.35–3.51(1H, m), 3.50(2H, s), 3.72(3H, s), 4.76(1H, d, J=8Hz), 5.52(1H, s), 5.87(1H, d, J=6.5Hz), 7.26–7.35(5H, m), 7.44(1H, d, J=1Hz) | (FAB) m/z; 427($MH^+$) |
| I-90 | | 0.83(3H, t, J=7.5Hz), 1.52(2H, q, J=7.5Hz), 1.72(3H, s), 2.00–2.15(1H, m), 2.65–2.77(2H, m), 2.86(3H, s), 2.96–3.32(3H, m), 3.65(3H, s), 5.52(1H, s), 5.81(1H, d, J=6.5Hz), 7.38(1H, s) | (FAB) m/z; 310($MH^+$) |

TABLE 22

| Compound No. | Structural Formulas | $^1$H-NMR (δ ppm in CDCl$_3$) | MS |
|---|---|---|---|
| I-91 | | 1.78(3H, s), 2.10–2.21(3H, m), 2.65–2.96(2H, m), 3.23(1H, dt, J=7.0, 8.0Hz), 3.51–3.66(2H, m), 3.73(3H, s), 3.98(2H, s), 5.30(1H, s), 5.53–5.84(1H, m), 5.87–5.95(2H, m), 7.46(1H, s) | (FAB) m/z; 320(MH$^+$) |
| I-92 | | 1.76(3H, s), 2.07–2.19(1H, m), 2.62(1H, t, J=7Hz), 2.72–2.91(1H, m), 3.07(2H, t, J=7Hz), 3.19(1H, dt, J=7.0, 7.5Hz), 3.42–3.60(2H, m), 3.72(3H, s), 4.99(1H, t, J=5Hz), 5.53(1H, s), 5.87(1H, d, J=7Hz), 6.84(1H, d, J=3Hz), 6.96(1H, d, J=4Hz), 5.68(1H, dd, J=1, 5Hz), 7.44(1H, s) | (FAB) m/z; 364(MH$^+$) |
| I-93 | | 2.02(3H, s), 2.07–2.15(1H, m), 2.65–2.78(2H, m), 2.93(3H, s), 3.14(1H, dt, J=7.0, 8.0Hz), 3.37(2H, t, J=4Hz), 3.66(3H, s), 3.75–3.83(2H, m), 3.86–3.95(2H, m), 4.96(1H, t, J=4.5Hz), 5.52(1H, s), 5.82(1H, d, J=6Hz), 7.38(1H, s) | (FAB) m/z; 354(MH$^+$) |
| I-94 | | 1.09–1.25(2H, m), 1.59–1.86(6H, m), 2.08–2.18(1H, m), 2.53–2.85(6H, m), 3.15–3.26(1H, m), 3.72(3H, s), 4.08–4.23(2H, m), 5.53(1H, br), 5.83–5.86(1H, m), 7.12–7.34(5H, m), 7.46(1H, d, J=4Hz) | (FAB) m/z; 412(MH$^+$) |
| I-95 | | 1.10(3H, t, J=7Hz), 1.77(3H, s), 2.07–2.21(1H, m), 2.27–2.53(2H, m), 2.44(2H, q, J=7Hz), 2.63–2.86(2H, m), 3.16–3.28(1H, m), 3.53–3.58(4H, m), 3.73(3H, s), 5.54(1H, br), 5.86(1H, d, J=7Hz), 7.46(1H, d, J=1Hz) | (FAB) m/z; 351(MH$^+$) |

TABLE 23

| Compound No. | Structural Formulas | $^1$H-NMR (δ ppm in CDCl$_3$) | MS |
|---|---|---|---|
| I-96 | | 1.77(3H, s), 2.08–2.20(1H, m), 2.62–2.85(2H, m), 3.15–3.26(1H, m), 3.33–3.44(2H, m), 3.41(6H, s), 4.41(1H, t, J=5Hz), 5.10(1H, t, J=6Hz), 5.52(1H, br), 5.88(1H, d, J=6Hz), 7.44(1H, d, J=1Hz) | (FAB) m/z; 342(MH$^+$) |
| I-97 | | 1.16(3H, t, J=7Hz), 1.78(3H, s), 2.13–2.23(1H, m), 2.51(1H, br), 2.67–2.85(2H, m), 3.17–3.61(5H, m), 3.73(3H, s), 3.73–3.80(2H, m), 5.53(1H, br), 5.96(1H, d, J=6Hz), 7.44(1H, s) | (FAB) m/z; 326(MH$^+$) |
| I-98 | | 1.75(3H, s), 2.07–2.19(1H, m), 2.61(1H, t, J=7Hz), 2.70–2.85(1H, m), 2.78(2H, t, J=6Hz), 3.18(1H, q, J=7Hz), 3.45(2H, q, J=6Hz), 3.72(3H, s), 3.80(3H, s), 4.86(1H, t, J=6Hz), 5.52(1H, br), 5.86(1H, d, J=7Hz), 6.82–6.89(2H, m), 7.09–7.13(2H, m), 7.45(1H, d, J=1Hz) | (FAB) m/z; 388(MH$^+$) |
| I-99 | | 1.75(3H, s), 2.07–2.20(1H, m), 2.62(1H, t, J=7Hz), 2.73–2.81(1H, m), 2.85(2H, t, J=6Hz), 3.18(1H, q, J=7Hz), 3.48(2H, q, J=6Hz), 3.72(3H, s), 4.91(1H, t, J=6Hz), 5.53(1H, br), 5.86(1H, d, J=7Hz), 6.87–6.99(3H, m), 7.22–7.36(1H, m), 7.44(1H, d, J=1Hz) | (FAB) m/z; 376(MH$^+$) |
| I-100 | | 1.74(3H, s), 2.05–2.18(1H, m), 2.62(1H, t, J=7Hz), 2.72–2.85(3H, m), 3.18(1H, q, J=7Hz), 3.45(2H, q, J=6Hz), 3.73(3H, s), 4.93(1H, t, J=6Hz), 5.52(1H, br), 5.64(1H, br), 5.87(1H, d, J=7Hz), 6.76–6.82(2H, m), 7.01–7.07(2H, m), 7.44(1H, s) | (FAB) m/z; 374(MH$^+$), 372(M—H)$^-$ |

TABLE 24

| Compound No. | Structural Formulas | ¹H-NMR (δ ppm in CDCl₃) | MS |
| --- | --- | --- | --- |
| I-101 | | 1.77(3H, s), 2.00–2.21(2H, m), 2.62–2.85(2H, m), 3.15–3.26(1H, m), 3.41–3.48(2H, m), 3.57–3.65(4H, m), 3.70–8.00(2H, m), 3.73(3H, s), 5.35(1H, t, J=6Hz), 5.52(1H, br), 5.89(1H, d, J=7Hz), 7.45(1H, d, J=1Hz) | (FAB) m/z; 342(MH⁺) |
| I-102 | | 0.91(3H, t, J=7.5Hz), 0.93(3H, t, J=7.5Hz), 1.10–1.60(4H, m), 1.77(3H, s), 2.05–2.20(1H, m), 2.63(1H, t, J=7.0Hz), 2.70–2.85(1H, m), 3.20(1H, dt, J=8.0, 7.0Hz), 3.38–3.61(1H, m), 3.73(3H, s), 4.58(1H, d, J=9.6Hz), 5.53(1H, s), 5.86(1H, d, J=7.0Hz), 7.46(1H, d, J=1.0Hz). | (FAB) m/z; 324(MH⁺) |
| I-103 | | 1.76(3H, s), 1.40–2.20(14H, m), 2.60–2.80(2H, m), 3.20(1H, dt, J=7.5, 7.0Hz), 3.72(3H, s), 4.81(1H, d, J=8.5Hz), 5.52(1H, s), 5.87(1H, d, J=6.5Hz), 7.45(1H, d, J=1.0Hz). | (FAB) m/z; 350(MH⁺) |
| I-104 | | 1.40–1.70(7H, m), 1.77(3H, s), 2.08–2.26(1H, m), 2.64(1H, t, J=7.0Hz), 2.79(1H, dd, J=7.5, 16.0Hz), 3.03–3.35(3H, m), 3.66(2H, t, J=6.0Hz), 3.72(3H, s), 4.91(1H, t, J=6.0Hz), 5.52(1H, s), 5.87(1H, d, J=6.5Hz), 7.45(1H, d, J=1.0Hz). | (FAB) m/z; 340(MH⁺) |
| I-105 | | 1.70(2H, quint, J=6.5Hz), 1.77(3H, s), 2.11–2.24(1H, m), 2.24(6H, s), 2.40(2H, t, J=6.5Hz), 2.62(1H, t, J=7.5Hz), 2.79(1H, dd, J=16.5, 8.0Hz), 3.20(1H, q, J=8.0Hz), 3.32(2H, q, J=6.0Hz), 3.72(3H, s), 5.53(1H, s), 5.82(1H, d, J=7.0Hz), 6.18(1H, t, J=5.0Hz), 7.46(1H, d, J=1.0Hz). | (FAB) m/z; 339(MH⁺) |

TABLE 25

| Compound No. | Structural Formulas | $^1$H-NMR (δ ppm in CDCl$_3$) | MS |
| --- | --- | --- | --- |
| I-106 | | 1.77(3H, s), 2.05–2.21(1H, m), 2.63–2.85(2H, m), 3.20(1H, dt, J=7.5, 7.0Hz), 3.72(3H, s), 4.41(2H, d, J=6.0Hz), 5.24(1H, t, J=6.0Hz), 5.53(1H, s), 5.93(1H, d, J=6.5Hz), 7.20(2H, d, J=8.5Hz), 7.33(2H, d, J=8.5Hz), 7.45(1H, d, J=1.0Hz). | (FAB) m/z; 428(MH$^+$) |
| I-107 | | 1.75(3H, s), 2.08–2.20(1H, m), 2.62(1H, t, J=7.0Hz), 2.74–2.82(1H, m), 2.82(2H, t, J=7.0Hz), 3.18(1H, q, J=7.5Hz), 3.46(2H, dd, J=7.0, 13.5Hz), 3.72(3H, s), 4.88(1H, t, J=5.5Hz), 5.53(1H, br), 5.86(1H, d, J=6.5Hz), 6.96–7.04(2H, m), 7.12–7.19(2H, m), 7. | (FAB) m/z; 376(MH$^+$), 193 |
| I-108 | | 1.76(3H, s), 2.08–2.20(1H, m), 2.62–2.84(2H, m), 3.19(1H, dt, J=7.0, 7.5Hz), 3.72(3H, s), 4.37(2H, d, J=6.0Hz), 5.26(1H, t, J=5.5Hz), 5.53(1H, br), 5.92(1H, d, J=6.5Hz), 6.98–7.07(2H, m), 7.24–7.30(2H, m), 7.44(1H, s) | (FAB) m/z; 362(MH$^+$), 193 |
| I-109 | | 1.76(3H, s), 2.04–2.21(1H, m), 2.62–2.84(2H, m), 3.19(1H, dt, J=7.0, 7.5Hz), 3.72(3H, s), 4.38(2H, d, J=6.0Hz), 5.23(1H, t, J=5.5Hz), 5.53(1H, br), 5.92(1H, d, J=6.5Hz), 7.21–7.34(4H, m), 7.44(1H, s) | (FAB) m/z; 378(MH$^+$), 193 |
| I-110 | | 1.76(3H, d, J=1.0Hz), 2.08–2.20(1H, m), 2.62–2.84(2H, m), 3.19(1H, q, J=7.5Hz), 3.72(3H, s), 4.40(1H, dd, J=1.5, 5.5Hz), 5.24(1H, t, J=5.5Hz), 5.52(1H, br), 5.92(1H, d, J=6.5Hz), 6.25(1H, d, J=3.0Hz), 6.33(1H, dd, J=2.0, 3.0Hz), 7.37(1H, d, J=1.0Hz), 7.44(1H, d, J=1.0Hz) | (FAB) m/z; 334(MH$^+$), 193 |

TABLE 26

| Compound No. | Structural Formulas | ¹H-NMR (δ ppm in CDCl₃) | MS |
| --- | --- | --- | --- |
| I-111 | | 1.43–1.66(6H, m), 1.77(3H, d, J=1.5Hz), 2.06–2.21(1H, m), 2.66(1H, t, J=7.0Hz), 2.74–2.86(1H, m), 3.21(1H, dt, J=7.0, 8.0Hz), 3.45–3.66(4H, m), 3.73(3H, s), 5.54(1H, br), 5.85(1H, d, J=7.0Hz), 7.46(1H, d, J=1.0Hz) | (FAB) m/z; 322(MH⁺), 193 |
| I-112 | | 1.76(3H, s), 1.87(2H, quint, J=7.5Hz), 2.08–2.30(1H, m), 2.62–2.85(4H, m), 3.19(1H, q, J=7.0Hz), 3.26(2H, dd, J=7.0, 13.0Hz), 3.72(3H, s), 4.91(1H, t, J=5.5Hz), 5.52(1H, br), 5.87(1H, d, J=6.5Hz), 7.16–7.34(m, 5H), 7.45(1H, d, J=1.0Hz) | (FAB) m/z; 372(MH⁺), 193 |
| I-113 | | 0.50–0.63(2H, m), 0.67–0.82(2H, m), 1.76(3H, s), 2.08–2.21(1H, m), 2.62–2.66(2H, m), 2.73–2.85(1H, m), 3.19(1H, dt, J=7.0, 7.5Hz), 3.72(3H, s), 5.08(1H, br), 5.52(1H, br), 5.89(1H, d, J=6.5Hz), 7.44(1H, d, J=0.5Hz) | (FAB) m/z; 294(MH⁺), 193 |
| I-114 | | 1.78(3H, s), 2.07–2.22(1H, m), 2.62–2.94(6H, m), 3.22(1H, dt, J=7.0, 8.0Hz), 3.73(3H, s), 3.75–3.81(4H, m), 5.55(1H, br), 5.88(1H, d, J=7.0Hz), 7.45(1H, d, J=1.0Hz) | (FAB) m/z; 340(MH⁺), 193 |
| I-115 | | 1.74(3H, s), 2.07–2.20(1H, m), 2.61(1H, t, J=7.0Hz), 2.72–2.84(1H, m), 3.01(2H, t, J=6.5Hz), 3.17(1H, dt, J=7.5, 8.5Hz), 3.60(2H, q, J=6.5Hz), 3.72(3H, s), 4.94(1H, t, J=5.5Hz), 5.52(1H, br), 5.88(1H, d, J=6.5Hz), 7.04–7.22(3H, m), 7.37–7.45(2H, m), 7.61(1H, d, J=8.0Hz), 8.06(1H, br) | (FAB) m/z; 396(M⁺) |

TABLE 27

| Compound No. | Structural Formulas | ¹H-NMR (δ ppm in CDCl₃) | MS |
|---|---|---|---|
| I-116 | | 1.78(3H, s), 2.09–2.21(1H, m), 2.66–2.85(2H, m), 3.20(1H, dt, J=7.0, 7.5Hz), 3.73(3H, s), 4.44(2H, d, J=6.5Hz), 5.54–5.58(2H, m), 5.94(1H, d, J=6.5Hz), 7.22(2H, d, J=6.0Hz), 7.45(1H, d, J=1.0Hz), 8.56–8.59(2H, m) | FAB m/z; 345(MH⁺) |
| I-117 | | 1.77(3H, m), 2.05–2.13(1H, m), 2.15–2.28(1H, m), 2.24(6H, s), 2.44(2H, t, J=7.0Hz), 2.57–2.85(2H, m), 3.20(1H, dt, J=7.0, 7.5Hz), 3.30(1H, dt, J=5.5, 6.0Hz), 3.72(3H, s), 5.40–5.60(2H, m), 5.88(1H, d, J=6.5Hz), 7.45(1H, d, J=1.0Hz) | (FAB) m/z; 325(MH⁺) |
| I-118 | | 1.44–1.61(6H, m), 1.78(3H, s), 2.06–2.20(1H, m), 2.30–2.54(6H, m), 2.62–2.85(2H, m), 3.21(1H, dt, J=7.0, 8.0Hz), 3.31(2H, dt, J=5.5, 6.0Hz), 3.73(3H, s), 5.45–5.60(2H, m), 5.87(1H, d, J=7.0Hz), 7.46(1H, d, J=1.0Hz) | (FAB) m/z; 365(MH⁺) |
| I-119 | | 1.75(3H, s), 2.07–2.19(1H, m), 2.58–2.65(1H, m), 2.72–2.77(1H, m), 2.85(2H, t, J=7.0Hz), 3.18(1H, dt, J=7.0, 8.0Hz), 3.44–3.55(2H, m), 3.72(3H, s), 4.89(1H, t, J=6.0Hz), 5.53(1H, br), 5.86(1H, d, J=6.5Hz), 7.18–7.37(5H, m), 7.45(1H, d, J–1.0Hz) | (FAB) m/z; 358(MH⁺), 193 |
| I-120 | | 1.78(3H, d, J=2.0Hz), 2.10–2.22(1H, m), 2.75–2.92(4H, m), 3.25(1H, q, J=7.5Hz), 3.70–3.78(2H, m), 3.73(3H, s), 4.66(2H, s), 5.54(1H, br), 5.93(1H, dd, J=2.0, 6.5Hz), 7.08–7.25(4H, m), 7.46(1H, s) | (FAB) m/z; 370(MH⁺), 193 |

TABLE 28

| Compound No. | Structural Formulas | $^1$H—NMR (δ ppm in CDCl$_3$) | MS |
|---|---|---|---|
| I-121 | 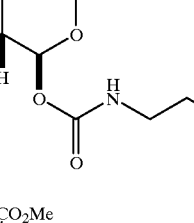 | 1.77–1.86(2H, m), 1.77(3H, s), 2.07–2.20(1H, m), 2.59–2.67(1H, m), 2.73–2.85(1H, m), 3.20(1H, q, J=7.5Hz), 3.30–3.39(2H, m), 3.34 (3H, s), 3.47(2H, t, J=6.0Hz), 3.72(3H, s), 5.33(1H, t, J=5.5Hz), 5.52(1H, br), 5.85 (1H, d, J=7.0 Hz), 7.45(1H, d, J=1.0Hz) | (FAB) m/z ; 326 (MH$^+$), 193 |
| I-122 | 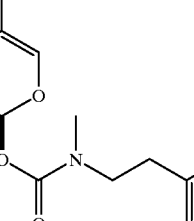 | 1.71(3H, s), 2.03–2.14(1H, m), 2.64–2.77(4H, m), 2.83 (3H, s), 3.14 (1H, dt, J=6.0, 8.0Hz), 3.44 (2H, dd, J=7.0, 12.5Hz), 3.65(3H, s), 3.72(3H, s), 3.75(3H, s), 5.51 (1H, br), 5.82(1H, d, J=5.5Hz), 6.67–6.86(3H, m), 7.37(1H, s) | (FAB) m/z ; 431 (MH$^+$) |
| I-123 | 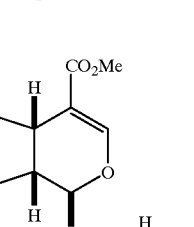 | 1.77(3H, d, J=1.0Hz), 2.06–2.21 (1H, m), 2.61–2.85(2H, m), 3.20 (1H, dt, J=7.0, 8.0Hz), 3.72(3H, s), 3.86(2H, t, J=6.0Hz), 4.94–5.01(1H, m), 5.14–5.27(2H, m), 5.53 (1H, br), 5.76–5.96(2H, m), 5.89 (1H, d, J=6.5Hz), 7.45(1H, d, J=1.0Hz) | (FAB) m/z ; 294 (MH$^+$), 193 |
| I-124 | 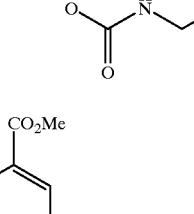 | 1.67–1.76(2H, m), 1.77(3H, s), 2.07–2.20(1H, m), 2.44–2.50(6H, m), 2.59–2.66(1H, m), 2.73–2.86(1H, m), 3.20(1H, dt, J=7.5, 8.0Hz), 3.34(2H, q, J=6.0Hz), 3.68–3.72 (4H, m), 3.72(3H, s), 5.53(1H, br), 5.83(1H, d, J=7.0Hz), 6.35–6.39(1H, m), 7.45(1H, d, J=1.0 Hz) | (FAB) mz/ ; 381 (MH$^+$) |
| I-125 | 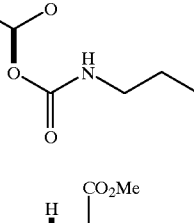 | 1.7(3H, d, J=1.5Hz), 2.09–2.22 (1H, m), 2.67–2.86(2H, m), 3.21 (1H, ddd, J=1.0, 8.0, 14.0Hz), 3.72(3H, s), 3.89(4H, dd, J=6.0, 12.5Hz), 5.09–5.22(4H, m), 5.52 (1H, d, J=1.5Hz), 5.65–5.92(2H, m), 5.95(1H, d, J=6.5Hz), 7.44 (1H, d, J=1.0Hz) | (FAB) m/z ; 334 (MH$^+$), 193 |

TABLE 29

| Compound No. | Structural Formulas | $^1$H—NMR (δ ppm in CDCl$_3$) | MS |
|---|---|---|---|
| I-126 | | 1.75(3H, s), 2.08–2.21(1H, m), 2.62–2.85(2H, m), 3.19(1H, q, J=7.5 Hz), 3.72(3H, s), 4.46(2H, d, J=6.0Hz), 5.29(1H, t, J=6.0Hz), 5.51(1H, br), 5.91(1H, d, J=6.5 Hz), 7.01–7.16(2H, m), 7.23–7.39 (2H, m), 7.43(1H, d, J=1.0Hz) | (FAB) m/z ; 362 (MH$^+$), 193 |
| I-127 | | 1.77(3H, s), 2.08–2.22(1H, m), 2.64–2.85(2H, m), 3.20(1H, q, J=7.5 Hz), 3.72(3H, s), 4.41(2H, d, J=6.5Hz), 5.28(1H, t, J=6.5Hz), 5.53(1H, br), 5.93(1H, d, J=6.5 Hz), 6.98–7.09(3H, m), 7.29–7.38 (1H, m), 7.45(1H, d, J=0.5Hz) | (FAB) m/z ; 362 (MH$^+$), 193 |
| I-128 | | 1.77(3H, s), 2.08–2.21(1H, m), 2.64–2.85(2H, m), 3.20(1H, dt, J=7.0, 7.5Hz), 3.72(3H, s), 4.48(2H, dd, J=3.0, 6.0Hz), 5.31(1H, t, J=6.0Hz), 5.53(1H, br), 5.94(1H, d, J=6.5Hz), 7.45–7.58(5H, m) | (FAB) m/z ; 412 (MH$^+$), 193 |
| I-129 | | 1.76(3H, s), 2.08–2.21(1H, m), 2.62–2.84(2H, m), 3.19(1H, dt, J=7.0, 7.5Hz), 3.72(3H, s), 4.31(2H, d, J=6.0Hz), 5.16(1H, t, J=6.0 Hz), 5.52(1H, br), 5.92(1H, d, J=6.5Hz), 5.95(2H, s), 6.75–6.79 (3H, m), 7.44(1H, d, J=1.0Hz) | (FAB) m/z ; 387 (M$^+$), 193 |
| I-130 | | 1.79(3H, s), 2.10–2.23(1H, m), 2.67–2.88(2H, m), 3.19–3.32(5H, m), 3.67–3.73(4H, m), 3.73(3H, s), 5.55(1H, br), 5.91(1H, d, J=7.0 Hz), 7.05–7.15(3H, m), 7.38(1H, t, J=8.0Hz), 7.46(1H, d, J=1.0 Hz) | (FAB) m/z ; 466 (M$^+$), 193 |

TABLE 30

| Compound No. | Structural Formulas | $^1$H—NMR (δ ppm in CDCl$_3$) | MS |
| --- | --- | --- | --- |
| I-131 | | 1.72(3H, s), 2.08–2.20(1H, m), 2.64–2.84(2H, m), 3.19(1H, dt, J=7.8Hz), 3.72(3H, s), 4.59(2H, d, J=6Hz), 5.51(1H, br), 5.92(1H, d, J=6Hz), 6.77–6.91(1H, m), 7.19–7.31(3H, m), 7.41(1H, d, J=1Hz), 7.54(1H, br), 10.45(1H, br) | (EI) m/z ; 383 (M$^+$) |
| I-132 | | 1.77(3H, br), 2.13–2.22(1H, m), 2.69–2.86(2H, m), 3.21(1H, dt, J=7, 8Hz), 3.73(3H, s), 4.17(1H, d, J=5Hz), 4.20(1H, d, J=5Hz), 5.47–5.60(1H, m), 5.54(1H, br), 5.97(1H, d, J=6Hz), 7.42(1H, d, J=1Hz) | (EI) m/z ; 261 (M$^+$—OMe) |
| I-133 | | 1.78(3H, br), 2.05–2.19(1H, m), 2.65–2.81(2H, m), 3.20(1H, dt, J=7, 8Hz), 3.73(3H, s), 4.44(2H, s), 5.54(1H, br), 5.91(1H, d, J=6Hz), 7.32(1H, s), 7.42(2H, d, J=8Hz), 7.87(2H, d, J=8Hz) | |
| I-134 | | 1.77(3H, br), 2.09–2.20(1H, m), 2.61–2.87(5H, m), 3.20(1H, dt, J=7, 8Hz), 3.56(2H, t, J=6Hz), 3.72(3H, s), 5.30–5.40(1H, m), 5.53(1H, br), 5.86(1H, d, J=7Hz), 7.44(1H, d, J=1Hz) | |
| I-135 | | 1.26(3H, t, J=7Hz), 1.76(3H, s), 1.87(2H, t, J=7Hz), 2.07–2.20(1H, m), 3.37(2H, t, J=7Hz), 2.60–2.85(2H, m), 3.17–3.33(3H, m), 3.72(3H, s), 4.14(2H, q, J=7Hz), 5.06(1H, t, J=6Hz), 5.52(1H, s), 5.86(1H, d, J=7Hz), 7.45(1H, d, J=1Hz) | (FAB m/z ; 368 (MH$^+$) |

TABLE 31

| Compound No. | Structural Formulas | ¹H—NMR (δ ppm in CDCl₃) | MS |
|---|---|---|---|
| I-136 | | 1.78(3H, d, J=2Hz), 2.07–2.22(1H, m), 2.61–2.92(2H, m), 2.96(6H, s), 3.22(1H, dt, J=7, 8Hz), 3.72 (3H, s), 5.53(1H, s), 5.85(1H, d, J=7Hz), 7.46(1H, d, J=1Hz) | (FAB) m/z ; 282 (MH⁺) |
| I-137 | | 1.78(3H, d, J=1Hz), 2.05–2.25(1H, m), 2.68–2.86(2H, m), 3.22(1H, dt, J=7, 8Hz), 3.73(3H, s), 3.78 (3H, s), 5.53(1H, d, J=1Hz), 5.97 (1H, d, J=6Hz), 7.44(1H, d, J= 1Hz), 7.62(1H, s) | (FAB) m/z ; 284 (MH⁺) |
| I-138 | | 1.38–1.78(1H, m), 1.78(3H, s), 1. 84(1H, br), 2.18–2.23(1H, m), 2. 73–2.85(2H, m), 3.21(1H, dt, J=7. 8Hz), 3.48–3.58(4H, m), 3.73(3H, s), 3.74–3.84(2H, m), 3.90(2H, t, J=5Hz), 5.53(1H, s), 5.99(1H, d, J=6Hz), 7.44(1H, d, J=1Hz) | (FAB) m/z ; 342 (MH⁺) |
| I-139 | | 0.17–0.25(2H, m), 0.48–0.58(2H, m), 0.88–1.06(1H, m), 1.78(3H, s), 2.04–2.22(1H, m), 2.61–2.85 (2H, m), 3.09(2H, t, J=6.5Hz), 3. 20(1H, dt, J=7.0, 7.5Hz), 3.72 (3H, s), 4.97(1H, br), 5.52(1H, s), 5.89(1H, d, J=6.5Hz), 7.45 (1H, d, J=1Hz) | (FAB) m/z ; 308 (MH⁺) |
| I-140 | | 1.79(3H, s), 2.17–2.38(1H, m), 2. 58–2.87(4H, m), 3.25(1H, dt, J=7. 0, 7.5Hz), 3.70–3.76(2H, m), 3.73 (3H, s), 4.17(2H, s), 5.30(1H, s), 5.90–6.07(2H, m), 7.26–7.37 (5H, m), 7.47(1H, s) | (FAB) m/z ; 396 (MH⁺) |

TABLE 32

| Compound No. | Structural Formulas | $^1$H—NMR (δ ppm in CDCl$_3$) | MS |
| --- | --- | --- | --- |
| I-141 | | 1.47(3H, t, J=7Hz), 1.79(3H, s), 2.04–2.22(1H, m), 2.65–2.87(2H, m), 3.00–3.15(4H, m), 3.24(1H, dt, J=7, 8Hz), 3.68–3.83(4H, m), 3.73(3H, s), 4.08(2H, q, J=7Hz), 5.55(1H, s), 5.91(1H, d, J=7Hz), 6.84–7.04(4H, m), 7.47(1H, d, J=1Hz) | (FAB) m/z ; 442 (M$^+$) |
| I-142 | | 1.77(3H, s), 1.97–2.20(3H, m), 2.61–2.85(2H, m), 3.15–3.26(1H, m), 3.41(2H, q, J=6Hz), 3.61 (2H, t, J=6Hz), 3.73(3H, s), 5.04(1H, t, J=6Hz), 5.53(1H, br), 5.88(1H, d, J=7Hz), 7.44(1H, d, J=1Hz) | (FAB) m/z ; 330 (MH$^+$) |
| I-143 | | 1.76(3H, s), 2.08–2.21(1H, m), 2.63–2.85(2H, m), 3.14–3.25(1H, m), 3.72(3H, s), 4.36(2H, d, J=6Hz), 5.22(1H, t, J=6Hz), 5.53 (1H, br), 5.92(1H, d, J=6Hz), 7.15–7.20(2H, m), 7.45–7.49(3H, m) | (FAB) m/z ; 422 (MH$^+$) |
| I-144 | | 1.78(3H, s), 2.08–2.21(1H, m), 2.65–2.85(2H, m), 3.16–3.27(1H, m), 3.73(3H, s), 3.78(3H, s), 3.97(1H, dd, J=5, 18Hz), 4.08 (1H, dd, J=5, 18Hz), 5.39(1H, t, J=5Hz), 5.53(1H, br), 5.90 (1H, d, J=6Hz), 7.44(1H, d, J=1 Hz) | (FAB) m/z ; 326 (MH$^+$) |
| I-145 | | 1.75(3H, s), 2.08–2.20(1H, m), 2.60–2.92(4H, m), 3.12–3.38(3H, m), 3.71(3H, s), 4.48–4.64(1H, m), 5.22(1H, d, J=8Hz), 5.52 (1H, br), 5.91(1H, d, J=6Hz), 7.16–7.26(4H, m), 7.44(1H, s) | (FAB) m/z ; 370 (MH$^+$) |

TABLE 33

| Compound No. | Structural Formulas | $^1$H—NMR ($\delta$ ppm in CDCl$_3$) | MS |
| --- | --- | --- | --- |
| I-146 | | 1.74(3H, s), 2.05–2.19(1H, m), 2.60(1H, t, J=7Hz), 2.73–2.85 (3H, m), 3.18(1H, q, J=7Hz), 3.45(2H, q, J=7Hz), 3.72(3H, s), 3.87(3H, s), 4.94(1H, t, J=7 Hz), 5.52(1H, br), 5.60(1H, br), 5.86(1H, d, J=7Hz), 6.65–6.69 (2H, m), 6.85(1H, d, J=9Hz), 7.44(1H, d, J=1Hz) | (FAB) m/z ; 403 (M$^+$) |
| I-147 | | 1.77(3H, s), 1.80–2.20(2H, m), 2.65–2.75(2H, m), 2.80–3.10(2H, m), 3.20(1H, q, J=7.0Hz), 3.72(3H, s), 3.70–3.90(4H, m), 4.11(1H, t, J=5.0Hz), 5.52(1H, s,), 5.78(1H, d, J=7.0Hz), 5.89(1H, d, J=6.0 Hz), 7.44(1H, s). | (FAB) m/z ; 328 (MH$^+$) |
| I-148 | | 1.77(3H, d, J=1.5Hz), 2.05–2.20 (1H, m), 2.28(2H, t, J=7.5Hz), 2.62(1H, t, J=7.0Hz), 2.73–2.92 (1H, m), 3.20(1H, dt, J=7.0, 8.0 Hz), 3.72(3H, s), 4.03–4.11(4H, m), 5.53(1H, br), 5.77(1H, d, J= 7.0Hz), 7.45(1H, d, J=1.0Hz) | (FAB) m/z ; 294 (MH$^+$), 193 |
| I-149 | | 1.79(3H, s), 2.09–2.23(1H, m), 2.66–2.87(2H, m), 3.06–3.08(4H, m), 3.23(1H, ddd, J=1.0, 8.0, 15.0 Hz), 3.68–3.73(4H, m), 3.73(3H, s), 5.55(1H, br), 5.90(1H, d, J= 7.0Hz), 6.89–7.12(4H, m), 7.47 (1H, d, J=1.0Hz) | (FAB) m/z ; 416 (M$^+$) |
| I-150 | | 1.76(3H, s), 2.07–2.20(1H, m), 2.55–2.85(2H, m), 2.59(2H, t, J=6.5 Hz), 3.20(1H, q, J=7.5Hz), 3.35 (2H, dt, J=6.0, 6.5Hz), 3.72(H, s), 5.19(1H, t, J=6.0Hz), 5.52 (1H, br), 5.87(1H, d, J=6.5Hz), 7.20–7.39(5H, m), 7.44(1H, d, J= 1.0Hz) | (FAB) m/z ; 404 (MH$^+$) |

TABLE 34

| Compound No. | Structural Formulas | ¹H—NMR (δ ppm in CDCl₃) | MS |
|---|---|---|---|
| I-151 | | 1.18(3H, t, J=7Hz), 1.77(3H, s), 2.11–2.20(1H, m), 2.64–2.85(2H, m), 3.18–3.34(3H, m), 3.72(3H, s), 4.79–4.91(1H, m), 5.88(1H, d, J=7Hz), 7.45(1H, d, J=1Hz) | (EI) m/z ; 250 (M⁺—OMe) |
| I-152 | | 1.78(3H, br), 2.19–2.24(1H, m), 2.76–2.88(2H, m), 3.19–3.29(1H, m), 3.74(3H, s), 4.51(2H, s), 5.55(1H, t, J=2Hz), 6.01(1H, d, J=6Hz), 7.41(1H, d, J=1Hz), 7.97–8.10(1H, m) | |
| I-153 | | 1.80(3H, br), 2.14–2.26(1H, m), 2.75–2.87(2H, m), 3.20–3.30(1H, m), 3.73(3H, s), 5.54(1H, d, J=1Hz), 6.13(1H, d, J=5Hz), 7.43 (1H, d, J=1Hz), 7.46–7.62(3H, m), 7.82–7.86(2H, m), 8.18(1H, br) | |
| I-154 | | 1.80(3H, br), 2.13–2.25(1H, m), 2.76–2.89(2H, m), 3.20–3.30(1H, m), 3.74(3H, s), 5.55(1H, br), 6.02(1H, d, J=6Hz), 6.82–6.93(3H, m), 7.46(1H, d, J=1Hz), 7.98–8.12 (1H, m) | (EI) m/z ; 365 (M⁺) |
| I-155 | | 1.18(3H, d, J=7Hz), 1.20(3H, d, J=7Hz), 1.77(3H, br), 2.05–2.20 (1H, m), 2.60–2.85(2H, m), 3.19 (1H, dt, J=7, 8Hz), 3.72(3H, s), 3.77–3.95(1H, m), 5.52(1H, br), 5.87(1H, d, J=7Hz), 7.45(1H, d, J=1Hz) | (EI) m/z ; 264 (M⁺—OMe) |

TABLE 35

| Compound No. | Structural Formulas | $^1$H—NMR (δ ppm in CDCl$_3$) | MS |
| --- | --- | --- | --- |
| I-156 | | 1.80(3H, br), 2.05–2.23(1H, m), 2.71–2.88(2H, m), 3.24(1H, dt, J=6, 7Hz), 3.74(3H, s), 5.55(1H, d, J=2Hz), 6.02(1H, d, J=6Hz), 6.77 (1H, br), 6.98–7.42(4H, m), 7.46 (1H, d, J=1Hz) | |
| I-157 | | 1.79(3H, s), 2.11–2.23(1H, m), 2.73–2.86(2H, m), 3.16–3.26(1H, m), 3.73(3H, s), 5.53–5.55(1H, m), 6.02(1H, d, J=6Hz), 6.28(1H, br), 6.91–7.03(2H, m), 7.16–7.31(1H, m), 7.46(1H, d, J=1Hz) | (EI) m/z ; 334 (M$^+$—OMe) |
| I-158 | | 1.81(3H, br), 2.12–2.25(1H, m), 2.73–2.89(2H, m), 3.26(1H, dt, J=7, 8Hz), 3.74(3H, s), 5.54(1H, d, J=1Hz), 6.03(1H, d, J=6Hz), 7.02–7.18(4H, m), 7.46(1H, d, J=1Hz), 8.02–8.15(1H, m) | (FAB) m/z ; 348 (MH$^+$) |
| I-159 | | 1.80(3H, s), 2.12–2.25(1H, m), 2.76–2.87(2H, m), 3.24(1H, dt, J=7, 8Hz), 3.74(3H, s), 5.55(1H, br), 6.03(1H, d, J=6Hz), 6.78(1H, br), 7.29–7.47(4H, m), 7.46(1H, d, J=1Hz) | (FAB) m/z ; 408 (MH$^+$) |
| I-160 | | 1.08(3H, s), 2.13–2.25(1H, m), 2.70–2.88(23H, m), 3.25(1H, dt, J=7, 8Hz), 3.74(3H, s), 5.55(1H, d, J=2Hz), 6.06(1H, d, J=6Hz), 7.04 (1H, br), 7.34–7.76(4H, m), 7.46 (1H, s) | (EI) m/z ; 366 (M$^{'}$—OMe) |

TABLE 36

| Compound No. | Structural Formulas | $^1$H—NMR ($\delta$ ppm in CDCl$_3$) | MS |
| --- | --- | --- | --- |
| I-161 | (structure with CO$_2$Me, fused bicyclic ring with methyl, O, and carbamate linked to 4-methoxyphenyl) | 1.80(3H, s), 2.11–2.25(1H, m), 2.70–2.87(2H, m), 3.24(1H, dt, J=7.8Hz), 3.73(3H, s), 3.79(3H, s), 5.54(1H, br), 6.00(1H, d, J=6Hz), 6.83(1H, br), 6.84–6.90(2H, m), 7.30–7.76(2H, m), 7.46(1H, d, J=1Hz) | (EI) m/z ; 359 (M$^+$) |
| I-162 | (structure with CO$_2$Me, fused bicyclic ring with methyl, O, and carbamate linked to 4-chlorophenyl) | 1.80(3H, s), 2.12–2.25(1H, m), 2.72–2.88(2H, m), 3.25(1H, dt, J=7.8Hz), 3.74(3H, s), 5.55(1H, br), 6.03(1H, d, J=6Hz), 6.80(1H, br), 7.28–7.40(4H, m), 7.45(1H, d, J=1Hz) | (FAB) m/z ; 364 (MH$^+$) |
| I-163 | (structure with CO$_2$Me, fused bicyclic ring with methyl, O, and carbamate linked to 3,4-dichlorophenyl) | 1.79(3H, s), 2.13–2.24(1H, m), 2.74–2.88(2H, m), 3.25(1H, dt, J=7.8Hz), 3.74(3H, s), 5.55(1H, br), 6.04(1H, d, J=6Hz), 6.85(1H, br), 7.22–7.41(2H, m), 7.45(1H, d, J=1Hz), 7.65(1H, d, J=2Hz) | (FAB) m/z ; 398 (MH$^+$) |
| I-164 | (structure with CO$_2$Me, fused bicyclic ring with methyl, O, and carbamate linked to 2-CF$_3$-4-chlorophenyl) | 1.80(3H, d, J=1Hz), 2.10–2.23 (1H, m), 2.71–2.89(2H, m), 3.20–3.31(1H, m), 3.74(3H, s), 5.56 (1H, br), 5.95(1H, d, J=6Hz), 6.98(1H, br), 7.47(1H, d, J=1 Hz), 7.54(1H, dd, J=2, 9Hz), 7.60(1H, d, J=2Hz), 8.08(1H, d, J =9Hz) | (FAB) m/z ; 432 (MH$^+$) |
| I-165 | (structure with CO$_2$Me, fused bicyclic ring with methyl, O, and carbamate linked to 4-OCF$_3$-phenyl) | 1.80(3H, s), 2.13–2.25(1H, m), 2.74–2.88(2H, m), 3.20–3.30(1H, m), 3.74(3H, s), 5.55(1H, br), 6.03(1H, d, J=6Hz), 6.86(1H, br), 7.17–7.21(2H, m), 7.43–7.48 (2H, m), 7.46(1H, d, J=1Hz) | (FAB) m/z ; 414 (MH$^+$) |

TABLE 37

| Compound No. | Structural Formulas | $^1$H—NMR ($\delta$ ppm in CDCl$_3$) | MS |
|---|---|---|---|
| I-166 | (structure) | 1.80(3H, s), 2.13–2.26(1H, m), 2.76–2.88(2H, m), 3.21–3.31(1H, m), 3.74(3H, s), 5.55(1H, br), 6.07(1H, d, J=6Hz), 7.19(1H, br), 7.36–7.48(3H, m), 7.63–7.69 (1H, m), 7.83(1H, br) | (FAB) m/z ; 355 (MH$^+$) |
| I-167 | (structure) | 1.39(3H, t, J=7Hz), 1.80(3H, s) , 2.13–2.25(1H, m), 2.75–2.89 (3H, m), 3.20–3.31(1H, m), 3.74 (3H, s), 4.36(2H, q, J=7Hz), 5. 55(1H, br), 6.05(1H, d, J=6Hz) , 7.01(1H, br), 7.46(1H, d, J=1 Hz), 7.48–7.52(2H, m), 8.00–8. | (FAB) m/z ; 402 (MH$^+$) |
| I-168 | (structure) | 1.81(3H, s), 2.14–2.27(1H, m), 2.77–2.89(2H, m), 3.22–3.32(1H, m), 3.74(3H, s), 5.56(1H, br), 6.09(1H, d, J=6Hz), 7.25(1H, br), 7.45(1H, d, J=1Hz), 7.58– 7.65(2H, m), 8.20–8.28(2H, m) | (FAB) mz/ ; 375 (MH$^+$) |
| I-169 | (structure) | 1.79(3H, s), 2.10–2.26(1H, m), 2.70–2.87(2H, m), 3.19–3.29(1H, m), 3.73(3H, s), 5.54(1H, br), 6.01(1H, d, J=6Hz), 6.78(1H, br), 7.10–7.15(2H, m), 7.28–7.32 (2H, m), 7.46(1H, d, J=1Hz) | (FAB) m/z ; 344 (MH$^+$) |
| I-170 | (structure) | 1.80(3H, d, J=1Hz), 2.11–2.25 (1H, m), 2.72–2.88(2H, m), 3.19– 3.37(1H, m), 3.74(3H, s), 5.54 (1H, br), 6.03(1H, d, J=6Hz), 6.79(1H, br), 7.07–7.15(1H, m), 7.29–7.44(4H, m), 7.46(1H, d, J =1Hz) | (FAB) mz/ ; 330 (MH$^+$) |

TABLE 38

| Compound No. | Structural Formulas | $^1$H—NMR (δ ppm in CDCl$_3$) | MS |
| --- | --- | --- | --- |
| I-171 | | 1.80(3H s), 2.13–2.29(1H, m), 2.61(3H, s), 2.76–2.88(2H, m), 3.20–3.31(1H, m), 3.74(3H, s), 5.54(1H, br), 6.05(1H, d, J=6 Hz), 7.37(1H, br), 7.40–7.48 (2H, m), 7.67–7.79(2H, m), 8.02 (1H, s) | (FAB) m/z ; 372 (MH$^+$) |
| I-172 | | 1.80(3H, s), 2.05–2.25(1H, m), 2.47(3H, s), 2.71–2.88(2H, m), 3.24 (1H, q, J=7.0Hz), 5.54(1H, s), 6.02(1H, d, J=6.0Hz), 6.71(1H, s), 7.24(2H, d, J=8.5Hz), 7.35 (2H, d, J=8.5Hz), 7.46(1H, d, J= 1.0Hz) | (FAB) m/z ; 375 (M$^+$). |
| I-173 | | 1.78(3H, br s), 2.08–2.21(1H, m), 2.63–2.85(2H, m), 3.21(1H, dt, J=7, 8Hz), 3.53–3.68(4H, m), 3.73(3H, s), 5.25–5.35(1H, m), 5.53(1H, br s), 5.89(1H, d, J=6Hz), 7.44(1H,d, J=1Hz) | (EI) m/z; 284 (M$^+$—OMe) |
| I-174 | | 1.59(3H, br s), 2.07–2.20(1H, m), 2.59–2.82(2H, m), 2.85(3H, d, J= 5Hz), 3.19(1H, dt, J=7, 8Hz), 3.72 (3H, s), 4.76–4.86(1H, m), 5.52(1H, br s), 5.88(1H, d, J=7Hz), 7.45 (1H, d, J=1Hz) | (FAB) m/ z; 278 (MH$^+$) |
| I-175 | | 0.89(3H, t, J=6Hz), 1.08(3H, d, J =6Hz), 1.19–1.29(9H, m), 1.39–1.54 (2H, m), 1.73–1.92(2H, m), 2.15–2.26(1H, m), 2.91(1H, dt, J=7, 8Hz), 3.21(2H, q, J=6Hz), 3.72 (3H, s), 4.83–4.91(1H, m), 5.90 (1H, d, J=5Hz), 7.37(1H, d, J=1Hz) | (EI) m/z ; 308 (M$^+$—OMe) |

TABLE 39

| Compound No. | Structural Formulas | $^1$H—NMR ($\delta$ ppm in CDCl$_3$) | MS |
| --- | --- | --- | --- |
| I-176 | | 1.10(3H, d, J=6Hz), 1.16–1.28(1H, m), 1.39–1.43(1H, m), 1.77–1.93 (3H, m), 2.14–2.30(1H, m), 2.93 (1H, dt, J=7, 8Hz), 3.73(3H, s), 4.05–4.29(2H, m), 5.30–5.40(1H, m), 5.98(1H, d, J=4Hz), 7.33(1H, d, J=1Hz) | (EI) m/z ; 263 (M$^+$—OMe) |
| I-177 | | 1.09(3H, d, J=6Hz), 1.15–1.34(1H, m), 1.37–1.55 81H, m), 1.74–1.96 (3H, m), 2.15–2.31(1H, m), 2.93 (1H, dt, J=7, 8Hz), 3.72(3H, s), 4.53(2H, d, J=5Hz), 5.95(1H, d, J =5Hz), 6.11–7.11(1H, m), 7.18–7.30 (2H, m), 7.37(1H, d, J=1Hz), 7.68 (1H, dt, J=7, 8Hz), 8.55(1H, d, J =5Hz) | (FAB) m/z; 347 (MH$^+$) |
| I-178 | | 1.08(3H, s, J=6Hz), 1.16–1.29(1H, m), 1.37–1.55(1H, m), 1.71–1.95 (3H, m), 2.13–2.28(1H, m), 2.90 (1H, dt, J=7, 8Hz), 3.71(3H, s), 4.42(2H, d, J=6Hz), 5.70–5.80(1H, m), 5.96(1H, d, J=5Hz), 7.28(1H, dd, J=2, 8Hz), 7.35(1H, d, J= 1Hz), 7.67(1H, d, J=8Hz), 8.50(1H, d, J=2Hz), 8.53(1H, s) | (FAB) m/z ; 347 (MH$^+$) |
| I-179 | | 1.09(3H, d, J=6Hz), 1.16–1.28(1H, m), 1.37–1.51(1H, m), 1.73–1.93 (3H, m), 2.15–2.29(1H, m), 2.93 (1H, dt, J=7, 8Hz), 3.72(3H, s), 4.90(2H, br), 5.90(1H, d, J=5Hz), 7.36(1H, d, J=1Hz) | (FAB) m/z ; 256 (MH$^+$) |
| I-180 | | 1.10(3H, d, J=6Hz), 1.15–1.27(1H, m), 1.37–1.51(1H, m), 1.75–1.93 (3H, m), 2.17–2.27(1H, m), 2.47–2. 53(4H, m), 2.57(2H, t, J=5Hz), 2. 93(1H, dt, J=7, 8Hz), 3.47–3.57 (4H, m), 3.64(2H, t, J=5Hz), 3.72 (3H, s), 5.91(1h, d, J=5Hz), 7.37 (1H, d, J=1Hz) | (FAB) m/z ; 369 (MH$^+$) |

TABLE 40

| Compound No. | Structural Formulas | $^1$H—NMR ($\delta$ ppm in CDCl$_3$) | MS |
|---|---|---|---|
| I-181 | | 1.08(3H, d, J=6Hz), 1.19–1.25(1H, m), 1.43–1.59(2H, m), 1.71–2.04 (6H, m), 2.16–2,26(1H, m), 2.91 (1H, q, J=7Hz), 3.14–3.21(1H, m), 3.42–3.52(1H, m), 3.72(3H, s), 3.77–4.04(3H, m), 5.20(1H, b),5.89 (1H, q, J=2.5Hz), 7.36(1H, s) | (FAB) m/z; 340 (MH$^+$) |
| I-182 | | 1.07(3H, d, J=6Hz), 1.18–1.35(1H, m), 1.38–1.49(1H, m), 1.67–1.92 (3H, m), 2.17–2.24(1H, m), 2.85–3.11 (3H, m), 3.60–3.70(2H, m), 3.71 (3H, s), 5.74(1H, t, J=6Hz), 5.89 (1H, d, J=5Hz), 7.09–7.22(2H, m), 7.36(1H, d, J=1Hz), 7.58–7.67 (1H, m), 8.52–8.56(1H, m) | (FAB) m/z; 361 (MH$^+$) |
| I-183 | | 1.09(3H, d, J=6Hz), 1.14–1.26(1H, m), 1.40–1.55(1H, m), 1.71–1.93 (3H, m), 2.14–2.39(12H, m), 2.91 (1H, dt, J=7.0, 7.5Hz), 3.71(3H, s), 4.40(2H, d, J=6Hz), 5.15(3H, t, J=5Hz), 5.95(1H, d, J=5Hz), 7.31–7.40(6H, m) | (FAB) m/z; 346 (MH$^+$) |
| I-184 | | 1.06(3H, d, J=6Hz), 1.14–1.28(1H, m), 1.34–1.45(1H, m), 1.74–1.93 (3H, m), 2.04–2.33(1H, m), 2.83–2.89 (1H, m), 2.95(3H, s), 3.66(3H, s), 4.45(2H, d, J=2Hz), 5.88(1H, d, J=5Hz), 7.19–7.39(6H, m) | (FAB) m/z; 360 (MH$^+$) |
| I-185 | | 1.08(3H, d, J=6Hz), 1.19–1.25(1H, m), 1.38–1.45(1H, m), 1.72–1.92 (3H, m), 2.18–2.24(1H, m), 2.83–2.95 (3H, m), 3.47(2H, td, J=6.7Hz), 3.72(3H, s), 4.89(1H, t, J=6Hz), 5.89(1H, d, J=5Hz), 6.99–7.26 (4H, m), 7.36(1H, d, J=1Hz) | (FAB) m/z; 378 (MH$^+$) |

TABLE 41

| Compound No. | Structural Formulas | $^1$H—NMR (δ ppm in CDCl$_3$) | MS |
| --- | --- | --- | --- |
| I-186 | | 1.08(3H, d, J=6Hz), 1.19–1.26(1H, m), 1.43–1.56(1H, m), 1.70–2.09 (3H, m), 2.13–2.30(1H, m), 2.90 (1H, dt, J=7.5, 8.0Hz), 3.71(3H, s), 3.80(3H, s), 4.33(2H, d, J=6Hz), 5.07(1H, br), 5.94(1H, d, J=5Hz), 6.87(2H, d, J=9Hz), 7.23 (2H, d, J=9Hz), 7.37(1H, s) | (FAB) m/z; 376 (MH$^+$) |
| I-187 | | 1.09(3H, d, J=6Hz), 1.17–1.28(1H, m), 1.40–1.51(1H, m), 1.71–1.93 (4H, m), 2.14–2.31(1H, m), 2.92 (1H, d.t. J=7, 8Hz), 3.34–3.46(2H, m), 3.72(3H, s), 3.72–3.81(2H, m), 5.30(1H, s), 5.92(1H, d, J=5Hz), 7.36(1H, s) | (FAB) m/z ; 300 (MH$^+$) |
| I-188 | | 1.09(3H, d, J=6Hz), 1.12–1.28(1H, m), 1.37–1.56(1H, m), 1.78–1.92 (3H, m), 2.91–2.24(1H, m), 2.92 (1H, dt, J=7.0, 7.5Hz), 3.17–3.50 (4H., m), 3.65–3.76(4H, m), 3.72 (3H, s), 5.94(1H, d, J=5Hz), 7.37 (1H, d, J=1Hz) | (FAB) m/z ; 326 (MH$^+$) |
| I-189 | | 1.06(3H, d, J=6Hz), 1.12–1.25(1H, m), 1.32–1.50(1H, m), 1.78–1.83 (3H, m), 2.15(8H, s), 2.37(2H, t, J=7Hz), 2.86(3H, s), 3.23–3.32 (2H, m), 3.64(3H, s), 5.82(1H, d, J=4.5Hz), 7.31(1H, s) | (FAB) m/z ; 341 (MH$^+$) |
| I-190 | | 0.91(3H, s), 0.85(3H, s), 1.09 (3H, d, J=6Hz), 1.19–1.26(1H, m), 1.39–1.50(1H, m), 1.70–1.95(4H, m), 2.14–2.31(1H, m), 2.92(1H, q, J=7Hz), 3.04(2H, t, J=7Hz), 3.72 (3H, s), 4.88(1H, t, J=6Hz), 5.91 (1H, d, J=5Hz), 7.37(1H, s) | (FAB) m/z ; 312 (MH$^+$) |

TABLE 42

| Compound No. | Structural Formulas | $^1$H—NMR (δ ppm in CDCl$_3$) | MS |
|---|---|---|---|
| I-191 | | 0.88–1.04(2H, m), 1.09(3H, d, J=6Hz), 1.16–1.27(5H, m), 1.39–1.50 (2H, m), 1.70–1.92(7H, m), 2.14–2.39 (1H, m), 2.91(1H, dt, J=7.0, 7.5Hz), 3.05(2H, t, J=6Hz), 3.72 (3H, s), 4.85–4.91(1H, m), 5.90 (1H, d, J=5Hz), 7.37(1H, d, J=1Hz) | (FAB) m/z; 352 (MH$^+$) |
| I-192 | | 1.08(3H, d, J=6Hz), 1.13–1.25(1H, m), 1.40–1.50(3H, m), 1.73–2.30 (8H, m), 2.78–2.97(3H, m), 3.34–3.59 (1H, m), 3.49(2H, s), 3.72(3H, s), 4.71(1H, d, J=8Hz), 5.90(1H, d, J=5Hz), 7.21–7.30(5H, m), 7.36 (1H, d, J=1Hz) | (FAB) m/z; 429 (MH$^+$) |
| I-193 | | 0.82(3H, t, J=7,5Hz), 1.06(3H, d, J=6Hz), 1.16–1.23(1H, m),1.34–1.59 (3H, m), 1.75–1.91(3H, m), 2.06–2.22(1H, m), 2.84(2H, s), 2.92 (2H, s), 3.18(2H, t, J=7Hz), 3.64 (3H, s), 5.80(1H, d, J=5Hz), 7.31 (1H, s) | (FAB) m/z; 312 (MH$^+$) |
| I-194 | | 1.10(3H, d, J=6Hz), 1.13–1.28(1H, m), 1.37–1.51(1H, m), 1.79–1.89 (3H, m), 2.15–2.23(3H, m), 2.94 (1H, dt, J=6.5, 7.0Hz), 3.53–3.61 (2H, m), 3.72(3H, s), 3.91–3.98 (2H, m), 5.60–5.71(1H, m), 5.82–5.87 (1H, m), 5.94(1H, d, J=5Hz), 7.38(1H, s) | (FAB) m/z; 322 (MH$^+$) |
| I-195 | | 1.08(3H, d, J=6Hz), 1.19–1.27(1H, m), 1.36–1.51(1H, m), 1.70–1.95 (3H, m), 2.13–2.30(1H, m), 2.91 (1H, dt, J=7.0, 7.5Hz), 3.71(3H, s), 4.40(2H, d, J=6Hz), 5.22(1H, t, J=6Hz), 5.93(1H, d, J=5Hz), 6.74–6.91(2H, m), 7.28–7.37(2H, m) | (FAB) m/z; 382 (MH$^+$) |

TABLE 43

| Compound No. | Structural Formulas | $^1$H—NMR (δ ppm in CDCl$_3$) | MS |
|---|---|---|---|
| I-196 | | 1.09(3H, d, J=6Hz), 1.14–1.25(1H, m), 1.32–1.52(1H, m), 1.72–1.91 (3H, m), 2.09–2.36(1H, m), 2.92 (1H, dt, J=7.0, 7.5Hz), 3.72(3H, s), 4.36(2H, d, J=5Hz), 5.16–5.22 (1H, m), 5.95(1H, d, J=5Hz), 7.14 (1H, dd, J=2, 8Hz), 7.35–7.44(3H, m) | (FAB) m/z; 414 (MH$^+$) |
| I-197 | | 1.08(3H, d, J=6Hz), 1.15–1.25(1H, m), 1.39–1.54(1H, m), 1.73–1.93 (3H, m), 2.16–2.24(1H, m), 2.90 (1H, dt, J=7.0, 7.5Hz), 3.06(2H, t, J=7Hz), 3.50(2H, q, J=6Hz), 3.72 (3H, s), 4.95(1H, br), 5.90 (1H, d, J=5Hz), 6.84(1H, d, J=2.5Hz), 7.00(1H, d, J=4Hz), 7.18 (1H, dd, J=1, 5Hz), 7.36(1H, d, J=1Hz) | (FAB) m/z ; 366 (MH$^+$) |
| I-198 | | 1.06(3H, d, J=6Hz), 1.12–1.25(1H, m), 1.31–1.43(1H, m), 1.76–1.91 (3H, m), 2.07–2.18(1H, m), 2.81– 2.92(1H, m), 2.91(3H, s), 3.34(2H, d, J=4.5Hz), 3.65(3H, s), 3.74– 3.82(2H, m), 3.85–3.94(2H, m), 4.94 (1H, t, J=4.5Hz), 5.80(1H, d, J= 5Hz), 7.31(1H, d, J=1Hz) | (FAB) m/z; 356 (MH$^+$) |
| I-199 | | 0.92–1.29(6H, m), 1.35–1.53(1H, m), 1.55–1.95(6H, m), 2.15–2.31 (1H, m), 2.52–2.96(5H, m), 3.72 (3H, s), 4.01–4.22(2H, m), 5.84– 5.94(1H, m), 7.08–7.33(5H, m), 7.38(1H, d, J=5Hz) | (FAB) m/z; 414 (MH$^+$) |
| I-200 | | 1.09(3H, t, J=7Hz), 1.10(3H, d, J=6Hz), 1.17–1.32(1H, m), 1.37– 1.55(1H, m), 1.75–2.00(3H, m), 2.15–2.30(1H, m), 2.31–2.53(2H, m), 2.43(2H, d, J=7Hz), 2.87– 2.98(1H, m), 3.40–3.62(4H, m), 3.72(3H, s), 5.91(1H, d, J=5Hz), 7.37(1H, d, J=1Hz) | (FAB) m/z; 353 (MH$^+$) |

TABLE 44

| Compound No. | Structural Formulas | $^1$H—NMR (δ ppm in CDCl$_3$) | MS |
|---|---|---|---|
| I-201 | | 1.09(3H, d, J=6Hz), 1.14–1.32 (1H, m), 1.37–1.55(1H, m), 1.71–1.95(3H, m), 2.14–2.30(1H, m), 2.86–2.97(1H, m), 3.28–3.46(2H, m), 3.40(6H, s), 3.72(3H, s), 4.40(1H, t, J=5Hz), 5.05(1H, t, J=6Hz), 5.91(1H, d, J=5Hz), 7.35(1H, d, J=1Hz) | (FAB) m/z; 344 (MH$^+$) |
| I-202 | | 1.09(3H, d, J=6Hz), 1.14–1.32 (1H, m), 1.37–1.55(1H, m), 1.71–1.92(3H, m), 2.14–2.30(1H, m), 2.47(1H, br), 2.86–2.97(1H, m), 3.35–3.64(6H, m), 3.68–3.77(2H, m), 3.72(3H, s), 5.53(1H, t, J=6Hz), 5.92(1H, d, J=5Hz), 7.36(1H, d, J=1Hz) | (FAB) m/z; 344 (MH$^+$) |
| I-203 | | 1.10(3H, d, J=6Hz), 1.13(3H, t, J=7Hz), 1.13–1.33(1H, m), 1.38–1.56(1H, m), 1.77–1.96(3H, m), 2.16–2.31(1H, m), 2.52(1H, br), 2.85–2.99(1H, m), 3.27–3.57 (4H, m), 3.72(3H, s), 3.72–3.83 (2H, m), 5.93(1H, d, J=5Hz), 7.37(1H, d, J=1Hz) | (FAB) m/z; 328 (MH$^+$) |
| I-204 | | 1.07(3H, d, J=6Hz), 1.14–1.31 (1H, m), 1.35–1.53(1H, m), 1.68–1.96(3H, m), 2.14–2.30(1H, m), 2.77(2H, t, J=6Hz), 2.83–2.94 (1H, m), 3.43(2H, q, J=6Hz), 3.71(3H, s), 3.78(3H, s), 4.96 (1H, t, J=6Hz), 5.89(1H, d, J=5 Hz), 6.82–6.88(2H, m), 7.08–7.12 (2H, m), 7.36(1H, d, J=1Hz) | (FAB) m/z; 389 (M$^+$) |
| I-205 | | 1.08(3H, d, J=6Hz), 1.14–1.31 (1H, m), 1.35–1.53(1H, m), 1.69–1.96(3H, m), 2.14–2.30(1H, m), 2.84(2H, t, J=7Hz), 2.84–2.95 (1H, m), 3.47(2H, q, J=7Hz), 4.94(1H, t, J=7Hz), 5.90(1H, d, J=5Hz), 6.88–6.98(3H, m), 7.22–7.33(1H, m), 7.36(1H, d, J=1Hz) | (FAB) m/z; 378 (MH$^+$) |

TABLE 45

| Compound No. | Structural Formulas | $^1$H—NMR ($\delta$ ppm in CDCl$_3$) | MS |
| --- | --- | --- | --- |
| I-206 | | 1.07(3H, d, J=6Hz), 1.14–1.30 (1H, m), 1.35–1.53(1H, m), 1.68–1.95(3H, m), 2.14–2.29(1H, m), 2.75(2H, t, J=7Hz), 2.84–2.95 (1H, m), 3.43(2H, q, J=7Hz), 3.72(3H, s), 4.91(1H, t, J=7Hz), 5.90(1H, d, J=5Hz), 6.76–6.83 (2H, m), 7.01–7.05(2H, m), 7.36 (1H, d, J=1Hz) | (FAB) m/z ; 376 (MH$^+$) |
| I-207 | | 0.92(6H, t, J=7.5Hz), 1.09(3H, d, J=6.0Hz), 1.10–2.00(9H, m), 2.05–2.30(1H, m), 2.91(1H, dt, J=7.5, 7.0Hz), 3.43–3.62(1H, m), 3.72 (3H, s), 4.59(1H, d, J=9.0Hz), 5.90(1H, d, J=5.0Hz), 7.38(1H, d, J=1.0Hz). | (FAB) m/z ; 326 (MH$^+$) |
| I-208 | | 1.08(3H, d, J=6.0Hz), 1.10–2.00 (18H, m), 2.09–2.30(1H, m), 2.91 (1H, dt, J=7.5, 7.0Hz), 3.72(3H, s), 4.76(1H, d, J=8.0Hz), 5.86 (1H, d, J=5.0Hz), 7.36(1H, d, J= 1.0Hz). | (FAB) m/z ; 352 (MH$^+$) |
| I-209 | | 1.09(3H, d, J=6.0Hz), 1.10–2.00 (12H, m), 2.05–2.34(1H, m), 2.91 (1H, q, J=7.5Hz), 3.18–3.31(2H, m), 3.55–3.72(2H, m), 3.72(3H, s), 4.85(1H, t, J=5.0Hz), 5.90 (1H, d, J=5.0Hz), 7.36(1H, d, J= 1.0Hz) | (FAB) m/z ; 342 (MH$^+$) |
| I-210 | | 1.09(3H, d, J=6.0Hz), 1.10–2.00 (6H, m), 1.69(2H, quint, J=6.5 Hz), 2.24(6H, s), 2.38(2H, t, J= 6.5Hz), 2.91(1H, dt, J=7.6, 7.4 Hz), 3.30(2H, q, J=6.0Hz), 3.72 (3H, s), 5.86(1H, d, J=5.5Hz), 5.99(1H, t, J=5.0Hz), 7.37(1H, d, J=1.0Hz). | (FAB) m/z ; 341 (MH$^+$). |

TABLE 46

| Compound No. | Structural Formulas | $^1$H—NMR (δ ppm in CDCl$_3$) | MS |
|---|---|---|---|
| I-211 | | 1.09(3H, d, J=6.0Hz), 1.14–1.32 (1H, m), 1.37–1.55(1H, m), 1.66–2.04(3H, m), 2.2(1H, m), 2.91(1H, dt, J=7.5, 7.0Hz), 3.71(3H, s), 4.40(2H, d, J=6.0Hz), 5.29(1H, t, J=6.0Hz), 5.95(1H, d, J=5.0 Hz), 7.19(2H, d, J=8.5Hz), 7.33 (2H, d, J=8,5Hz), 7.35(1H, s). | (FAB) m/z ; 430 (MH$^+$) |
| I-212 | | 1.08(3H, d, J=6,0Hz), 1.14–1.53 (2H, m), 1.68–2.02(3H, m), 2.14–2.30(1H, m), 2.78–2.91(3H, m), 3.45(2H, dd, J=7.0, 13.0Hz), 3.72 (3H, s), 4.85(1H, t, J=5.5Hz), 5.89(1H, d, J=5.0Hz), 6.95–7.23 (4H, m), 7.35(1H, d, J=1.0Hz) | (FAB) m/z ; 378 (MH$^+$), 195 |
| I-213 | | 1.08(3H, d, J=6.0Hz), 1.14–1.27 (1H, m), 1.31–1.55(1H, m), 1.71–2.02(3H, m), 2.14–2.30(1H, m), 2.90 (1H, q, J=7.5Hz), 3.71(3H, s), 4.36(2H, d, J=6,0Hz), 5.15–5.21 (1H, m), 5.95(1H, d, J=5.0Hz), 6.98–7.08(2H, m), 7.28–7.32(2H, m), 7.36(1H, d, J=1.0Hz) | (FAB) m/z ; 364 (MH$^+$), 195 |
| I-214 | | 1.09(3H, d, J=6.0Hz), 1.14–1.32 (1H, m), 1.36–1.55(1H, m), 1.71–2.02(3H, m), 2.08–2.36(1H, m), 2.91 (1H, q, J=7.5Hz), 3.71(3H, s), 4.36(2H, d, J=6.0Hz), 5.19(1H, t, J=6.0Hz), 5.94(1H, d, J=5.0 Hz), 7.11–7.40(5H, m) | (FAB) m/z ; 380 (MH$^+$), 195 |
| I-215 | | 1.08(3H, d, J=6.0Hz), 1.14–1.31 (1H, m),1.37–1.55(1H, m), 1.70–1.96(3H, m), 2.08–2.30(1H, m), 2.91 (1H, q, J=7.5Hz), 3.71(3H, s), 4.29–4.47(2H, m), 5.16(1H, t, J= 5.5Hz), 5.94(1H, d, J=5.0Hz), 6.24–6.34(2H, m), 7.32–7.39(2H, m) | (FAB) m/z ; 336 (MH$^+$), 195 |

TABLE 47

| Compound No. | Structural Formulas | $^1$H—NMR (δ ppm in CDCl$_3$) | MS |
|---|---|---|---|
| I-216 | | 1.10(3H, d, J=6.0Hz), 1.14–1.31 (1H, m), 1.46–1.58(7H, m), 1.75–1.96(3H, m), 2.13–2.31(1H, m), 2.92 (1H, q, J=7.0Hz), 3.35–3.62(4H, m), 3.72(3H, s), 5.90(1H, d,J=5.0Hz), 7.38(1H, d, J=1.0Hz) | (FAB) m/z ; 324 (MH$^+$), 195 |
| I-217 | | 1.08(3H, d, J=6.0Hz), 1.14–1.27 (1H, m), 1.31–1.54(1H, m), 1.70–2.01(4H, m), 2.09–2.35(1H, m), 2.66 (2H, t, J=7.5Hz), 2.91(1H, dt, J=7.0, 7.5Hz), 3.25(2H, dd, J=7.0, 13.5Hz), 3.72(3H, s), 4.84(1H, t, J=5.5Hz), 5.90(d, 1H, J=5.0 Hz), 7.16–7.33(5H, m), 7.36(1H, d, J=1.0Hz) | (FAB) m/z ; 374 (MH$^+$), 195 |
| I-218 | | 0.42–0.67(2H, m), 0.69–0.88(2H, m), 1.08(3H, d, J=6.0Hz), 1.15–1.31(1H, m), 1.36–1.54(1H, m), 1.66 –1.94(3H, m), 2.14–2.30(1H, m), 2.50–2.70(1H, m), 2.90(1H, q, J=7.5Hz), 3.72(3H, s), 5.05(1H, br), 5.91(1H, d, J=5.0Hz), 7.36 (1H, s) | (FAB) m/z ; 296 (MH$^+$), 195 |
| I-219 | | 1.10(3H, d, J=6.0Hz), 1.14–1.32 (1H, m), 1.37–1.55(1H, m), 1.79–1.94(3H, m), 2.16–2.31(1H, m), 2.58 –2.67(4H, m), 2.92(1H, q, J=7.0 Hz), 3.72(3H, s), 3.73—3.86(4H, m), 5.92(1H, d, J=5.0Hz), 7.37 (1H, d, J=1.0Hz) | (FAB) m/z ; 342 (MH$^+$), 195 |

TABLE 47-continued

| Compound No. | Structural Formulas | $^1$H—NMR ($\delta$ ppm in CDCl$_3$) | MS |
|---|---|---|---|
| I-220 | | 1.07(3H, d, J=6.0Hz), 1.13–1.27 (1H, m), 1.30–1.53(1H, m), 1.67–1.96(2H, m), 2.13–2.29(1H, m), 2.88 (1H, q, J=7.5Hz), 2.97–3.10(2H, m), 3.46–3.64(2H, m), 3.71(3H, s), 4.90(1H, t, J=6.0Hz), 5.91 (1H, d, J=5.0Hz), 7.04–7.25(4H, m), 7.31–7.41(2H, m), 7.61(1H, d, J=8.0Hz), 8.07(1H, br) | (FAB) m/z ; 398 (M$^+$), 195 |

TABLE 48

| Compound No. | Structural Formulas | $^1$H—NMR ($\delta$ ppm in CDCl$_3$) | MS |
|---|---|---|---|
| I-221 | | 1.10(3H, d, J=6.0Hz), 1.15–1.28 (1H, m), 1.33–1.56(1H, m), 1.73–1.93(3H, m), 2.14–2.31(1H, m), 2.91 (1H, q, J=7.5Hz), 3.72(3H, s), 4.42(2H, d, J=6.0Hz), 5.52(1H, t, J=6.0Hz), 5.96(1H, d, J=4.5 Hz), 7.13–7.34(2H, m), 7.36(1H, d, J=1.0Hz), 8.55—8.58(2H, m) | (FAB) m/z ; 347 (MH$^+$), 195 |
| I-222 | | 1.09(3H, d, J=6.0Hz), 1.15–1.31 (1H, m), 1.37–1.55(1H, m), 1.71–1.96(4H, m), 2.24(6H, s), 2.43(2H, t, J=6.0Hz), 2.92(1H, dt, J=7.0, 7.5Hz), 3.30(2H, dt, J=5.5, 6.0 Hz), 3.72(3H, s), 5.40–5.44(1H, m), 5.91(1H, d, J=5.0Hz), 7.36 (1H, d, J=1.0Hz) | (FAB) m/z ; 327 (MH$^+$), 195 |
| I-223 | | 1.09(3H, d, J=6.0Hz), 1.14–1.32 (1H, m), 1.40–1.60(6H, m), 1.72–1.97(4H, m), 2.45(2H, t, J=6.0 Hz), 2.93(1H, dt, J=7.0, 7.5Hz), 3.31(2H, q, J=6.0Hz), 3.72(3H, s), 5.44–5.48(1H, m), 5.90(1H, d, J=5.0Hz), 7.37(1H, d, J=1.0Hz) | (FAB) m/z ; 367 (MH$^+$) |

TABLE 48-continued

| Compound No. | Structural Formulas | $^1$H—NMR (δ ppm in CDCl$_3$) | MS |
| --- | --- | --- | --- |
| I-224 | | 1.08(3H, d, J=6.0Hz), 1.15–1.25 (1H, m), 1.31–1.53(1H, m), 1.68–1.96(3H, m), 2.14–2.30(1H, m), 2.81–2.94(3H, m), 3.48(2H, q, J=6,5 Hz), 3.71(3H, s), 4.86(1H, t, J=6.0Hz), 5.90(1H, d, J=5.0Hz), 7.18–7.33(5H, m), 7.36(1H, d, J=1.0 Hz) | (FAB) m/z ; 360 (MH$^+$), 195 |
| I-225 | | 1.11(3H, d, J=6.0Hz), 1.15–1.33 (1H, m), 1.39–1.52(1H, m), 1.87–1.97(3H, m), 2.17–2.33(1H, m), 2.82–3.00(3H, m), 3.65–3.78(2H, m), 3.73(3H, s), 4.63(2H, d, J=10.5 Hz), 5.97(1H, dd, J=1.5, 5.0Hz), 7.07–7.25(4H, m), 7.38(1H, m) | (FAB) m/z ; 372 (MH$^+$), 195 |

TABLE 49

| Compound No. | Structural Formulas | $^1$H—NMR (δ ppm in CDCl$_3$) | MS |
| --- | --- | --- | --- |
| I-226 | | 1.09(3H, d, J=6.0Hz), 1.14–1.31(1H, m), 1.36–1.54(1H, m), 1.71–1.96(5H, m), 2.15–2.31(1H, m), 2.91(1H, dt, J=7.0, 7.5Hz), 3.29–3.38(2H, m), 3.34 (3H, s), 3.47(2H, t, J=6.0Hz), 3.72 (3H, s), 5.24–5.30(1H, m), 5.89(1H, d, J=5.5Hz), 7.36(1H, d, J=1.0Hz)MS | (FAB) m/z ; 328 (MH$^+$), 195 |
| I-227 | | 1.04(3H, d, J=6.0Hz), 1.08–1.23(1H, m), 1.33–1.50(1H, m), 1.72–1.86(3H, m), 2.05–2.19(1H, m), 2.71(2H, t, J=7.5Hz), 2.80–2.88(1H, m), 2.81(3H, s), 3.41(2H, t, J=7.5Hz), 3.64(3H, s), 3.73(3H, s), 3.74(3H, s), 5.79 (1H, d, J=4.5Hz), 6.67(1H, dd, J=2.0, 8.0Hz), 6.67(1H, d, J=2.0Hz), 6.84 (1H, d, J=8.0Hz), 7.30(1H, d, J=1.0 Hz) | (FAB) m/z ; 433 (MH$^+$), 195 |

TABLE 49-continued

| Compound No. | Structural Formulas | ¹H—NMR (δ ppm in CDCl₃) | MS |
| --- | --- | --- | --- |
| I-228 | | 1.09(3H, d, J=6.0Hz), 1.14–1.27(1H, m), 1.32–1.54(1H, m), 1.71–1.96(3H, m), 2.15–2.31(1H, m), 2.92(1H, q, J=7.5Hz), 3.72(3H, s), 3.85(2H, t, J=6.0Hz), 4.92–4.98(1H, m), 5.13–5,26 (2H, m), 5.76–5.95(1H, m), 5.92(1H, d, J=5.0Hz), 7.36(1H, d, J=1.0Hz) | (FAB) m/z ; 296 (MH⁺), 195 |
| I-229 | | 1.09(3H, d, J=6.0Hz), 1.14–1.28(1H, m), 1.32–1.53(1H, m), 1.64–1.95(5H, m), 2.16–2.35(1H, m), 2.43–2.53(6H, m), 2.91(1H, dt, J=7.0, 7.5Hz), 3.32 (2H, q, J=6.0Hz), 3.67–3.71(4H, m), 3.72(3H, s), 5.87(1H, d, J=5.5Hz), 6.27(1H, t, J=5.0Hz), 7.37(1H, d, J=1.0Hz) | (FAB) m/z ; 383 (MH⁺) |
| I-230 | | 1.09(3H, d, J=6.0Hz), 1.14–1.28(1H, m), 1.32–1,55(1H, m), 1.74–1.96(3H, m), 2.15–2.31(1H, m), 2.91(1H, q, J=7.0Hz), 3.72(3H, s), 3.78–3.93(4H, m), 5.06–5.21(4H, m), 5.63–5,89(2H, m), 5.93(1H, d, J=5.0Hz), 7.36(1H, d, J=1.0Hz) | (FAB) m/z; 336 (MH⁺), 195 |

TABLE 50

| Compound No. | Structural Formulas | ¹H—NMR (δ ppm in CDCl₃) | MS |
| --- | --- | --- | --- |
| I-231 | | 1.08(3H, d, J=6.0Hz), 1.13–1.27 (1H, m), 1.31–1.56(1H, m), 1.70–1.95(3H, m), 2.14–2.30(1H, m), 2.91 (1H, dt, J=7.0, 7.5Hz), 3.71(3H, s), 4.45(2H, d, J=6.0Hz), 5.22 (1H, t, J=6.0Hz), 5.93(1H, d, J=5.0Hz), 7.01–7.16(2H, m), 7.23–7.39(2H, m), 7.35(1H, d, J=1.5Hz) | (FAB) m/z; 364 (MH⁺), 195 |

TABLE 50-continued

| Compound No. | Structural Formulas | ¹H—NMR (δ ppm in CDCl₃) | MS |
|---|---|---|---|
| I-232 | | 1.09(3H, d, J=6.0Hz), 1.14–1.27 (1H, m), 1.32–1.55(1H, m), 1.72–1.96(3H, m), 2.14–2.30(1H, m), 2.91 (1H, dt, J=7.0, 7.5Hz), 3.71(3H, s), 4.40(2H, d, J=6.0Hz), 5.25 (1H, t, J=6.0Hz), 5.95(1H, d, J=5.0Hz), 6.93–7.09(3H, m), 7.26–7.33(1H, m), 7.36(1H, d, J=1.0Hz) | (FAB) m/z; 364 (MH⁺), 195 |
| I-233 | | 1.09(3H, d, J=6.0Hz), 1.15–1.27 (1H, m), 1.32–1.55(1H, m), 1.73–1.96(3H, m), 2.14–2.30(1H, m), 2.92 (1H, dt, J=6.0, 7.5Hz), 3.71(3H, s), 4.46(2H, dd, J=1.0, 6.5Hz), 5.30(1H, t, J=6.5Hz), 5.95(1H, d, J=5.0Hz), 7.36(1H, d, J=1.0 Hz), 7.42–7.58(4H, m) | (FAB) m/z ; 414 (MH⁺), 195 |
| I-234 | | 1.08(3H, d, J=6.0Hz), 1.14–1.27 (1H, m), 1.31–1.55(1H, m), 1.71–1.96(3H, m), 2.14–2.30(1H, m), 2.90 (1H, dt, J=7.0, 7.5Hz), 3.71(3H, s), 4.29(2H, d, J=6.0Hz), 5.11 (1H, t, J=6.0Hz), 5.94(1H, d, J=4.5Hz), 5.95(2H, sd), 6.76–6.79 (3H, m), 7.36(1H, d, J=1.0Hz) | (FAB) m/z ; 389 (M⁺), 195 |
| I-235 | | 1.11(3H, d, J=6.0Hz), 1.17–1.29 (1H, m), 1.33–1.57(1H, m), 1.78–1.96(3H, m), 2.17–2.33(1H, m), 2.95 (1H, q, J=7.0Hz), 3.20–3.24(4H, m), 3.67–3.73(4H, m), 3.73(3H, s), 5.95(1H, d, J=5.0Hz), 7.05–7.15(3H, m), 7.34–7.42(1H, m ), 7.38 (1H, d, J=1.0Hz) | (FAB) m/z ; 468 (M⁺), 195 |

TABLE 51

| Compound No. | Structural Formulas | ¹H—NMR (δ ppm in CDCl₃) | MS |
|---|---|---|---|
| I-236 | | 1.09(3H, d, J=6Hz), 1.15–1.27(1H, m), 1.39–1.54(1H, m), 1.74–1.93 (3H, m), 2.18–2.27(1H, m), 2.81–3.02(3H, m), 3.54(2H, q, J=6Hz), 3.72(3H, s), 5.28–5.38(1H, m), 5.90 (1H, d, J=5Hz), 7.35(1H, d, J=1Hz) | |
| I-237 | | 1.09(3H, d, J=6Hz), 1.20–1.30(4H, m), 1.31–1.51(1H, m), 1.73–1.96 (5H, m), 2.15–2.29(1H, m), 2.30–2.42(2H, m), 2.91(1H, dt, J=7.0, 7.5Hz), 3.22–3.35(2H, m), 3.72(3H, s), 4.10–4.21(2H, m), 5.01(1H, t, J=6Hz), 5.89(1H, d, J=5Hz), 7.36 (1H, s) | (FAB) m/z ; 370 (MH⁺) |
| I-238 | | 1.09(3H, d, J=6Hz), 1.15–1.28(1H, m), 1.39–1.68(1H, m), 1.74–1.92 (3H, m), 2.14–2.31(1H, m), 2.93 (1H, dt, J=7.0, 7.5Hz), 3.72(3H, s), 3.76(3H, s), 5.99(1H, d, J=4Hz), 7.35(1H, d, J=1Hz), 7.65 (1H, s) | |
| I-239 | | 1.09(3H, d, J=6Hz), 1.12–1.26(1H, m), 1.36–1.51(1H, m), 1.78–1.93 (3H, m), 2.15–2.31(1H, m), 2.75–2.98(7H, m), 3.72(3H, s), 5.88(1H, d, J=5Hz), 7.37(1H, s) | (FAB) m/z; 284 (MH⁺) |
| I-240 | | 1.10(3H, d, J=6Hz), 1.15–1.33(1H, m), 1.38–1.57(1H, m), 1.75–1.94 (3H, m), 2.11–2.37(1H, m), 2.91 (1H, dt, J=7.0, 7.5Hz), 3.19(2H, br), 3.44–3.58(4H, m), 3.73(3H, s), 3.78(2H, t, J=5Hz), 3.89(2H, t, J=5Hz), 5.96(1H, d, J=5Hz), 7.36(1H, d, J=1Hz), (MH⁺) | (FAB) m/z ; 344 (MH⁺) |

TABLE 52

| Compound No. | Structural Formulas | $^1$H—NMR ($\delta$ ppm in CDCl$_3$) | MS |
|---|---|---|---|
| I-241 | | 0.16–0.24(2H, m), 0.48–0.57(2H, m), 0.98–1.04(1H, m), 1.09(3H, d, J=6Hz), 1.19–1.37(1H, m), 1.40–1.55(1H, m), 1.74–1.93(3H, m), 2.14–2.35(1H, m), 2.92(1H, dt, J=7.0, 7.5Hz), 3.07(1H, d, J=7Hz), 3.10 (1H, d, J=7Hz), 3.72(3H, s), 4.94 (1H, m), 5.91(1H, d, J=5Hz), 7.37 (1H, d, J=1Hz) | (FAB) m/z ; 310 (MH$^+$) |
| I-242 | | 1.11(3H, d, J=5.5Hz), 1.21–1.28 (1H, m), 1.42–1.53(1H, m), 1.86–1.98(3H, m), 2.17–2.25(1H, m), 2.50–2.70(2H, m), 2.96(1H, dt, J=7.0. 7.5Hz), 3.65–3.83(2H, m), 3.73 (3H, s), 4.12–4.18(2H, m), 5.73–6.14(2H, m), 7.24–7.39(6H, m) | (FAB) m/z ; 398 (MH$^+$) |
| I-243 | | 1.11(3H, d, J=6Hz), 1.18–1.27(1H, m), 1.42–1.49(1H, m), 1.46(3H, t, J=7Hz), 1.78–1.97(3H, m), 2.16–2.32(1H, m), 2.89–3.16(5H, m), 2.65–3.72(4H, m), 3.73(3H, s), 4.08 (2H, q, J=7Hz), 5.96(1H, d, J=5Hz), 6.84–7.05(4H, m), 7.39(1H, d, J=1Hz) | (FAB m/z; 444 (M$^+$) |
| I-244 | | 1.09(3H, d, J=6Hz), 1.15–1.28 (1H, m), 1.32–1.59(1H, m), 1.70–2.34(6H, m), 2.86–2.97(1H, m), 3.42(2H, q, J=6Hz), 3.61(2H, t), J=6Hz), 3.72(3H, s), 5.03(1H, t, J=6Hz), 5.90(1H, d, J=5Hz) , 7.36(1H, d, J=1Hz) | (FAB) m/z ; 332 (MH$^+$) |
| I-245 | | 1.08(3H, d, J=6Hz), 1.14–1.27 (1H, m), 1.32–1.55(1H, m), 1.71–1.96(3H, m), 2.14–2.30(1H, m), 2.85–2.96(1H. m), 3.71(3H, s), 4.35(2H, d, J=6Hz), 5.20(1H, t, J=6Hz), 5.94(1H, d, J=5Hz), 7.12–7.26(2H, m), 7.36(1H, d, J=1Hz), 7.45–7.51(2H, m) | (FAB m/z ; 424 (MH$^+$) |

TABLE 53

| Compound No. | Structural Formulas | ¹H—NMR (δ ppm in CDCl₃) | MS |
|---|---|---|---|
| I-246 | | 1.09(3H, d, J=6Hz), 1.15–1.27 (1H, m), 1.32–1.55(1H, m), 1.74–1.91(3H, m), 2.15–2.31(1H, m), 2.88–2.99(1H, m), 3.72(3H, s), 3.78(3H, s), 3.96(1H, dd, J=5.18Hz), 4.07(1H, dd, J=5.18Hz), 5.36(1H, t, J=5Hz), 5.93(1H, d, J=5Hz), 7.37(1H, d, J=1Hz) | (FAB) m/z; 328 (MH⁺) |
| I-247 | | 1.08(3H, d, J=6Hz), 1.14–1.26 (1H, m), 1.37–1.51(1H, m), 1.68–1.90(3H, m), 2.13–2.29(1H, m), 2.79–2.94(3H, m), 3.26–3.37(2H, m), 3.71(3H, s), 4.47–4.88(1H, m), 5.06(1H, d, J=8Hz), 5.93 (1H, d, J=5Hz), 7.15–7,26(4H, m), 7.35(1H, d, J=1Hz) | (FAB) m/z; 372 (MH⁺) |
| I-248 | | 1.07(3H, d, J=6Hz), 1.13–1.30 (1H, m), 1.35–1.53(1H, m), 1.68–1.96(3H, m), 2.14–2.30(1H, m), 2.76(2H, t, J=7Hz), 2.82–2.94 (1H, m), 3.44(2H, q, J=7Hz), 3.71(3H, s), 3.87(3H, s), 4.92 (1H, t, J=7Hz), 5.63(1H, br), 5.89(1H, d, J=5Hz), 6.85(6.69 (2H, m), 6.85(1H, d, J=9Hz), 7, 35(1H, d, J=1Hz) | (FAB) m/z ; 405 (M⁺) |
| I-249 | | 1.09(3H, d, J=6.0Hz), 1.15–1,32 (1H, m), 1.35–1.56(1H, m), 1.73–1.95(2H, m), 2.93(1H, dt), J=7.5, 7.0(Hz), 3.73(3H, s), 3.70–4.00 (5H, m), 5.61(1H, d, J=7,5Hz), 5.92(1H, d, J=4.5Hz), 7.36(1H,d, J=1.0Hz) | (FAB) m/z ; 330 (MH⁺) |
| I-250 | | 1.09(3H, d, J=6.0Hz), 1.13–1.27 (1H, m), 1.31–1.61(1H, m), 1.71–1.96(3H, m), 2.15–2.34(1H, m), 2.27 (2H, t, H=7.5Hz), 2.90(1H, q, J=7.0Hz), 3.72(3H, s), 4.05(4H, t, J=7.5Hz), 5.81(1H, d, J=5.5Hz), 7.55(1H, d, J=1.0Hz) | (FAB) m/z ; 296 (MH⁺), 195 |

TABLE 54

| Compound No. | Structural Formulas | $^1$H—NMR (δ ppm in CDCl$_3$) | MS |
| --- | --- | --- | --- |
| I-251 | | 1.11(3H, d, J=6.0Hz), 1.15–1.29 (1H, m), 1.33–1.56(1H, m), 1.78–1.97(3H, m), 2.17–2.32(1H, m), 2.95 (1H, q, J=7.0Hz), 3.00–3.17(4H, m), 3.67–3.73(4H, m), 3.73(3H, s), 5.95(1H, d, J=5.0Hz), 6.88–7.12(4H, m), 7.38(1H, d, J=1.0Hz) | (FAB) m/z ; 418 (M$^+$), 195 |
| I-252 | | 1.05(3H, d, J=6.0Hz), 1.12–1.29 (1H, m), 1.36–1.54(1H, m), 1.68–1.90(3H, m), 2.12–2.28(1H, m), 2.89 (1H, dt, J=7.0, 7.5Hz), 3.70(3H, s), 4.60(2H, d, J=6.0Hz), 5.93 (1H, d, J=4.5Hz), 6.79–6.87(1H, m), 7.21–7.39(4H, m), 7.54–7.56 (2H, m) | (FAB) m/z ; 386 (MH$^+$) |
| I-253 | | 1.09(3H, d, J=6.0Hz), 1.14–1.32 (1H, m), 1.37–1.59(1H, m), 1.71–1.92(3H, m), 2.15–2.31(1H, m), 2.58 (2H, t, J=6.5Hz), 2.92(1H, dt, J =7.0, 7.5Hz), 3.34(2H, dt, J=6.0, 6.5Hz), 3.72(5H, s, 5.14(1H, t, J=6.0Hz), 5.90(1H, d, J=5.0 Hz), 7.20–7.39(6H, m) | (FAB) m/z ; 406 (MH$^+$), 195 |
| I-254 | | 1.08(3H, d, J=6Hz), 1.15–1.58(2H, m), 1.73–1.95(2H, m), 2.17–2.31 (2H, m), 2.84(3H, d, J=5Hz), 2.91 (1H, dt, J=7.8Hz), 3.72(3H, s), 4.71–4.84(1H, m), 5.90(1H, d, J= 5Hz), 7.36(1H, d, J=1Hz) | (EI) m/z ; 238 (M$^+$—OMe) |
| I-255 | | 1.11(3H, d, J=6Hz), 1.17–1.39(1H, m), 1.42–1.59(2H, m), 1.80–1.95 (2H, m), 2.16–2.33(1H, m), 2.97 (1H, dt, J=7, 8Hz), 3.73(3H, s), 6.04(1H, d, J=4Hz), 6.85(1H, br), 7.21–7.40(2H, m), 7.36(1H, s), 7.65(1H, d, J=2Hz) | |

TABLE 55

| Compound No. | Structural Formulas | $^1$H-NMR ($\delta$ ppm in CDCl$_3$) | MS |
| --- | --- | --- | --- |
| I-256 | | 1.12 (3H, d, J = 6Hz), 1.17–1.34 (2H, m), 1.42–1.59 (1H, m), 1.83–1.95 (2H, m), 2.17–2.34 (1H,m), 2.98 (1H, dt, J = 7, 8Hz), 3.73 (3H, s), 6.03 (1H, d, J = 4Hz), 6.79–6.94 (3H, m), 7.37 (1H, d, J = 1Hz), 7.98–8.10 (1H, m) | (EI) m/z: 367 (M$^+$) |
| I-257 | | 1.12 (3H, d, J = 6Hz), 1.23–1.29 (1H, m), 1.42–1.59 (1H, m), 1.80–1.99 (3H, m), 2.18–2.34 (1H, m), 2.98 (1H, dt, J = 7, 8Hz), 3.73 (3H, s), 6.04 (1H, d, J = 4Hz), 6.97–7.15 (4H, m), 7.38 (1H, d, J = 1Hz), 8.06–8.18 (1H, m) | (EI) m/z: 349 (M$^+$) |
| I-258 | | 1.09 (3H, d, J = 6Hz), 1.13–1.28 (1H, m), 1.34–1.56 (1H, m), 1.76–1.95 (3H, m), 2.15–2.31 (1H, m), 2.93 (1H, dt, J = 7, 8Hz), 3.51–3.68 (4H, m), 3.72 (3H, s), 6.20–5.32 (1H, m), 5.92 (1H, d, J = 5Hz), 7.36 (1H, d, J = 1Hz) | (EI) m/z: 286 (M$^+$ $^-$OMe) |
| I-259 | | 1.11 (3H, d, J = 6Hz), 1.17–1.29(1H, m), 1.77–1.95 (3H, m), 2.18–2.33 (1H, m), 2.97 (1H, dt, J = 7, 8Hz), 3.73 (3H, s), 6.03 (1H, d, J = 4Hz), 6.74 (1H, br), 7.28–7.46 (5H, m) | |
| I-260 | | 1.11 (3H, d, J = 6Hz), 1.17–1.29 (1H, m), 1.41–1.56 (1H, m), 1.77–1.98 (3H, m), 2.17–2.33 (1H, m), 2.97 (1H, dt, J = 7, 8Hz), 3.73 (3H, s), 6.03 (1H, d, J = 4Hz), 6.77 (1H, br), 7.27–7.39 (4H, m), 7.37 (1H, d, J =1Hz) | (EI) m/z: 365 (M$^+$) |

TABLE 56

| Compound No. | Structural Formulas | ¹H—NMR (δ ppm in CDCl₃) | MS |
|---|---|---|---|
| I-261 | | 1.09(3H, d, J=6Hz), 1.19(6H, d, J=6Hz), 1.21–1.56(2H, m), 1.73–1.93 (3H, m), 2.14–2.30(1H, m), 2.91 (1H, dt, J=7.8Hz), 3.72(3H, s), 3.77–3.94(1H, m), 4.64–4.71(1H, m), 5.90(1H, d, J=5Hz), 7.37(1H, d, J=1Hz) | (FAB) m/z ; 298 (MH⁺) |
| I-262 | | 1.09(3H, d, J=6Hz), 1.17(3H, t, J=7Hz), 1.27–1.55(1H, m), 1.73–1.93 (3H, m), 2.14–2.30(1H, m), 2.91 (1H, dt, J=7.8Hz), 3.19–3.33(2H, m), 3.72(3H, s), 4.83–4.93(1H, m), 5.90(1H, d, J=5Hz), 7.37(1H, d, J=1Hz) | (FAB) m/z ; 284 (MH⁺) |
| I-263 | | 1.11(3H, d, J=6Hz), 1.16–1.34(1H, m), 1.40–1.55(1H, m), 1.76–1.95 (3H, m), 2.61–2.32(1H, m), 2.96 (1H, dt, J=7.0, 7.5Hz), 3.73(3H, s), 3.79(3H, s), 6.02(1H, d, J=5Hz), 6.61(1H, br), 6.86(2H, d, J=9Hz), 7.29–7.41(2H, m), 7.38(1H, d, J=1Hz) | (FAB) m/z ; 361 (M⁺) |
| I-264 | | 1.11(3H, d, J=6Hz), 1.22–1.29(1H, m), 1.41–1.56(1H, m), 1.81–1.99 (3H, m), 2.17–2.33(1H, m), 2.97 (1H, dt, J=7.8Hz), 3.73(3H, s), 6.03(1H, d, J=4.5Hz), 6.76(1H, br), 7.02(2H, t, J=8.5Hz), 7.33–7.38(3H, m) | (FAB) m/z ; 349 (M⁺) |
| I-265 | | 1.2(3H, d, J=6Hz), 1.19–1.30 (1H, m), 1.35–1.55(1H, m), 1.80–1.95(3H, m), 2.16–2.36(1H, m), 2.93–3.04(1H, m), 3.74(3H, s), 6.01(1H, d, J=4Hz), 6.94(1H, br), 7.38(1H, d, J=1Hz), 7.53 (1H, dd, J=2, 9Hz), 7.59(1H, d, J=2Hz), 8.10(1H, d, J=9Hz) | (FAB) m/z ; 434 (MH⁺) |

TABLE 57

| Compound No. | Structural Formulas | $^1$H—NMR ($\delta$ ppm in CDCl$_3$) | MS |
|---|---|---|---|
| I-266 | (cyclopenta-pyran with CO$_2$Me, Me, H, H substituents; O-C(=O)-NH-C$_6$H$_4$-OCF$_3$) | 1.11(3H, d, J=6Hz), 1.17–1.34 (1H, m), 1.41–1.59(1H, m), 1.78–1.98(3H, m), 2.17–2.33(1H, m), 2.92–3.02(1H, m), 3.73(3H, s), 6.04(1H, d, J=4Hz), 6.92(1H, br), 7.16–7.20(2H, m), 7.37(1H, d, J=1Hz), 7.34–7.48(2H, m) | (FAB) m/z ; 415 (M$^+$) |
| I-267 | (same core; O-C(=O)-NH-C$_6$H$_4$-CN) | 1.12(3H, d, J=6Hz), 1.17–1.34 (1H, m), 1.42–1.63(1H, m), 1.78–1.99(3H, m), 2.12–2.35(1H, m), 2.93–3.03(1H, m), 3.73(3H, s), 6.07(1H, d, 4Hz), 7.25(1H, br) , 7.36–7.47(3H, m), 7.65–7.69 (1H, m), 7.82(1H, br) | (FAB) m/z; 357 (MH$^+$) |
| I-268 | (same core; O-C(=O)-NH-C$_6$H$_4$-CO$_2$Et) | 1.12 (3H, d, J=6Hz), 1.17–1.30 (1H, m), 1.39(3H, t, J=7Hz), 1. 46–1.56(1H, m), 1.79–1.99(3H, m) , 2.17–2.34(1H, m), 2.39–3.03 (1H, m), 3.73(3H, s), 4.36(2H, q, J=7Hz), 6.05(1H, d, J=4Hz), 6.89(1H, br), 7.37(1H, d, J=1 Hz), 7.46–7.50(2H, m), 7.99–8.05 (2H, m) | (FAB) m/z; 404 (MH$^+$) |
| I-269 | (same core; O-C(=O)-NH-C$_6$H$_4$-NO$_2$) | 1.12(3H, d, J=6Hz), 1.17–1.35 (1H, m), 1.44–1.58(1H, m), 1.79–1.99(3H, m), 2.17–2.34(1H, m), 2.94–3.04(1H, m), 3.74(3H, s), 6.09(1H, d, J=4Hz), 7.29(2H, br), 7.36(1H, d, J=1Hz), 7.57–7.65(2H, m), 8.19–8,26(2H, m) | |
| I-270 | (same core; O-C(=O)-NH-C$_6$H$_4$-CH$_3$) | 1.10(3H, d, J=6Hz), 1.16–1.33 (1H, m), 1.40–1.57(1H, m), 1.76–1.98(3H, m), 2.16–2.28(1H, m), 2.90–3.01(1H, m), 3.72(3H, s), 6.02(1H, d, J=5Hz), 6.84(1H, br), 7.09–7.19(2H, m), 7.28–7.32 (2H, m), 7.37(1H, d, J=1Hz) | (FAB) m/z ; 345 (M$^+$) |

TABLE 58

| Compound No. | Structural Formulas | ¹H—NMR (δ ppm in CDCl₃) | MS |
| --- | --- | --- | --- |
| I-271 | | 1.10(3H, d, J=6Hz), 1.17–1.33 (1H, m), 1.40–1.58(1H, m), 1.56–1.98(3H, m), 2.16–2.32(1H, m), 2.91–3.02(1H, m), 3.72(3H, s), 6.04(1H, d, J=4Hz), 6.98(1H, br), 7.05–7.12(1H, m), 7.27–7.44 (5H, m) | (FAB) m/z ; 332 (MH⁺) |
| I-272 | | 1.10(3H, d, J=6Hz), 1.16–1.33 (1H, m), 1.41–1.60(1H, m), 1.78–1.96(3H, m), 2.09–2.32(1H, m), 2.90–3.00(1H, m), 3.70(3H, s), 6.11(1H, d, J=4Hz), 7.32(1H, d, J=1Hz), 7.43–7.57(3H, m), 7.84 –7.88(2H, m) | (FA) m/z ; 360 (MH⁺) |
| I-273 | | 1.11(3H, d, J=6Hz), 1.17–1.34 (1H, m), 1.41–1.59(1H, m), 1.78–1.99(3H, m), 2.16–2.33(1H, m), 2.60(3H, s), 6.06(1H, d, J=4Hz) , 7.32(1H, br), 7.27–7.47(2H, m), 7.67–7.78(2H, m), 8.01(1H, s) | (FAB) m/z ; 374 (MH⁺) |
| I-274 | | 1.11(3H, d, J=6Hz), 1.17–1.34 (1H, m), 1.42–1.60(1H, m), 1.79–1,94(3H, m), 2.15–2.31(1H, m), 2.91–3.01(1H, m), 3.73(3H, s), 4.51(3H, s), 6.02(1H, d, J=3Hz) , 7.32(1H, d, J=1Hz), 8.32(1H, br) | |
| I-275 | | 1.11(3H, d, J=6.0Hz), 1.12–1.34 (1H, m), 1.41–1.57(1H, m), 1.77–2. 02(3H, m), 2.12–2.33(1H, m), 2. 47(3H, s), 2.97(1H, dt, J=7.5, 7. 0Hz), 3.73(3H, s), 6.03(1H, d, J =4.5Hz), 6.68(1H, s), 7.25(2H, d, J=8,5Hz), 7.34(2H, d, J=8.5 Hz), 7.37(1H, d, J=1.0Hz) | (FAB) m/z ; 377 (M°) |

TABLE 59

| Compound No. | Structural Formulas | $^1$H—NMR (δ ppm in CDCl$_3$) | MS |
|---|---|---|---|
| I-276 | 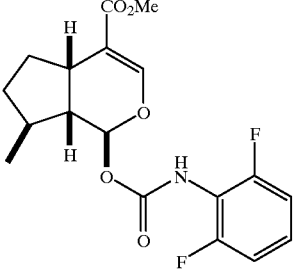 | 1.10(3H, d, J=6.0Hz), 1.17–1.27 (1H, m), 1.33–1.58(1H, m), 1.78–1.94(3H, m), 2.14–2.31(1H, m), 2.90 –2.95(1H, m), 3.73(3H, m), 6.02 (1H, d, J=4.5Hz), 6.25(1H, br), 6.89–7.02(2H, m), 7.15–7.25(1H, m), 7.37(1H, d, J=1.0Hz) | (FAB) m/z ; 368 (MH$^+$), 195 |
| I-277 | 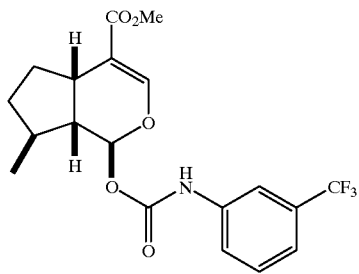 | 1.12(3H, d, J=6.0Jz), 1.17–1.34 (1H, m), 1.42–1.57(1H, m), 1.78–1.99(3H, m), 2.17–2.33(1H, m), 2.98 (1H, dt, J=6.5, 7.5Hz), 3.73(3H, m), 6.06(1H, d, J=4.0Hz), 7.00 (1H, br), 7.33–7,49(3H, m), 7.58–7.63(1H, m), 7.75(1H, br) | (FAB) m/z ; 400 (MH$^+$), 195 |
| I-278 | 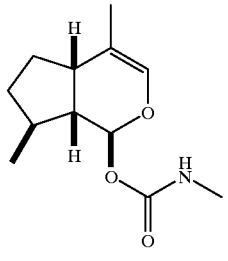 | 1.07(3H, d, J=6Hz), 1.11–1.30(2H, m), 1.53(3H, s), 1.70–2.0(4H, m), 2,43–2.51(1H, m), 2.82(3H, d, J= 4Hz), 4.67–4.81(1H, m), 5.85(1H, d, J=4Hz), 5.98(1H, s) | |
| I-279 | 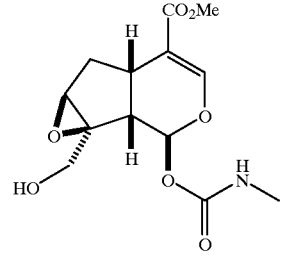 | 1.28(3H, t, J=7Hz), 1.49(1H, dd, J= 10, 14Hz), 1.92(1H, dd, J=4, 9Hz), 2.51(1H, dd, J=7, 10Hz), 2.71(1H, dd, J=11, 14 Hz), 2.82–2.94(1H, m), 2,89(3H, d, J=5Hz), 3.55(1H, s), 3.68(1H, dd, J=9, 13Hz), 4.01(1H, dd, J=4, 13Hz), 4.18(2H, q, J=7Hz), 5.0.6–5.09(1H, m), 5.73(1H, d,J= 10Hz), 7.41(1H, s) | |
| I-280 | 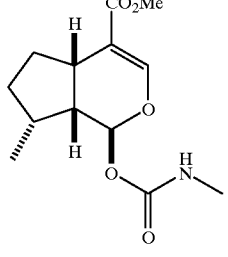 | 1.02(3H, d, J=7Hz), 1.28–1.60(2H, m), 1.78–1.92(1H, m), 2.10–2.35(3H, m), 2.84(3H, d, J=5Hz), 2.92(1H, dt, J=8, 9Hz), 3.71(3H, s), 4.80 (1H, br), 5.99(1H, d, J=7Hz), 7.39 (1H, s) | (EI) m/z ; 269 (M$^+$) |

TABLE 60

| Compound No. | Structural Formulas | ¹H—NMR (δ ppm in CDCl₃) | MS |
| --- | --- | --- | --- |
| I-281 | | 0.98(3H, d, J=7Hz), 1.24–2.23(3H, m), 2.26–2.36(1H, m), 2.73(3H, s), 2.85–2.95(1H, m), 5.89(1H, d, J=5Hz), 7.10(1H, s) | |
| I-282 | | 1.06(3H, d, J=7Hz), 1.21–1.47(2H, m), 1.51–1.96(3H, m), 2.17–2.32(2H, m), 2.40–2.52(4H, m), 2.57(2H, t, J=6Hz), 2.83(3H, d, J=5Hz), 3.03–3.24(1H, m), 3.52–3.80(6H, m), 4.87–4.90(1H, m), 6.02(1H, d, J=5Hz), 6.48(1H, d, J=1Hz) | |
| I-283 | | 1.07(3H, d, J=6Hz), 1.11–1.27(1H, m), 1.43–1.50(1H, m), 1.53(3H, s), 1.66–1.98(4H, m), 2.43–2.39(1H, m), 2.82(3H, d, J=5Hz), 4.63–4.76(1H, m), 5.85(1H, d, J=4Hz), 5.98(1H, s) | |
| I-284 | | 1.42(3H, s), 1.51(1H, ddd, J=1, 8.13Hz), 2.50(1H, dd, J=7, 10Hz)(, 2.62–2.72(1H, m), 2.83–2.96(1H, m), 3.25(3H, s), 3.33(1H, s), 3.43(3H, s), 3.72(3H, s), 6.43(1H, d, J=10Hz), 7.41(1H, d, J=1Hz) | (EI) m/z; 313(M⁺) |
| I-285 | | 1.49(3H, s), 1.59–1.71(1H, m), 2.58—2.82(3H, m), 3.06(3H, s), 3.31(1H, s), 3.40(3H, s), 3.73(3H, s), 7.17(1H, d, J=4Hz), 7.40(1H, s) | |

TABLE 61

| Compound No. | Structural Formulas | ¹H—NMR (δ ppm in CDCl₃) | MS |
|---|---|---|---|
| I-286 | | 1.43(3H, s), 1.45–1.57(1H, m), 2.53–2.75(2H. m), 2.93(1H, dt, J=8, 9Hz), 3.32(1H, s), 3.73 (3H, s), 6.03(1H, d, J=10Hz), 7.44(1H, s), 7.45–7.69(3H, m), 8.12–8.16(2H, m) | |
| I-287 | | 1.60–1.68(1H, m), 2.10–2.22(1H, m), 2.77–2.89(1H, m), 2.81(3H, d, J=5Hz), 2.84(3H, d, J=5Hz), 3.23(1H, q, J=8Hz), 3.73(3H, s), 4.62(1H, d, J=12Hz), 4.66–4.77(1H, m), 4.89(1H, d, J=12Hz), 5.22–5.35(1H, m), 5.68 (1H, d, J=8Hz), 5.92(1H, br), 7,48(1H, d, J=1Hz) | (FAB) m /z; 341 (MH⁺) |
| I-288 | | 2.12–2.24(1H, m), 2.77–2.99(2H, m), 3.25(1H, q, J=8Hz), 3.52–3.69(8H, m), 3.74(3H, s), 4.53 (1H, d, J=13Hz), 4.90(1H, d, J=13Hz), 5.13–5.21(1H, m), 5.70–5.73(1H, m), 5.71(1H, d, J=8Hz), 5.94(1H, br), 7.48(1H, d, J=12Hz) | |
| I-289 | | 1.30–2.15(3H, m), 2.52–2.70(3H, m), 3.40(1H, t, J=13Hz), 3.48 (1H, d, J=13Hz), 3.72(3H, s), 3.99(1H, d, J=13Hz), 4.35(1H, dd, J=5, 12Hz), 7.60(1H, s) | |
| I-290 | | 1.43–1.57(1H, m), 2.46–2.73(3H, m), 2.83(3H, d, J=5Hz), 3.34–3.46(2H, m), 3.71(3H, s), 4.03 (1H, d, J=13Hz), 4.43(1H, dd, J =5, 11Hz), 4.57(1H, J=3Hz), 4. 75(1H, br), 7.60(1H, s) | |

TABLE 62

| Compound No. | Structural Formulas | ¹H—NMR (δ ppm in CDCl₃) | MS |
|---|---|---|---|
| I-291 | | 1.43–1.55(1H, m), 2.50–2.70(3H, m), 3.34–3.46(2H, m), 3.50–3.66(4H, m), 3.71(3H, s), 4.07(1H, d, J=13Hz), 4.42(1H, dd, J=5, 11Hz), 4.56(1H, d, J=13Hz), 5.24(1H, br), 7.60(1H, s) | |
| I-292 | | 2.02–2.17(1H, m), 2.81–2.94(2H, m), 3.09(1H, dt, J=7, 8Hz), 3.51(1H, t, J=11Hz), 3.71(3H, s), 4.13(2H, s), 4.41(1H, dd, J=5, 11Hz), 5.92(1H, br), 7.30(1H, ddd, J=1, 8, 11Hz), 7.43(1H, J=1, 8, 11Hz), 7.66(1H, s), 7.85(1H, dd, J=1, 8Hz), 7.89(1H, dd, J=1, 8Hz) | |
| I-293 | | 1.65–1.96(2H, m), 2.22–2.36(1H, m), 2.49–2.61(6H, m), 3.06–3.16(3H, m), 3.63–371(6H, m), 3.74(3H, s), 4.40(1H, dd, J=4, 11Hz), 5.97(1H, s), 7.68(1H, s) | |
| I-294 | | 0.89(3H, t, J=6Hz), 1.14–1.57(4H, m), 1.28(8H, br), 1.77–2.28(4H, m), 2.64–2.73(1H, m), 3.40(0.5H, t, J=11Hz), 3.47(0.5H, t, J=12Hz), 3.70(1.5H, s), 3.71(1.5H, s), 4.02(0.5H, dd, J=3, 12Hz), 4.12(0.5H, dd, J=4, 11Hz), 5.56(0.5H, s), 7.56(0.5H, s), 7.60(0.5H, s) | (EI) m/z; 266(M⁺) |
| I-295 | | 2.03–2.17(1H, m), 2.68–2.87(3H, d, J=5Hz), 3.08(1H, q, J=8Hz), 3.42(1H, t, J=11Hz), 3.73(3H, s), 4.27(1H, dd, J=5, 11Hz), 4.65(2H, q, J=9Hz), 5.86(1H, s), 7.67(1H, s) | (EI) mz/; 236 (M⁺—OMe) |

TABLE 63

| Compound No. | Structural Formulas | $^1$H—NMR (δ ppm in CDCl$_3$) | MS |
|---|---|---|---|
| I-296 | | 2.03–2.18(1H, m), 2.67–2.97(2H, m), 3.09(1H, dt, J=7, 8Hz), 3.43(1H, t, J=11Hz), 3.50–3.65(4H, m), 3.73 (3H, s), 4.27(1H, dd, J=5, 11Hz), 4.66(2H, q, J=8Hz), 5.15(1H, br), 5.88(1H, br), 7.67(1H, d, J=1Hz) | |
| I-297 | | 1.26–1.48(2H, m), 1.86–1.90(1H, m), 2.21–2.38(2H, m), 2.53–2.84(2H, m), 3.46–3.65(5H, m), 3.72(3H, s), 4.01–4.22(3H, m), 5.12(1H, br), 7.58(0.6H, s), 7.61(0.4H, s) | |
| I-298 | | 0.89(3H, t, J=7Hz), 1.29–1.56(10H, m), 2.04–2.14(1H, m), 2.37–2.69(3H, m), 3.26(1H, s), 3.38(1H, dt, J=10, 12Hz), 3.71(3H, s), 4.21–4.29 (1H, m), 7.48(1H, s) | |
| I-299 | | 0.88(3H, t, J=6Hz), 1.28(6H, br), 1.44–1.60(2H, m), 1.96–2.31(3H, m), 2.58–2.96(2H, m), 2.85(3H, d, J=5Hz), 3.17(1H, dt, J=6, 8Hz), 3.72 (3H, s), 4.71–4.85(1H, m), 5.52(1H, br), 5.87(1H, d, J=7JHz), 7.44(1H, s) | (EI) m/z; 306 (M$^+$—OMe) |
| I-300 | | 0.89(3H, t, J=6Hz), 1.26–1.53(2H, m), 1.28(10H, m), 1.67–2.30(4H, m), 2.77–2.96(1H, m), 2.84(3H, d, J=5Hz), 3.72(3H, s), 4.71–4.85(1H, m), 5.84(0.7H, d, J=6Hz), 5.96(0.3H, d, J=7Hz), 7.39(0.7H, s), 7.44 0.3H, s) | |

TABLE 64
| Compound No. | Structural Formulas | ¹H—NMR (δ ppm in CDCl₃) | MS |
|---|---|---|---|
| I-301 | 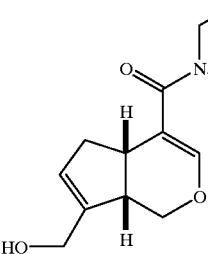 | 1.67–2.14(3H, m), 2.43–2.88(8H, m), 3.22(1H, dt, J=7Hz), 3.24–3.78(7H, m), 4.17–4.24(1H, m), 4.25(2H, s), 5.76(1H, s), 6.74(1H, d, J=1Hz) | |
| I-302 | 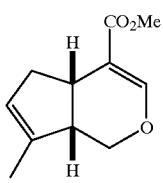 | 1.74(3H, t, J=1Hz), 1.95–2.11(1H, m), 2.49–2.59(1H, m), 2.73–2.88(1H, m), 3.04(1H, dt, J=7, 8Hz), 3.43 (1H, t, J=11Hz), 3.72(3H, s), 4.19 (1H, dd, J=5, 11Hz), 5.47(1H, t, J= 1Hz), 7.66(1H, d, 1Hz) | |
| I-303 | 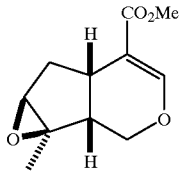 | 1.36–2.11(2H, m), 1.43(3H, s), 2.26 –2.38(1H, m), 2.52–2.70(2H, m), 3. 26(1H, s), 3.71(3H, s), 4.26(1H, dd, J=5, 11Hz), 7.85(1H, s) | |
| I-304 | 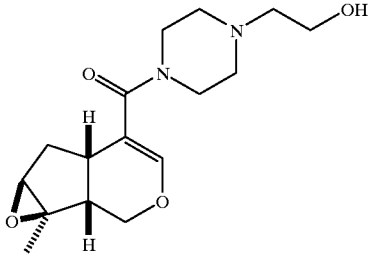 | 1.43(3H, s), 1.46–1.59(1H, m), 2.32 –2.72(10H, m), 3.25(1H, s), 3.35 (1H, dd, J=11, 12Hz), 3.53–3.70(6H, m), 4.20(1H, dd, J=5, 11Hz), 6.65 (1H, d, J=1Hz) | |
| I-305 | 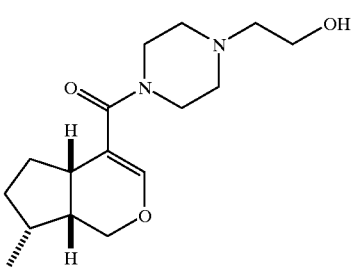 | 1.08(3H, d, J=7Hz), 1.14–1.35(2H, m), 1.66–2.07(4H, m), 2.45–2.52(4H, m), 2.56(2H, t, J=6Hz), 2.93(1H, dt, J=7, 9Hz), 3.48–3.79(8H, m), 4. 0.2(1H, dd, J=4, 11Hz), 6.64(1H, d, J=2Hz) | |

TABLE 65

| Compound No. | Structural Formulas | $^1$H—NMR ($\delta$ ppm in CDCl$_3$) | MS |
|---|---|---|---|
| I-306 | | 1.08(3H, d, J=6Hz), 1.16–1.30(2H, m), 1.73–2.03(5H, m), 2.47(3H, m), 2.63(2H, t, J=5Hz), 2.79(3H, d, J=5Hz), 2.92(1H, t, J=7Hz), 3.49–3.78 (5H, m), 4.02(1H, dd, J=4, 11Hz), 4.20(2H, t, J=5Hz), 4.72(1H, br), 6.62(1H, d, J=1Hz) | |
| I-307 | | 1.77(3H, s), 2.13–2.24(1H, m), 2.61 –2.78(2H, m), 2.86(3H, d, J=5Hz), 3.13–3.28(1H, m), 4.82(1H, br), 5. 53(1H, br), 5.90(1H, d, J=7Hz), 7. 56(1H, s), 9.52(1H, br) | (FAB) m/ z: 254 (MH$^+$) |
| I-308 | | 1.81(3H, br), 2.16–2.28(1H, m), 2. 74–2.88(2H, m), 3.24(1H, dt, J=7. 8Hz), 5.55(1H, br), 6.03(1H, d, J= 6Hz), 6.82–6.95(3H, m), 7.51(1H, d, J=1Hz), 7.96–8.06(1H, m), 15.19 (1H, br) | (FAB) m/ z; 352 (MH$^+$) |
| I-309 | | 1.79(3H, s), 1.95–2.05(1H, m), 2.39 –2.65(89H, m), 2.78–2.80(1H, m), 2. 83(3H, d, J=5Hz), 3.33–3.78(7H, m), 5.13(1H, br), 5.47(1H, s), 6.03 (1H, s, J=5Hz), 6.45(1H, d, J=1Hz) | |
| I-310 | | 1.77(3H, d, J=1Hz), 2.14–2.18(1H, m), 2.64–2.77(2H, m), 2.84(3H, d, J =5Hz), 2.86(3H, d, J=5Hz), 3.24(1H, q, J=8Hz), 4.89(1H, br), 5.50(2H, br), 5.85(1H, d, J=7Hz), 7.13(1H, s) | |

TABLE 66

| Compound No. | Structural Formulas | $^1$H—NMR ($\delta$ ppm in CDCl$_3$) | MS |
|---|---|---|---|
| I-311 | | 1.18(3H, d, J=6Hz), 1.21(3H, d, J=6Hz), 1.80(3H, s), 1.94–2.03(1H, m), 2.44–2.80(3H, s), 2.84(3H, d, J=5Hz), 3.33–3.59(3H, m), 3.97–4.05 (1H, m), 4.23–4.31(1H, m), 4.87–5.00(1H, m), 5.47(1H, br), 6.02(1H, d, J=5Hz), 6.45(1H, d, J=1Hz) | |
| I-312 | | 1.28(3H, t, J=7Hz), 1.76(3H, s), 2.09–2.21(1H, m), 2.60–2.77(2H, m), 2.85(3H, d, J=5Hz), 3.20(1H, dt, J=7, 8Hz), 4.18(2H, q, J=7Hz), 4.81 (1H, br), 5.52(1H, s), 5.87(1H, d, J=7Hz), 7.44(1H, s) | (EI) m/z 236 (M$^+$—OEt) |
| I-313 | | 1.76(3H, s), 2.07–2.37(1H, m), 2.61–2.82(2H, m), 2.72(3H, s), 3.16–3.32(1H, m), 5.49(1H, br), 5.79(1H, d, J=6Hz), 7.17(1H, s) | |
| I-314 | | 2.12–3.08(3H, m), 2.84(3H, d, J=5Hz), 3.22–3.38(1H, m), 3.73(3H, s), 4.82(1H, br), 4.92(1H, br), 5.06(1H, br), 5.92(1H, d, J=10Hz), 6.02(1H, br), 7.48(1H, s) | |
| I-315 | | 1.64–1.92(2H, br), 2.08–2.32(1H, m), 2.84(3H, d, J=5Hz), 3.26(1H, q, J=8Hz), 3.73(3H, s), 4.26(2H, br), 5.06(1H, br), 5.84(1H, d, J=7Hz), 5.85(1H, br), 7.46(1H, d, J=1Hz) | |

TABLE 67

| Compound No. | Structural Formulas | $^1$H—NMR (δ ppm in CDCl$_3$) | MS |
|---|---|---|---|
| II-1 | | 1.07–1.19(1H, m), 1.77(3H, s), 2.19–2.23(1H, m), 2.63–2.77(2H, m), 3.23(1H, q, J=8Hz), 3.53–3.85 (4H, m), 5.18(2H, d, J=2Hz), 5.25–5.30(1H, m), 5.53(1H, br), 5.89 (1H, d, J=7Hz), 7.35(5H, s), 7.50 (1H, d, J=1Hz | |
| II-2 | | 1.40–1.55(1H, m), 1.44(3H, s), 2.29–2.94(3H, m), 3.28(1H, s), 3.59 –3.70(4H, m), 5.17(2H, d, J= 11Hz), 5.30(1H, br), 5.73(1H, d, J=10Hz), 7.35(5H, s), 7.45(1H, s) | |
| II-3 | | 1.21–1.26(1H, m), 1.55(3H, s), 2.42–2.47(1H, m), 2.96–3.05(1H, m), 3.28(1H, s), 3.46–3.64(5H, m), 5.13–5.25(3H, m), 6.44(1H, d, J= 1Hz), 7.35(1H, s) | |
| II-4 | | 1.19–1.45(1H, m), 1.55(3H, s),2.00–2.14(1H, m), 2.60(1H, d, J= 9Hz), 2.88–2.96(1H, m), 3.27(1H, s), 3.34–3.73(4H, m), 6.44(1H, s), 6.93(1H, br), 7.25(1H, s), 10.65(1H, br) | |

TABLE 67-continued

| Compound No. | Structural Formulas | $^1$H—NMR (δ ppm in CDCl$_3$) | MS |
| --- | --- | --- | --- |
| II-5 | | 1.83(3H, s), 2.14–2.27(1H, m), 2.75–2.90(2H, m), 3.29(1H, dt, J=7, 8Hz), 3.74(3H, s), 5.56(1H, d, J=1Hz), 5.95(1H, d, J=6Hz), 7.18–7.47(6H, m)MS (EI) m/z; 330(M$^+$) | |

TABLE 68

| Compound No. | Structural Formulas | $^1$H—NMR (δ ppm in CDCl$_3$) | MS |
| --- | --- | --- | --- |
| II-6 | | 1.13(3H, d, J=6Hz), 1.20–1.31(1H, m), 1.45–1.63(1H, m), 1.86–1.96 (3H, m), 2.04–2.43(1H, m), 3.04 (1H, dt, J=6.5, 7.0Hz), 3.74(3H, s), 5.99(1H, d, J=3.5Hz), 7.18–7.30(3H, m), 7.35–7.44(3H, m) | |
| II-7 | | 1.13–1.34(4H, m), 1.37–1.42(3H, m), 2.09–2.18(1H, m), 2.68(1H, dt, J=7, 8Hz), 2.83–2.96(1H, m), 3.21(1H, dt, J=8, 9Hz), 3.34–3.86 (2H, m), 4.29(2H, s), 4.76(0.5H, d, J=8Hz), 4.91(0.5H, d, J=8Hz), 4.96–4.99(0.5H, m), 5.09(0.5H, q, J=5Hz), 5.84–5.88(1H, m), 6.30–7.50(1H, br), 7.61(1H, d, J=3Hz) | |
| II-8 | | 1.14–1.47(11H, m), 2.13–2.22(1H, m), 2.70–3.63(4H, m), 4.13–4.53 (5H, m), 4.78(1H, q, J=5Hz), 5.78 (1H, br), 7.56(1H, J=1Hz) | |
| II-9 | | 1.29(3H, t, J=7Hz), 1.60–1.94(1H, m), 2.00–2.15(1H, m), 2.45(1H, t, J=8Hz), 2.82–2.96(2H, m), 3.22 (1H, dt, J=8, 9Hz), 4.20(2H, q, J=7Hz), 4.32(2H, s), 4.78–4.84(1H, m), 5.88(1H, s), 7.53(1H, d, J=1Hz) | |

TABLE 68-continued
| Compound No. | Structural Formulas | $^1$H—NMR (δ ppm in CDCl$_3$) | MS |
|---|---|---|---|
| II-10 | 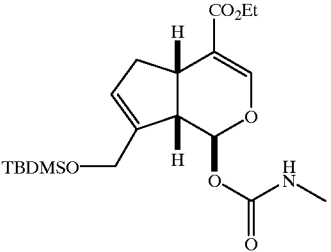 | 0.07(6H, s), 0.91(9H, s), 1.28 (3H, t, J=7Hz), 2.13–2.25(1H, m), 2.79–2.92(1H, m), 2.86(3H, d, J=5Hz), 3.25(1H, dt, J=7, 8Hz), 4.15 –4.26(2H, m), 4.83(1H, br), 5.80 (1H, br), 5.88(1H, d, J=7Hz), 7.45 (1H, d, J=1Hz) | |
TABLE 69
| Compound No. | Structural Formulas | $^1$H—NMR (δ ppm in CDCl$_3$) | MS |
|---|---|---|---|
| II-11 | 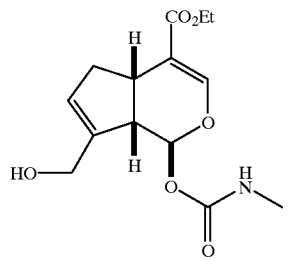 | 1.17–1.28(1H, m), 1.28(3H, t, J=7Hz), 2.14–2.27(1H, m), 2.84(3H, d, J=5Hz), 2.84–2.95(2H, m), 3.25 (1H, dt, J=7, 8Hz), 4.14–4.25(4H, m), 4.92(1H, br), 5.85(1H, d, J=7Hz), 5.87(1H, br), 7.46(1H, d, J=1Hz) | |
| II-12 | 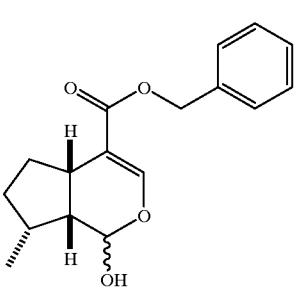 | 1.13(2.1H, d, J=7Hz), 1.15(0.9H, d, J=7Hz), 1.18–2.38(5H, m), 2.87–2.95(1H, m), 5.04–5.26(1H, m), 5.15(1H, d, J=8Hz), 5.18(1H, d, J=8Hz), 7.35(5H, s), 7.47(1H, s) | |
| II-13 | 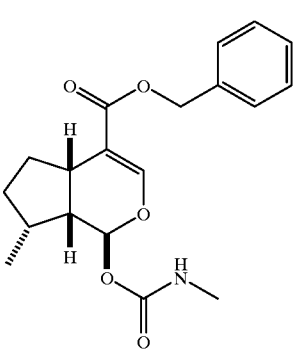 | 1.01(3H, d, J=7Hz), 1.04–1.37(1H, m), 1.81–1,87(1H, m), 2.12–2.32 (3H, m), 2.79–2.82(1H, m), 2.84 (3H, d, J=5Hz), 2.94(1H, q, J=8Hz), 4.79(1H, br), 5.13–5.22(2H, m), 5.99(1H, d, J=7Hz), 7.35(5H, s), 7.45(1H, s) | |

TABLE 69-continued

| Compound No. | Structural Formulas | $^1$H—NMR (δ ppm in CDCl$_3$) | MS |
| --- | --- | --- | --- |
| II-14 | | 1.08(3H, d, J=6Hz), 1.15–1.32(1H, m), 1.43–1.59(1H, m), 1.71–1.96 (3H, m), 2.15–2.31(1H, m), 2.79–2.95(1H, m), 2.84(3H, d, J=5Hz), 4.74–4.86(1H, m), 5.92(1H, d, J=5Hz), 7.48(1H, d, J=1Hz), 11.26 (1H, br) | (FAB) m/z; 256 (MH$^+$) |
| II-15 | | 1.08(3H, d, J=6Hz), 1.16–1.33(1H, m), 1.39–1.59(2H, m), 1.65–2.01 (4H, m), 2.06(3H, s), 2,65(1H, dt, J=6, 7Hz), 2.83(3H, d, J=5Hz), 4.37(1H, d, J=12Hz), 4.59(1H, d, J=12Hz), 4.79–4.91(1H, m), 5.83 (1H, d, J=5Hz), 6.35(1H, br) | |

TABLE 70

| Compound No. | Structural Formulas | $^1$H—NMR (δ ppm in CDCl$_3$) | MS |
| --- | --- | --- | --- |
| II-16 | | 2.03–2.18(1H, m), 2.09(3H, s), 2.66–2.97(2H, m), 3.09(1H, dt, J=7, 8Hz), 3.43(1H, t, J=12Hz), 3.73 (3H, s), 4.27(1H, dd, J=5, 12Hz), 4.64(2H, q, J=13Hz), 5.89(1H, br), 7.68(1H, s) | |
| II-17 | | 1.51(1H, t, J=6Hz), 2.02–2.17(1H, m), 2.74–2.99(2H, m), 3.08(1H, dt, J=7, 8Hz), 3.47(1H, t, J=11Hz), 4.22–4.33(3H, m), 5.79(1H, s), 7.68(1H, s) | |
| II-18 | | 2.00–2.13(1H, m), 2.78–2.99(2H, m), 3.13(1H, q, J=8Hz), 3.57(1H, dd, J=4, 11Hz), 3.72(3H, s), 3.92 (1H, d, J=10Hz), 4.06(1H, d, J=10Hz), 4.30(1H, dd, J=10Hz), 5.98 (1H, br), 7.67(1H, d, J=1Hz) | |

TABLE 70-continued

| Compound No. | Structural Formulas | $^1$H—NMR ($\delta$ ppm in CDCl$_3$) | MS |
| --- | --- | --- | --- |
| II-19 | | 1.16–1.25(1H, m), 2.27–2.31(1H, m), 3.05–3.19(2H, m), 3.42(1H, t, J=11Hz), 3.74(3H, s), 4.45(1H, dd, J=5, 11Hz), 7.10(1H, t, J= 1Hz), 7.71(1H, s), 8.18(1H, br) | |
| II-20 | | 0.91(3H, t, J=7Hz), 1.30–1.43(4H, m), 2.11–2.28(3H, m), 2.76–3.09 (3H, m), 3.35(1H, t, J=11Hz), 3.73 (3H, s), 4.23(1H, dd, J=4, 11Hz), 5.41–5.54(1H, m), 7.79–7.88(2H, m), 7.68(1H, s) | |

TABLE 71

| Compound No. | Structural Formulas | $^1$H—NMR ($\delta$ ppm in CDCl$_3$) | MS |
| --- | --- | --- | --- |
| II-21 | | 1.56–1.66(1H, m), 2.64–2.83(3H, m), 3.41(1H, t, J=11Hz), 3.72(3H, s), 3.89(1H, s), 5.01(1H, ddd, J =1, 4, 11Hz), 7.61(1H, s), 9.14 (1H, s) | |
| II-22 | | 0.91(3H, t, J=7Hz), 1.29–1.57(5H, m), 2.13–2.20(2H, m), 2.45–2.61 (1H, m), 2.65–2.73(2H, m), 3.35 (1H, t, J=10Hz), 3.45(1H, s), 3.71 (3H, s), 4.20(1H, dd, J=5, 10Hz), 5.54–5.75(2H, m), 7.59(1H, s) | |
| II-23 | | 0.90(3H, t, J=7Hz), 1.10–1.24(3H, m), 1.29–1.39(6H, m), 2.12–2.25 (3H, m), 2.61–3.01(3H, m),3.18 (1H, dt, J=7, 8Hz), 3.34–3.78(2H, m), 3.73(3H, s), 4.74(1H, d, J= 8Hz), 4.87(0.5H, q, J=5Hz), 5.03 (0.5H, q, J=5Hz), 5.45–6.12(3H, m), 7.49(0.5H, s), 7.52(0.5H, s) | |

TABLE 71-continued

| Compound No. | Structural Formulas | $^1$H—NMR (δ ppm in CDCl$_3$) | MS |
|---|---|---|---|
| II-24 | | 0.88(3H, t, J=6Hz), 1.12–1.40 (12H, m), 1.97–2.95(7H, m), 3.14 (1H, q, J=8Hz), 3.35–3.81(2H, m), 3.72(3H, s), 4.74(1H, d, J=7Hz), 4.90(0.5H, q, J=7Hz), 5.04(0.5H, q, J=5Hz), 5.51(1H, br), 7.47(0.5H, s), 7.49(0.5H, s) | |
| II-25 | | 0.89(3H, t, J=6Hz), 1.29(7H, br), 1.96–2.48(5H, m), 2.75–3.38(3H, m), 3.73(3H, s), 4.83–4.91(1H, m), 5.54(1H, br), 7.49(1H, d, J=1Hz) | |

TABLE 72

| Compound No. | Structural Formulas | $^1$H—NMR (δ ppm in CDCl$_3$) | MS |
|---|---|---|---|
| II-26 | | 0.99–1.39(3H, m), 1.08(3H, d, J=7Hz), 1.61–1.94(3H, m), 2.22–2.32 (1H, m), 2.76(1H, dt, J=8Hz), 3.52 (1H, dd, J=4, 11Hz), 4.06(1H, dd, J=4, 11Hz), 7.70(1H, d, J=1Hz) | |
| II-27 | | 1.15–1.25(3H, m), 1.38(1.5H, d, J=5Hz), 1.39(1.5H, d, J=5Hz), 1.84 (3H, d, J=2Hz), 2.01–2.17(1H, m), 2.45–2.53(1H, m), 2.73–2.85(1H, m), 3.16(1H, q, J=8Hz), 3.40–3.85 (3H, m), 4.76(1H, d, J=8Hz), 4.88–4.95(0.5H, m), 5.06(0.5H, q, J=5Hz), 5.53(1H, br), 7.58(0.5H, s), 7.61(0.5H, s), 9.52(1H, br) | (FAB m/z; 269 (MH$^+$) |
| II-28 | | 1.89(1.5H, t, J=7Hz), 1.21(1.5H, t, J=7Hz), 1.38(1.5H, d, J=5Hz), 1.39(1.5H, d, J=5Hz), 1.83(1.5H, d, J=2Hz), 1.85(1.5H, d, J=2Hz), 1.99–2.14(1H, m), 2.48(1H, t, J=8Hz), 2.74–2.86(1H, m), 3.18(1H, dt, J=8, 9Hz), 3.39(3H, s), 3.47–3.62(2H, m), 3.74–3.85(2H, m), 4.92(0.5H), q, J=7Hz), 5.06(0.5H, q, J=5Hz), 5.38(1H, d, J=9Hz), 5.41 (1H, d, J=9Hz), 5.53(1H br), 7.55 (0.5H, d, J=1Hz), 7.57(0.5H, d, J=1Hz). | (FAB) m/z; 357 (MH$^+$) |

TABLE 72-continued

| Compound No. | Structural Formulas | $^1$H—NMR (δ ppm in CDCl$_3$) | MS |
| --- | --- | --- | --- |
| II-29 | [structure] | 1.87(3H, d, J=2Hz), 1.96–2.11(1H, m), 2.75–2.89(1H, m), 3.19(1H, dt, J=7, 9Hz), 3.39(3H, s), 3.44 (1H, d, J=5Hz), 3.54–3.59(2H, m), 3.78–3.83(2H, m), 5.38(1H, d, J=10Hz), 5.41(1H, d, J=10Hz), 5.55 (0.8H, d, J=2Hz), 5.66(0.2H, br), 7.57(1H, d, J=1Hz) | (FAB) m/z; 285 (MH$^+$) |

TABLE 73

| Compound No. | Structural Formulas | $^1$H—NMR (δ ppm in CDCl$_3$) | MS |
| --- | --- | --- | --- |
| II-30 | [structure] | 1.77(3H, s), 2.09–2.23(1H, m), 2.61 –2.80(2H, m), 2.85(3H, d, J=5Hz), 3.20(1H, dt, J=7, 8Hz), 3.39(3H, s), 3.54–3.58(2H, m), 3.77–3.82(2H, m), 4.86–4.92(1H, m), 5.38(1H, d, J=10Hz), 5.41(1H, d, J=10Hz), 5.53 (1J, br s), 5.90(1H, d, J=7Hz), 7.52(1H, d, J=1Hz) | (FAB) m/z; 342 (MH$^+$) |
| II-31 | [structure] | 1.81(3H, s), 2.15–2.26(1H, m), 2.73–2.90(2H, m), 3.27(1H, q, J=7Hz), 3.39(3H, s), 3.54–3.59(2H, m), 3.78–3.83(2H, m), 5.39(1H, d, J=10Hz), 5.43(1H, d, J=10Hz), 5.56(1H, br), 6.03(1H, d, J=9Hz), 6.84–6.94(3H, m), 7.53(1H, d, J=11Hz), 7.95–8.15(1H, m) | (FAB) m/z; 440 (MH$^+$) |

TABLE 74

| Compound No. | Structural Formulas |
| --- | --- |
| III-1 | [structure] |
| III-2 | [structure] |

TABLE 74-continued

| Compound No. | Structural Formulas |
|---|---|
| III-3 | (structure) |
| III-4 | (structure) |
| III-5 | (structure) |
| III-6 | (structure) |
| III-7 | (structure) |
| III-8 | (structure) |
| III-9 | (structure) |
| III-10 | (structure) |
| III-11 | (structure) |

[Sample Preparation]

Samples were prepared using the present compounds of Compound No. I-60 through I-315. More specifically, 32 µl of a 20 mL sample solution dissolved in dimethylsulfoxide (DMSO) were removed and brought to a volume of 1 ml with phosphate-buffered saline (PBS) to prepare a sample solution having a concentration of 0.32 mM (containing 3.2% DMSO).

[Cell Migration Assay (CMA) Test]

After disseminating the 7th subculture of HUVEC obtained from the first generation at 4 ml/well ($3.0 \times 10^5$ cells/well) in a collagen-coated 6-well plate (NUNC), the cells were cultured for 48 hours at 37° C. in the presence of 5% $CO_2$. The cells reached nearly a completely confluent state as a result of this culturing.

A double-edged, disposable razor blade was divided into four sections, of which one of those sections was pinched between a pair of forceps. Using this piece of razor blade, the cell surface in the above confluent state was scraped off.

After washing the surface of the wells from which the cells had been scraped off with medium, 4.0 ml of fresh M199 (2+) medium were placed in the wells. 4.0 ml of M199 medium were added to the control (−) well.

125 µl of sample solution (0.32 mM, containing 3.2% dimethylsulfoxide) were added to the wells.

125 µl of PBS solution containing 3.2% dimethylsulfoxide were added to the control wells instead of sample. The cells were cultured for 24 hours at 37° C. in the presence of 5% $CO_2$. After discarding the culture liquid, the cells were fixed for 30 minutes with methanol. Next, after fixing the cells for 4 hours with Giemsa stain, the plates were washed with tap water and air dried.

Measurement of cell migration was performed by microscopically counting the number of cells that had newly migrated within the range of a 1 mm×1 mm block. More specifically, as shown in FIG. 1, a line on the edge of the gradation (block) was aligned with the line formed as a result of scraping off the cells, and, for example, the number of cells in block 1 (1-A,B,C,D,E) were all counted within a 5×5 gradation (1 square=200 μm×200 μm) printed on the eyepiece lens, and that number was taken to be the number of cells of block 1. The total number of cells counted in blocks 1 through 5 were then totaled to determine the overall total number of cells. Four fields were counted for each well.

Evaluation was performed determining the cell migration inhibitory rate (%) according to the following equation.

Inhibitory rate=100−((number of migrating cells to which sample was added−number of migrating cells of control (−))×100/ (number of migrating cells of control (+)−number of migrating cells of control (−)))

If this inhibitory rate was 80% or more, cell migration was assessed as being remarkable.

[Tube Formation Assay (TFA) Test]

The testing method used for these compounds was the same as that used for the compounds of Compound No. 1 through 60 previously described.

TABLE 75

| Compound No. | Inhibition rate (%) | |
|---|---|---|
| | CMA | TFA |
| I-61 | 82.1 | 18.9 |
| I-62 | 10.6 | 28.4 |
| I-63 | 14.2 | 41.7 |
| I-64 | 9.4 | 5.2 |
| I-65 | 73.4 | 32.4 |
| I-66 | 30.5 | 19.7 |
| I-67 | 29.5 | 19.7 |
| I-68 | 65.6 | 9.2 |
| I-69 | 18.8 | 18.0 |
| I-70 | 7.1 | 75.4 |
| I-71 | 25.4 | 4.1 |
| I-72 | 42.9 | 5.9 |
| I-73 | 15.6 | 8.2 |
| I-74 | 23.4 | 5.8 |
| I-75 | 11.7 | 4.3 |
| I-76 | 7.6 | 4.6 |
| I-77 | 5.9 | 7.2 |
| I-78 | 23.4 | 5.1 |
| I-79 | 13.7 | 4.7 |
| I-80 | 5.9 | 8.1 |
| I-81 | 31.2 | 8.3 |
| I-82 | 13.7 | 5.5 |
| I-83 | 50.0 | 21.4 |
| I-84 | 8.8 | 21.9 |
| I-85 | 31.0 | 15.6 |
| I-86 | 9.9 | 5.2 |
| I-87 | 8.0 | 8.6 |
| I-88 | 16.5 | 4.7 |
| I-89 | 9.9 | 31.3 |
| I-90 | 4.3 | 22.8 |

TABLE 76

| Compound No. | Inhibition rate (%) | |
|---|---|---|
| | CMA | TFA |
| I-91 | 21.6 | 5.1 |
| I-92 | 8.1 | 15.2 |
| I-93 | 5.8 | 2.4 |

TABLE 76-continued

| Compound No. | Inhibition rate (%) | |
|---|---|---|
| | CMA | TFA |
| I-94 | 3.9 | 6.2 |
| I-95 | 9.8 | 4.5 |
| I-96 | 5.9 | 19.7 |
| I-97 | 7.7 | 29.1 |
| I-98 | 2.7 | 3.8 |
| I-99 | 9.9 | 8.6 |
| I-100 | 21.9 | 23.3 |
| I-101 | 15.7 | 6.3 |
| I-102 | 15.6 | 8.2 |
| I-103 | 5.1 | 8.3 |
| I-104 | 24.1 | 3.8 |
| I-105 | 14.9 | 5.6 |
| I-106 | 6.7 | 26.8 |
| I-107 | 31.2 | 4.4 |
| I-108 | 11.7 | 3.0 |
| I-109 | 21.5 | 7.2 |
| I-110 | 7.8 | 4.6 |
| I-111 | 9.4 | 2.9 |
| I-112 | 6.8 | 7.9 |
| I-113 | 34.4 | 7.9 |
| I-114 | 9.4 | 6.8 |
| I-115 | 3.1 | 6.8 |
| I-116 | 5.6 | 6.9 |
| I-117 | 28.1 | 26.8 |
| I-118 | 31.3 | 5.1 |
| I-119 | 18.8 | 4.2 |
| I-120 | 3.1 | 7.8 |

TABLE 77

| Compound No. | Inhibition rate (%) | |
|---|---|---|
| | CMA | TFA |
| I-121 | 7.1 | 9.4 |
| I-122 | 10.3 | 9.1 |
| I-123 | 8.0 | 14.1 |
| I-124 | 5.7 | 2.6 |
| I-125 | 17.2 | 2.6 |
| I-126 | 6.5 | 4.0 |
| I-127 | 5.3 | 5.3 |
| I-128 | 8.7 | 9.4 |
| I-129 | 4.3 | 19.5 |
| I-130 | 7.5 | 5.5 |
| I-134 | 19.5 | 7.2 |
| I-132 | 15.6 | 3.9 |
| I-133 | 3.9 | 9.5 |
| I-134 | 7.1 | 8.6 |
| I-135 | 23.4 | 4.7 |
| I-136 | 8.3 | 15.6 |
| I-137 | 3.3 | 6.4 |
| I-138 | 3.5 | 2.5 |
| I-139 | 9.7 | 25.6 |
| I-140 | 3.3 | 5.2 |
| I-141 | 12.5 | 23.1 |
| I-142 | 9.8 | 3.7 |
| I-143 | 5.9 | 8.1 |
| I-144 | 31.2 | 7.5 |
| I-145 | 27.3 | 17.5 |
| I-146 | 17.2 | 7.8 |
| I-147 | 41.0 | 10.3 |
| I-148 | 3.4 | 5.1 |
| I-149 | 7.5 | 8.7 |
| I-150 | 5.4 | 32.3 |

TABLE 78

| Compound No. | Inhibition rate (%) CMA | TFA |
|---|---|---|
| I-151 | 35.9 | 38.1 |
| I-152 | 33.7 | 51.0 |
| I-153 | 22.3 | 19.0 |
| I-154 | 151.0 | 56.2 |
| I-155 | 19.9 | 45.7 |
| I-156 | 5.8 | 10.9 |
| I-157 | 7.7 | 12.9 |
| I-158 | 7.3 | 8.5 |
| I-159 | 39.5 | 9.8 |
| I-160 | 6.3 | 13.8 |
| I-161 | 14.4 | 8.2 |
| I-162 | 8.9 | 7.5 |
| I-163 | 5.6 | 11.5 |
| I-164 | 5.9 | 2.5 |
| I-165 | 12.5 | 7.5 |
| I-166 | 8.7 | 9.1 |
| I-167 | 4.1 | 5.1 |
| I-168 | 17.2 | 4.2 |
| I-169 | 12.6 | 13.7 |
| I-170 | 6.7 | 12.9 |
| I-171 | 3.0 | 5.8 |
| I-172 | 5.5 | 8.7 |
| I-173 | 107.5 | 11.4 |
| I-174 | 12.9 | 67.0 |
| I-175 | 19.5 | 7.5 |
| I-176 | 11.7 | 2.2 |
| I-177 | 5.0 | 15.0 |
| I-178 | 6.3 | 5.8 |
| I-179 | 81.3 | 5.2 |
| I-180 | 50.0 | 7.7 |

TABLE 79

| Compound No. | Inhibition rate (%) CMA | TFA |
|---|---|---|
| I-181 | 2.3 | 3.2 |
| I-182 | 3.9 | 9.6 |
| I-183 | 25.4 | 8.7 |
| I-184 | 37.1 | 7.4 |
| I-185 | 15.6 | 4.9 |
| I-186 | 6.3 | 5.5 |
| I-187 | 31.3 | 11.7 |
| I-188 | 7.1 | 10.2 |
| I-189 | 8.5 | 4.7 |
| I-190 | 21.8 | 12.8 |
| I-191 | 8.0 | 6.0 |
| I-192 | 7.8 | 4.5 |
| I-193 | 5.3 | 6.7 |
| I-194 | 5.5 | 3.0 |
| I-195 | 15.7 | 3.7 |
| I-196 | 27.6 | 6.2 |
| I-197 | 20.0 | 4.5 |
| I-198 | 7.9 | 2.9 |
| I-199 | 25.0 | 6.0 |
| I-200 | 25.0 | 5.6 |
| I-201 | 8.5 | 18.5 |
| I-202 | 6.5 | 26.2 |
| I-203 | 5.9 | 15.8 |
| I-204 | 7.7 | 3.5 |
| I-205 | 8.7 | 2.0 |
| I-206 | 33.6 | 14.2 |
| I-207 | 5.5 | 4.4 |
| I-208 | 7.6 | 8.2 |
| I-209 | 8.9 | 4.9 |
| I-210 | 8.0 | 8.9 |

TABLE 80

| Compound No. | Inhibition rate (%) CMA | TFA |
|---|---|---|
| I-211 | 32.1 | 20.4 |
| I-212 | 21.5 | 7.8 |
| I-213 | 21.5 | 6.2 |
| I-214 | 11.7 | 5.7 |
| I-215 | 21.5 | 8.1 |
| I-216 | 9.4 | 3.7 |
| I-217 | 9.4 | 7.2 |
| I-218 | 25.0 | 5.4 |
| I-219 | 6.3 | 30.6 |
| I-220 | 25.0 | 7.4 |
| I-221 | 15.6 | 24.5 |
| I-222 | 3.7 | 20.8 |
| I-223 | 18.8 | 17.9 |
| I-224 | 15.6 | 10.5 |
| I-225 | 25.0 | 5.5 |
| I-226 | 17.2 | 15.3 |
| I-227 | 17.2 | 7.4 |
| I-228 | 7.2 | 2.7 |
| I-229 | 19.5 | 3.0 |
| I-230 | 28.7 | 6.4 |
| I-231 | 9.7 | 5.9 |
| I-232 | 6.5 | 2.9 |
| I-233 | 5.5 | 4.1 |
| I-234 | 7.3 | 7.3 |
| I-235 | 6.5 | 9.3 |
| I-236 | 28.1 | 10.4 |
| I-237 | 6.9 | 7.8 |
| I-238 | 5.9 | 17.8 |
| I-239 | 7.8 | 5.7 |
| I-240 | 8.5 | 7.4 |

TABLE 81

| Compound No. | Inhibition rate (%) CMA | TFA |
|---|---|---|
| I-241 | 12.6 | 5.1 |
| I-242 | 5.1 | 4.8 |
| I-243 | 6.7 | 8.1 |
| I-244 | 19.5 | 5.2 |
| I-245 | 27.3 | 6.3 |
| I-246 | 23.4 | 4.9 |
| I-247 | 23.4 | 9.7 |
| I-248 | 2.2 | 5.7 |
| I-249 | 44.0 | 11.1 |
| I-250 | 8.0 | 4.1 |
| I-251 | 8.7 | 7.9 |
| I-252 | 8.2 | 5.4 |
| I-253 | 25.1 | 5.7 |
| I-254 | 4.7 | 4.6 |
| I-255 | 6.5 | 6.0 |
| I-256 | 5.0 | 4.0 |
| I-257 | 8.0 | 3.5 |
| I-258 | 5.7 | 3.8 |
| I-259 | 5.0 | 2.9 |
| I-260 | 8.9 | 2.5 |
| I-261 | 37.5 | 32.1 |
| I-262 | 6.3 | 8.8 |
| I-263 | 7.2 | 5.5 |
| I-264 | 6.7 | 29.2 |
| I-265 | 6.3 | 3.3 |
| I-266 | 9.4 | 4.9 |
| I-267 | 14.9 | 5.8 |
| I-268 | 8.4 | 7.6 |
| I-269 | 19.5 | 8.3 |
| I-270 | 28.7 | 5.9 |

TABLE 82

| Compound No. | Inhibition rate (%) CMA | Inhibition rate (%) TFA |
|---|---|---|
| I-271 | 21.6 | 35.1 |
| I-272 | 5.7 | 7.9 |
| I-273 | 3.8 | 17.5 |
| I-274 | 14.9 | 7.0 |
| I-275 | 7.7 | 2.0 |
| I-276 | 5.7 | 8.2 |
| I-277 | 12.7 | 84.4 |
| I-278 | 125.2 | 20.2 |
| I-279 | 45.1 | 13.2 |
| I-280 | 72.4 | 14.9 |
| I-281 | 27.9 | 31.1 |
| I-282 | 5.8 | 6.0 |
| I-283 | 9.1 | 11.0 |
| I-284 | 32.5 | 23.1 |
| I-285 | 6.5 | 7.7 |
| I-286 | 26.6 | 21.2 |
| I-287 | 35.2 | 30.1 |
| I-288 | 15.9 | 2.4 |
| I-289 | 9.4 | 17.1 |
| I-290 | 51.5 | 13.5 |
| I-291 | 7.0 | 44.5 |
| I-292 | 57.9 | 23.5 |
| I-293 | 69.3 | 11.2 |
| I-294 | 4.5 | 7.8 |
| I-295 | 5.6 | 7.9 |
| I-296 | 19.9 | 21.3 |
| I-297 | 15.2 | 11.2 |
| I-298 | 7.8 | 9.5 |
| I-299 | 5.9 | 8.8 |
| I-300 | 8.0 | 14.6 |

TABLE 83

| Compound No. | Inhibition rate (%) CMA | Inhibition rate (%) TFA |
|---|---|---|
| I-301 | 56.0 | 15.9 |
| I-302 | 26.6 | 12.5 |
| I-303 | 6.1 | 30.6 |
| I-304 | 9.4 | 11.2 |
| I-305 | 7.6 | 23.1 |
| I-306 | 25.1 | 22.6 |
| I-307 | 52.5 | 50.2 |
| I-308 | 32.1 | 23.2 |
| I-309 | 48.0 | 5.2 |
| I-310 | 20.7 | 20.1 |
| I-311 | 7.6 | 10.7 |
| I-312 | 34.9 | 41.8 |
| I-313 | 60.2 | 27.0 |
| I-314 | 47.2 | 9.4 |
| I-315 | 36.4 | 8.6 |

Industrial Feasibility

As described above, a vascularization inhibitor having for its active ingredient a novel compound according to the persent invention has remarkable vascularization inhibitory effects unaccompanied by serious adverse side effects, which is useful for the treatment and prevention of various diseases accompanied by abnormal acceleration of vascularization.

Further, the compound according to the present has excellent solubility characteristics, which is suitable for using as pharmaceutical.

We claim:

1. A compound represented by the following general formula (II)

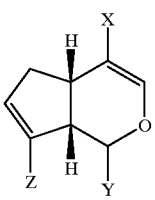

(II)

wherein:

X represents a $C_{1-5}$ alkyl group or —$COR^1$, and $R^1$ is:
(a) a hydroxyl group or —OM, wherein —OM is a pharmacologically allowable salt or M is an alkali metal atom,
(b) a $C_{1-10}$ alkoxyl group, $C_{2-10}$ alkenyloxyl group or $C_{4-15}$ alkedienyloxyl group and wherein each may or may not be substituted with a phenyl group,
(c) a furfuryloxyl group, phenoxyl group or $C_{3-10}$ cycloalkyloxyl group, or
(d) —$NR^4R^5$ wherein $R^4$ and $R^5$ may be respectively identical or different, and each represents
a hydrogen atom,
$C_{3-10}$ cycloalkyl group,
phenyl group,
a five-membered or six-membered ring system containing one or more heteroatoms selected from
nitrogen,
oxygen or
sulfur atoms,
$C_{1-10}$ alkyl group which may or may not be substituted with a
mercapto group,
—$CO_2R^6$ wherein $R^6$ is a $C_{1-5}$ alkyl group,
phenyl group or
nitrogen-containing aromatic group; or
$R^4$ and $R^5$ and are bonded to form a heterocycloalkyl group, and said heterocycloalkyl group is a five-membered or six-membered ring system that contains as a heteroatom only the nitrogen atom at which $R^4$ and $R^5$ are bonded, or which contains a different nitrogen atom or oxygen atom, and said heterocycloalkyl group may or may not be substituted with a $C_{1-5}$ alkyl group which may or may not be substituted with a hydroxyl group or —OCONH—$R^7$ wherein $R^7$ is a hydrogen atom or $C_{1-5}$ alkyl group;

Y represents a hydrogen atom or the following formula:

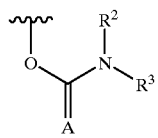

wherein $R^2$ and $R^3$ may be respectively identical or different, and each represents:
(a) a hydrogen atom, $C_{1-10}$ alkyl group which may be a straight or branched chain, $C_{2-10}$ alkenyl group, $C_{3-10}$ cycloalkyl group, $C_{1-10}$ alkylamino group, $C_{1-10}$ alkoxyl group, $C_{3-10}$ heterocycloalkyl group, phenyl group, phenyl $C_{1-5}$ alkyl group, naphthyl group, or cyclic amino group containing a heteroatom selected from nitrogen, oxygen or sulfur atoms, wherein each of said groups may or may not be substituted with a halogen atom, hydroxyl group, mercapto group, nitro group, cyano group, —SO$_2$NH$_2$ group, hydroxy C$_{1-5}$ alkoxy group, C$_{1-5}$ alkylamino group, C$_{1-5}$ alkylcarbonyl group, C$_{1-5}$ alkylthio group, benzylthio group, halogenated C$_{1-5}$ alkyl group, halogenated C$_{1-5}$ alkoxy group and —CO$_2$R$^8$ wherein R$^8$ is a C$_{1-5}$ alkyl group, C$_{3-10}$ cycloalkyl group or five-membered or six-membered ring system that may be condensed with a benzene ring and contains one or more heteroatoms selected from nitrogen, oxygen or sulfur atoms;

(b) —COR$^9$ wherein R$^9$ is a phenyl group or a C$_{1-5}$ alkyl group which may or may not be substituted with a halogen atom; or (c) R$^2$ and R$^3$ are bonded to form a heterocycloalkyl group or heterocyclolalkenyl group, and said heterocycloalkyl group or heteroycloalkenyl group is a four-membered, five-membered or six-membered ring system that may be condensed with a benzene ring, and contains as a heteroatom only the nitrogen atom at which R$^2$ and R$^3$ are bonded, or which contains a different nitrogen atom, oxygen atom or sulfur atom, wherein said ring system may or may not be substituted with a C$_{1-5}$ alkyl group, hydroxy C$_{1-5}$ alkyl group, phenyl group, phenyl C$_{1-5}$ alkyl group, halogenated phenyl group, C$_{1-5}$ alkoxyphenyl group or halogenated C$_{1-5}$ alkylphenyl group; and A represents an oxygen atom or sulfur atom; and Z represents a C$_{1-10}$ alkyl group which may or may not be substituted with a hydroxyl group, halogen atom, —O—R$^{10}$, —OCO—R$^{11}$, —OCOO—R$^{12}$ or —OCONH—R$^{13}$ wherein R$^{10}$ through R$^{13}$ may be a hydrogen atom or C$_{1-5}$ alkyl group that may be substituted with a halogen atom; or wherein said C$_{1-10}$ alkyl group may or may not be substituted with —CO—R$^{14}$, or —CH$_2$—S—R$^{15}$;

wherein R$^{14}$ and R$^{15}$ each represents a five membered or six membered ring system that may be condensed with a benzene ring and contains one or more heteroatoms selected from nitrogen, oxygen or sulfur atoms, or a hydroxy C$_{1-5}$ alkyl group.

2. A compound represented by the following general formula (III):

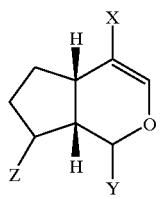

(III)

wherein:

X represents a C$_{1-5}$ alkyl group or —COR$^1$, and R$^1$ is:

(a) a hydroxyl group or —OM, wherein —OM is a pharmacologically allowable salt or M is an alkali metal atom, (b) a C$_{1-10}$ alkoxyl group, C$_{2-10}$ alkenyloxyl group or C$_{4-15}$ alkedienyloxyl group and wherein each may or may not be substituted with a phenyl group, (c) a furfuryloxyl group, phenoxyl group or C$_{3-10}$ cycloalkyloxyl group, or (d) —NR$^4$R$^5$ wherein R$^4$ and R$^5$ may be respectively identical or different, and each represents a hydrogen atom, C$_{3-10}$ cycloalkyl group, phenyl group, a five-membered or six-membered ring system containing one or more heteroatoms selected from
nitrogen,
oxygen or
sulfur atoms, C$_{1-10}$ alkyl group which may or may not be substituted with a
mercapto group,
—CO$_2$R$^6$ wherein R$^6$ is a C$_{1-5}$ alkyl group,
phenyl group or
nitrogen-containing aromatic group; or R$^4$ and R$^5$ and are bonded to form a heterocycloalkyl group, and said heterocycloalkyl group is a five-membered or six-membered ring system that contains as a heteroatom only the nitrogen atom at which R$^4$ and R$^5$ are bonded, or which contains a different nitrogen atom or oxygen atom, and said heterocycloalkyl group may or may not be substituted with a C$_{1-5}$ alkyl group which may or may not be substituted with a hydroxyl group or —OCONH—R$^7$ wherein R$^7$ is a hydrogen atom or C$_{1-5}$ alkyl group;

Y represents a hydrogen atom or the following formula:

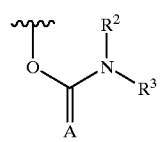

wherein R$^2$ and R$^3$ may be respectively identical or different, and each represents:

(a) a hydrogen atom, C$_{1-10}$ alkyl group which may be a straight or branched chain, C$_{2-10}$ alkenyl group, C$_{3-10}$ cycloalkyl group, C$_{1-10}$ alkylamino group, C$_{1-10}$ alkoxyl group, C$_{3-10}$ heterocycloalkyl group, phenyl group, phenyl C$_{1-5}$ alkyl group, naphthyl group, or cyclic amino group containing a heteroatom selected from nitrogen, oxygen or sulfur atoms, wherein each of said groups may or may not be substituted with a halogen atom, hydroxyl group, mercapto group, nitro group, cyano group, —SO$_2$NH$_2$ group, hydroxy C$_{1-5}$ alkoxy group, C$_{1-5}$ alkylamino group, C$_{1-5}$ alkylcarbonyl group, C$_{1-5}$ alkylthio group, benzylthio group, halogenated C$_{1-5}$ alkyl group, halogenated C$_{1-5}$ alkoxy group and —CO$_2$R$^8$ wherein R$^8$ is a C$_{1-5}$ alkyl group, C$_{3-10}$ cycloalkyl group or five-membered or six-membered ring system that may be condensed with a benzene ring and contains one or more heteroatoms selected from nitrogen, oxygen or sulfur atoms;

(b) —COR$^9$ wherein R$^9$ is a phenyl group or a C$_{1-5}$ alkyl group which may or may not be substituted with a halogen atom; or (c) R$^2$ and R$^3$ are bonded to form a heterocycloalkyl group or heterocyclolalkenyl group, and said heterocycloalkyl group or heteroycloalkenyl group is a four-membered, five-membered or six-membered ring system that may be condensed with a benzene ring, and contains as a heteroatom only the nitrogen atom at which R$^2$ and R$^3$ are bonded, or which contains a different nitrogen atom, oxygen atom or sulfur atom, wherein said ring system may or may not be substituted with a C$_{1-5}$ alkyl group, hydroxy C$_{1-5}$ alkyl group, phenyl group, phenyl $C_{1-5}$ alkyl group, halogenated phenyl group, $C_{1-5}$ alkoxyphenyl group or halogenated $C_{1-5}$ alkylphenyl group; and A represents an oxygen atom or sulfur atom; and Z represents a $C_{1-10}$ alkyl group which may or may not be substituted with a hydroxyl group, halogen atom, —O—$R^{10}$, —OCO—$R^{11}$, —OCOO—$R^{12}$ or —OCONH—$R^{13}$
wherein $R^{10}$ through $R^{13}$ may be a hydrogen atom or $C_{1-5}$ alkyl group that may be substituted with a halogen atom; or wherein said $C_{1-10}$ alkyl group may or may not be substituted with —CO—$R^{14}$, or —CH$_2$—S—$R^{15}$ wherein $R^{14}$ and $R^{15}$ each represents a five membered or six membered ring system that may be condensed with a benzene ring and contains one or more heteroatoms selected from nitrogen, oxygen or sulfur atoms, or a hydroxy $C_{1-5}$ alkyl group.

3. A compound represented by the following general formula (IV):

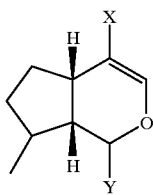

(IV)

wherein:

Y represents a hydrogen atom or the following formula:

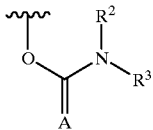

wherein $R^2$ and $R^3$ may be respectively identical or different, and each represents:

(a) a hydrogen atom, $C_{1-10}$ alkyl group which may be a straight or branched chain, $C_{2-10}$ alkenyl group, $C_{3-10}$ cycloalkyl group, $C_{1-10}$ alkylamino group, $C_{1-10}$ alkoxyl group, $C_{3-10}$ heterocycloalkyl group, phenyl group, phenyl $C_{1-5}$ alkyl group, naphthyl group, or cyclic amino group containing a heteroatom selected from nitrogen, oxygen or sulfur atoms, wherein each of said groups may or may not be substituted with a halogen atom, hydroxyl group, mercapto group, nitro group, cyano group, —SO$_2$NH$_2$ group, hydroxy $C_{1-5}$ alkoxy group, $C_{1-5}$ alkylamino group, $C_{1-5}$ alkylcarbonyl group, $C_{1-5}$ alkylthio group, benzylthio group, halogenated $C_{1-5}$ alkyl group, halogenated $C_{1-5}$ alkoxy group and —CO$_2$R$^8$
wherein $R^8$ is a $C_{1-5}$ alkyl group, $C_{3-10}$ cycloalkyl group or five-membered or six-membered ring system that may be condensed with a benzene ring and contains one or more heteroatoms selected from nitrogen, oxygen or sulfur atoms;

(b) —COR$^9$ wherein $R^9$ is a phenyl group or a $C_{1-5}$ alkyl group which may or may not be substituted with a halogen atom; or (c) $R^2$ and $R^3$ are bonded to form a heterocycloalkyl group or heterocyclolalkenyl group, and said heterocycloalkyl group or heteroycloalkenyl group is a four-membered, five-membered or six-membered ring system that may be condensed with a benzene ring, and contains as a heteroatom only the nitrogen atom at which $R^2$ and $R^3$ are bonded, or which contains a different nitrogen atom, oxygen atom or sulfur atom, wherein said ring system may or may not be substituted with a $C_{1-5}$ alkyl group, hydroxy $C_{1-5}$ alkyl group, phenyl group, phenyl $C_{1-5}$ alkyl group, halogenated phenyl group, $C_{1-5}$ alkoxyphenyl group or halogenated $C_{1-5}$ alkylphenyl group; and A represents an oxygen atom or sulfur atom.

4. A compound represented by the following general formula (VI):

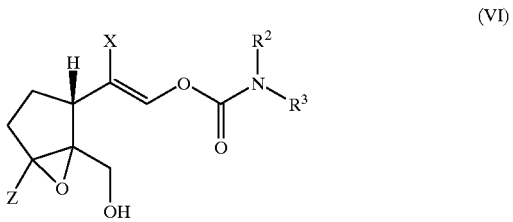

(VI)

wherein:

X represents a $C_{1-5}$ alkyl group or —COR$^1$, and $R^1$ is:

(a) a hydroxyl group or —OM, wherein —OM is a pharmacologically allowable salt or M is an alkali metal atom, (b) a $C_{1-10}$ alkoxyl group, $C_{2-10}$ alkenyloxyl group or $C_{4-15}$ alkedienyloxyl group and wherein each may or may not be substituted with a phenyl group, (c) a furfuryloxyl group, phenoxyl group or $C_{3-10}$ cycloalkyloxyl group, or (d) —NR$^4$R$^5$ wherein $R^4$ and $R^5$ may be respectively identical or different, and each represents
a hydrogen atom,
$C_{3-10}$ cycloalkyl group,
phenyl group,
a five-membered or six-membered ring system containing one or more heteroatoms selected from
nitrogen,
oxygen or
sulfur atoms,
$C_{1-10}$ alkyl group which may or may not be substituted with a
mercapto group,
—CO$_2$R$^6$ wherein $R^6$ is a $C_{1-5}$ alkyl group,
phenyl group or
nitrogen-containing aromatic group; or
$R^4$ and $R^5$ and are bonded to form a heterocycloalkyl group, and said heterocycloalkyl group is a five-membered or six-membered ring system that contains as a heteroatom only the nitrogen atom at which $R^4$ and $R^5$ are bonded, or which contains a different nitrogen atom or oxygen atom, and said heterocycloalkyl group may or may not be substituted with a $C_{1-5}$ alkyl group which may or may not be substituted with a hydroxyl group or —OCONH—$R^7$ wherein $R^7$ is a hydrogen atom or $C_{1-5}$ alkyl group;

$R^2$ and $R^3$ may be respectively identical or different, and each represents:

(a) a hydrogen atom, $C_{1-10}$ alkyl group which may be a straight or branched chain, $C_{2-10}$ alkenyl group, $C_{3-10}$ cycloalkyl group, $C_{1-10}$ alkylamino group, $C_{1-10}$ alkoxyl group, $C_{3-10}$ heterocycloalkyl group, phenyl group, phenyl $C_{1-5}$ alkyl group, naphthyl group, or cyclic amino group containing a heteroatom selected from nitrogen, oxygen or sulfur atoms, wherein each of said groups may or may not be substituted with a halogen atom, hydroxyl group, mercapto group, nitro group, cyano group, —$SO_2NH_2$ group, hydroxy $C_{1-5}$ alkoxy group, $C_{1-5}$ alkylamino group, $C_{1-5}$ alkylcarbonyl group, $C_{1-5}$ alkylthio group, benzylthio group, halogenated $C_{1-5}$ alkyl group, halogenated $C_{1-5}$ alkoxy group and —$CO_2R^8$ wherein $R^8$ is a $C_{1-5}$ alkyl group, $C_{3-10}$ cycloalkyl group or five-membered or six-membered ring system that may be condensed with a benzene ring and contains one or more heteroatoms selected from nitrogen, oxygen or sulfur atoms;

(b) —$COR^9$ wherein $R^9$ is a phenyl group or a $C_{1-5}$ alkyl group which may or may not be substituted with a halogen atom; or (c) $R^2$ and $R^3$ are bonded to form a heterocycloalkyl group or heterocyclolalkenyl group, and said heterocycloalkyl group or heteroycloalkenyl group is a four-membered, five-membered or six-membered ring system that may be condensed with a benzene ring, and contains as a heteroatom only the nitrogen atom at which $R^2$ and $R^3$ are bonded, or which contains a different nitrogen atom, oxygen atom or sulfur atom, wherein said ring system may or may not be substituted with a $C_{1-5}$ alkyl group, hydroxy $C_{1-5}$ alkyl group, phenyl group, phenyl $C_{1-5}$ alkyl group, halogenated phenyl group, $C_{1-5}$ alkoxyphenyl group or halogenated $C_{1-5}$ alkylphenyl group; and Z represents a $C_{1-10}$ alkyl group which may or may not be substituted with a hydroxyl group, halogen atom, —O—$R^{10}$, —OCO—$R^{11}$, —OCOO—$R^{12}$ or —OCONH—$R^{13}$ wherein $R^{10}$ through $R^{13}$ may be a hydrogen atom or $C_{1-5}$ alkyl group that may be substituted with a halogen atom; or wherein said $C_{1-10}$ alkyl group may or may not be substituted with —CO—$R^{14}$, or —$CH_2$—S—$R^{15}$ wherein $R^{14}$ and $R^{15}$ each represents a five membered or six membered ring system that may be condensed with a benzene ring and contains one or more heteroatoms selected from nitrogen, oxygen or sulfur atoms, or a hydroxy $C_{1-5}$ alkyl group.

5. A compound represented by the following general formula (IX)

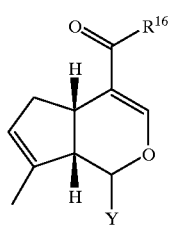

(IX)

wherein, Y represents a hydrogen atom or the following formula:

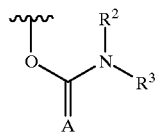

wherein $R^2$ and $R^3$ may be respectively identical or different, and each represents:

(a) a hydrogen atom, $C_{1-10}$ alkyl group which may be a straight or branched chain, $C_{2-10}$ alkenyl group, $C_{3-10}$ cycloalkyl group, $C_{1-10}$ alkylamino group, $C_{1-10}$ alkoxyl group, $C_{3-10}$ heterocycloalkyl group, phenyl group, phenyl $C_{1-5}$ alkyl group, naphthyl group, or cyclic amino group containing a heteroatom selected from nitrogen, oxygen or sulfur atoms, wherein each of said groups may or may not be substituted with a halogen atom, hydroxyl group, mercapto group, nitro group, cyano group, —$SO_2NH_2$ group, hydroxy $C_{1-5}$ alkoxy group, $C_{1-5}$ alkylamino group, $C_{1-5}$ alkylcarbonyl group, $C_{1-5}$ alkylthio group, benzylthio group, halogenated $C_{1-5}$ alkyl group, halogenated $C_{1-5}$ alkoxy group and —$CO_2R^8$ wherein $R^8$ is a $C_{1-5}$ alkyl group, $C_{3-10}$ cycloalkyl group or five-membered or six-membered ring system that may be condensed with a benzene ring and contains one or more heteroatoms selected from nitrogen, oxygen or sulfur atoms;

(b) —$COR^9$ wherein $R^9$ is a phenyl group or a $C_{1-5}$ alkyl group which may or may not be substituted with a halogen atom; or (c) $R^2$ and $R^3$ are bonded to form a heterocycloalkyl group or heterocyclolalkenyl group, and said heterocycloalkyl group or heteroycloalkenyl group is a four-membered, five-membered or six-membered ring system that may be condensed with a benzene ring, and contains as a heteroatom only the nitrogen atom at which $R^2$ and $R^3$ are bonded, or which contains a different nitrogen atom, oxygen atom or sulfur atom, wherein said ring system may or may not be substituted with a $C_{1-5}$ alkyl group, hydroxy $C_{1-5}$ alkyl group, phenyl group, phenyl $C_{1-5}$ alkyl group, halogenated phenyl group, $C_{1-5}$ alkoxyphenyl group or halogenated $C_{1-5}$ alkylphenyl group; and A represents an oxygen atom or sulfur atom; and $R^{16}$ represents a hydroxyl group, methoxyl group or —OM wherein —OM is a pharmacologically allowable salt or M is an alkali metal atom.

6. A compound represented by the following general formula (X):

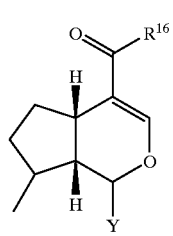

(X)

wherein:

Y represents a hydrogen atom or the following formula:

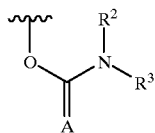

wherein $R^2$ and $R^3$ may be respectively identical or different, and each represents:

(a) a hydrogen atom, $C_{1-10}$ alkyl group which may be a straight or branched chain, $C_{2-10}$ alkenyl group, $C_{3-10}$ cycloalkyl group, $C_{1-10}$ alkylamino group, $C_{1-10}$ alkoxyl group, $C_{3-10}$ heterocycloalkyl group, phenyl group, phenyl $C_{1-5}$ alkyl group, naphthyl group, or cyclic amino group containing a heteroatom selected from nitrogen, oxygen or sulfur atoms, wherein each of said groups may or may not be substituted with a halogen atom, hydroxyl group, mercapto group, nitro group, cyano group, —$SO_2NH_2$ group, hydroxy $C_{1-5}$ alkoxy group, $C_{1-5}$ alkylamino group, $C_{1-5}$ alkylcarbonyl group, $C_{1-5}$ alkylthio group, benzylthio group, halogenated $C_{1-5}$ alkyl group, halogenated $C_{1-5}$ alkoxy group and —$CO_2R^8$
wherein $R^8$ is a $C_{1-5}$ alkyl group, $C_{3-10}$ cycloalkyl group or five-membered or six-membered ring system that may be condensed with a benzene ring and contains one or more heteroatoms selected from nitrogen, oxygen or sulfur atoms;

(b) —$COR^9$ wherein $R^9$ is a phenyl group or a $C_{1-5}$ alkyl group which may or may not be substituted with a halogen atom; or (c) $R^2$ and $R^3$ are bonded to form a heterocycloalkyl group or heterocyclolalkenyl group, and said heterocycloalkyl group or heteroycloalkenyl group is a four-membered, five-membered or six-membered ring system that may be condensed with a benzene ring, and contains as a heteroatom only the nitrogen atom at which $R^2$ and $R^3$ are bonded, or which contains a different nitrogen atom, oxygen atom or sulfur atom, wherein said ring system may or may not be substituted with a $C_{1-5}$ alkyl group, hydroxy $C_{1-5}$ alkyl group, phenyl group, phenyl $C_{1-5}$ alkyl group, halogenated phenyl group, $C_{1-5}$ alkoxyphenyl group or halogenated $C_{1-5}$ alkylphenyl group; and A represents an oxygen atom or sulfur atom; and $R^{16}$ represents a hydroxyl group, methoxyl group or —OM wherein —OM is a pharmacologically allowable salt or M is an alkali metal atom.

7. A composition for vascularization inhibition comprising as the active ingredient at least one compound as set forth in any one of claims 1, 2, 3, 4, 5, or 6 and a pharmaceutically acceptable carrier.

* * * * *